(12) United States Patent
Ginty et al.

(10) Patent No.: US 12,252,457 B2
(45) Date of Patent: Mar. 18, 2025

(54) COMPOSITIONS AND METHODS FOR REDUCING TACTILE DYSFUNCTION, ANXIETY, AND SOCIAL IMPAIRMENT

(71) Applicant: President and Fellows of Harvard College, Cambridge, MA (US)

(72) Inventors: David D. Ginty, Boston, MA (US); Lauren L. Orefice, Boston, MA (US); Jinbo Lee, Andover, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 1099 days.

(21) Appl. No.: 17/056,069

(22) PCT Filed: May 22, 2019

(86) PCT No.: PCT/US2019/033581
§ 371 (c)(1),
(2) Date: Nov. 17, 2020

(87) PCT Pub. No.: WO2019/226808
PCT Pub. Date: Nov. 28, 2019

(65) Prior Publication Data
US 2021/0206714 A1 Jul. 8, 2021

Related U.S. Application Data

(60) Provisional application No. 62/823,360, filed on Mar. 25, 2019, provisional application No. 62/674,770, filed on May 22, 2018.

(51) Int. Cl.
C07C 229/48 (2006.01)
A61P 25/02 (2006.01)
A61P 25/04 (2006.01)

(52) U.S. Cl.
CPC ............ *C07C 229/48* (2013.01); *A61P 25/02* (2018.01); *A61P 25/04* (2018.01)

(58) Field of Classification Search
CPC ............... C07C 229/48; C07C 2601/16; A61P 25/02; A61P 25/04; A61P 25/00
See application file for complete search history.

(56) References Cited

U.S. PATENT DOCUMENTS 3,243,427 A    3/1966  Recder et al.
3,516,988 A    6/1970  Schmitt
(Continued)

FOREIGN PATENT DOCUMENTS

CN    103933036 A    7/2014
EP     0167919 A2    1/1986
(Continued)

OTHER PUBLICATIONS

U.S. Pat. No. 9,586,890, Database Caplus [Online] Chemical Abstracts Service, Columbus, Ohio, US; 2017. (Year: 2017).*
(Continued)

*Primary Examiner* — Deborah D Carr
(74) *Attorney, Agent, or Firm* — Wolf, Greenfield & Sacks, P.C.

(57) ABSTRACT

The present invention features novel peripherally-restricted isoguvacine analogs with reduced blood brain barrier permeability and methods of use thereof for reducing tactile dysfunction, social impairment, and anxiety in a subject diagnosed with Autism Spectrum Disorder, Rett syndrome, Phelan McDermid syndrome, or Fragile X syndrome.

22 Claims, 112 Drawing Sheets

(56) References Cited

U.S. PATENT DOCUMENTS

| | | | |
|---|---|---|---|
| 3,862,149 | A | 1/1975 | Cortel et al. |
| 4,065,451 | A | 12/1977 | McCaully et al. |
| 4,122,265 | A | 10/1978 | Jaunin |
| 4,382,938 | A | 5/1983 | Kaplan et al. |
| 4,460,592 | A | 7/1984 | Kaplan et al. |
| 4,492,695 | A | 1/1985 | Kaplan et al. |
| 4,820,834 | A | 4/1989 | Evans et al. |
| 4,879,293 | A | 11/1989 | Hiraga et al. |
| 5,618,824 | A | 4/1997 | Schmidt et al. |
| 5,776,930 | A | 7/1998 | Lynch, Jr. et al. |
| 5,786,357 | A | 7/1998 | Young et al. |
| 6,927,290 | B2 | 8/2005 | Miki et al. |
| 7,456,173 | B2 | 11/2008 | Jerussi et al. |
| 8,980,887 | B2 | 3/2015 | Yang et al. |
| 9,586,890 | B2 * | 3/2017 | Statsyuk ............. C07D 307/84 |
| 11,434,244 | B2 | 9/2022 | Ginty et al. |
| 11,547,706 | B2 | 1/2023 | Orefice et al. |
| 12,077,512 | B2 | 9/2024 | Ginty et al. |
| 2006/0084806 | A1 | 4/2006 | Sridharan et al. |
| 2007/0015810 | A1 | 1/2007 | Cuberes |
| 2008/0312279 | A1 | 12/2008 | Warren et al. |
| 2010/0150944 | A1 | 6/2010 | Hilbush et al. |
| 2011/0046090 | A1 | 2/2011 | Barlow et al. |
| 2012/0095217 | A1 | 4/2012 | Ritter et al. |
| 2014/0066504 | A1 | 3/2014 | Hochman |
| 2015/0051151 | A1 | 2/2015 | Eisenbach-Schwartz et al. |
| 2015/0203486 | A1 | 7/2015 | Bently et al. |
| 2015/0313913 | A1 | 11/2015 | Catterall et al. |
| 2016/0193169 | A1 | 7/2016 | Hoffman |
| 2017/0197967 | A1 | 7/2017 | Pasricha et al. |
| 2020/0179374 | A1 | 6/2020 | Orefice et al. |
| 2021/0128508 | A1 | 5/2021 | Hoffman et al. |
| 2021/0206771 | A1 | 7/2021 | Ginty et al. |
| 2022/0162173 | A1 | 5/2022 | Ginty et al. |
| 2022/0233133 | A1 | 7/2022 | Ginty et al. |
| 2023/0031479 | A1 | 2/2023 | Orefice et al. |
| 2023/0051850 | A1 | 2/2023 | Ginty et al. |

FOREIGN PATENT DOCUMENTS

| | | | | |
|---|---|---|---|---|
| WO | WO 1996/031210 | A1 | 4/1996 | |
| WO | WO 97/49690 | A1 | 12/1997 | |
| WO | WO 1999/051594 | A1 | 10/1999 | |
| WO | WO 2002/028831 | A1 | 4/2002 | |
| WO | WO 03/051274 | A2 | 6/2003 | |
| WO | WO 2004/106310 | A1 | 12/2004 | |
| WO | WO 2008/003044 | A2 | 1/2008 | |
| WO | WO 2008/022396 | A1 | 8/2008 | |
| WO | WO 2010/017047 | A1 | 2/2010 | |
| WO | WO 2013/154712 | A1 | 10/2013 | |
| WO | WO-2014100438 | A1 * | 6/2014 | ............. A61P 25/00 |
| WO | WO 2014/123909 | A1 | 8/2014 | |
| WO | WO 2014/138791 | A1 | 9/2014 | |
| WO | WO 2015/013715 | A2 | 1/2015 | |
| WO | WO 2015/052076 | A1 | 4/2015 | |
| WO | WO 2017/214442 | A1 | 12/2017 | |
| WO | WO 2018/114663 | A1 | 6/2018 | |
| WO | WO 2019/103658 | A2 | 5/2019 | |
| WO | 2020/237043 | A1 | 11/2020 | |

OTHER PUBLICATIONS

Ruben Agudo et al: "Achieving Regio- and Enantioselectivity of P450-Catalyzed Oxidative CH Activation of Small Functionalized Molecules by Structure-Guided Directed Evolution", CHEMBIOCHEM, vol. 13, No. 10, 2012, pp. 1465-1473. (Year: 2012).*

Kuznetsov S G et Al: "Synthesis of cyclic amino alcohols with cholinolytic properties", Zhurnal Obshchei Khimii [Russian Journal of Organic Chemistry], Nauka, RU, vol. 29, 1959, pp. 2421-2428. (Year: 1959).*

Extended European Search Report for Application No. 19806972.6, mailed Feb. 9, 2022.

No Author Listed, CAS RN: 2098817-47-9. 2017. 3 pages.

Agudo et al., Achieving regio- and enantioselectivity of P450-catalyzed oxidative CH activation of small functionalized molecules by structure-guided directed evolution.Chembiochem. Jul. 9, 2012;13(10):1465-73. doi: 10.1002/cbic.201200244. Epub Jun. 1, 20128.

Kuznetsov et al., Synthesis of cyclic I1-5,7 amino alcohols with cholinolytic properties.Zhurnal Obshchei Khimii [Russian Journal of Organic Chemistry]. Jan. 1, 1959; 29: 2421-2428.

Partial Supplementary European Search Report, mailed Jan. 24, 2020, in connection with Application No. EP 17811036.7.

Extended European Search Report, mailed Jun. 24, 2020, in connection with Application No. EP 17811036.7.

Invitation to Pay Additional Fees, mailed Sep. 11, 2017, in connection with Application No. PCT/US2017/036621.

International Search Report and Written Opinion, mailed Nov. 9, 2017, in connection with Application No. PCT/US2017/036621.

International Preliminary Report on Patentability, mailed Oct. 29, 2018, in connection with Application No. PCT/US2017/036621.

International Search Report and Written Opinion, mailed Jul. 25, 2019, in connection with Application No. PCT/US2019/033581.

International Preliminary Report on Patentability, mailed Dec. 3, 2020, in connection with Application No. PCT/US2019/033581.

Invitation to Pay Additional Fees, mailed Jul. 19, 2019, in connection with Application No. PCT/US2019/034390.

International Search Report and Written Opinion, mailed Sep. 19, 2019, in connection with Application No. PCT/US2019/034390.

International Preliminary Report on Patentability, mailed Dec. 10, 2020, in connection with Application No. PCT/US2019/034390.

Invitation to Pay Additional Fees, mailed Jun. 4, 2020, in connection with Application No. PCT/US2020/024564.

International Search Report and Written Opinion, mailed Jul. 28, 2020, in connection with Application No. PCT/US2020/024564.

International Search Report and Written Opinion, mailed Aug. 17, 2020, in connection with Application No. PCT/US2020/033984.

[No Author Listed] PubChem. 4-Methyl-1-{ [2-(4-chlorophenyl)-imidazo[1,2-a]pyridin-3-yl]-methylcarbonyl}-piperazine. Accessed Jul. 11, 2019; created Feb. 8, 2017; modified Jul. 10, 2019. https://pubchem.ncbi.nlm.nih.gov/compound/13068199. 7 pages.

[No Author Listed] PubChem. Compound Summary for SID 319566201. Available Date Dec. 8, 2016; [Retrieved on Jul. 2, 2019]. Retrieved from the internet. https://pubchem.ncbi.nlm.nih.gov/substance/319566201.

[No Author Listed] Pubmed-Cid: 614001. Create Date: Mar. 27, 2005. pp. 1-11.

[No Author Listed] Pubmed-Cid: 4506. Create Date: Mar. 25, 2005. pp. 1-47.

[No Author Listed] Pubmed-Cid: 13068199. Create Date: Feb. 8, 2007. pp. 1-7.

[No Author Listed] Pubmed-Cid: 19842214. Create Date: Dec. 5, 2007. pp. 1-7.

[No Author Listed] Caplus Registry No. 952499-78-4. 1,2-a]pyridine-3-acetamide, N-(2-aminoethyl)-6,8-dichloro-2-(4-chlorophenyl)-N-(phenylmethyl). Entered STN: Nov. 6, 2007. 5 pages.

[No Author Listed] Caplus Registry No. 952499-71-7. Carbamic acid, N-[2-[[2-[6,8-dichloro-2-(4-chlorophenyl)imidazo[1,2-a]pyridin-3-yl]acetyl](phenylmethyl)amino]ethyl]-, 1,1-dimethylethyl ester. Entered STN: Nov. 6, 2007. 5 pages.

[No Author Listed] Caplus Registry No. 952499-50-2. [1,2-a]pyridine-3-acetamide, 6,8-dichloro-2-(4-chlorophenyl)-N-[2-[(7-nitro-2,1,3-benzoxadiazol-4-yl)amino]ethyl]-N-(phenylmethyl)- Entered STN: Nov. 6, 2007. 6 pages.

[No Author Listed] Caplus Registry No. 1616667-55-0. Carbamic acid, N,N-diethyl-, 6-(5-chloro-2-pyridinyl)-6,7-dihydro-7-oxo-5H-pyrrolo[3,4-b]pyrazin-5-yl ester entered STN: Jul. 23, 2014. 9 pages.

Akyol et al., Generating somatic mosaicism with a Cre recombinase-microsatellite sequence transgene. Nat Methods. Mar. 2008;5(3):231-3.

Amaral et al., The amygdala and autism: implications from non-human primate studies. Genes Brain Behav. Oct. 2003;2(5):295-302.

(56) References Cited

OTHER PUBLICATIONS

Amaral, The amygdala, social behavior, and danger detection. Ann N Y Acad Sci. Dec. 2003;1000(1):337-47.

Anagnostou et al., Intranasal oxytocin versus placebo in the treatment of adults with autism spectrum disorders: a randomized controlled trial. Mol Autism. Dec. 2012;3(1):16.

Antoine et al., Increased Excitation-Inhibition Ratio Stabilizes Synapse and Circuit Excitability in Four Autism Mouse Models. Neuron. Feb. 20, 2019;101(4):648-61.

Bader et al., Neurophysiological findings in the Rett syndrome, I: EMG, conduction velocity, EEG and somatosensory-evoked potential studies. Brain Dev. Jan. 1, 1989;11(2):102-9.

Baio et al., Prevalence of Autism Spectrum Disorder Among Children Aged 8 Years—Autism and Developmental Disabilities Monitoring Network, 11 Sites, United States, 2014. MMWR Surveill Summ. Apr. 27, 2018; 67(6): 1-23.

Berge et al., Pharmaceutical salts. J Pharm Sci. Jan. 1977;66(1):1-19.

Bhattacherjee et al., Neuronal cytoskeletal gene dysregulation and mechanical hypersensitivity in a rat model of Rett syndrome. Proceedings of the National Academy of Sciences. Aug. 15, 2017; 114(33): E6952-E6961.

Bowery et al., Characteristics of GABAB receptor binding sites on rat whole brain synaptic membranes. Br J Pharmacol. Jan. 1983; 78(1): 191-206.

Boyle et al., The behavioral phenotype of FMR1 mutations. Am J Med Genet C Semin Med Genet. Nov. 15, 2010; 154(4): 469-76.

Braat et al., The GABAA Receptor as a Therapeutic Target for Neurodevelopmental Disorders. Neuron. Jun. 3, 2015;86(5):1119-30.

Brandt et al., Impaired peripheral somatosensory function in children with Prader—Willi syndrome. Neuropediatrics. Jun. 1998; 29(30): 124-6.

Carlton et al., Peripheral GABA(A) receptors: evidence for peripheral primary afferent depolarization. Neuroscience. Jul. 1, 1999; 93(2): 713-22.

Cascio, Somatosensory processing in neurodevelopmental disorders. J Neurodev Disord. Jun. 2010;2(2):62-9.

Cellot et al., GABAergic signaling as therapeutic target for autism spectrum disorders. Front Pediatr. Jul. 8, 2014;2:70.

Chen et al., Presynaptic GABAergic inhibition regulated by BDNF contributes to neuropathic pain induction. Nature communications. Oct. 30, 2014; 5: 5331.

Cheng et al., Relationship between the inhibition constant (KI) and the concentration of inhibitor which causes 50 per cent inhibition (I50) of an enzymatic reaction. Biochem. Pharmacol. Dec. 1973; 22(23):3099-3108.

Choi et al., The maternal interleukin-17a pathway in mice promotes autism-like phenotypes in offspring. Science. Feb. 26, 2016; 351(6276): 933-9.

Coury et al., Use of psychotropic medication in children and adolescents with autism spectrum disorders. Pediatrics. Nov. 1, 2012; 130(Suppl 2): S69-76.

Crozier et al., MrgD activation inhibits KCNQ/M-currents and contributes to enhanced neuronal excitability. The Journal of neuroscience: the official journal of the Society for Neuroscience. Apr. 18, 2007; 27(16): 4492-6.

Dawes et al., Immune or Genetic-Mediated Disruption of CASPR2 Causes Pain Hypersensitivity Due to Enhanced Primary Afferent Excitability. Neuron. Feb. 21, 2018; 97(4): 806-22.

Dorrn et al.,Developmental sensory experience balances cortical excitation and inhibition. Nature. Jun. 2010; 465(7300): 932-6.

Downs et al., Linking MECP2 and pain sensitivity: the example of Rett syndrome. Am J Med Genet A. May 2010; 152(5): 1197-205.

Du et al., Local GABAergic signaling within sensory ganglia controls peripheral nociceptive transmission. J Clin Invest. May 1, 2017; 127(5): 1741-56.

Enna et al., The role of GABA in the mediation and perception of pain. Adv Pharmacol. Jan. 1, 2006; 54: 1-27.

Erickson et al., STX209 (arbaclofen) for autism spectrum disorders: an 8-week open-label study. J Autism Dev Disord. Apr. 1, 2014; 44(4): 958-64.

Fier et al., Synthesis and late-stage functionalization of complex molecules through C-H fluorination and nucleophilic aromatic substitution. J Am Chem Soc. Jul. 16, 2014;136(28):10139-47. doi: 10.1021/ja5049303. Epub Jul. 1, 2014.

Filice et al., Reduction in parvalbumin expression not loss of the parvalbumin-expressing GABA interneuron subpopulation in genetic parvalbumin and shank mouse models of autism. Mol Brain. Dec. 9, 2016; 10.

Flegel et al., RNA- Seq Analysis of Human Trigeminal and Dorsal Root Ganglia with a Focus on Chemoreceptors. PLoS One. Jun. 12, 2015; 10(6): e0128951.

Fukuda et al., Delayed maturation of neuronal architecture and synaptogenesis in cerebral cortex of Mecp2-deficient mice. J Neuropathol Exp Neurol. Jun. 1, 2005; 64(6): 537-44.

Golombok et al., Cognitive impairment in long-term benzodiazepine users. Psychol Med. May 1988; 18(2): 365-74.

Groeneveld et al., Measuring blood-brain barrier penetration using the NeuroCart, a CNS test battery. Drug Discov Today Technol. Jun. 1, 2016; 20: 27-34.

Guastella et al. The effects of a course of intranasal oxytocin on social behaviors in youth diagnosed with autism spectrum disorders: a randomized controlled trial. J Child Psychol Psychiatry. Apr. 2015; 56(4): 444-52.

Gudex, Adverse effects of benzodiazepines. Soc Sci Med. Jan. 1, 1991; 33(5): 587-96.

Guy et al., A mouse Mecp2-null mutation causes neurological symptoms that mimic Rett syndrome. Nat Genet. Mar. 2001;27(3):322-6.

Haas et al., Peripheral nerve findings in Rett syndrome. J Child Neurol. Jan. 1988; 3(1_Suppl): S25-30.

Hadjikhani et al., Bumetanide for autism: more eye contact, less amygdala activation. Sci Rep. Feb. 26, 2018; 8(1): 3602.

Hagerman et al., Neuropathy as a presenting feature in fragile X-associated tremor/ataxia syndrome. Am J Med Genet A. Oct. 1, 2007; 143(19): 2256-60.

Han et al. SHANK3 Deficiency Impairs Heat Hyperalgesia and TRPV1 Signaling in Primary Sensory Neurons. Neuron. Dec. 21, 2016; 92(6): 1279-93.

Hanack et al., GABA blocks pathological but not acute TRPV1 pain signals. Cell. Feb. 12, 2015; 160(4): 759-770.

Hasegawa et al., Analyzing somatosensory axon projections with the sensory neuron-specific Advillin gene. The Journal of neuroscience: the official journal of the Society for Neuroscience. Dec. 26, 2007; 27(52): 14404-14.

Hashemi et al., The Number of Parvalbumin-Expressing Interneurons Is Decreased in the Medial Prefrontal Cortex in Autism. Cereb Cortex. Mar. 1, 2017; 27(3): 1931-43.

He et al., Critical period inhibition of NKCC1 rectifies synapse plasticity in the somatosensory cortex and restores adult tactile response maps in fragile X mice. Mol Psychiatry. Nov. 2019; 24(11):1732-47.

Hill et al., 3H-baclofen and 3H-GABA bind to bicuculline-insensitive GABA B sites in rat brain. Nature. Mar. 1981; 290(5802): 149-152.

Howes et al., Autism spectrum disorder: Consensus guidelines on assessment, treatment and research from the British Association for Psychopharmacology. J Psychopharmacol. Jan. 2018; 32(1): 3-29.

Hubel et al., The period of susceptibility to the physiological effects of unilateral eye closure in kittens. The Journal of physiology. Feb. 1, 1970; 206(2): 419-36.

Janak et al., From circuits to behaviour in the amygdala. Nature. Jan. 2015; 517(7534): 284-92.

Jaramillo et al., Novel Shank3 mutant exhibits behaviors with face validity for autism and altered striatal and hippocampal function. Autism Res. Jan. 2017; 10(1): 42-65.

Jellinger et al., Neuropathology of Rett syndrome. Acta Neuropathol. Mar. 1, 1988; 76(2): 142-58.

Jevtovic-Todorovic et al., Early exposure to common anesthetic agents causes widespread neurodegeneration in the developing rat

(56) References Cited

OTHER PUBLICATIONS brain and persistent learning deficits. The Journal of neuroscience: the official journal of the Society for Neuroscience. Feb. 1, 2003; 23(3): 876-82.

Jiao et al., A key mechanism underlying sensory experience-dependent maturation of neocortical GABAergic circuits in vivo. Proceedings of the National Academy of Sciences. Jul. 19, 2011; 108(29): 12131-6.

Khalfa et al., Peripheral auditory asymmetry in infantile autism. Eur J Neurosci. Feb. 2001; 13(3): 628-32.

King et al., Lack of efficacy of citalopram in children with autism spectrum disorders and high levels of repetitive behavior: citalopram ineffective in children with autism. Arch Gen Psychiatry. Jun. 1, 2009; 66(6): 583-90.

Kodish et al., Pharmacotherapy for anxiety disorders in children and adolescents. Dialogues in clinical neuroscience. Dec. 2011; 13(4): 439-452.

Konig et al., Integrator or coincidence detector? The role of the cortical neuron revisited. Trends Neurosci. Apr. 1, 1996; 19(4): 130-7.

Krishnan et al., MeCP2 regulates the timing of critical period plasticity that shapes functional connectivity in primary visual cortex. Proceedings of the National Academy of Sciences. Aug. 25, 2015; 112(34): E4782-91.

Krogsgaard-Larsen et al., A new class of GABA agonist. Nature. 1977; 268: 53-55.

Krogsgaard-Larsen et al., Structure-activity studies on the inhibition of GABA binding to rat brain membranes by muscimol and related compounds. J Neurochem. Jun. 1978; 30(6): 1377-82.

Krogsgaard-Larsen et al., THIP, isoguvacine, isoguvacine oxide, and related GABA agonists. Adv Biochem Psychopharmacol. 1981; 29: 69-76.

Laquintana et al., N-Benzyl-2-(6,8-dichloro-2-(4-chlorophenyl)imidazo[1,2-a]pyridin-3-yl)-N-(6-(7-nitrobenzo[c][1,2,5]oxadiazol-4-ylamino)hexyl)acetamide as a New Fluorescent Probe for Peripheral Benzodiazepine Receptor and Microglial Cell Visualizationt. Bioconjugate Chem. 2007;18(5):1397-1407.

Lau et al., Temporal control of gene deletion in sensory ganglia using a tamoxifen-inducible Advillin-Cre-ERT2 recombinase mouse. Mol Pain. Dec. 21, 2011; 7: 1744-8069.

Lemonnier et al., Effects of bumetanide on neurobehavioral function in children and adolescents with autism spectrum disorders. Transl Psychiatry. Mar. 2017; 7(3): e1056.

Levy et al., The effect of the GABA antagonists bicuculline and picrotoxin on primary afferent terminal excitability. Brain research. Aug. 11, 1972; 43(1): 171-80.

Lyst et al., Rett syndrome mutations abolish the interaction of MeCP2 with the NCoR/SMRT co-repressor. Nature neuroscience. Jul. 2013; 16(7): 898-902.

Mammen et al., Infant Avoidance during a Tactile Task Predicts Autism Spectrum Behaviors in Toddlerhood. Infant Ment Health J. Nov. 2015; 36(6): 575-87.

Marin, Interneuron dysfunction in psychiatric disorders. Nat Rev Neurosci. Feb. 2012; 13(2): 107-120.

Mazurek et al., Anxiety, sensory over-responsivity, and gastrointestinal problems in children with autism spectrum disorders. J Abnorm Child Psychol. Jan. 1, 2013; 41(1): 165-76.

Mei et al., Adult restoration of Shank3 expression rescues selective autistic-like phenotypes. Nature. Feb. 2016; 530(7591): 481-4.

Nadeau et al., Treatment of comorbid anxiety and autism spectrum disorders. Neuropsychiatry. Dec. 2011;1(6):567-78.

Nelson et al., Excitatory/Inhibitory Balance and Circuit Homeostasis in Autism Spectrum Disorders. Neuron. Aug. 19, 2015; 87(4): 684-98.

Obradovic et al., Silencing the alpha2 subunit of gamma-aminobutyric acid type A receptors in rat dorsal root ganglia reveals its major role in antinociception posttraumatic nerve injury. Anesthesiology. Sep. 1, 2015; 123(3): 654-67.

Oginsky et al., Hyperexcitability of Mesencephalic Trigeminal Neurons and Reorganization of Ion Channel Expression in a Rett Syndrome Model. J Cell Physiol. May 2017; 232(5): 1151-64.

Orefice et al., Peripheral Mechanosensory Neuron Dysfunction Underlies Tactile and Behavioral Deficits in Mouse Models of ASDs. Cell. Jul. 14, 2016; 166(2): 299-313.

Page et al., GABA(B) receptors inhibit mechanosensitivity of primary afferent endings. The Journal of neuroscience: the official journal of the Society for Neuroscience. Oct. 1, 1999; 19(19): 8597-8602.

Pajouhesh et al., Medicinal chemical properties of successful central nervous system drugs. NeuroRx. Oct. 1, 2005; 2(4): 541-553.

Peca et al., Shank3 mutant mice display autistic-like behaviours and striatal dysfunction. Nature. Apr. 2011; 472(7344): 437-442.

Peixoto et al., Early hyperactivity and precocious maturation of corticostriatal circuits in Shank3B(-/-) mice. Nature neuroscience. May 2016; 19(5): 716-24.

Perche et al., Early Retinal Defects in Fmr1(-/y) Mice: Toward a Critical Role of Visual Dys-Sensitivity in the Fragile X Syndrome Phenotype? Front Cell Neurosci. Apr. 6, 2018; 12: 96.

Phelan et al., The 22q13.3 Deletion Syndrome (Phelan-McDermid Syndrome). Mol Syndromol. 2011; 2(3-5): 186-201.

Price et al., Fragile X mental retardation protein (FMRP) and the spinal sensory system. Results Probl Cell Differ. 2012; 54, 41-59.

Ray et al., Comparative transcriptome profiling of the human and mouse dorsal root ganglia: an RNA-seq-based resource for pain and sensory neuroscience research. Pain. Jul. 2018; 159(7): 1325-1345.

Romermann et al., Multiple blood-brain barrier transport mechanisms limit bumetanide accumulation, and therapeutic potential, in the mammalian brain. Neuropharmacology. May 1, 2017; 117: 182-94.

Rudolph et al., Beyond classical benzodiazepines: novel therapeutic potential of GABAA receptor subtypes. Nat Rev Drug Discov. Sep. 2011; 10(9): 685-97.

Schultz et al., Sensory hypersensitivity predicts repetitive behaviours in autistic and typically-developing children. Autism: the international journal of research and practice. May 2019; 23(4): 1028-41.

Shank et al., Ion and temperature effects on the binding of gamma-aminobutyrate to its receptors and the high-affinity transport system. J. Neurochem. Jun. 1990;54(6):2007-15.

Simons et al., Early experience of tactile stimulation influences organization of somatic sensory cortex. Nature. Apr. 1987; 326(6114): 694-7.

Sohal et al., Parvalbumin neurons and gamma rhythms enhance cortical circuit performance. Nature. Jun. 2009; 459(7247): 698-702.

Tata et al., Lack of cognitive recovery following withdrawal from long-term benzodiazepine use. Psychol Med. Feb. 1994; 24(1): 203-13.

Tomassy et al. Developmental abnormalities of cortical interneurons precede symptoms onset in a mouse model of Rett syndrome. J Neurochem. Oct. 2014; 131(1): 115-27.

Tomchek et al., Sensory processing in children with and without autism: a comparative study using the short sensory profile. Am J Occup Ther. Mar. 1, 2007; 61(2): 190-200.

Torres et al., Autism: the micro-movement perspective. Front Integr Neurosci. Jul. 24, 2013;7: 32.

Usoskin et al., Unbiased classification of sensory neuron types by large- scale single-cell RNA sequencing. Nature neuroscience. Jan. 2015; 18(1): 145-53.

Veenstra-Danderweele et al., Arbaclofen in Children and Adolescents with Autism Spectrum Disorder: A Randomized, Controlled, Phase 2 Trial. Neuropsychopharmacology. Jun. 2017; 42(7): 1390-8.

Wang et al., Striatopallidal dysfunction underlies repetitive behavior in Shank3-deficient model of autism. The Journal of Clinical Investigation. May 1, 2017; 127(5): 1978-90.

Watanabe et al., Disruption of the epilepsy KCNQ2 gene results in neural hyperexcitability. J Neurochem. Jul. 2000; 75(1): 28-33.

Wiesel et al., Extent of recovery from the effects of visual deprivation in kittens. Journal of neurophysiology. Nov. 1, 1965; 28(6): 1060-72.

(56) References Cited

OTHER PUBLICATIONS

Wiggins et al., Brief report: sensory abnormalities as distinguishing symptoms of autism spectrum disorders in young children. J Autism Dev Disord. Jul. 1, 2009; 39(7): 1087-91.
Womelsdorf et al., Dynamic circuit motifs underlying rhythmic gain control, gating and integration. Nature neuroscience. Aug. 2014; 17(8): 1031-9.
Yatawara et al., The effect of oxytocin nasal spray on social interaction deficits observed in young children with autism: a randomized clinical crossover trial. Mol Psychiatry. Sep. 2016; 21(9): 1225-31.
Yi et al., Autism- associated SHANK3 haploinsufficiency causes Ih channelopathy in human neurons. Science. May 6, 2016; 352(6286): aaf2669.
Zeilhofer et al., Fast synaptic inhibition in spinal sensory processing and pain control. Physiological reviews. Jan. 2012; 92(1): 193-235.
Zheng et al., Suppression of KCNQ/M (Kv7) potassium channels in dorsal root ganglion neurons contributes to the development of bone cancer pain in a rat model. Pain. Mar. 1, 2013; 154(3): 434-48.
Zikopoulos et al., Altered neural connectivity in excitatory and inhibitory cortical circuits in autism. Front Hum Neurosci. Sep. 27, 2013; 7: 609.
Partial European Search Report, mailed Sep. 16, 2021, in connection with Application No. 19810786.4.
Extended European Search Report, mailed Dec. 20, 2021, in connection with Application No. 19810786.4.
Extended European Search Report for Application No. 20779891.9, mailed Nov. 21, 2022.
International Preliminary Report on Patentability, mailed Oct. 7, 2021, in connection with Application No. PCT/US2020/024564.
Extended European Search Report for Application No. 20810565.0, mailed Jun. 29, 2023.
International Preliminary Report on Patentability for Application No. PCT/US2020/033984, mailed Dec. 2, 2021.
Abrahams et al., Advances in autism genetics: on the threshold of a new neurobiology. Nat Rev Genet. May 2008;9(5):341-55. doi: 10.1038/nrg2346.
Banerjee et al., Impairment of cortical GABAergic synaptic transmission in an environmental rat model of autism. Int J Neuropsychopharmacol. Jul. 2013; 16(6):1309-18. doi: 10.1017/S1461145712001216. Epub Dec. 11, 2012.
Boitano et al., Structure activity studies of a novel cytotoxic benzodiazepine. Bioorg Med Chem Lett. Oct. 6, 2003;13(19):3327-30. doi: 10.1016/s0960-894x(03)00683-8.
Bowery et al., Isoguvacine, isonipecotic acid, muscimol and N-methyl isoguvacine on the GABA receptor in rat sympathetic ganglia. Experientia. Sep. 15, 1978;34(9):1193-5. doi: 10.1007/BF01922953.
Braff et al., Human studies of prepulse inhibition of startle: normal subjects, patient groups, and pharmacological studies. Psychopharmacology (Berl.). Jul. 2001;156(2-3):234-58. doi: 10.1007/s002130100810.
Cascio et al., Tactile Perception in Adults with Autism: a Multidimensional Psychophysical Study. J Autism Dev Disord. Jan. 2008;38(1):127-37. doi: 10.1007/s10803-007-0370-8. Epub Apr. 6, 2007.
Dalai et al., Exploring selectivity requirements for peripheral versus central benzodiazepine receptor binding affinity: QSAR modeling of 2-phenylimidazo[1,2-a]pyridine acetamides using topological and physicochemical descriptors. Indian J Biochem Biophys. Apr. 2006;43(2):105-18.
Denora et al., 2-Phenyl-imidazo[1,2-a]pyridine compounds containing hydrophilic groups as potent and selective ligands for peripheral benzodiazepine receptors: synthesis, binding affinity and electrophysiological studies. J Med Chem. Nov. 13, 2008;51(21):6876-88. doi: 10.1021/jm8006728. Epub Oct. 4, 2008.
Drasbek et al., THIP, a hypnotic and antinociceptive drug, enhances an extrasynaptic GABAA receptor-mediated conductance in mouse neocortex. Cereb Cortex. Aug. 2006;16(8):1134-41. doi: 10.1093/cercor/bhj055. Epub Oct. 12, 2005.
Gebhardt et al., Maturation of prepulse inhibition (PPI) in childhood: Maturation of PPI in childhood. Psychophysiology. Apr. 2012;49(4):484-8. doi: 10.1111/j.1469-8986.2011.01323.x. Epub Dec. 16, 2011.
Guetzoyan et al., Flow chemistry synthesis of zolpidem, alpidem and other GABA agonists and their iological evaluation through the use of in-line frontal affinity chromatography. Chemical Science. 2013; 4(2): 764-69.
Gupta et al., Quantitative structure-activity relationship studies on some nonbenzodiazepine series of compounds acting at the benzodiazepine receptor. Bioorg Med Chem. Nov. 1998;6(11):2213-8. doi: 10.1016/s0968-0896(98)00169-2.
Hanson et al., Structural requirements for eszopiclone and zolpidem binding to the gamma-aminobutyric acid type-A (GABAA) receptor are different. J Med Chem. Nov. 27, 2008;51(22):7243-52. doi: 10.1021/jm800889m.
Hoehn-Saric et al., Effects of THIP on chronic anxiety. Psychopharmacology (Berl). 1983;80(4):338-41. doi: 10.1007/BF00432116.
Kanner, Autistic disturbances of affective contact. Nerv Child. 1943; 2: 217-250.
Kohl et al., Prepulse Inhibition of the Acoustic Startle Reflex in High Functioning Autism. PLoS ONE. Mar. 18, 2014;9(3):e92372. doi: 10.1371/journal.pone.0092372. eCollection 2014.
Lopez-Mendoza et al., Visible light/Ir(III) photocatalytic initiation of xanthate-based radical-chain reactions: Xanthate group transfer and oxidative addition to aromatic systems. Tetrahedron. Apr. 2018; 74(38):5494-5502.
Lozano et al., Modulation of the GABAergic pathway for the treatment of fragile X syndrome. Neuropsychiatr Dis Treat. Sep. 16, 2014;10:1769-79. doi: 10.2147/NDT.S42919. eCollection 2014.
Maddox et al., The Accuracy of the ADOS-2 in Identifying Autism among Adults with Complex Psychiatric Conditions. J Autism Dev Disord. Sep. 2017;47(9):2703-2709. doi: 10.1007/s10803-017-3188-z.
Madsen et al., Increased Prepulse Inhibition and Sensitization of the Startle Reflex in Autistic Children: Sensorimotor gating in autistic children. Autism Res. Feb. 2014;7(1):94-103. doi: 10.1002/aur. 1337. Epub Oct. 4, 2013.
No Author Listed, Annex to ESOP (EP19810786). Jan. 1, 2021. 84 pages.
No Author Listed, Pubchem CID 3393. Flurazepam compound summary. Entered Mar. 25, 2005. 81 pages.
Ogata et al., 5-Aryl-1,5-dihydro-2H-1,4-benzodiazepin-2-one derivatives as antianxiety agents. J Med Chem. Jun. 1977;20(6):776-81. doi: 10.1021/jm00216a008.
Olmos-Serrano et al., The GABA(A) receptor agonist THIP ameliorates specific behavioral deficits in the mouse model of fragile X syndrome. Dev Neurosci. 2011;33(5):395-403. doi: 10.1159/000332884. Epub Nov. 8, 2011.
Orefice et al., Targeting Peripheral Somatosensory Neurons to Improve Tactile-Related Phenotypes in ASD Models. Cell. Aug. 8, 2019;178(4):867-886.e24. doi: 10.1016/j.cell.2019.07.024.
Orefice, Peripheral Somatosensory Neuron Dysfunction: Emerging Roles in Autism Spectrum Disorders. Neuroscience. Oct. 1, 2020;445:120-129. doi: 10.1016/j.neuroscience.2020.01.039. Epub Feb. 6, 2020.
Pardridge, Drug transport across the blood-brain barrier. J Cereb Blood Flow Metab. Nov. 2012;32(11):1959-72. doi: 10.1038/jcbfm. 2012.126. Epub Aug. 29, 2012.
Paulson et al., Blood-brain barrier transfer and cerebral uptake of antiepileptic drugs. Clin Pharmacol Ther. Oct. 1982;32(4):466-77. doi: 10.1038/clpt.1982.190.
Pavlovsky et al., Synthesis and anticonvulsant activity of 3- alkoxy-1,2-dihydro-3H-1,4-benzodiazepin-2-ones. Pharmaceutical Chemistry Journal. 2012; 46(9): 540-545. DOI: 10.1007/s11094-012-0842-9.
Roland et al., Quinazolines et benzodiazépines-1,4. LXI) Imidazo[5,1-c]benzodiazepines-1,4. 1973; 56(7):2569-2583. Helvetica Chimica Acta. Retrieved from the Internet: URL: https://api.wiley.com/onlinelibrary/tdm/v1/articles/10.1002%2Fhlca.19730560742>.

(56) References Cited

OTHER PUBLICATIONS

Roy et al., QSAR modeling of peripheral versus central benzodiazepine receptor binding affinity of 2-phenylimidazo[1,2-a]pyridineacetamides using optimal descriptors calculated with Smiles. QSAR Comb Sci. 2007; 26(4): 460-468.

Salamon, Conners Scale for ADHD Assessment. WebMD. Jul. 12, 2020. available at https://www.webmd.com/add-adhd/childhood-adhd/conners-rating-scale#:-:text=The%20Conners%20rating%20scale%20is,%2C%20home%20life%2C%20and%20relationships. 2 pages.

Samanta et al., Search for Structural Requirements of 2-Phenylimidazo[1,2-a] pyridineacetamide Analogs to Improve Affinity and Selectivity towards Central and/or Peripheral Benzodiazepine Receptors. Internet Electronic Journal of Molecular Design. Jul. 2007; 6(7): 183-99.

Silverman et al., Behavioural phenotyping assays for mouse models of autism. Nat Rev Neurosci. Jul. 2010; 11(7):490-502. doi: 10.1038/nrn2851.

Swerdlow et al., Sensorimotor gating of the startle reflex: what we said 25 years ago, what has happened since then, and what comes next. J Psychopharmacol. Nov. 2016;30(11): 1072-1081. doi: 10.1177/0269881116661075. Epub Aug. 18, 2016.

Trapani et al., Structure-activity relationships and effects on neuroactive steroid synthesis in a series of 2-phenylimidazo[1,2-a]pyridineacetamide peripheral benzodiazepine receptors ligands. J Med Chem. Jan. 13, 2005;48(1):292-305. doi: 10.1021/jm049610q.

Trapani et al., Synthesis and binding affinity of 2-phenylimidazo[1,2-alpha]pyridine derivatives for both central and peripheral benzodiazepine receptors. A new series of high-affinity and selective ligands for the peripheral type. J Med Chem. Sep. 12, 1997;40(19):3109-18. doi: 10.1021/jm970112+.

Tuccinardi et al., A virtual screening study of the 18 kDa translocator protein using pharmacophore models combined with 3D-QSAR studies. ChemMedChem. Oct. 2009;4(10):1686-94. doi: 10.1002/cmdc.200900254.

Voos et al., Autistic traits are associated with diminished neural response to affective touch. Soc Cogn Affect Neurosci. Apr. 2013;8(4):378-86. doi: 10.1093/scan/nss009. Epub Jan. 20, 2012.

Waszczak et al., GABAergic actions of THIP in vivo and vitro: a comparison with muscimol and GABA. Eur J Pharmacol. Jul. 11, 1980;65(1):21-9. doi: 10.1016/0014-2999(80)90204-6.

Wright, Cognition and behavior: Sensory sensitivity tied to autism, Oct. 10, 2012, available at https://www.spectrumnews.org/news/cognition-and-behavior-sensory-sensitivity-tied-to-autism/.

Öhler et al., Synthesis of (3-amino-1-alkenyl) phosphonic acids from allylic α- and γ- hydroxyphosphonates. Sigmatropic rearrangement of dialkyl(1-azido-2-alkenyl) phosphonates (*Darstellung von (3-Amino-1-alkenyl)phosphonsäuren aus allylischen α- und γ-Hydroxyphosphonaten. Sigmatrope Umlagerung von (1-Azido-2-alkenyl)phosphonsäureestern*). Liebigs Annalen der Chemie. 1993; 3: 269-280.

No Author Listed, "More GABA" for Autism and Epilepsy? Not so Simple. Epiphany, An Alternative Reality for Classic Autism—Based on Today's Science. Dec. 23, 2015. Accessed at: https://www.epiphanyasd.com/2015/12/more-gaba-for-autism-and-epilepsy-not.html [last accessed: Aug. 7, 2024].

* cited by examiner

Key

Wash, 30s $EC_{100}$ GABA, 2s

Test conc 1-5, 2s

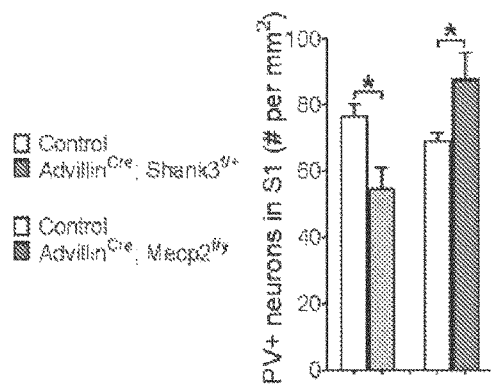 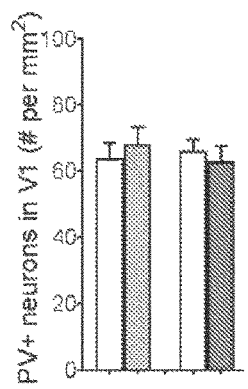 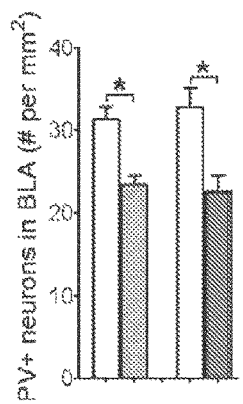
FIG. 16D     FIG. 16E     FIG. 16F
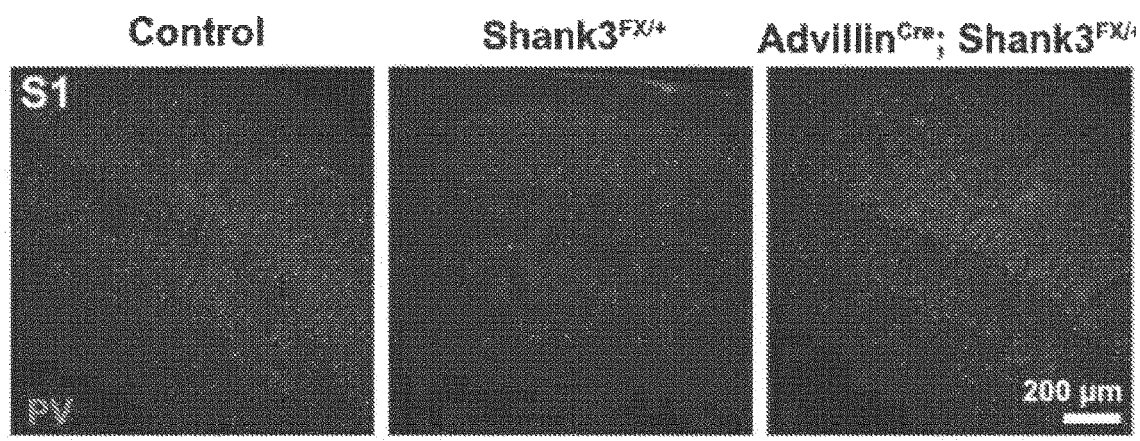
FIG. 16G
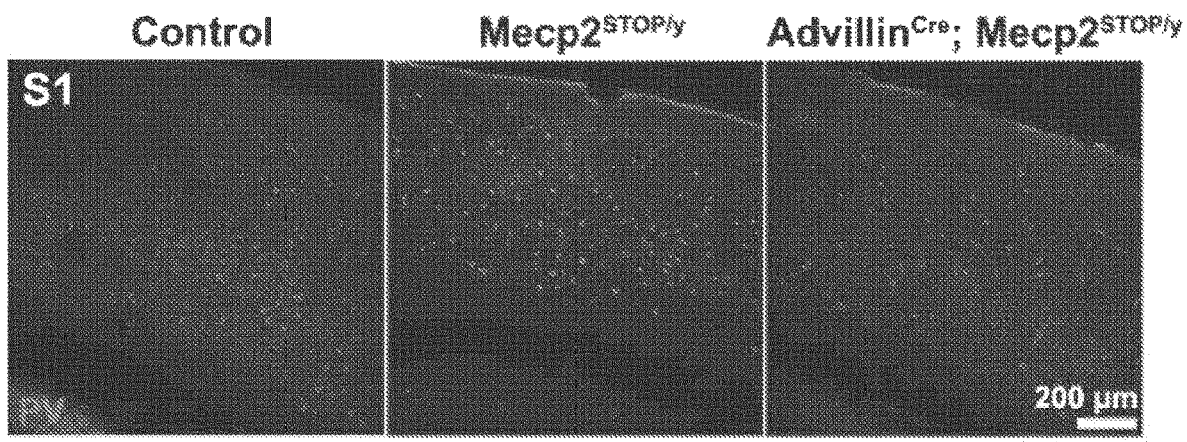
FIG. 16H

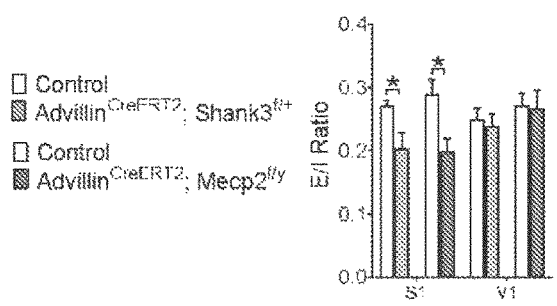
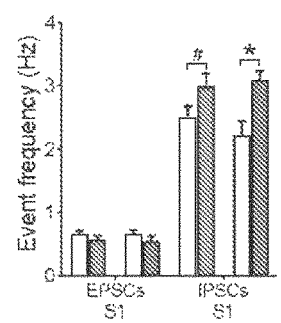
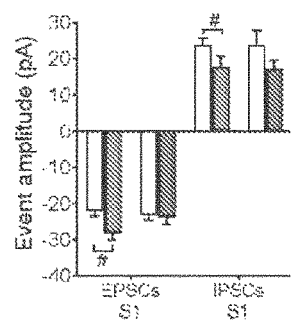
FIG. 16R          FIG. 16S          FIG. 16T
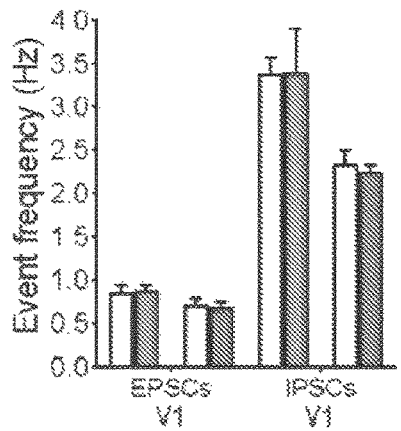
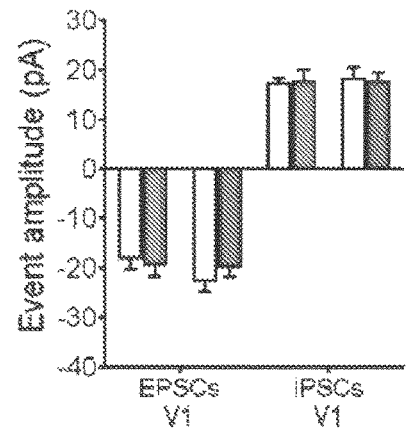
FIG. 16U          FIG. 16V
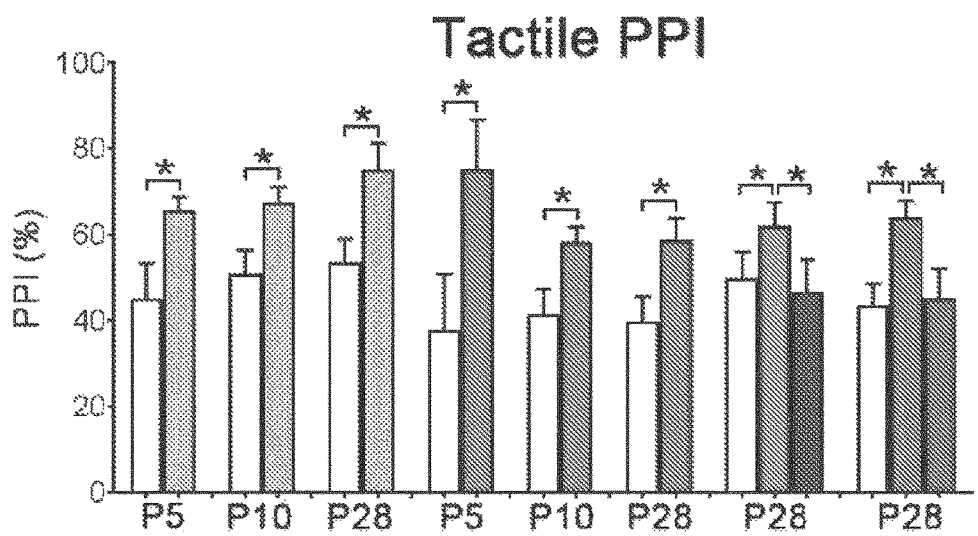
FIG. 17A

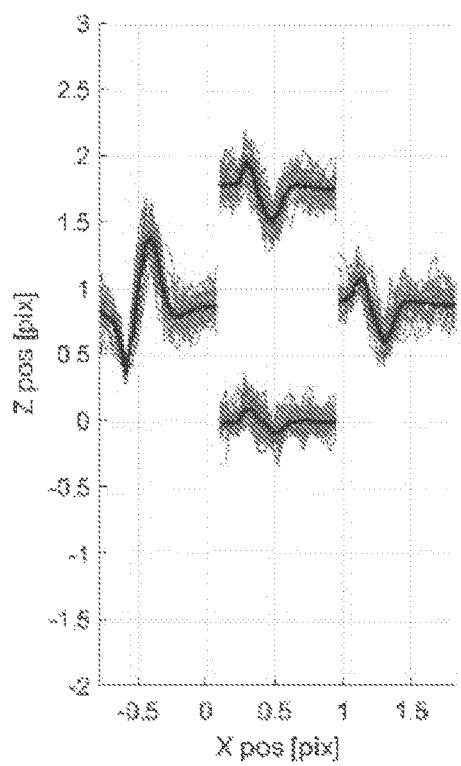
FIG. 20E
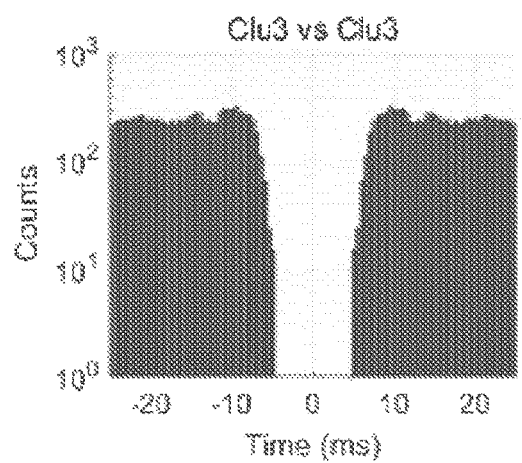 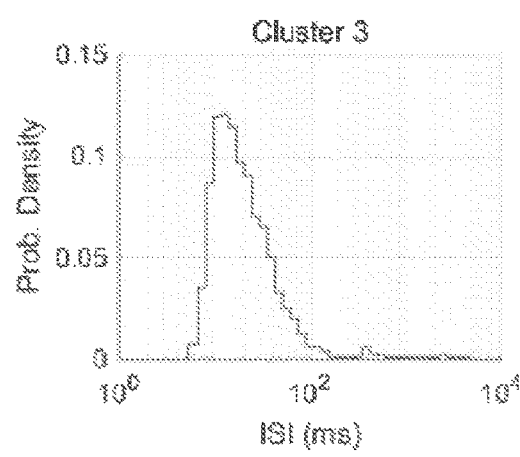
FIG. 20F                FIG. 20G

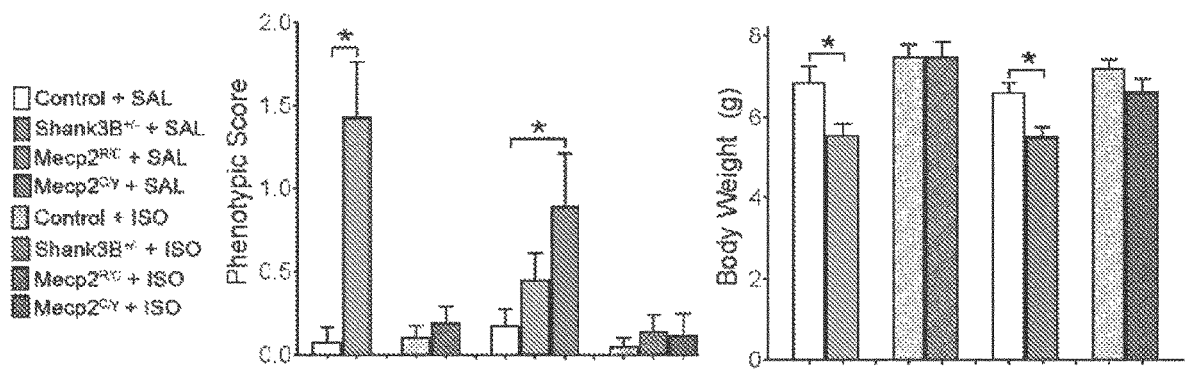
FIG. 21B
FIG. 21C
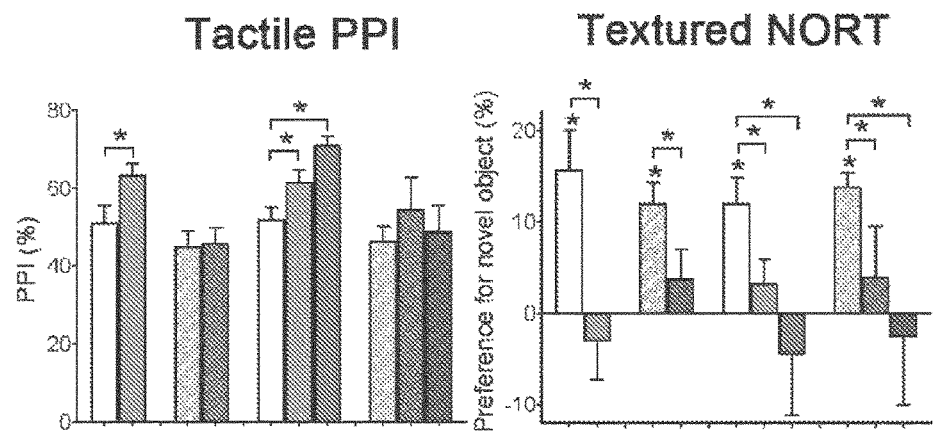
FIG. 21D
FIG. 21E
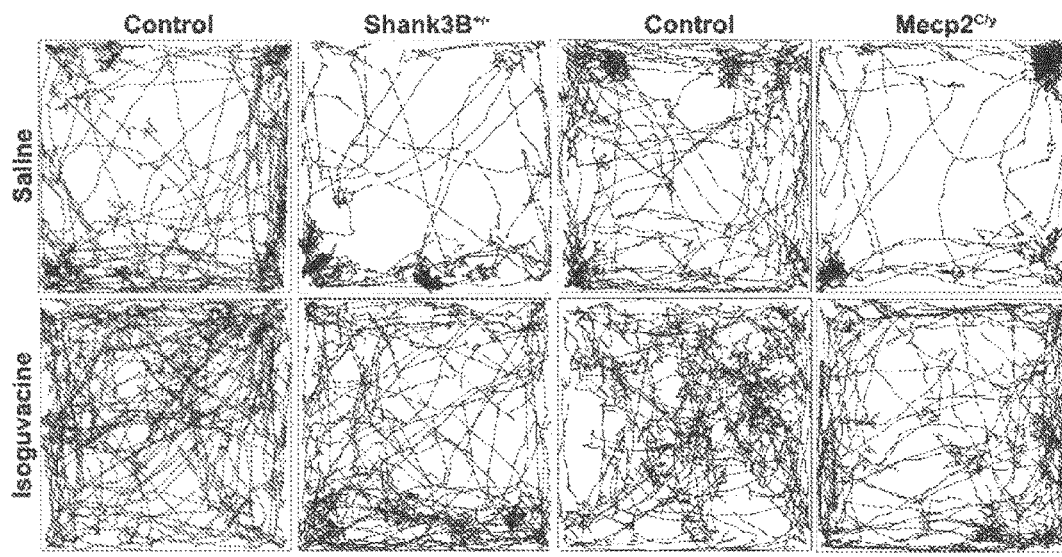
FIG. 21F

| | Novel Mouse | Novel Object | Center | Pred. for novel mouse | Novel Mouse | Familiar Mouse | Center | Pred. for novel mouse |
|---|---|---|---|---|---|---|---|---|
| Control (n = 18) | 263.88 +/- 13.89 | 206.09 +/- 11.51 | 60.83 +/- 7.31 | Yes p = 0.0044 | 266.66 +/- 14.71 | 194.74 +/- 15.65 | 69.39 +/- 8.60 | Yes p = 0.0010 |
| Shank2B-/- (n=14) | 229.65 +/- 16.28 | 241.22 +/- 16.23 | 60.57 +/- 15.20 | No p = 0.8332 | 232.76 +/- 21.85 | 228.87 +/- 20.62 | 69.81 +/- 15.40 | No p = 0.9839 |
| Control (n=13) | 288 +/- 19.62 | 206.77 +/- 14.46 | 44.99 +/- 4.97 | Yes p = 0.0002 | 271.72 +/- 20.42 | 202.45 +/- 18.17 | 65.53 +/- 7.91 | Yes p = 0.0093 |
| Cdx2Cre; Shank3F/F (n = 13) | 267.49 +/- 17.54 | 224.91 +/- 14.83 | 49.26 +/- 7.04 | No p = 0.0826 | 259.89 +/- 13.57 | 226.42 +/- 14.49 | 59.41 +/- 6.07 | No p = 0.4217 |
| Control (n = 36) | 283.90 +/- 6.78 | 204.95 +/- 7.08 | 46.19 +/- 3.13 | Yes p < 0.0001 | 271.14 +/- 9.50 | 209.71 +/- 9.38 | 57.29 +/- 3.93 | Yes p < 0.0001 |
| AdvillinCre; Shank3F/F (n = 26) | 252.47 +/- 11.46 | 227.63 +/- 11.22 | 48.93 +/- 3.31 | No p = 0.0957 | 243.84 +/- 13.48 | 228.95 +/- 16.07 | 57.81 +/- 6.29 | No p = 0.6429 |
| Control (n = 33) | 293.48 +/- 9.66 | 220.17 +/- 8.82 | 68.05 +/- 6.24 | Yes p < 0.0001 | 309.71 +/- 12.97 | 252.41 +/- 26.55 | 65.75 +/- 13.29 | No p = 0.0647 |
| AdvillinCre; Shank3F/F (n = 9) | 243.45 +/- 19.71 | 233.07 +/- 21.07 | 72.19 +/- 10.93 | No p = 0.5463 | 228.08 +/- 12.46 | 226.55 +/- 11.11 | 81.37 +/- 4.58 | Yes p < 0.0001 |
| AdvillinCre; Mrgp2-/- (n = 23) | 264.43 +/- 12.41 | 243.93 +/- 12.20 | 90.95 +/- 9.22 | No p = 0.5892 | 267.54 +/- 10.08 | 250.49 +/- 10.41 | 97.08 +/- 7.93 | No p = 0.5851 |
| AdvillinCre; Mrgp2-/- (n = 20) | 260.78 +/- 9.52 | 264.92 +/- 8.30 | 62.79 +/- 10.73 | No p = 0.8334 | 230.24 +/- 16.08 | 257.71 +/- 21.14 | 93.88 +/- 14.06 | No p = 0.3159 |
| Control (n = 21) | 270.17 +/- 8.95 | 206.97 +/- 8.92 | 44.70 +/- 4.66 | Yes p = 0.0042 | 285.29 +/- 14.92 | 206.93 +/- 14.92 | 98.62 +/- 7.27 | Yes p = 0.0102 |
| Shank3F/F (n = 35) | 236.44 +/- 13.28 | 244.02 +/- 13.54 | 50.65 +/- 3.79 | No p = 0.9917 | 233.63 +/- 13.97 | 223.63 +/- 11.08 | 72.26 +/- 6.54 | No p = 0.8429 |
| Cdx2Cre; Shank3F/F (n = 29) | 288.71 +/- 9.49 | 213.25 +/- 10.26 | 46.39 +/- 2.40 | Yes p = 0.9761 | 244.02 +/- 15.30 | 219.74 +/- 16.99 | 63.49 +/- 6.53 | No p = 0.2631 |
| Control (n = 26) | 272.47 +/- 10.07 | 224.59 +/- 9.24 | 33.70 +/- 4.91 | Yes p = 0.0043 | 207.64 +/- 13.33 | 222.26 +/- 13.71 | 51.23 +/- 4.87 | Yes p = 0.0007 |
| Shank3F/F (n = 26) | 247.48 +/- 13.63 | 244.32 +/- 16.28 | 38.96 +/- 3.29 | Yes p = 0.0064 | 243.38 +/- 15.61 | 230.29 +/- 15.29 | 36.64 +/- 6.91 | No p = 0.7090 |
| AdvillinCre; Shank3F/F (n = 24) | 269.67 +/- 9.07 | 221.67 +/- 8.87 | 39.37 +/- 3.55 | Yes p = 0.0064 | 269.85 +/- 12.40 | 216.50 +/- 12.95 | 53.91 +/- 6.98 | Yes p = 0.0380 |

FIG. 29

COMPOSITIONS AND METHODS FOR REDUCING TACTILE DYSFUNCTION, ANXIETY, AND SOCIAL IMPAIRMENT

REFERENCE TO RELATED APPLICATIONS

This application is a national stage filing under 35 U.S.C. § 371 of international PCT application, PCT/US2019/033581, filed May 22, 2019, which claims priority under 35 U.S.C. § 119 (e) to U.S. Provisional Application, U.S. Ser. No. 62/674,770, filed on May 22, 2018, and to U.S. Provisional Application, U.S. Ser. No. 62/823,360, filed on Mar. 25, 2019, each of which is incorporated herein by reference in their entirety.

STATEMENT AS TO FEDERALLY SPONSORED RESEARCH

This invention was made with government support under NS097344 and NS101057 awarded by the National Institutes of Health. The government has certain rights in the invention.

BACKGROUND OF THE INVENTION

Autism spectrum disorder (ASD) is a highly prevalent class of neurodevelopmental disorders characterized by impairments in social communication and interactions, as well as restricted and repetitive behaviors. Rates of ASD diagnoses are increasing, and the CDC identifies one in every 59 children in the United States as having ASD. In the United States alone, it is estimated that the ASD-related healthcare costs exceed 230 billion dollars per year, or 1.4 million per individual with ASD over their lifetime. A majority of ASD patients (60.9%) report altered tactile sensitivity in both glabrous (smooth) and hairy skin, and altered sensitivity to vibration and thermal pain. As with idiopathic or non-syndromic ASD, pervasive developmental disorders that cause syndromic forms of ASD are also associated with disrupted somatosensation. For example, abnormalities in tactile perception are observed in patients with Phelan McDermid Syndrome (PMS) and Fragile X syndrome, which are both highly associated with ASD and are caused by mutations in Shank3 and Fmr1, respectively. Similarly, tactile hypersensitivity is common in patients with Rett syndrome (RTT), which is caused by mutations in the X-linked methyl-CpG-binding protein 2 (Mecp2) gene. There is an inverse correlation between the presence of ASD traits in human subjects and their neural responses to C-low-threshold mechanoreceptor (LTMR)-targeted affective touch. Currently, there are no FDA-approved treatments for ASD. Thus, a critical need exists for novel therapeutic approaches to treat ASD and related disorders such as Rett syndrome, Phelan McDermid Syndrome, and Fragile X syndrome.

SUMMARY OF THE INVENTION

In one aspect, the invention features a compound having the structure of Formula (I):

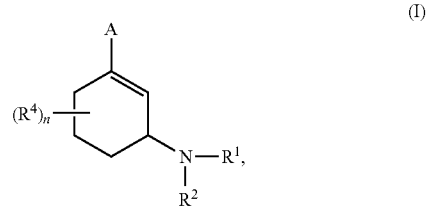

wherein
n=1, 2, 3, 4, 5, 6, 7, or 8;
each of $R^1$ and $R^2$ is, independently, hydrogen, deuterium, optionally substituted $C_{1-6}$ alkyl, or optionally substituted $C_{3-6}$ cycloalkyl, wherein $R^1$ and $R^2$ are covalently linked;
each $R^4$ is, independently, hydrogen, deuterium, halogen, $C_{1-4}$ alkoxy, $C_{1-6}$ alkyl, $CF_3$, $CH_3S$, $CH_3SO_2$, or $NO_2$; and
A is a carboxylic acid, a carboxylic acid biomimetic, or optionally substituted $C_{1-6}$ carboxylic acid alkyl ester;
or a pharmaceutically acceptable salt thereof.

In some embodiments, the compound has the structure of Formula (Ia) or (Ib):

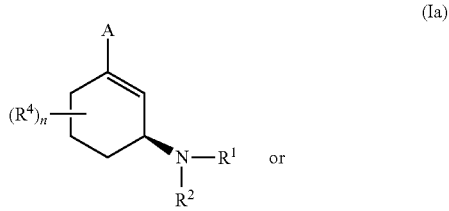

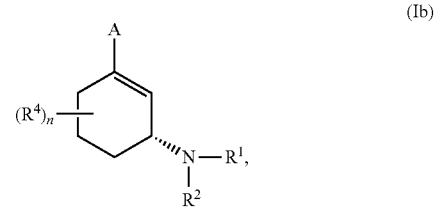

or a pharmaceutically acceptable salt thereof.

In some embodiments, A is a carboxylic acid, optionally substituted $C_{1-6}$ carboxylic acid alkyl ester, or has the structure of:

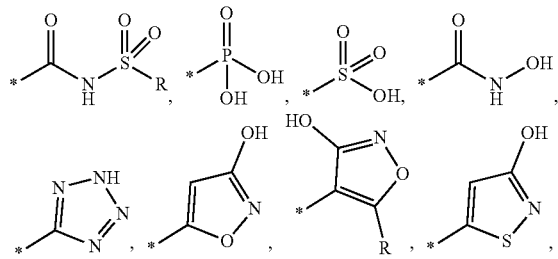

-continued

[Chemical structures shown: various heterocyclic bioisosteres including hydroxy-isothiazole, hydroxy-thiadiazole, tetrazolone, triazolidinedione, oxadiazolone, hydroxy-triazole, oxazolidinedione, thiazolidinedione, hydroxy-imidazole, hydroxy-cyclobutenedione (squaric acid), and amino-hydroxy-cyclobutenedione]

In some embodiments, the compound has the structure of Formula (II):

(II)

[Chemical structure of Formula (II): cyclohexene with OR³ ester, (R⁴)ₙ substituents, and NR¹R² group]

wherein n=1, 2, 3, 4, 5, 6, 7, or 8;

each of $R^1$ and $R^2$ is, independently, hydrogen, deuterium, optionally substituted $C_{1-6}$ alkyl, or optionally substituted $C_{3-6}$ cycloalkyl, wherein $R^1$ and $R^2$ are covalently linked;

$R^3$ is hydrogen, deuterium, or optionally substituted $C_{1-6}$ alkyl; and each $R^4$ is, independently, hydrogen, deuterium, halogen, $C_{1-4}$ alkoxy, $C_{1-6}$ alkyl, $CF_3$, $CH_3S$, $CH_3SO_2$, or $NO_2$;

or a pharmaceutically acceptable salt thereof.

In some embodiments, the compound has the structure of Formula (IIa) or Formula (IIb):

(IIa)

[Chemical structure of Formula (IIa)]

or (IIb)

[Chemical structure of Formula (IIb)]

or a pharmaceutically acceptable salt thereof.

In some embodiments, the compound has the structure of Formula (III):

(III)

[Chemical structure of Formula (III)]

wherein each of $R^1$ and $R^2$ is, independently, hydrogen, deuterium, or optionally substituted $C_{1-6}$ alkyl; and $R^3$ is hydrogen, deuterium, or optionally substituted $C_{1-6}$ alkyl;

or a pharmaceutically acceptable salt thereof.

In some embodiments, the compound has the structure of Formula (IIIa) or Formula (IIIb):

(IIIa)

[Chemical structure of Formula (IIIa)]

or (IIIb)

[Chemical structure of Formula (IIIb)]

or a pharmaceutically acceptable salt thereof.

In some embodiments, each of $R^1$ and $R^2$ is, independently, hydrogen or $C_{1-4}$ alkyl; and $R^3$ is hydrogen or $C_{1-4}$ alkyl.

In some embodiments, each of $R^1$ and $R^2$ is, independently, hydrogen or 01-2 alkyl; and $R^3$ is hydrogen or $C_{1-2}$ alkyl.

In some embodiments, the compound has the structure of:

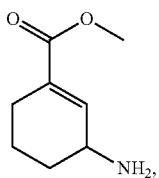
1

2

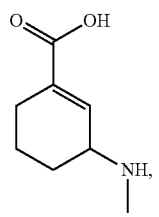
3

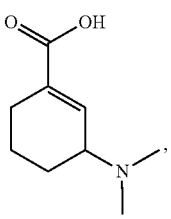
4

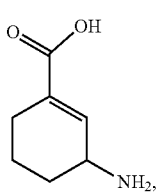
5

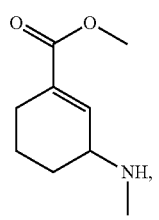
6

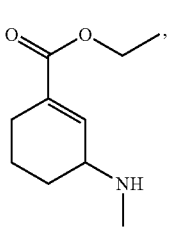
7

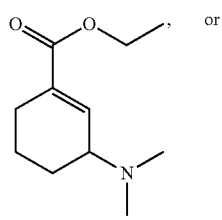
8

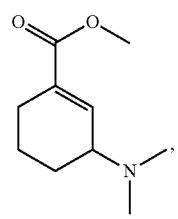
9 or a pharmaceutically acceptable salt thereof.

In some embodiments, the compound has the structure of:

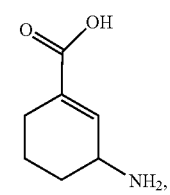
5 or a pharmaceutically acceptable salt thereof.

In some embodiments, the compound has the structure of:

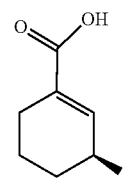
5a or

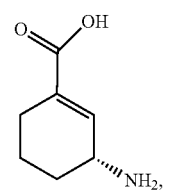
5b or a pharmaceutically acceptable salt thereof.

In some embodiments, the compound has the structure of:

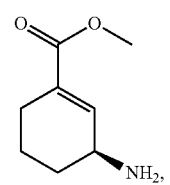
1a

-continued
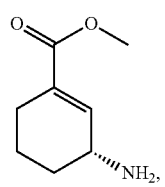   1b
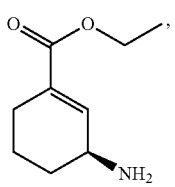   2a
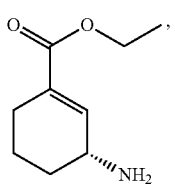   2b
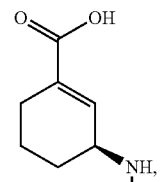   3a
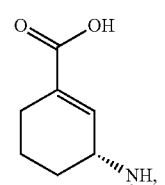   3b
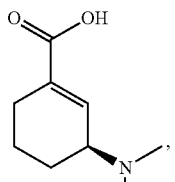   4a
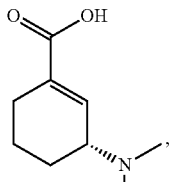   4b
-continued
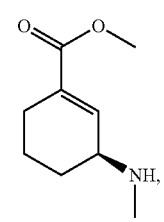   6a
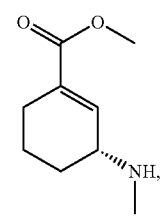   6b
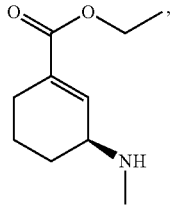   7a
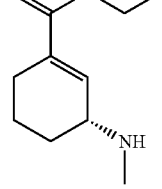   7b
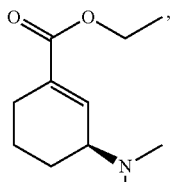   8a
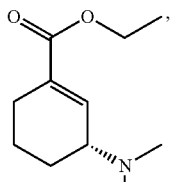   8b
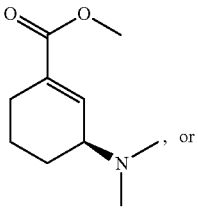   9a

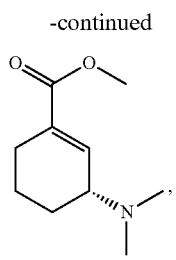

or a pharmaceutically acceptable salt thereof.

In another aspect, the invention features a pharmaceutical composition comprising a compound as described herein (e.g., the compounds of any one of Formulas (I)-(III); e.g., the compounds of Table 1) and a pharmaceutically acceptable excipient.

In another aspect, the invention features a method of reducing tactile dysfunction in a human subject diagnosed with Autism Spectrum Disorder (ASD), Rett syndrome (RTT), Phelan McDermid syndrome (PMS), or Fragile X syndrome, comprising administering to the subject a compound of any of the above embodiments (e.g., the compounds of any one of Formulas (I)-(III); e.g., the compounds of Table 1) in an amount and for a duration sufficient to reduce the tactile dysfunction.

In another aspect, the invention features a method of reducing anxiety or social impairment in a human subject diagnosed with ASD, RTT, PMS, or Fragile X syndrome, comprising administering to the subject a compound of any of the above embodiments (e.g., the compounds of any one of Formulas (I)-(III); e.g., the compounds of Table 1) in an amount and for a duration sufficient to reduce the anxiety or social impairment.

In another aspect, the invention features a method of treating pain in a human subject in need thereof, comprising administering to the subject a compound of any of the above embodiments (e.g., the compounds of any one of Formulas (I)-(III); e.g., the compounds of Table 1) in an amount and for a duration sufficient to reduce the pain.

In another aspect, provided herein is a compound of any of the above embodiments (e.g., the compounds of any one of Formulas (I)-(III); e.g., the compounds of Table 1) for use in a method of reducing tactile dysfunction in a human subject diagnosed with Autism Spectrum Disorder (ASD), Rett syndrome (RTT), Phelan McDermid syndrome (PMS), or Fragile X syndrome.

In another aspect, provided herein is a compound of any of the above embodiments (e.g., the compounds of any one of Formulas (I)-(III); e.g., the compounds of Table 1) for use in a method of reducing anxiety or social impairment in a human subject diagnosed with ASD, RTT, PMS, or Fragile X syndrome.

In another aspect, provided herein is a compound of any of the above embodiments (e.g., the compounds of any one of Formulas (I)-(III); e.g., the compounds of Table 1) for use in a method of treating pain in a human subject in need thereof, comprising administering to the subject a compound of any of the above embodiments (e.g., the compounds of any one of Formulas (I)-(III); e.g., the compounds of Table 1) in an amount and for a duration sufficient to reduce the pain.

Definitions

As used herein, the terms "Autism Spectrum Disorder" or "ASD" refer to a heterogeneous group of neurodevelopmental disorders as classified in the fifth revision of the American Psychiatric Association's Diagnostic and Statistical Manual of Mental Disorders 5th edition (DSM-5). The DSM-5 redefined the autism spectrum to encompass the prior (DSM-IV-TR) diagnosis of autism, Asperger syndrome, pervasive developmental disorder not otherwise specified, childhood disintegrative disorder, and Rett syndrome. The autism spectrum disorders are characterized by social deficits and communication difficulties, stereotyped or repetitive behaviors and interests, and in some cases, cognitive delays. For example, an ASD is defined in the DSM-5 as exhibiting (i) deficits in social communication and interaction not caused by general developmental delays (must exhibit three criteria including deficits in social-emotional reciprocity, deficits in nonverbal communication, and deficits in creating and maintaining relationships appropriate to developmental level), (ii) demonstration of restricted and repetitive patterns of behavior, interest or activities (must exhibit two of the following four criteria: repetitive speech, repetitive motor movements or repetitive use of objects, adherence to routines, ritualized patterns of verbal or nonverbal, or strong resistance to change, fixated interests that are abnormally intense of focus, and over or under reactivity to sensory input or abnormal interest in sensory aspects of environment), (iii) symptoms must be present in early childhood, and (iv) symptoms collectively limit and hinder everyday functioning. The term "ASD" is also contemplated herein to include Dravet's syndrome and autistic-like behavior in non-human animals.

As used herein, the terms "Rett syndrome" or "RTT" refer to an X-linked disorder that affects approximately one in ten-thousand girls. Patients go through four stages: Stage I) Following a period of apparently normal development from birth, the child begins to display social and communication deficits, similar to those seen in other autism spectrum disorders, between six and eighteen months of age. The child shows delays in their developmental milestones, particularly for motor ability, such as sitting and crawling. Stage II) Beginning between one and four years of age, the child goes through a period of regression in which they lose speech and motor abilities, developing stereotypical midline hand movements and gait impairments. Breathing irregularities, including apnea and hyperventilation also develop during this stage. Autistic symptoms are still prevalent at this stage. Stage III) Between age two and ten, the period of regression ends and symptoms plateau. Social and communication skills may show small improvements during this plateau period, which may last for most of the patients' lives. Stage IV) Motor ability and muscle deterioration continues. Many girls develop severe scoliosis and lose the ability to walk.

As used herein, the terms "Phelan McDermid syndrome" or "PMS" refer to rare genetic condition caused by a deletion or other structural change of the terminal end of chromosome 22 in the 22q13 region or a disease-causing mutation of the Shank3 gene. Although the range and severity of symptoms may vary, PMS is generally thought to be characterized by neonatal hypotonia (low muscle tone in the newborn), normal growth, absent to severely delayed speech, moderate to profound developmental delay, and minor dysmorphic features. People who have PMS often show symptoms in very early childhood, sometimes at birth and within the first six months of life.

As used herein, the term "Fragile X syndrome" refers to an X chromosome-linked condition that is characterized by a visible constriction near the end of the X chromosome, at locus q27.3 that causes intellectual disability, behavioral and learning challenges and various physical characteristics Fragile X syndrome is the most common inherited form of mental retardation and developmental disability. Males with Fragile X syndrome usually have mental retardation and often exhibit characteristic physical features and behavior. Fragile X syndrome is characterized by behavior similar to autism and attention deficit disorder, obsessive-compulsive tendencies, hyperactivity, slow development of motor skills and anxiety fear disorder. When these disabilities are severe and occur simultaneously, the condition is sometimes described as autism, and may be associated with any degree of intelligence. Other characteristics are a likable, happy, friendly personality with a limited number of autistic-like features such as hand-flapping, finding direct eye contact unpleasant, and some speech and language problems. Physical features may include large ears, long face, soft skin and large testicles (called "macroorchidism") in post-pubertal males. Connective tissue problems may include ear infections, flat feet, high arched palate, double-jointed fingers and hyper-flexible joints.

As used herein, the term "tactile dysfunction" refers to exhibiting symptoms such as withdrawing when being touched, refusing to eat certain "textured" foods and/or to wear certain types of clothing, complaining about having hair or face washed, avoiding getting hands dirty (e.g., glue, sand, mud, finger-paint), and using finger tips rather than whole hands to manipulate objects. Tactile dysfunction may lead to a misperception of touch and/or pain (hyper- or hyposensitive) and may lead to self-imposed isolation, general irritability, distractibility, and hyperactivity.

As used herein, the term "anxiety" refers to emotions characterized by feelings of tension, worried thoughts and physical changes like increased blood pressure. Anxiety can be characterized by having recurring intrusive thoughts or concerns, avoiding certain situations (e.g., social situations) out of worry, and physical symptoms such as sweating, trembling, dizziness, or a rapid heartbeat.

As used herein, the term "social impairment" refers to a distinct dissociation from and lack of involvement in relations with other people. It can occur with various mental and developmental disorders, such as autism. Social impairment may occur when an individual acts in a less positive way or performs worse when they are around others as compared to when alone. Nonverbal behaviors associated with social impairment can include deficits in eye contact, facial expression, and gestures that are used to help regulate social interaction. Often there is a failure to develop age-appropriate friendships. Social impairment can also include a lack of spontaneous seeking to share achievements or interests with other individuals. A person with social impairment may exhibit a deficit in social reciprocity with individuals, decreased awareness of others, lack of empathy, and lack of awareness of the needs of others.

As used herein, the terms "blood brain barrier" and "BBB" refer to a transvascular permeability barrier that tightly controls entry of substances into the brain. The capillaries that perfuse the brain are lined with special endothelial cells that lack fenestrations and are sealed by endothelial tight junctions. The tight endothelium provides a physical barrier that together with metabolic barriers forms the basis of the BBB.

As used herein, the term "reduced permeability" refers to peripherally acting compositions of the compounds described herein that have decreased (e.g., by 10%, 20%, 30%, 40%, 50%, 60%, 70%, 80%, 90%, or 100%) ability to cross the blood brain barrier.

As used herein, the term "reducing" refers to decreasing (e.g., by 1%, 2%, 3%, 4%, 5%, 6%, 7%, 8%, 9%, 10%, 20%, 30%, 40%, 50%, 60%, 70%, 80%, 90%, 95%, 97%, 99%, or about 100%) the side effects or symptoms (e.g., tactile sensitivity, social impairment, or anxiety) of patients diagnosed with ASD, RTT, PMS, or Fragile X syndrome.

As used herein, the terms "treatment" or "treating" refer to reducing, decreasing, decreasing the risk of progression, or decreasing the side effects of (e.g., by 1%, 2%, 3%, 4%, 5%, 6%, 7%, 8%, 9%, 10%, 20%, 30%, 40%, 50%, 60%, 70%, 80%, 90%, 95%, 97%, 99%, or about 100%) a particular disease or condition (e.g., tactile dysfunction, anxiety, and social impairment, e.g., ASD, RTT, PMS, and Fragile X syndrome). Reducing, decreasing, decreasing the risk of progression, or decreasing the side effects of are relative to a subject who did not receive treatment, e.g., a control, a baseline, or a known control level or measurement.

As used herein, the terms "effective amount" or "therapeutically effective amount" refers to an amount of a compound of the invention sufficient to produce a desired result, for example, reducing (e.g., by 10%, 20%, 30%, 40%, 50%, 60%, 70%, 80%, 90%, or 100%) tactile dysfunction, social impairment, or anxiety in a subject upon administration of a composition containing a compound described herein. The increase or reduction related to administration of an effective amount of a compound may be calculated relative to levels or symptoms, as applicable, in a subject that has not been administered a compound of the invention or relative to the subject prior to administration of a compound of the invention. The increase or reduction may also be calculated relative to a control or baseline average.

As used herein, the term "subject," refers to any animal (e.g., a mammal, e.g., a human). A subject to be treated according to the methods described herein may be one who has been diagnosed with a developmental disorder (e.g., ASD, RTT, PMS, and Fragile X syndrome) as having such a condition or one at risk of developing the condition. Diagnosis may be performed by any method or technique known in the art. One skilled in the art will understand that a subject to be treated according to the present invention may have been subjected to standard tests or may have been identified, without examination, as one at high risk due to the presence of one or more risk factors. In certain particular embodiments, the subject is a human. In certain particular embodiments, the subject is an adult. In certain particular embodiments, the subject is an adolescent. In other particular embodiments, the subject is a child. In certain embodiments, the child is less than 12 years of age. In certain embodiments, the child is less than 10 years of age. In certain embodiments, the child is less than 8 years of age. In certain embodiments, the child is less than 6 years of age. In certain embodiments, the child is less than 4 years of age. In certain embodiments, the child is less than 2 years of age. In certain embodiments, the child is 2-4 years of age. In certain embodiments, the child is 4-6 years of age. In certain embodiments, the child is 6-8 years of age. In certain embodiments, the child is 8-10 years of age. In certain embodiments, the child is greater than 12 years of age.

As used herein, the term "pharmaceutical composition," refers to a composition containing a compound described herein (e.g., a compound of Formulas (I)-(III); e.g., the compounds of Table 1), formulated with a pharmaceutically acceptable excipient, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); for intrathecal administration (e.g., as a sterile preservative-free composition in a solvent system suitable for intrathecal use); or in any other formulation described herein.

As used herein, the terms "pharmaceutically acceptable excipient" or "pharmaceutically acceptable carrier," refer to any ingredient in a pharmaceutical composition other than compounds described herein (e.g., a vehicle capable of suspending or dissolving the active agent) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene, calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

As used herein, the term "pharmaceutically acceptable salt," refers to those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in Pharmaceutical Salts: Properties, Selection, and Use, (Eds. P. H. Stahl and CG. Wermuth), Wiley-VCH, 2008. The salts can be prepared in situ during the final isolation and purification of the compounds described herein by reacting the free base group with a suitable organic acid.

Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

The term "alkyl," as used herein, refers to a branched or straight-chain monovalent saturated aliphatic hydrocarbon radical of 1 to 20 carbon atoms (e.g., 1 to 16 carbon atoms, 1 to 10 carbon atoms, or 1 to 6 carbon atoms). An alkylene is a divalent alkyl group.

The term "heteroalkyl," as used herein, refers to an alkyl group, as defined herein, in which one or more of the constituent carbon atoms have been replaced by nitrogen, oxygen, or sulfur. In some embodiments, the heteroalkyl group can be further substituted with 1, 2, 3, or 4 substituent groups as described herein for alkyl groups. Examples of heteroalkyl groups are an "alkoxy" which, as used herein, refers to alkyl-O— (e.g., methoxy and ethoxy). A heteroalkylene is a divalent heteroalkyl group. Heteroalkyl groups also include alkylamino groups.

The term "alkylamino," as used herein, refers to a heteroalkyl group, as defined herein, in which one or more of the constituent carbon atoms have been replaced by nitrogen. In some embodiments, the heteroalkyl group can be further substituted with 1, 2, 3, or 4 substituent groups as described herein for alkyl groups. Examples of alkylamino groups are methylamino and ethylamino.

The term "amino," as used herein, represents $N(R^{N1})_2$, wherein each $R^{N1}$ is, independently, H, OH, $NO_2$, $N(R^{N2})_2$, $SO_2OR^{N2}$, $SO_2R^{N2}$, $SOR^{N2}$, an N-protecting group, alkyl, alkoxy, aryl, arylalkyl, cycloalkyl, or acyl (e.g., acetyl, trifluoroacetyl, or others described herein), wherein each of these recited $R^{N1}$ groups can be optionally substituted; or two $R^{N1}$ combine to form an alkylene or heteroalkylene, and wherein each $R^{N2}$ is, independently, H, alkyl, or aryl. The amino groups of the invention can be an unsubstituted amino (i.e., $NH_2$) or a substituted amino (i.e., $N(R^{N1})_2$).

The term "carboxylic acid biomimetic," as used herein, refers to a moiety that can replace a carboxylic acid moiety on a compound as described herein, without substantially effecting the biological activity of the molecule. Exemplary carboxylic acid mimetic moieties are described herein.

The term "cycloalkyl," as used herein, represents a monovalent saturated or unsaturated non-aromatic cyclic hydrocarbon group from three to eight carbons, unless otherwise specified, and is exemplified by cyclopropyl, cyclobutyl, cyclopentyl, cyclohexyl, cycloheptyl, bicycle heptyl, and the like. When the cycloalkyl group includes one carbon-carbon double bond, the cycloalkyl group can be referred to as a "cycloalkenyl" group. Exemplary cycloalkenyl groups include cyclopentenyl, cyclohexenyl, and the like. The cycloalkyl groups of this invention can be optionally substituted with: (1) $C_1$-$C_7$ acyl (e.g., carboxyaldehyde); (2) $C_1$-$C_{20}$ alkyl (e.g., $C_1$-$C_6$ alkyl, $C_1$-$C_6$ alkoxy-$C_1$-$C_6$ alkyl, $C_1$-$C_6$ alkylsulfinyl-$C_1$-$C_6$ alkyl, amino-$C_1$-$C_6$ alkyl, azido-$C_1$-$C_6$ alkyl, (carboxyaldehyde)-$C_1$-$C_6$ alkyl, halo-$C_1$-$C_6$ alkyl (e.g., perfluoroalkyl), optionally substituted hydroxyl-$C_1$-$C_6$ alkyl, nitro-$C_1$-$C_6$ alkyl, or $C_1$-$C_6$ thioalkoxy-$C_1$-$C_6$ alkyl); (3) $C_1$-$C_{20}$ alkoxy (e.g., $C_1$-$C_6$ alkoxy, such as perfluoroalkoxy); (4) $C_1$-$C_6$ alkylsulfinyl; (5) $C_6$-$C_{10}$ aryl; (6) amino; (7) $C_1$-$C_6$ alk-$C_6$-$C_{10}$ aryl; (8) azido; (9) $C_{3-8}$ cycloalkyl; (10) $C_1$-$C_6$ alk-$C_{3-8}$ cycloalkyl; (11) halo; (12) $C_1$-$C_{12}$ heterocyclyl (e.g., $C_1$-$C_{12}$ heteroaryl); (13) ($C_1$-$C_{12}$ heterocyclyl)oxy; (14) optionally substituted hydroxyl; (15) nitro; (16) $C_1$-$C_{20}$ thioalkoxy (e.g., $C_1$-$C_6$ thioalkoxy); (17) —$(CH_2)_qCO_2R^{A'}$, where q is an integer from zero to four, and $R^{A'}$ is selected from the group consisting of (a) $C_1$-$C_6$ alkyl, (b) $C_6$-$C_{10}$ aryl, (c) hydrogen, and (d) $C_1$-$C_6$ alk-$C_6$-$C_{10}$ aryl; (18) —$(CH_2)_qCONR^{B'}R^{C'}$, where q is an integer from zero to four and where $R^{B'}$ and $R^{C'}$ are independently selected from the group consisting of (a) hydrogen, (b) $C_6$-$C_{10}$ alkyl, (c) $C_6$-$C_{10}$ aryl, and (d) $C_1$-$C_6$ alk-$C_6$-$C_{10}$ aryl;

(19) —$(CH_2)_qSO_2R^{D'}$, where q is an integer from zero to four and where $R^{D'}$ is selected from the group consisting of (a) $C_6$-$C_{10}$ alkyl, (b) $C_6$-$C_{10}$ aryl, and (c) $C_1$-$C_6$ alk-$C_6$-$C_{10}$ aryl; (20) —$(CH_2)_qSO_2NR^{E'}R^{F'}$, where q is an integer from zero to four and where each of $R^{E'}$ and $R^{F'}$ is, independently, selected from the group consisting of (a) hydrogen, (b) $C_6$-$C_{10}$ alkyl, (c) $C_6$-$C_{10}$ aryl, and (d) $C_1$-$C_6$ alk-$C_6$-$C_{10}$ aryl; (21) optionally substituted thiol; (22) $C_6$-$C_{10}$ aryloxy; (23) $C^{3-8}$ cycloalkoxy; (24) $C_6$-$C_{10}$ aryl-$C_1$-$C_6$ alkoxy; (25) $C_1$-$C_6$ alkl-$C_1$-$C_{12}$ heterocyclyl (e.g., $C_1$-$C_6$ alk-$C_1$-$C_{12}$ heteroaryl); (26) oxo; (27) $C_2$-$C_{20}$ alkenyl; and (28) $C_2$-$C_{20}$ alkynyl. In some embodiments, each of these groups can be further substituted as described herein. For example, the alkylene group of a $C_1$-alkaryl or a $C_1$-alkheterocyclyl can be further substituted with an oxo group to afford the respective aryloyl and (heterocyclyl)oyl substituent group.

The term "halogen," as used herein, refers to bromine, chlorine, iodine, or fluorine.

The term "N-protecting group," as used herein, represents those groups intended to protect an amino group against undesirable reactions during synthetic procedures. Commonly used N-protecting groups are disclosed in Greene, "Protective Groups in Organic Synthesis," $3^{rd}$ Edition (John Wiley & Sons, New York, 1999). N-protecting groups include acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L or D, L-amino acids such as alanine, leucine, and phenylalanine; sulfonyl-containing groups such as benzenesulfonyl, and p-toluenesulfonyl; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, and phenylthiocarbonyl, arylalkyl groups such as benzyl, triphenylmethyl, and benzyloxymethyl, and silyl groups, such as trimethylsilyl. Preferred N-protecting groups are alloc, formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "O-protecting group," as used herein, represents those groups intended to protect an oxygen containing (e.g., phenol, optionally substituted hydroxyl, or carbonyl) group against undesirable reactions during synthetic procedures. Commonly used O-protecting groups are disclosed in Greene, "Protective Groups in Organic Synthesis," $3^{rd}$ Edition (John Wiley & Sons, New York, 1999), which is incorporated herein by reference. Exemplary O-protecting groups include acyl, aryloyl, or carbamyl groups, such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, t-butyldimethylsilyl, tri-iso-propylsilyloxymethyl, 4,4'-dimethoxytrityl, isobutyryl, phenoxyacetyl, 4-isopropylpehenoxyacetyl, dimethylformamidino, and 4-nitrobenzoyl; alkylcarbonyl groups, such as acyl, acetyl, propionyl, pivaloyl, and the like; optionally substituted arylcarbonyl groups, such as benzoyl; silyl groups, such as trimethylsilyl (TMS), tert-butyldimethylsilyl (TBDMS), tri-iso-propylsilyloxymethyl (TOM), triisopropylsilyl (TIPS), and the like; ether-forming groups with the optionally substituted hydroxyl, such methyl, methoxymethyl, tetrahydropyranyl, benzyl, p-methoxybenzyl, trityl, and the like; alkoxycarbonyls, such as methoxycarbonyl, ethoxycarbonyl, isopropoxycarbonyl, n-isopropoxycarbonyl, n-butyloxycarbonyl, isobutyloxycarbonyl, sec-butyloxycarbonyl, t-butyloxycarbonyl, 2-ethylhexyloxycarbonyl, cyclohexyloxycarbonyl, methyloxycarbonyl, and the like; alkoxyalkoxycarbonyl groups, such as methoxymethoxycarbonyl, ethoxymethoxycarbonyl, 2-methoxyethoxycarbonyl, 2-ethoxyethoxycarbonyl, 2-butoxyethoxycarbonyl, 2-methoxyethoxymethoxycarbonyl, allyloxycarbonyl, propargyloxycarbonyl, 2-butenoxycarbonyl, 3-methyl-2-butenoxycarbonyl, and the like; haloalkoxycarbonyls, such as 2-chloroethoxycarbonyl, 2-chloroethoxycarbonyl, 2,2,2-trichloroethoxycarbonyl, and the like; optionally substituted arylalkoxycarbonyl groups, such as benzyloxycarbonyl, p-methylbenzyloxycarbonyl, p-methoxybenzyloxycarbonyl, p-nitrobenzyloxycarbonyl, 2,4-di nitrobenzyloxycarbonyl, 3,5-dimethylbenzyloxycarbonyl, p-chlorobenzyloxycarbonyl, p-bromobenzyloxy-carbonyl, fluorenylmethyloxycarbonyl, and the like; and optionally substituted aryloxycarbonyl groups, such as phenoxycarbonyl, p-nitrophenoxycarbonyl, o-nitrophenoxycarbonyl, 2,4-di nitrophenoxycarbonyl, p-methyl-phenoxycarbonyl, m-methylphenoxycarbonyl, o-bromophenoxycarbonyl, 3,5-dimethylphenoxycarbonyl, p-chlorophenoxycarbonyl, 2-chloro-4-nitrophenoxy-carbonyl, and the like); substituted alkyl, aryl, and alkaryl ethers (e.g., trityl; methylthiomethyl; methoxymethyl; benzyloxymethyl; siloxymethyl; 2,2,2,-trichloroethoxymethyl; tetrahydropyranyl; tetrahydrofuranyl; ethoxyethyl; 1-[2-(trimethylsilyl)ethoxy]ethyl; 2-trimethylsilylethyl; t-butyl ether; p-chlorophenyl, p-methoxyphenyl, p-nitrophenyl, benzyl, p-methoxybenzyl, and nitrobenzyl); silyl ethers (e.g., trimethylsilyl; triethylsilyl; triisopropylsilyl; dimethylisopropylsilyl; t-butyldimethylsilyl; t-butyldiphenylsilyl; tribenzylsilyl; triphenylsilyl; and diphenymethylsilyl); carbonates (e.g., methyl, methoxymethyl, 9-fluorenylmethyl; ethyl; 2,2,2-trichloroethyl; 2-(trimethylsilyl)ethyl; vinyl, allyl, nitrophenyl; benzyl; methoxybenzyl; 3,4-dimethoxybenzyl; and nitrobenzyl); carbonyl-protecting groups (e.g., acetal and ketal groups, such as dimethyl acetal, 1,3-dioxolane, and the like; acylal groups; and dithiane groups, such as 1,3-dithianes, 1,3-dioptionally substituted thiolane, and the like); carboxylic acid-protecting groups (e.g., ester groups, such as methyl ester, benzyl ester, t-butyl ester, orthoesters, and the like; and oxazoline groups.

The alkyl, alkenyl, alkynyl, heteroalkyl, heteroalkenyl, heteroalkynyl, carbocyclyl (e.g., cycloalkyl), aryl, heteroaryl, and heterocyclyl groups may be substituted or unsubstituted. When substituted, there will generally be 1 to 4 substituents present, unless otherwise specified. Substituents include, for example: aryl (e.g., substituted and unsubstituted phenyl), carbocyclyl (e.g., substituted and unsubstituted cycloalkyl), halogen (e.g., fluoro), hydroxyl, heteroalkyl (e.g., substituted and unsubstituted methoxy, ethoxy, or thioalkoxy), heteroaryl, heterocyclyl, amino (e.g., $NH_2$ or mono- or dialkyl amino), azido, cyano, nitro, or thiol. Aryl, carbocyclyl (e.g., cycloalkyl), heteroaryl, and heterocyclyl groups may also be substituted with alkyl (unsubstituted and substituted such as arylalkyl (e.g., substituted and unsubstituted benzyl)).

Those skilled in the art will appreciate that certain compounds described herein can exist in one or more different isomeric (e.g., stereoisomers, geometric isomers, tautomers) and/or isotopic (e.g., in which one or more atoms has been substituted with a different isotope of the atom, such as hydrogen substituted for deuterium) forms. Unless otherwise indicated or clear from context, a depicted structure can be understood to represent any such isomeric or isotopic form, individually or in combination.

Compounds of the invention can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbents or eluant). That is, certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms and represent the configuration of substituents around one or more chiral carbon atoms. Enantiomers of a compound can be prepared, for example, by separating an enantiomer from a racemate using one or more well-known techniques and methods, such as, for example, chiral chromatography and separation methods based thereon. The appropriate technique and/or method for separating an enantiomer of a compound described herein from a racemic mixture can be readily determined by those of skill in the art. "Racemate" or "racemic mixture" means a compound containing two enantiomers, wherein such mixtures exhibit no optical activity; i.e., they do not rotate the plane of polarized light. "Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration. "R," "S," "S*," "R*," "E," "Z," "cis," and "trans," indicate configurations relative to the core molecule. Certain of the disclosed compounds may exist in atropisomeric forms. Atropisomers are stereoisomers resulting from hindered rotation about single bonds where the steric strain barrier to rotation is high enough to allow for the isolation of the conformers. The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods. When the stereochemistry of a disclosed compound is named or depicted by structure, the named or depicted stereoisomer is at least 60%, 70%, 80%, 90%, 99% or 99.9%) by weight relative to the other stereoisomers. When a single enantiomer is named or depicted by structure, the depicted or named enantiomer is at least 60%, 70%, 80%, 90%, 99% or 99.9% by weight optically pure. When a single diastereomer is named or depicted by structure, the depicted or named diastereomer is at least 60%, 70%, 80%, 90%, 99% or 99.9% by weight pure. Percent optical purity is the ratio of the weight of the enantiomer or over the weight of the enantiomer plus the weight of its optical isomer. Diastereomeric purity by weight is the ratio of the weight of one diastereomer or over the weight of all the diastereomers.

When the stereochemistry of a disclosed compound is named or depicted by structure, the named or depicted stereoisomer is at least 60%, 70%, 80%, 90%, 99% or 99.9% by mole fraction pure relative to the other stereoisomers. When a single enantiomer is named or depicted by structure, the depicted or named enantiomer is at least 60%, 70%, 80%, 90%, 99% or 99.9% by mole fraction pure. When a single diastereomer is named or depicted by structure, the depicted or named diastereomer is at least 60%, 70%, 80%, 90%, 99% or 99.9% by mole fraction pure. Percent purity by mole fraction is the ratio of the moles of the enantiomer or over the moles of the enantiomer plus the moles of its optical isomer. Similarly, percent purity by moles fraction is the ratio of the moles of the diastereomer or over the moles of the diastereomer plus the moles of its isomer. When a disclosed compound is named or depicted by structure without indicating the stereochemistry, and the compound has at least one chiral center, it is to be understood that the name or structure encompasses either enantiomer of the compound free from the corresponding optical isomer, a racemic mixture of the compound or mixtures enriched in one enantiomer relative to its corresponding optical isomer. When a disclosed compound is named or depicted by structure without indicating the stereochemistry and has two or more chiral centers, it is to be understood that the name or structure encompasses a diastereomer free of other diastereomers, a number of diastereomers free from other diastereomeric pairs, mixtures of diastereomers, mixtures of diastereomeric pairs, mixtures of diastereomers in which one diastereomer is enriched relative to the other diastereomer(s) or mixtures of diastereomers in which one or more diastereomer is enriched relative to the other diastereomers. The invention embraces all of these forms.

In some embodiments, one or more compounds depicted herein may exist in different tautomeric forms. As will be clear from context, unless explicitly excluded, references to such compounds encompass all such tautomeric forms. In some embodiments, tautomeric forms result from the swapping of a single bond with an adjacent double bond and the concomitant migration of a proton. In certain embodiments, a tautomeric form may be a prototropic tautomer, which is an isomeric protonation states having the same empirical formula and total charge as a reference form. Examples of moieties with prototropic tautomeric forms are ketone—enol pairs, amide—imidic acid pairs, lactam—lactim pairs, amide—imidic acid pairs, enamine—imine pairs, and annular forms where a proton can occupy two or more positions of a heterocyclic system, such as, 1H- and 3H-imidazole, 1H-, 2H- and 4H-1,2,4-triazole, 1H- and 2H-isoindole, and 1H- and 2H-pyrazole. In some embodiments, tautomeric forms can be in equilibrium or sterically locked into one form by appropriate substitution. In certain embodiments, tautomeric forms result from acetal interconversion, e.g., the interconversion illustrated in the scheme below:

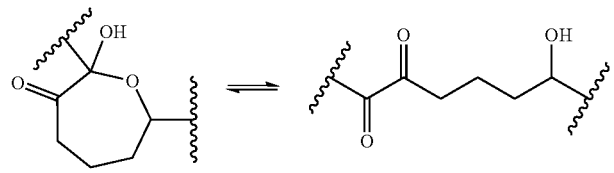 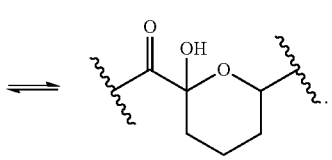

Those skilled in the art will appreciate that, in some embodiments, isotopes of compounds described herein may be prepared and/or utilized in accordance with the present invention. "Isotopes" refers to atoms having the same atomic number but different mass numbers resulting from a different number of neutrons in the nuclei. For example, isotopes of hydrogen include tritium and deuterium. In some embodiments, an isotopic substitution (e.g., substitution of hydrogen with deuterium) may alter the physiciochemical properties of the molecules, such as metabolism and/or the rate of racemization of a chiral center.

As is known in the art, many chemical entities (in particular many organic molecules and/or many small molecules) can adopt a variety of different solid forms such as, for example, amorphous forms and/or crystalline forms (e.g., polymorphs, hydrates, solvates, etc). In some embodiments, such entities may be utilized in any form, including in any solid form. In some embodiments, such entities are utilized in a particular form, for example in a particular solid form.

In some embodiments, compounds described and/or depicted herein may be provided and/or utilized in salt form.

In certain embodiments, compounds described and/or depicted herein may be provided and/or utilized in hydrate or solvate form.

At various places in the present specification, substituents of compounds of the present disclosure are disclosed in groups or in ranges. It is specifically intended that the present disclosure include each and every individual subcombination of the members of such groups and ranges. For example, the term "$C_1$-$C_6$ alkyl" is specifically intended to individually disclose methyl, ethyl, $C_3$ alkyl, $C_4$ alkyl, $C_5$ alkyl, and $C_6$ alkyl. Furthermore, where a compound includes a plurality of positions at which substitutes are disclosed in groups or in ranges, unless otherwise indicated, the present disclosure is intended to cover individual compounds and groups of compounds (e.g., genera and subgenera) containing each and every individual subcombination of members at each position. Herein a phrase of the form "optionally substituted X" (e.g., optionally substituted alkyl) is intended to be equivalent to "X, wherein X is optionally substituted" (e.g., "alkyl, wherein said alkyl is optionally substituted"). It is not intended to mean that the feature "X" (e.g. alkyl) per se is optional. As used herein, the term "optionally substituted X" (e.g., optionally substituted alkyl) means that X can be substituted with any substituent, e.g., any of the substituents described herein.

BRIEF DESCRIPTION OF THE DRAWINGS

FIGS. 10C-10D show dose-response curves for isoguvacine (FIG. 10C) and compound 5 (FIG. 10D) for agonism of the human GABAAα2β3γ2 receptor using an in vitro Cl-flux measurement. All compound response data has been normalized to the baseline peak current induced by addition of EC$_{100}$ GABA (30 μM) for 2 seconds for the agonist assay. FIG. 10C is a graph of data from a radio-ligand binding assay showing percent inhibition of GABA transporter activity in the presence of compound 5 or positive control NO-711.

FIG. 15A: Hairy skin sensitivity was measured using tactile PPI. Percent inhibition of the startle response to a 125 dB noise, when the startle noise is preceded by a light air puff (250 ms Student's unpaired t-test or one-way ANOVA with post-hoc Tukey's test, *, p<0.05. FIG. 15N: Quantification of average $R_h$ in large diameter DRG neurons cultured from control and Shank3B$^{+/-}$ mutant mice. Student's unpaired t-test, *, p<0.005.

FIGS. 16A-16V show loss of either Shank3 or Mecp2 in peripheral somatosensory neurons leads to abnormal forebrain interneuron development and microcircuit properties in a region-specific manner. FIG. 16A: Representative immunohistochemistry (IHC) images of parvalbumin (PV) immunoreactivity in control or Advillin$^{Cre}$; Mecp2$^{f/y}$ mutant mice, showing full sagittal brain sections and corresponding magnified sections of primary somatosensory cortex (S1) and primary visual cortex (V1), or transverse sections of basolateral amygdala (BLA). FIGS. 16C-16F: Quantification of the number of PV-positive (PV$^+$) neurons in S1 (FIG. 16D), V1 (FIG. 16E), and BLA (FIG. 16F) in mutant mice and their control littermates. Student's unpaired t-test, *, p<0.05. FIG. 16G: Representative IHC images of transverse S1 brain sections, showing PV immunoreactivity in control, Shank3$^{FX/+}$, or Advillin$^{Cre}$; Shank3$^{FX/+}$ mutant mice. FIG. 16H: Representative IHC images of transverse S1 brain sections, showing PV immunoreactivity in control, Mecp2$^{STOP/y}$, or Advillin$^{Cre}$; Mecp2$^{STOP/y}$ mutant mice. FIG. 16Q: Representative traces showing ePSCSs (-70 my hold) and iPSCs (0 mV hold) from S1 slices of control or Advillin$^{Cre}$; Mecp2$^{f/y}$ mutant mice. FIG. 16R: Quantification of excitatory/inhibitory (E/I) ratios in S1 or V1 slices from control and mutant mice. Student's unpaired t-test, *, p<0.05. FIGS. 16S-16T: Quantification of ePSC and iPSC event frequency (FIG. 16S) and event amplitude (FIG. 16T) in S1 slices from control and mutant mice. Two-way ANOVA with post-hoc Sidak's test, *, p<0.05. FIGS. 16U-16V: Quantification of ePSC and iPSC event frequency (FIG. 16U) and event amplitude (FIG. 16V) in V1 slices from control and mutant mice. Two-way ANOVA with post-hoc Sidak's test, *, p<0.05.

FIGS. 17A-17J show normal tactile sensitivity is necessary during early postnatal periods for normal brain development and behavior. FIG. 17A: Percent inhibition of the startle response to a 125 dB noise, when the startle noise is preceded by a light air puff in mutant mice and control littermates. Student's unpaired t-test or one-way ANOVA with post-hoc Tukey's test, *, p<0.05. Tamoxifen was administered to all littermates, over a five day period, beginning on the day noted for each condition. FIG. 17B: Discrimination index for textured NORT. Student's unpaired t-test or one-way ANOVA with post-hoc Tukey's test, *, p<0.05. FIG. 17C: Representative activity traces in the OF test for Shank3 mutant mice and control littermates. Tamoxifen (TAM) was administered over a five day period, beginning on the day noted for each condition. FIG. 17D: Representative activity traces in the OF test for Mecp2 mutant mice and control littermates. FIG. 17E: Percent time spent in the center of the OF chamber. Student's unpaired t-test or one-way ANOVA with post-hoc Tukey's test, *, p<0.05. FIG. 17F: Percent time spent in the open arms of the EPM. Student's unpaired t-test or one-way ANOVA with post-hoc Tukey's test, *, p<0.05. FIGS. 17G-17H: Representative heat maps of activity in the 3-chamber social interaction test during the "Sociability" (top panels) and "Social Novelty Preference" (bottom panels) portions of the assay, for Shank3 (FIG. 17G) or Mecp2 (FIG. 17H) mutant mice and their control littermates. FIG. 17I: Preference index for the percentage of time spent investigating the novel mouse in the "Sociability" portion of the 3-chamber social interaction test. Student's unpaired t-test or one-way ANOVA with post-hoc Tukey's test, *, p<0.05. FIG. 17J: Preference index for the percentage of time spent investigating the novel mouse in the "Social Novelty Recognition" portion of the 3-chamber social interaction test. Student's unpaired t-test or one-way ANOVA with post-hoc Tukey's test, *, p<0.05.

FIG. 18A: Intraperitoneal (i.p.) injection of AAV.FLEX.Gabrb3.mCherry into Advillin$^{Cre}$; Mecp2$^{C/y}$ mutant mice at P5 transduces peripheral sensory neurons, as evidenced by immunoreactivity for mCHERRY. Transduced large diameter neurons are immunoreactive for both mCHERRY and NF200. FIGS. 18M-18O: Quantification of the number of PV-positive (PV$^+$) neurons in S1 (FIG. 18M), V1 (FIG. 18N), and BLA (FIG. 18O) in mutant, mutant rescues and their control littermates. One-way ANOVA with post-hoc Tukey's test, *, p<0.05.

FIG. 19A: Percent inhibition of the startle response to a 125 dB noise, when the startle noise is preceded by a light air puff in mice following i.p. administration of either saline or 2 mg/kg midazolam treatment. Two-way ANOVA with post-hoc Sidak's test, *, p<0.05. FIG. 19N: Magnitude of startle response to a 125 dB noise in mice following i.p. administration of either saline or 2 mg/kg isoguvacine treatment. Responses are expressed as percent of startle response to a 125 dB noise. Two-way ANOVA with post-hoc Sidak's test, *, p<0.05.

FIGS. 20A-20O show isoguvacine attenuates tactile sensitivity through reduced excitability of peripheral, low-threshold mechanosensory neurons. FIG. 20A: Diagram for in vivo dorsal root ganglion (DRG) multi-unit electrode recordings, showing tetrode placement into the left L4 ganglia. FIGS. 20D-20G: Example unit identified during the spike sorting process. Average waveform at each electrode site (FIG. 20D, FIG. 20E), and inter-spike interval (FIG. 20F, FIG. 20G). FIG. 20O: Magnitude of startle response to a 125 dB noise in mice following i.p. administration of either saline or 2 mg/kg isoguvacine treatment. Responses are expressed as percent of startle response to a 125 dB noise. Two-way ANOVA with post-hoc Sidak's test, *, p<0.05.

FIG. 21A: Representative images of P21 control and Mecp2$^{C/y}$ mutant mice treated daily from P0-21 with either saline or isoguvacine (2 mg/kg). FIG. 21B: Average phenotypic score of P21 Shank3B$^{+/-}$ or Mecp2$^{C/y}$ mutant mice and control littermates treated daily with either saline or isoguvacine (2 mg/kg). One-way ANOVA with post-hoc Tukey's test, *, p<0.05. FIG. 21C: Average bodyweight of P21 Shank3B$^{+/-}$ or Mecp2$^{C/y}$ mutant mice and control littermates treated daily with either saline or isoguvacine (2 mg/kg). One-way ANOVA with post-hoc Tukey's test, *, p<0.05. FIG. 21D: Percent inhibition of the startle response to a 125 dB noise, when the startle noise is preceded by a light air puff in Shank3B$^{+/-}$, Mecp2$^{R/C}$ or Mecp2$^{C/y}$ mutant mice and control littermates treated daily from P0-42 with either saline or isoguvacine (2 mg/kg). One-way ANOVA with post-hoc Tukey's test, *, p<0.05. FIG. 21E: Discrimination index for textured NORT. One-way ANOVA with post-hoc Tukey's test, *, p<0.05. FIG. 21F: Representative activity traces in the OF test. FIG. 21O: Quantification of excitatory/inhibitory (E/I) ratio in S1 or V1 slices from control and mutant mice. One-way ANOVA with post-hoc Tukey's test, *, p<0.05.

FIG. 22A: IHC images of spinal cord (SC) dorsal horn lamina III/IV from control, Shank3B$^{-/-}$ or Advillin$^{Cre}$; Shank3$^{f/f}$ mice, showing SHANKS expression at vGLUT1+ presynaptic terminals for Aβ and Aδ LTMRs. FIG. 22R: IHC images of SC dorsal horn lamina III/IV from control, Shank3B$^{FX/FX}$ or Advillin$^{Cre}$; Shank3$^{FX/+}$ mice, showing KCNQ2 expression at vGLUT1+ presynaptic terminals.

FIG. 23A: IHC images of SC dorsal horn lamina III/IV from HCN1$^{-/-}$, Shank3B$^{-/-}$, Advillin$^{Cre}$; Shank3$^{f/f}$ mice and their control littermates, showing HCN1 expression at vGLUT1+ presynaptic terminals. FIG. 23Z: Discrimination index for textured NORT, 5-minute NORT and 1-hour NORT. One-way ANOVA with post-hoc Tukey's test, *, p<0.05.

FIG. 24A: Response to a light air puff stimulus alone mutant mice and their control littermates. Responses are expressed as percent of startle response to a 125 dB noise. Mice received five days of tamoxifen (TAM) treatment, beginning at either P5, P10 or P28. Student's unpaired t-test or one-way ANOVA with post-hoc Tukey's test, *, p<0.05. FIG. 24B: Magnitude of startle response to a 125 dB noise in mutant mice and control littermates. Student's unpaired t-test or one-way ANOVA with post-hoc Tukey's test, *, p<0.05. FIG. 24C: Percent inhibition of the startle response to a 125 dB noise (pulse), when the startle noise is preceded by tone prepulse in mutant mice and control littermates. FIG. 24D: Response to a non-startling acoustic noise (80 dB, 20 ms) in mutant mice and their control littermates. Responses are expressed as percent of startle response to a 125 dB startle noise. FIG. 24E: Discrimination index for 5-minute NORT. FIG. 24F: Discrimination index for 1-hour NORT. Student's unpaired t-test or one-way ANOVA with post-hoc Tukey's test, *, p<0.05. FIG. 24G: Average amount of time (seconds) spent physically interacting with both the familiar and novel object in the NOR tests in mutant mice and their control littermates. FIG. 24H: Average total distance traveled in the open field chamber for mutant mice and their control littermates. Student's unpaired t-test or one-way ANOVA with post-hoc Tukey's test, *, p<0.05. FIG. 24I: Percent decrease in startle response to a 125 dB noise during a 30-minute tactile PPI session, when comparing the first five startle responses to the last five responses to a 125 dB noise for mutant mice and their control littermates. Student's unpaired t-test or one-way ANOVA with post-hoc Tukey's test, *, p<0.05. FIG. 24J: Average number of marbles buried (out of 12) during a twenty-minute assay for mutant mice and their control littermates. Student's unpaired t-test or one-way ANOVA with post-hoc Tukey's test, *, p<0.05. FIG. 24K: Representative heat maps of activity in the 3-chamber social interaction test during the "Sociability" (top panels) and "Social Novelty Preference" (bottom panels) portions of the assay, for control, Shank3$^{FX/+}$ and Advillin$^{CreERT2}$; Shank3$^{FX/+}$ mice. TAM was administered from P28-32 to all littermates. FIG. 24L: Representative heat maps of activity in the 3-chamber social interaction test during the "Sociability" (top panels) and "Social Novelty Preference" (bottom panels) portions of the assay, for control, Mecp2$^{STOP/y}$ and Advillin$^{CreERT2}$; Mecp2$^{STOP/y}$ mice. TAM was administered from P28-32 to all littermates.

FIG. 25A: IHC images of transverse primary somatosensory cortex (S1), spinal cord, or DRG sections from a control mouse showing MeCP2 expression (top panels) or MeCP2, Hoescht and IB4 expression (bottom panels). FIG. 25B: IHC images of transverse primary somatosensory cortex (51), spinal cord, or DRG sections from an Advillin$^{CreERT2}$; Mecp2$^{f/y}$ mouse that received TAM treatment, showing MeCP2 expression (top panels) and MeCP2, Hoescht and IB4 expression (bottom panels). Note lack of MeCP2 expression in the DRG, while MeCP2 expression is normal in 51 and spinal cord sections. FIG. 25C: Average percentage of MeCP2+ DRG neurons in control mice or mice with sensory-neuron specific deletion of Mecp2 (Advillin$^{CreERT2}$; Mecp2$^{f/y}$), receiving five days of TAM beginning at P5, P10 or P28. Three to five DRGs were analyzed per mouse, and three to five mice per genotype and TAM date were included in the analysis. FIG. 25D: Average percentage of SHANK3+, vGLUT1+ puncta in spinal cord sections from control mice or mice with sensory-neuron specific deletion of Mecp2 (Advillin$^{CreERT2}$; Shank3$^{f/f}$), receiving five days of TAM beginning at P5, P10 or P28. Three to five spinal cord sections were analyzed per mouse, and three to five mice per genotype and TAM date were included in the analysis. FIG. 25E: IHC images of transverse spinal cord (SC) and DRG sections from a control mouse showing SHANK3 expression (top panels) or SHANK3 and vGLUT1 expression (bottom panels) in control mice. Note lack of SHANK3 expression in control SC at P7, and robust SHANKS expression in DRG at P7. FIG. 25F: Representative IHC images of transverse S1 brain sections, showing PV immunoreactivity in control, Adviffin$^{CreERT2}$; Shank3$^{f/+}$ or Advillin$^{CreERT2}$; Mecp2$^{f/y}$ mutant mice and their control littermates. TAM was administered from P28-32 to all littermates. FIG. 25G: Quantification of the number of PV$^+$ neurons in S1 of Advillin$^{CreERT2}$; Shank3$^{f/+}$ or Advillin$^{CreERT2}$; Mecp2$^{f/y}$ mutant mice and their control littermates. Mice received five days of TAM treatment, beginning at either P5, P10 or P28. Student's t-test, p<0.05. FIG. 25H: Quantification of the number of PV$^+$ neurons in V1 of Advillin$^{CreERT2}$; Shank3$^{f/+}$ or Advillin$^{CreERT2}$; Mecp2$^{f/y}$ mutant mice and their control littermates. Mice received five days of TAM treatment, beginning at either P5, P10 or P28. Student's t-test, p<0.05. FIG. 25I: Quantification of the number of PV⁺ neurons in BLA of Advillin$^{CreERT2}$; Shank3$^{f/+}$ or Advillin$^{CreERT2}$; Mecp2$^{f/y}$ mutant mice and their control littermates. Mice received five days of TAM treatment, beginning at either P5, P10 or P28. Student's t-test, p<0.05. FIG. 25J: IHC images of transverse primary somatosensory cortex (S1), spinal cord, or DRG sections from control and Advillin$^{CreERT2}$; Mecp2$^{STOP/y}$ mice showing MeCP2, Hoescht and IB4 expression with and without the TAM administration ('+TAM', –TAM'). TAM was administered from P28-32. FIG. 25K: Quantification of the number of PV⁺ neurons in S1 of control, mutant and mutant rescue mice. Mice received five days of TAM treatment, beginning at P28. One-way ANOVA with post-hoc Tukey's test, *, p<0.05. FIG. 25L: Quantification of the number of PV⁺ neurons in V1 of control, mutant and mutant rescue mice. Mice received five days of TAM treatment, beginning at P28. One-way ANOVA with post-hoc Tukey's test, *, p<0.05. FIG. 25M: Quantification of the number of PV⁺ neurons in BLA of control, mutant and mutant rescue mice. Mice received five days of TAM treatment, beginning at P28. One-way ANOVA with post-hoc Tukey's test, *, p<0.05.

FIG. 26A: Percentage of transduced DRG neurons (mCherry⁺ neurons) in mice that received P5 i.p. injection of AAV.FLEX.GABRB3. FIG. 26N: Representative heat maps of activity in the 3-chamber social interaction test during the "Sociability" (top panels) and "Social Novelty Preference" (bottom panels) portions of the assay, for control, Mecp2$^{C/y}$ and Advillin$^{Cre}$; Mecp2$^{C/y}$ mice.

FIGS. 27A-27B: Representative traces from large diameter neurons cultured from DRGs of control (FIG. 27A) and Mecp2$^{STOP/y}$ (FIG. 27B) mice during whole cell current clamp recordings, in which the minimal amount of current required to elicit an action potential in each neuron (rheobase, R$_h$), was determined in the absence or presence of 10 μm isoguvacine. FIG. 27C: Quantification of average R$_h$ in large diameter neurons cultured from DRGs of control mice during a baseline period and then in presence of 10 μm isoguvacine. Repeated measures one-way ANOVA, post-hoc Tukey's test, *, p<0.05. FIG. 27D: Quantification of average R$_h$ in large diameter neurons cultured from DRGs of control mice during a baseline period, followed application of 10 μm isoguvacine, then washout period. Repeated measures one-way ANOVA, post-hoc Tukey's test, *, p<0.05. FIG. 27E: Quantification of average R$_h$ in large diameter neurons cultured from DRGs of control and Mecp2$^{STOP/y}$ mice during a baseline period and then in presence of 10 μm isoguvacine. Repeated measures two-way ANOVA, post-hoc Tukey's test, *, p<0.05. FIG. 27F: Quantification of average R$_h$ in large diameter neurons cultured from DRGs of control and Shank3B$^{+/-}$ mice during a baseline period and then in presence of 10 μm isoguvacine. Repeated measures two-way ANOVA, post-hoc Tukey's test, *, p<0.05. FIG. 27G: Quantification of total I$_h$ density at each hyperpolarizing voltage step for large diameter neurons cultured from DRGs of control, Mecp2$^{STOP/y}$ and Shank3B$^{+/-}$ mutant mice. Repeated measures two-way ANOVA, not significant. FIG. 27H: GABA$_A$ receptor subunit RNA expression levels across peripheral somatosensory neuron subtypes, for the delta, epsilon, pi, and theta subunit types. FIG. 27I: Representative activity raster plots for multiple putative proprioceptors in multiple mice over the duration of a recording experiment in controls and Shank3B$^{+/-}$ mice. Mice received a subcutaneous injection of isoguvacine (2 mg/kg) during the experiment, and activity of proprioceptive units in response to a brush stimuli was assessed over a 90-minute period. FIG. 27J: Average firing frequency of proprioceptors over the duration of each recording experiment in controls and Shank3B$^{+/-}$ mice, following subcutaneous injection isoguvacine (2 mg/kg). Repeated measures, two-way ANOVA with post-hoc Dunnett's test, *p<0.05. FIG. 27K: Average brush stroke frequency over the duration of each recording experiment in all controls and mutant mice, following subcutaneous injection of either saline or isoguvacine (2 mg/kg). Repeated measures, one-way ANOVA with post-hoc Dunnett's test, *p<0.05.

FIG. 28A: Liquid chromatography mass spectrometry (LC-MS) quantified isoguvacine concentrations in brain homogenate samples of mice treated with isoguvacine (2 mg/kg, i.p.) from P1-42. Samples were obtained six hours following the final day of isoguvacine administration.

FIG. 28U: Quantification of ePSC and iPSC event frequency in S1 slices from Shank3B$^{+/-}$, Mecp2$^{R/C}$ or Mecp2$^{C/y}$ mutant mice and control littermates treated daily from P1-42 with either saline or isoguvacine (2 mg/kg). Two-way ANOVA with post-hoc Sidak's test, *, p<0.05.

FIG. 29 is related to FIGS. 15A-N.

DETAILED DESCRIPTION

The peripherally restricted GABA$_A$ receptor agonist, isoguvacine, is effective in preventing tactile hypersensitivity in Mecp2, Shank3, Gabrb3, Cntnap2, and Fmr1 genetic models as well as an environmental model of ASD. These results are similar to the reduced tactile sensitivity has been observed in mice treated with a CNS-penetrant benzodiazepine, midazolam. However, because midazolam and other FDA-approved benzodiazepines and nonbenzodiazepine GABA$_A$ receptor drugs reach the brain, these drugs also cause sedation, motor impairments, and other CNS-related complications, whereas isoguvacine does not cause sedation because of its peripheral site of action. Remarkably, long-term treatment of Mecp2 and Shank3 mutant mice with isoguvacine normalized body weight and improved overall phenotypic condition at weaning age, reduced hairy skin over-reactivity, improved brain development, and reduced anxiety-like behaviors and some social impairments in young adult mice. The GABA reuptake inhibitor compounds disclosed herein are effective at reducing tactile hypersensitivity in animal models for ASD and also reduce mechanical hypersensitivity in a rat model of neuropathic pain.

Figure 8:
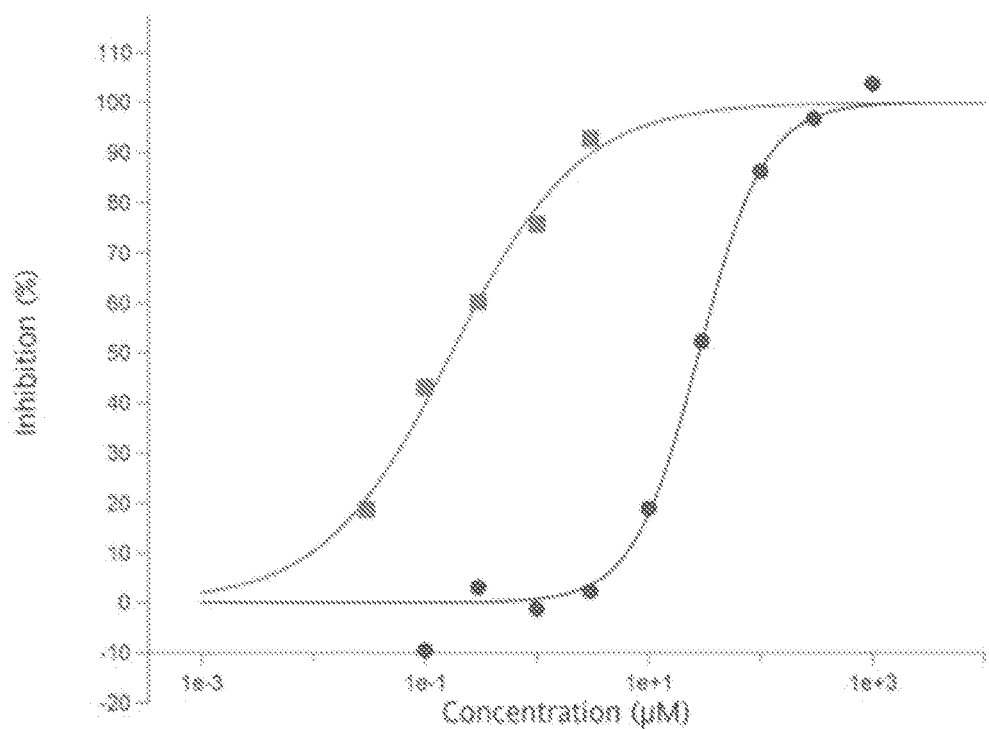
FIG. 8 is a graph of radio-ligand binding assay results showing percent inhibition of GABA transporter activity in the presence of Compound 5 or positive control NO-711. Two-way ANOVA with post-hoc Dunn's test, *, p<0.01, when comparing vehicle treatment mice to drug treatments.
Figure 9:
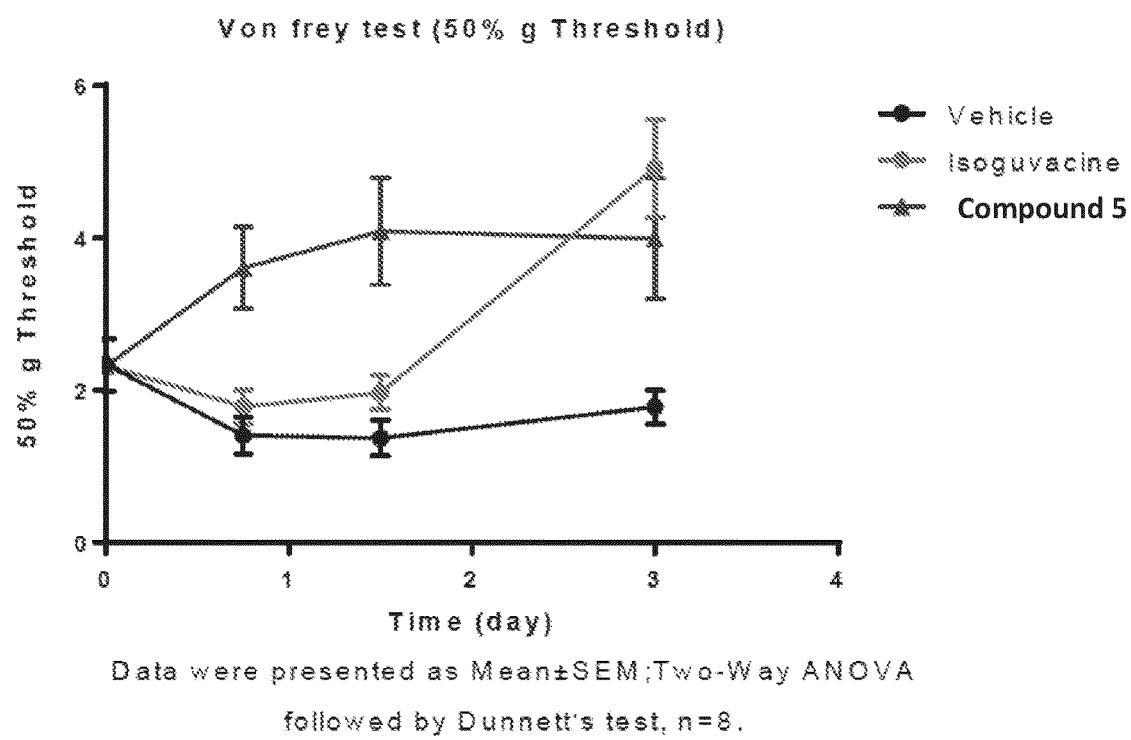
FIG. 9 is a graph showing results of fifty-percent withdrawal threshold to Von Frey fiber stimulation of the hindpaw glabrous skin in rats subject to spared nerve ligation (SNL) model of neuropathic pain. Following recovery from surgery, rats developed mechanical hypersensitivity. Mechanical hypersensitivity was assessed in SNL rats treated with either vehicle, isoguvacine or compound 5. Isoguvacine and compound 5 both reduce neuropathic pain sensitivity.
Figure 10A:
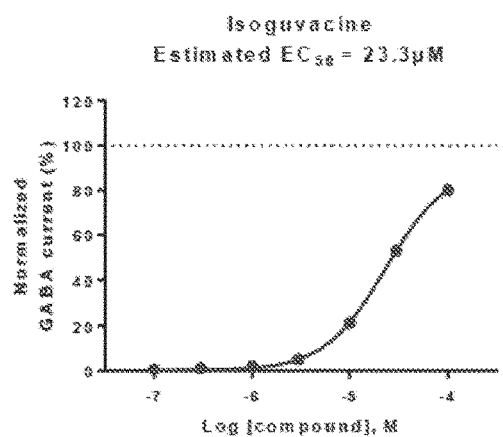
FIGS. 10A-10D show dose-response curves for isoguvacine (FIG. 10A) and compound 5 (FIG. 10B) for agonism of the human hGABAAα1β3γ2 receptor using an in vitro Cl-flux measurement.
Figure 10B:
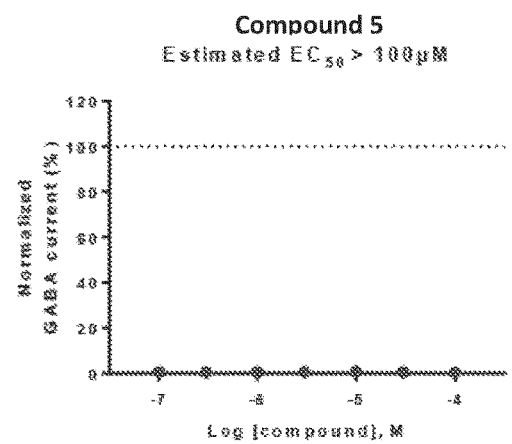
Figure 10C:
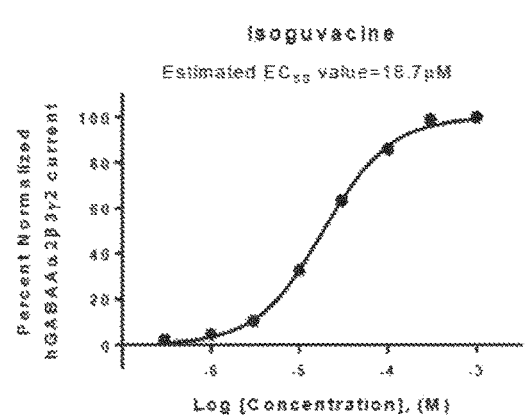
Figure 10D:
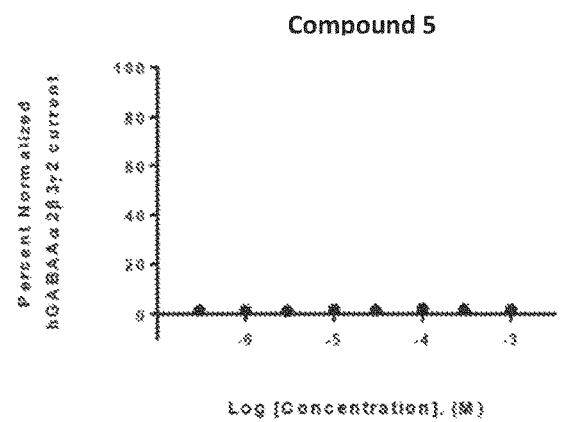
Figure 14:
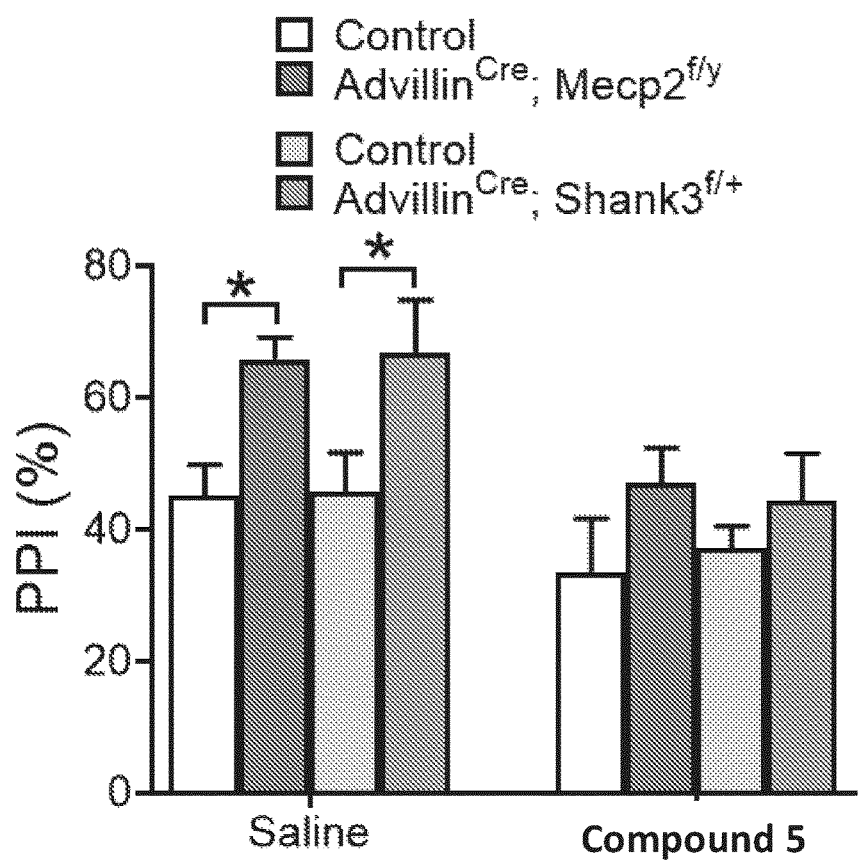
FIG. 14 is a graph showing tactile PPI performance in Mecp2 or Shank3 conditional mutant mice, and their control littermates, 30 minutes following administration of either saline or 2 mg/kg Compound 5. Compound 5 reduces hairy skin hypersensitivity in Mecp2 and Shank3 mutant mice. Two-way ANOVA, with post-hoc Holm-Sidak's test, *, p<0.05, when comparing mutants to control within same treatment.

Recent findings show that mouse peripheral sensory neurons contain α1β3γ2- and α2β3γ2-containing GABA$_A$ receptors (Zheng et al., in review; Example 6). Moreover, using a GABA$_A$ receptor chloride flux assay, it was found that isoguvacine potently activates both α1β3γ2- and α2β3γ2-containing GABA$_A$ receptors, with EC50 values of 23.3 μM and 18.7 μM (FIGS. 10A and 10C), respectively. Of note, human peripheral sensory neurons express only α2β3γ2-containing GABA$_A$ receptors. Compound 5 is not an agonist for the α1β3γ2-containing or α2β3γ2-containing GABA$_A$ receptor, but it is a potent GABA transporter inhibitor (FIGS. 10B, 10D and 8). Furthermore, acute administration of Compound 5 reduces hairy skin over-reactivity in two distinct models for ASD (FIG. 14).

The utility of peripherally-restricted GABA$_A$ receptor PAMs, agonists, and uptake inhibitors are not limited to treatment opportunities for ASD; the present findings also suggest that these drugs will be useful for treating touch over-reactivity and pain associated with other disease states, including Sensory Processing Disorder (SPD) and fibromyalgia, as well as mechanical allodynia associated with nerve injury, shingles, diabetic neuropathy, chemotherapy-induced neuropathy and other neuropathic pain states. Recent findings indicate that isoguvacine and Compound 5 reduce tactile over-reactivity (mechanical allodynia) in rodent models of neuropathic pain (FIG. 15).

A range of mouse genetic models of Autism Spectrum Disorder (ASD) combined with behavioral testing, synaptic analyses, and electrophysiology was used to define both the etiology of aberrant tactile sensitivity in ASD and the contribution of somatosensory dysfunction to the expression of ASD-like traits. It was found that mutations in genes associated with both syndromic and non-syndromic forms of ASD cause tactile dysfunction, and that the Rett Syndrome (RTT)-, Phelan McDermid syndrome (PMS)-, and ASD-associated genes Mecp2, Shank3, and Gabrb3 function cell autonomously in peripheral somatosensory neurons for normal tactile behaviors. Abnormalities in tactile perception are observed in patients with Phelan McDermid Syndrome (PMS) and Fragile X syndrome, which are both highly associated with ASD and are caused by mutations in Shank3 and Fmr1, respectively Similarly, tactile hypersensitivity is common in patients with Rett syndrome (RTT), which is caused by mutations in the X-linked methyl-CpG-binding protein 2 (Mecp2) gene. Tactile dysfunction associated with Mecp2 and Gabrb3 ASD models is caused by a deficiency of the β subunit of the $GABA_A$ receptor (GABRB3) and $GABA_A$ receptor-mediated presynaptic inhibition (PSI) of somatosensory inputs to the CNS. Shank3 mutant DRG neurons, which are associated with PMS, on the other hand, exhibit hyperexcitability. These somatosensory deficits during development contribute to aberrant social behaviors as well as anxiety-like behaviors in adulthood. These findings indicated that somatosensory neuron dysfunction underlies aberrant tactile perception in ASD, RTT, PMS, and Fragile X syndrome and that functional insufficiency of $GABA_A$ receptors or hyperactivity of peripheral sensory neurons cause tactile processing deficiency during development, which leads to anxiety-like behavior and social interaction deficits in adult mice. Thus, peripheral sensory neurons represent exciting, untested therapeutic targets for ASD, RTT, PMS, and Fragile X syndrome.

It has been found that deficits in peripheral sensory neurons, and not neurons in the brain, account for touch hypersensitivity in mouse models of ASD. Moreover, it has been found that touch hypersensitivity during development causes anxiety and social interaction deficits in adulthood. These findings raise the exciting possibility that GABA agents (e.g., GABA reuptake inhibitors or $GABA_A$ receptor agonists), which attenuate the activity of peripheral mechanosensory neurons, may be useful for treating tactile hypersensitivity and thus anxiety and social impairments in ASD patients. Treating young children with such GABA agents has traditionally been avoided because of undesirable side effects of these drugs in children. Indeed, there is great reluctance on the part of physicians to use FDA-approved $GABA_A$ receptor agonists and positive allosteric modulators because of undesirable side effects, including sedation, and serious complications associated with interference with brain development. Accordingly, it is desirable to use peripherally-restricted GABA agents (e.g., GABA reuptake inhibitors or $GABA_A$ receptor agonists), compounds that do not cross the blood-brain barrier, to treat tactile dysfunction and core ASD behaviors. Importantly, peripherally-restricted GABA agents should not promote undesirable side effects observed with all currently used, FDA-approved $GABA_A$ receptor agonists that act in the brain. The peripherally-restricted $GABA_A$ receptor agonist, isoguvacine, improves tactile hypersensitivity, anxiety-like behaviors and social impairments in three animal models of ASD tested (Mecp2, Shank3, and Fmr1 mutant mice), and the novel GABA reuptake inhibitor compounds disclosed herein are shown to be effective at reducing tactile hypersensitivity in animal models for ASD, and effective at reducing mechanical hypersensitivity in a rat model of neuropathic pain.

Accordingly, the present invention features novel peripherally-restricted GABA reuptake inhibitors with reduced blood brain barrier (BBB) permeability and methods of use thereof for reducing tactile dysfunction, social impairment, and/or anxiety in a subject diagnosed with ASD, RTT, PMS, or Fragile X syndrome.

Small Molecule Agents

Gamma-aminobutyrate (GABA) is synthesized primarily by the enzyme glutamate decarboxylase (GAD), which catalyzes the conversion of the excitatory neurotransmitter glutamate to GABA. GABA mediates a wide range of physiological functions, both in the CNS and in external tissues and organs, via binding to GABA receptor subtypes, $GABA_A$ and $GABA_B$. The most abundant subtype of $GABA_A$ receptors are ionotropic receptors comprised of multiple subunits that form ligand-gated chloride ion channels. The $GABA_A$ receptor subunits have been identified (alpha, beta, gamma, delta, epsilon, pi, and theta subunits), and each subunit is encoded by a separate gene. In addition, many subunits have multiple isoforms and/or splice variants, giving rise to a large degree of structural diversity.

The GABA reuptake inhibitors described herein have been modified such that they retain GABA reuptake inhibitory activity but can no longer penetrate the blood brain barrier, or such that they have reduced ability to permeate the blood brain barrier. Such compounds are "peripherally restricted," i.e., they are restricted to the peripheral nervous system. Critically, the peripherally restricted compounds disclosed herein maintain functionality as GABA reuptake inhibitors. The compounds disclosed herein have structures and physiochemical properties that maintain or improve their therapeutic activity, but limit their exposure to the CNS. In some embodiments, the compounds disclosed herein have physiochemical properties, such as Log P (water-octanol partition coefficient) values, polar surface area (PSA) and/or freely rotatable bonds (FRBs), which limit the ability of the compounds to penetrate the blood brain barrier and enter the CNS.

Peripherally restricted GABA reuptake inhibitors cannot penetrate the blood brain barrier, or have reduced blood brain barrier permeability, and target $GABA_A$ receptors in the peripheral nervous system.

Such compounds can be administered to a subject with ASD, RTT, PMS, or Fragile X syndrome to reduce tactile dysfunction, social impairment, and anxiety, while avoiding unwanted central effects such as sedation.

Peripherally restricted GABA agents can be administered to a subject with ASD, RTT, PMS, or Fragile X syndrome to reduce tactile dysfunction, social impairment, and anxiety. Suitable compounds include GABA reuptake inhibitors, $GABA_A$ receptor agonists, and positive allosteric modulators.

A compound or pharmaceutically acceptable salt thereof of any one of Formulas (I)-(III) may be administered to a subject to reduce social impairment, anxiety, or tactile dysfunction in patients diagnosed with ASD, RTT, PMS or Fragile X syndrome. Exemplary compounds that may be used in the compositions and methods described herein are listed in Table 1.

TABLE 1
| Compound | Structure |
|---|---|
| 1 | 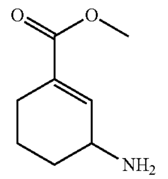 |
| 1a | 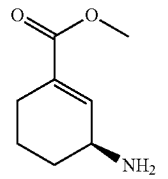 |
| 1b | 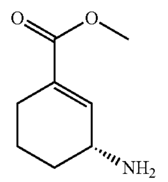 |
| 2 | 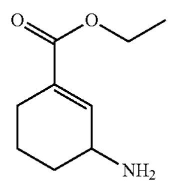 |
| 2a | 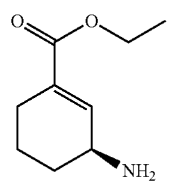 |
| 2b | 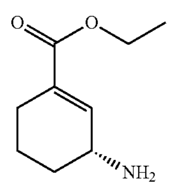 |
| 3 | 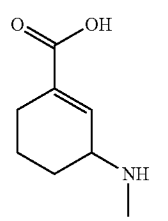 |
| 3a | 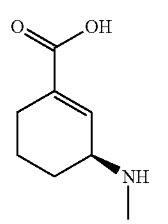 |
TABLE 1-continued
| Compound | Structure |
|---|---|
| 3b | 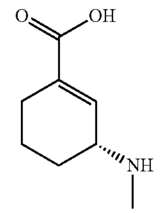 |
| 4 | 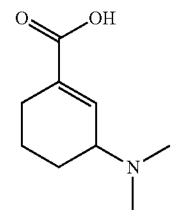 |
| 4a | 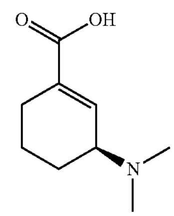 |
| 4b | 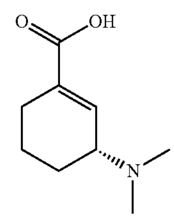 |
| 5 | 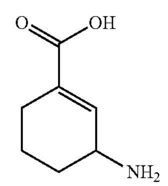 |
| 5a | 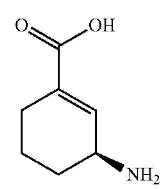 |
| 5b | 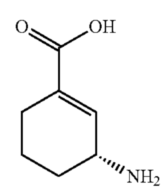 |

TABLE 1-continued
Compounds
| Compound | Structure |
|---|---|
| 6 | 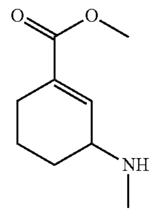 |
| 6a | 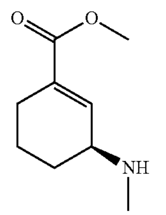 |
| 6b | 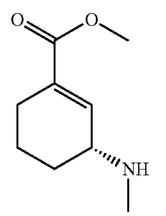 |
| 7 | 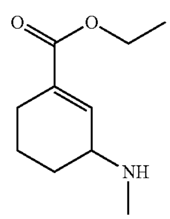 |
| 7a | 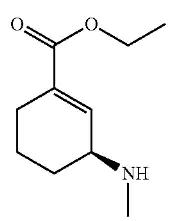 |
| 7b | 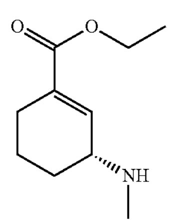 |
| 8 | 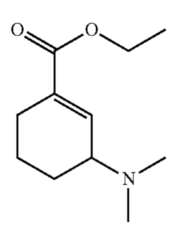 |
| 8a | 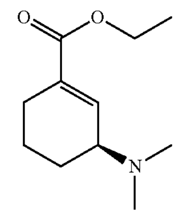 |
| 8b | 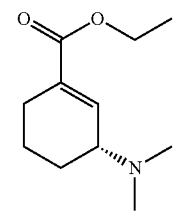 |
| 9 | 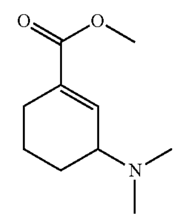 |
| 9a | 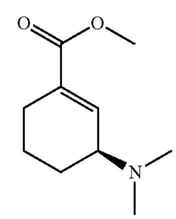 |
| 9b | 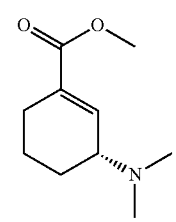 |
Compounds that may be used in the compositions and methods described herein include any compound having the structure of Formula (I):
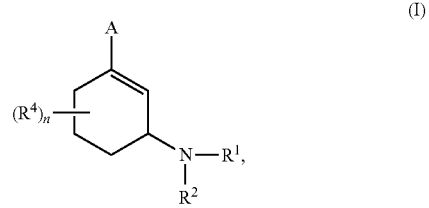

wherein
n=1, 2, 3, 4, 5, 6, 7, or 8;
each of $R^1$ and $R^2$ is, independently, hydrogen, deuterium, optionally substituted $C_{1-6}$ alkyl, or optionally substituted $C_{3-6}$ cycloalkyl, wherein $R^1$ and $R^2$ are covalently linked;
each $R^4$ is, independently, hydrogen, deuterium, halogen, $C_{1-4}$ alkoxy, $C_{1-6}$ alkyl, $CF_3$, $CH_3S$, $CH_3SO_2$, or $NO_2$; and
A is a carboxylic acid, a carboxylic acid biomimetic, or optionally substituted $C_{1-6}$ carboxylic acid alkyl ester;
or a pharmaceutically acceptable salt thereof.

In some embodiments, the compounds that may be used in the compositions and methods described herein include any compound having the structure of Formula (Ia) or Formula (Ib):

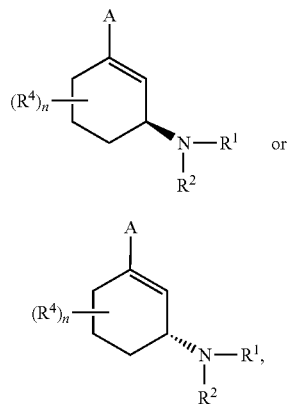

wherein
n=1, 2, 3, 4, 5, 6, 7, or 8;
each of $R^1$ and $R^2$ is, independently, hydrogen, deuterium, optionally substituted $C_{1-6}$ alkyl, or optionally substituted $C_{3-6}$ cycloalkyl, wherein $R^1$ and $R^2$ are covalently linked;
each $R^4$ is, independently, hydrogen, deuterium, halogen, $C_{1-4}$ alkoxy, $C_{1-6}$ alkyl, $CF_3$, $CH_3S$, $CH_3SO_2$, or $NO_2$; and
A is a carboxylic acid, a carboxylic acid biomimetic, or optionally substituted $C_{1-6}$ carboxylic acid alkyl ester;
or a pharmaceutically acceptable salt thereof.

In some embodiments, the compounds that may be used in the compositions and methods described herein include any compound having the structure of Formula (II):

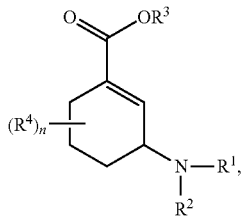

wherein
n=1, 2, 3, 4, 5, 6, 7, or 8;
each of $R^1$ and $R^2$ is, independently, hydrogen, deuterium, optionally substituted $C_{1-6}$ alkyl, or optionally substituted $C_{3-6}$ cycloalkyl, wherein $R^1$ and $R^2$ are covalently linked;
$R^3$ is hydrogen, deuterium, or optionally substituted $C_{1-6}$ alkyl; and
each $R^4$ is, independently, hydrogen, deuterium, halogen, $C_{1-4}$ alkoxy, $C_{1-6}$ alkyl, $CF_3$, $CH_3S$, $CH_3SO_2$, or $NO_2$;
or a pharmaceutically acceptable salt thereof.

In some embodiments, the compounds that may be used in the compositions and methods described herein include any compound having the structure of Formula (IIa) or Formula (IIb):

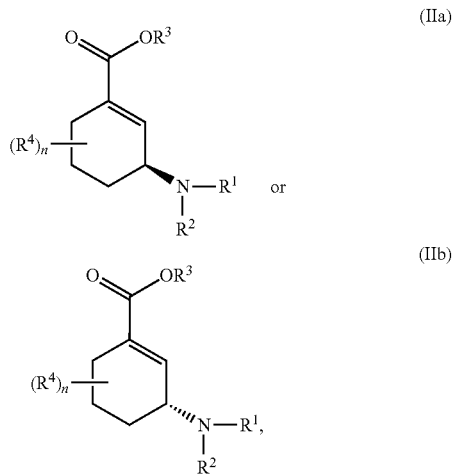

wherein
n=1, 2, 3, 4, 5, 6, 7, or 8;
each of $R^1$ and $R^2$ is, independently, hydrogen, deuterium, optionally substituted $C_{1-6}$ alkyl, or optionally substituted $C_{3-6}$ cycloalkyl wherein $R^1$ and $R^2$ are covalently linked;
$R^3$ is hydrogen, deuterium, or optionally substituted $C_{1-6}$ alkyl; and
each $R^4$ is, independently, hydrogen, deuterium, halogen, $C_{1-4}$ alkoxy, $C_{1-6}$ alkyl, $CF_3$, $CH_3S$, $CH_3SO_2$, or $NO_2$;
or a pharmaceutically acceptable salt thereof.

In some embodiments, the compounds that may be used in the compositions and methods described herein include any compound having the structure of Formula (III):

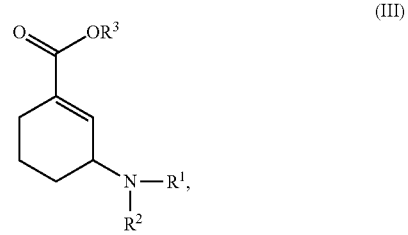

wherein
each of $R^1$ and $R^2$ is, independently, hydrogen, deuterium, or optionally substituted $C_{1-6}$ alkyl; and
$R^3$ is hydrogen, deuterium, or optionally substituted $C_{1-6}$ alkyl;
or a pharmaceutically acceptable salt thereof.

In some embodiments, the compounds that may be used in the compositions and methods described herein include any compound having the structure of Formula (IIIa) or Formula (IIIb):

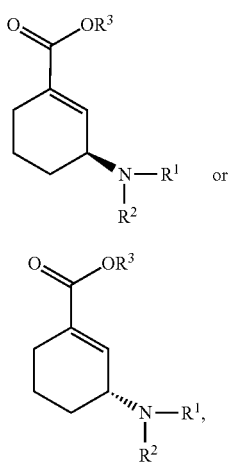

wherein
each of $R^1$ and $R^2$ is, independently, hydrogen, deuterium, or optionally substituted $C_{1-6}$ alkyl; and
$R^3$ is hydrogen, deuterium, or optionally substituted $C_{1-6}$ alkyl;
or a pharmaceutically acceptable salt thereof.

In a particular embodiment, the compound that may be used in the compositions and methods described herein is Compound 5:

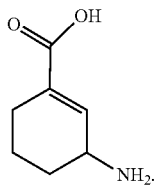

Variable n

In certain embodiments of the foregoing compounds, n is 1, 2, 3, 4, 5, 6, 7, or 8. In certain particular embodiments, n is 1. In certain particular embodiments, n is 2. In certain particular embodiments, n is 3. In certain particular embodiments, n is 4. In certain particular embodiments, n is 5. In certain particular embodiments, n is 6. In certain particular embodiments, n is 7. In certain particular embodiments, n is 8.

Variable A

In certain embodiments of the foregoing compounds, A is a carboxylic acid, a carboxylic acid biomimetic, or optionally substituted $C_{1-6}$ carboxylic acid alkyl ester. In certain embodiments, A is unsubstituted. In certain embodiments, A is substituted. In certain embodiments, A is a carboxylic acid, i.e., —$CO_2H$. In certain particular embodiments, A is a carboxylic acid alkyl ester, e.g., —$CO_2CH_3$, —$CO_2CH_2CH_3$, —$CO_2CH_2CH_2CH_3$, —$CO_2CH(CH_3)_2$, or —$CO_2CH_2CH_2CH_2CH_3$. In certain embodiments, A is a carboxylic acid biomimetic. Carboxylic acid biomimetics are moieties that can replace a carboxylic acid moiety on a compound without substantially effecting the biological activity (e.g., reducing the biological activity by less than 50%, 40%, 30%, 20%, 10%, 5%, 4%, 3%, 2%, 1%) of the molecule. Carboxylic acid biomimetics include, but are not limited to:

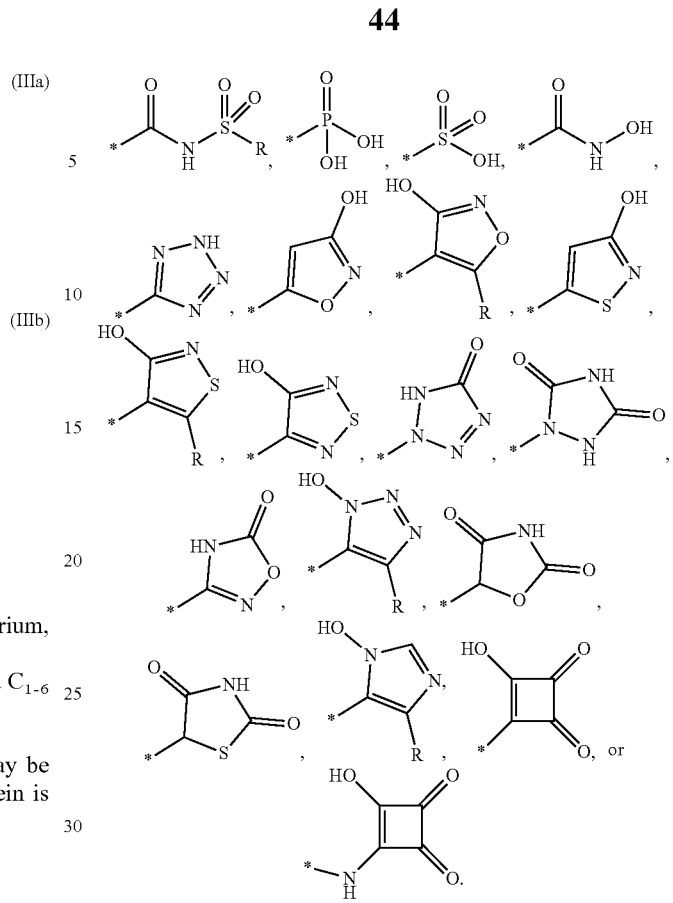

Variable $R^1$ $R^1$ is hydrogen, deuterium, optionally substituted 1-6 alkyl, or optionally substituted $C_{3-6}$ cycloalkyl; or $R^1$ and $R^2$ combine to form a 4-, 5-, or 6-membered ring.

In certain particular embodiments, $R^1$ is hydrogen. In certain particular embodiments, $R^1$ is deuterium. In certain particular embodiments, $R^1$ is $C_{1-6}$ alkyl, e.g., methyl, ethyl, propyl, isopropyl, butyl, pentyl, or hexyl. In certain embodiments, $R^1$ is unsubstituted 1-6 alkyl. In certain embodiments, $R^1$ is substituted 1_6 alkyl.

In certain particular embodiments, $R^1$ is $C_{3-6}$ cycloalkyl, e.g., cyclopropyl, cyclobuyl, cyclopentyl, or cyclohexyl. In certain embodiments, $R^1$ is unsubstituted $C_{3-6}$ cycloalkyl. In certain embodiments, $R^1$ is substituted $C_{3-6}$ cycloalkyl.

Variable $R^2$ $R^2$ is hydrogen, deuterium, optionally substituted 1-6 alkyl, or optionally substituted $C_{3-6}$ cycloalkyl; or $R^1$ and $R^2$ combine to form a 4-, 5-, or 6-membered ring.

In certain particular embodiments, $R^2$ is hydrogen. In certain particular embodiments, $R^2$ is deuterium. In certain particular embodiments, $R^2$ is $C_{1-6}$ alkyl, e.g., methyl, ethyl, propyl, isopropyl, butyl, pentyl, or hexyl. In certain embodiments, $R^2$ is unsubstituted 1-6 alkyl. In certain embodiments, $R^2$ is substituted 1-6 alkyl.

In certain particular embodiments, $R^2$ is $C_{3-6}$ cycloalkyl, e.g., cyclopropyl, cyclobuyl, cyclopentyl, or cyclohexyl. In certain embodiments, $R^2$ is unsubstituted $C_{3-6}$ cycloalkyl. In certain embodiments, $R^2$ is substituted $C_{3-6}$ cycloalkyl.

In embodiments, $R^1$ and $R^2$ combine to form a 4-membered ring, e.g., oxetanyl. In certain embodiments, $R^1$ and $R^2$ combine to form a 5-membered ring, e.g., pyrrolidinyl. In certain embodiments, $R^1$ and Recombine to form a 6-membered ring, e.g., piperidinyl, piperazinyl, or morpholinyl. In certain embodiments, the 4-, 5-, or 6-membered ring is unsubstituted. In certain embodiments, the 4-, 5-, or 6-membered ring is substituted.

Variable $R^3$

In certain embodiments, $R^3$ is hydrogen, deuterium, or optionally substituted $C_{1-6}$ alkyl. In certain particular embodiments, $R^3$ is hydrogen. In certain particular embodiments, $R^3$ is deuterium. In certain particular embodiments, $R^3$ is $C_{1-6}$ alkyl, e.g., methyl, ethyl, propyl, isopropyl, butyl, pentyl, or hexyl. In certain embodiments, $R^3$ is unsubstituted $C_{1-6}$ alkyl. In certain embodiments, $R^3$ is substituted $C_{1-6}$ alkyl.

Variable $R^4$

In certain embodiments, each $R^4$ is independently hydrogen, deuterium, halogen, $C_{1-4}$ alkoxy, $C_{1-6}$ alkyl, $CF_3$, $CH_3S$, $CH_3SO_2$, or $NO_2$. In certain particular embodiments, $R^4$ is hydrogen. In certain particular embodiments, $R^4$ is deuterium. In certain particular embodiments, $R^4$ is $C_{1-4}$ alkoxy, e.g., methoxy, ethoxyl, propoxy, or butoxy. In certain embodiments, $R^4$ is unsubstituted $C_{1-4}$ alkoxy. In certain embodiments, $R^4$ is substituted $C_{1-4}$ alkoxy. In certain particular embodiments, $R^4$ is $C_{1-6}$ alkyl, e.g., methyl, ethyl, propyl, isopropyl, butyl, pentyl, or hexyl. In certain embodiments, $R^4$ is unsubstituted $C_{1-6}$ alkyl. In certain embodiments, $R^4$ is substituted $C_{1-6}$ alkyl.

In some embodiments of any of the compounds described herein, an oxygen (e.g., oxygen in the carboxylic acid or $C_{1-6}$ carboxylic acid alkyl ester moiety) has an O-protecting group. An O-protecting group is intended to protect an oxygen containing (e.g., phenol, optionally substituted hydroxyl, or carbonyl) group against undesirable reactions during synthetic procedures. Commonly used O-protecting groups are disclosed in Greene, *Protective Groups in Organic Synthesis,* 3rd Edition (John Wiley & Sons, New York, 1999), which is incorporated herein by reference. Exemplary O-protecting groups include acyl, aryloyl, or carbamyl groups, such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, t-butyldimethylsilyl, tri-iso-propylsilyloxymethyl, 4,4'-dimethoxytrityl, isobutyryl, phenoxyacetyl, 4-isopropylpehenoxyacetyl, dimethylformamidino, and 4-nitrobenzoyl; alkylcarbonyl groups, such as acyl, acetyl, propionyl, pivaloyl, and the like; optionally substituted arylcarbonyl groups, such as benzoyl; silyl groups, such as trimethylsilyl (TMS), tert-butyldimethylsilyl (TBDMS), tri-iso-propylsilyloxymethyl (TOM), triisopropylsilyl (TIPS), and the like; ether-forming groups with the optionally substituted hydroxyl, such methyl, methoxymethyl, tetrahydropyranyl, benzyl, p-methoxybenzyl, trityl, and the like; alkoxycarbonyls, such as methoxycarbonyl, ethoxycarbonyl, isopropoxycarbonyl, n-isopropoxycarbonyl, n-butyloxycarbonyl, isobutyloxycarbonyl, sec-butyloxycarbonyl, t-butyloxycarbonyl, 2-ethyl hexyloxycarbonyl, cyclohexyloxycarbonyl, methyloxycarbonyl, and the like; alkoxyalkoxycarbonyl groups, such as methoxymethoxycarbonyl, ethoxymethoxycarbonyl, 2-methoxyethoxycarbonyl, 2-ethoxyethoxycarbonyl, 2-butoxyethoxycarbonyl, 2-methoxyethoxymethoxycarbonyl, allyloxycarbonyl, propargyloxycarbonyl, 2-butenoxycarbonyl, 3-methyl-2-butenoxycarbonyl, and the like; haloalkoxycarbonyls, such as 2-chloroethoxycarbonyl, 2-chloroethoxycarbonyl, 2,2,2-trichloroethoxycarbonyl, and the like; optionally substituted arylalkoxycarbonyl groups, such as benzyloxycarbonyl, p-methylbenzyloxycarbonyl, p-methoxybenzyloxycarbonyl, p-nitrobenzyloxycarbonyl, 2,4-dinitrobenzyloxycarbonyl, 3,5-dimethylbenzyloxycarbonyl, p-chlorobenzyloxycarbonyl, p-bromobenzyloxy-carbonyl, fluorenylmethyloxycarbonyl, and the like; and optionally substituted aryloxycarbonyl groups, such as phenoxycarbonyl, p-nitrophenoxycarbonyl, o-nitrophenoxycarbonyl, 2,4-dinitrophenoxycarbonyl, p-methyl-phenoxycarbonyl, m-methylphenoxycarbonyl, o-bromophenoxycarbonyl, 3,5-dimethylphenoxycarbonyl, p-chlorophenoxycarbonyl, 2-chloro-4-nitrophenoxy-carbonyl, and the like); substituted alkyl, aryl, and alkaryl ethers (e.g., trityl; methylthiomethyl; methoxymethyl; benzyloxymethyl; siloxymethyl; 2,2,2,-trichloroethoxymethyl; tetrahydropyranyl; tetrahydrofuranyl; ethoxyethyl; 1-[2-(trimethylsilyl)ethoxy]ethyl; 2-trimethylsilylethyl; t-butyl ether; p-chlorophenyl, p-methoxyphenyl, p-nitrophenyl, benzyl, p-methoxybenzyl, and nitrobenzyl); silyl ethers (e.g., trimethylsilyl; triethylsilyl; triisopropylsilyl; dimethylisopropylsilyl; t-butyldimethylsilyl; t-butyldiphenylsilyl; tribenzylsilyl; triphenylsilyl; and diphenymethylsilyl); carbonates (e.g., methyl, methoxymethyl, 9-fluorenylmethyl; ethyl; 2,2,2-trichloroethyl; 2-(trimethylsilyl)ethyl; vinyl, allyl, nitrophenyl; benzyl; methoxybenzyl; 3,4-dimethoxybenzyl; and nitrobenzyl); carbonyl-protecting groups (e.g., acetal and ketal groups, such as dimethyl acetal, 1,3-dioxolane, and the like; acylal groups; and dithiane groups, such as 1,3-dithianes, 1,3-dioptionally substituted thiolane, and the like); carboxylic acid-protecting groups (e.g., ester groups, such as methyl ester, benzyl ester, t-butyl ester, orthoesters, and the like; and oxazoline groups.

In some embodiments of any of any of the compounds described herein, a nitrogen (e.g., nitrogen in the amino moiety) has an N-protecting group. An N-protecting group is intended to protect an amino group against undesirable reactions during synthetic procedures. Commonly used N-protecting groups are disclosed in Greene, *Protective Groups in Organic Synthesis,* $3^{rd}$ Edition (John Wiley & Sons, New York, 1999). N-protecting groups include acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L or D, L-amino acids such as alanine, leucine, and phenylalanine; sulfonyl-containing groups such as benzenesulfonyl, and p-toluenesulfonyl; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, and phenylthiocarbonyl, arylalkyl groups such as benzyl, triphenylmethyl, and benzyloxymethyl, and silyl groups, such as trimethylsilyl. Preferred N-protecting groups are alloc, formyl, acetyl, benzoyl, pivaloyl, t-butylacetyl, alanyl, phenylsulfonyl, benzyl, t-butyloxycarbonyl (Boc), and benzyloxycarbonyl (Cbz).

Indications

The compounds described herein are useful in treating a neurological or psychiatric condition. In certain embodiments, the neurological condition is tactile dysfunction, anxiety, or social impairment in a subject diagnosed with ASD, RTT, PMS, or Fragile X syndrome.

Tactile Dysfunction

Tactile dysfunction includes exhibiting symptoms such as withdrawing when being touched, refusing to eat certain "textured" foods and/or to wear certain types of clothing, complaining about having hair or face washed, avoiding getting hands dirty (e.g., glue, sand, mud, finger-paint), and using finger tips rather than whole hands to manipulate objects. Tactile dysfunction may lead to a misperception of touch and/or pain (hyper- or hyposensitive) and may lead to self-imposed isolation, general irritability, distractibility, and hyperactivity.

Anxiety

Anxiety includes emotions characterized by feelings of tension, worried thoughts and physical changes like increased blood pressure. Anxiety can be characterized by having recurring intrusive thoughts or concerns, avoiding certain situations (e.g., social situations) out of worry, and physical symptoms such as sweating, trembling, dizziness or a rapid heartbeat.

Social Impairment

Social impairment involves a distinct dissociation from and lack of involvement in relations with other people. It can occur with various mental and developmental disorders, such as autism. Social impairment may occur when an individual acts in a less positive way or performs worse when they are around others as compared to when alone. Nonverbal behaviors associated with social impairment can include deficits in eye contact, facial expression, and gestures that are used to help regulate social interaction. Often there is a failure to develop age-appropriate friendships. Social impairment can also include a lack of spontaneous seeking to share achievements or interests with other individuals. A person with social impairment may exhibit a deficit in social reciprocity with individuals, decreased awareness of others, lack of empathy, and lack of awareness of the needs of others.

Autism Spectrum Disorder

ASD is a heterogeneous group of neurodevelopmental disorders as classified in the fifth revision of the American Psychiatric Association's Diagnostic and Statistical Manual of Mental Disorders 5th edition (DSM-5). The DSM-5 redefined the autism spectrum to encompass the prior (DSM-IV-TR) diagnosis of autism, Asperger syndrome, pervasive developmental disorder not otherwise specified, childhood disintegrative disorder, and Rett syndrome. The autism spectrum disorders are characterized by social deficits and communication difficulties, stereotyped or repetitive behaviors and interests, and in some cases, cognitive delays. For example, an ASD is defined in the DSM-5 as exhibiting (i) deficits in social communication and interaction not caused by general developmental delays (must exhibit three criteria including deficits in social-emotional reciprocity, deficits in nonverbal communication, and deficits in creating and maintaining relationships appropriate to developmental level), (ii) demonstration of restricted and repetitive patterns of behavior, interest or activities (must exhibit two of the following four criteria: repetitive speech, repetitive motor movements or repetitive use of objects, adherence to routines, ritualized patterns of verbal or nonverbal, or strong resistance to change, fixated interests that are abnormally intense of focus, and over or under reactivity to sensory input or abnormal interest in sensory aspects of environment), (iii) symptoms must be present in early childhood, and (iv) symptoms collectively limit and hinder everyday functioning. ASD is also contemplated herein to include Dravet's syndrome and autistic-like behavior in non-human animals.

Rett Syndrome

Rett syndrome is an X-linked disorder that affects approximately one in ten-thousand girls. Patients go through four stages: Stage I) Following a period of apparently normal development from birth, the child begins to display social and communication deficits, similar to those seen in other autism spectrum disorders, between six and eighteen months of age. The child shows delays in their developmental milestones, particularly for motor ability, such as sitting and crawling. Stage II) Beginning between one and four years of age, the child goes through a period of regression in which they lose speech and motor abilities, developing stereotypical midline hand movements and gait impairments. Breathing irregularities, including apnea and hyperventilation also develop during this stage. Autistic symptoms are still prevalent at this stage. Stage III) Between age two and ten, the period of regression ends and symptoms plateau. Social and communication skills may show small improvements during this plateau period, which may last for most of the patients' lives. Stage IV) Motor ability and muscle deterioration continues. Many girls develop severe scoliosis and lose the ability to walk.

Phelan McDermid syndrome

Phelan McDermid syndrome is a rare genetic condition caused by a deletion or other structural change of the terminal end of chromosome 22 in the 22q13 region or a disease-causing mutation of the Shank3 gene. Although the range and severity of symptoms may vary, PMS is generally thought to be characterized by neonatal hypotonia (low muscle tone in the newborn), normal growth, absent to severely delayed speech, moderate to profound developmental delay, and minor dysmorphic features. People who have PMS often show symptoms in very early childhood, sometimes at birth and within the first six months of life.

Fragile X Syndrome

Fragile X syndrome is an X chromosome-linked condition that is characterized by a visible constriction near the end of the X chromosome, at locus q27.3 that causes intellectual disability, behavioral and learning challenges and various physical characteristics Fragile X syndrome is the most common inherited form of mental retardation and developmental disability. Males with Fragile X syndrome usually have mental retardation and often exhibit characteristic physical features and behavior. Fragile X syndrome is characterized by behavior similar to autism and attention deficit disorder, obsessive-compulsive tendencies, hyperactivity, slow development of motor skills and anxiety fear disorder. When these disabilities are severe and occur simultaneously, the condition is sometimes described as autism, and may be associated with any degree of intelligence. Other characteristics are a likable, happy, friendly personality with a limited number of autistic-like features such as hand-flapping, finding direct eye contact unpleasant, and some speech and language problems. Physical features may include large ears, long face, soft skin and large testicles (called "macroorchidism") in post-pubertal males. Connective tissue problems may include ear infections, flat feet, high arched palate, double-jointed fingers and hyper-flexible joints.

Pain and Touch Sensitivity

The compounds described herein are useful in treating pain, and in treating touch over-reactivity and pain associated with disease states, including Sensory Processing Disorder (SPD) and fibromyalgia, as well as mechanical allodynia associated with nerve injury, shingles, diabetic neuropathy, chemotherapy-induced neuropathy and other neuropathic pain states.

Pharmaceutical Compositions

The compounds described herein (e.g., the compounds of Formulas (I)-(III); e.g., the compounds of Table 1) may be formulated into pharmaceutical compositions for administration to human subjects in a biologically compatible form suitable for administration in vivo. Pharmaceutical compositions typically include an active agent and a pharmaceutically acceptable excipient.

The compound can also be used in the form of the free base, in the form of salts, zwitterions, solvates, or as prodrugs, or pharmaceutical compositions thereof. All forms are within the scope of the invention. The compounds, salts, zwitterions, solvates, prodrugs, or pharmaceutical compositions thereof, may be administered to a patient in a variety of forms depending on the selected route of administration, as will be understood by those skilled in the art. The compounds described herein may be administered, for example, by oral, parenteral, buccal, sublingual, nasal, rectal, patch, pump, or transdermal administration, and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

For human use, the compounds described herein can be administered alone or in admixture with a pharmaceutical carrier selected with regard to the intended route of administration and standard pharmaceutical practice. Pharmaceutical compositions for use in accordance with the present invention thus can be formulated in a conventional manner using one or more physiologically acceptable carriers including excipients and auxiliaries that facilitate processing of compounds into preparations which can be used pharmaceutically.

The excipient or carrier is selected on the basis of the mode and route of administration. Suitable pharmaceutical carriers, as well as pharmaceutical necessities for use in pharmaceutical formulations, are described in Remington: The Science and Practice of Pharmacy, 22nd Ed., Allen, Ed. (2012), a well-known reference text in this field, and in the USP/NF (United States Pharmacopeia and the National Formulary). Examples of suitable excipients are lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents, e.g., talc, magnesium stearate, and mineral oil; wetting agents; emulsifying and suspending agents; preserving agents, e.g., methyl- and propylhydroxy-benzoates; sweetening agents; and flavoring agents. Other exemplary excipients are described in Handbook of Pharmaceutical Excipients, 6th Edition, Rowe et al., Eds., Pharmaceutical Press (2009).

These pharmaceutical compositions can be manufactured in a conventional manner, e.g., by conventional mixing, dissolving, granulating, dragee-making, levigating, emulsifying, encapsulating, entrapping, or lyophilizing processes. Methods well known in the art for making formulations are found, for example, in Remington: The Science and Practice of Pharmacy, 22nd Ed., Allen, Ed. (2012), and Encyclopedia of Pharmaceutical Technology, eds. J. Swarbrick and J. C. Boylan, 1988-1999, Marcel Dekker, New York. Proper formulation is dependent upon the route of administration chosen. The formulation and preparation of such compositions is well-known to those skilled in the art of pharmaceutical formulation. In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

Dosages

The dosage of the compounds described herein (e.g., the compounds of Formulas (I)-(III); e.g., the compounds of Table 1), or pharmaceutically acceptable salts or prodrugs thereof, or pharmaceutical compositions thereof, can vary depending on many factors, e.g., the pharmacodynamic properties of the compound, the mode of administration, the age, health, and weight of the recipient, the nature and extent of the symptoms, the frequency of the treatment, and the type of concurrent treatment, if any, and the clearance rate of the composition in the subject to be treated. One of skill in the art can determine the appropriate dosage based on the above factors. The active agent may be administered initially in a suitable dosage that may be adjusted as required, depending on the clinical response. In general, a suitable daily dose of an active agent will be that amount of the compound that is the lowest dose effective to produce a therapeutic effect. Such an effective dose will generally depend upon the factors described above.

In general, the dosage of a pharmaceutical composition or the active agent in a pharmaceutical composition may be in the range of from about 1 pg to about 10 g (e.g., 1 pg-10 pg, e.g., 2 pg, 3 pg, 4 pg, 5 pg, 6 pg, 7 pg, 8 pg, 9 pg, 10 pg, e.g., 10 pg-100 pg, e.g., 20 pg, 30 pg, 40 pg, 50 pg, 60 pg, 70 pg, 80 pg, 90 pg, 100 pg, e.g., 100 pg-1 ng, e.g., 200 pg, 300 pg, 400 pg, 500 pg, 600 pg, 700 pg, 800 pg, 900 pg, 1 ng, e.g., 1 ng-10 ng, e.g., 2 ng, 3 ng, 4 ng, 5 ng, 6 ng, 7 ng, 8 ng, 9 ng, 10 ng, e.g., 10 ng-100 ng, e.g., 20 ng, 30 ng, 40 ng, 50 ng, 60 ng, 70 ng, 80 ng, 90 ng, 100 ng, e.g., 100 ng-1 pg, e.g., 200 ng, 300 ng, 400 ng, 500 ng, 600 ng, 700 ng, 800 ng, 900 ng, 1 µg, e.g., 1-10 µg, e.g., 1 µg, 2 µg, 3 µg, 4 µg, 5 µg, 6 µg, 7 µg, 8 µg, 9 µg, 10 µg, e.g., 10 µg-100 µg, e.g., 20 µg, 30 µg, 40 µg, 50 µg, 60 µg, 70 µg, 80 µg, 90 pg, 100 µg, e.g., 100 µg-1 mg, e.g., 200 µg, 300 µg, 400 µg, 500 µg, 600 µg, 700 µg, 800 µg, 900 µg, 1 mg, e.g., 1 mg-10 mg, e.g., 2 mg, 3 mg, 4 mg, 5 mg, 6 mg, 7 mg, 8 mg, 9 mg, 10 mg, e.g., 10 mg-100 mg, e.g., 20 mg, 30 mg, 40 mg, 50 mg, 60 mg, 70 mg, 80 mg, 90 mg, 100 mg, e.g., 100 mg-1 g, e.g., 200 mg, 300 mg, 400 mg, 500 mg, 600 mg, 700 mg, 800 mg, 900 mg, 1 g, e.g., 1 g-10 g, e.g., 2 g, 3 g, 4 g, 5 g, 6 g, 7 g, 8 g, 9 g, 10 g).

The pharmaceutical composition or the active agent may also be administered as a unit dose form or as a dose per mass or weight of the patient from about 0.01 mg/kg to about 100 mg/kg (e.g., 0.01-0.1 mg/kg, e.g., 0.02 0.03 mg/kg, 0.04 mg/kg, 0.05 mg/kg, 0.06 mg/kg, 0.07 mg/kg, 0.08 mg/kg, 0.09 mg/kg, 0.1 mg/kg, e.g., 0.1-1 mg/kg, e.g., 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, e.g., 1-10 mg/kg, e.g., 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, e.g., 10-100 mg/kg, e.g., 20 mg/kg, 30 mg/kg, 40 mg/kg, 50 mg/kg, 60 mg/kg, 70 mg/kg, 80 mg/kg, 90 mg/kg, 100 mg/kg). The dose may also be administered as a dose per mass or weight of the patient per unit day (e.g., 0.1-10 mg/kg/day). The dosage regimen may be determined by the clinical indication being addressed (e.g., ASD, RTT, PMS, or Fragile X syndrome, e.g., tacile dysfunction, social impairment, or anxiety), as well as by various patient variables (e.g., weight, age, sex) and clinical presentation (e.g., extent or severity of tactile dysfunction, anxiety, or social impairment). Furthermore, it is understood that all dosages may be continuously given or divided into dosages given per a given time frame. The composition may be administered, for example, every hour, day, week, month, or year.

Formulations

The compounds described herein may be administered to patients or animals with a pharmaceutically acceptable diluent, carrier, or excipient, in unit dosage form. The compounds for use in treatment of ASD, RTT, PMS, or Fragile X syndrome may be produced and isolated by any standard technique known to those in the field of medicinal chemistry. Conventional pharmaceutical practice may be employed to provide suitable formulations or compositions to administer the compound to patients diagnosed with ASD, RTT, PMS, or Fragile X syndrome.

Exemplary routes of administration of the compounds, or pharmaceutical compositions thereof, used in the present invention include oral, sublingual, buccal, transdermal, intradermal, intramuscular, parenteral, intravenous, intraarterial, intracranial, subcutaneous, intraorbital, intraventricular, intraspinal, intraperitoneal, intranasal, inhalation, intrathecal and topical administration. The compounds may be administered with a pharmaceutically acceptable carrier.

Formulations for Oral Administration

The pharmaceutical compositions contemplated by the invention include those formulated for oral administration. Oral dosage forms can be, for example, in the form of tablets, capsules, a liquid solution or suspension, a powder, or liquid or solid crystals, which contain the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate), granulating and disintegrating agents (e.g., cellulose derivatives including microcrystalline cellulose, starches including potato starch, croscarmellose sodium, alginates, or alginic acid), binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol), and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

Formulations for oral administration may also be presented as chewable tablets, as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Controlled release compositions for oral use may be constructed to release the active drug by controlling the dissolution and/or the diffusion of the active drug substance. Any of a number of strategies can be pursued in order to obtain controlled release and the targeted plasma concentration versus time profile. In one example, controlled release is obtained by appropriate selection of various formulation parameters and ingredients, including, e.g., various types of controlled release compositions and coatings. Examples include single or multiple unit tablet or capsule compositions, oil solutions, suspensions, emulsions, microcapsules, microspheres, nanoparticles, patches, and liposomes. In certain embodiments, compositions include biodegradable, pH, and/or temperature-sensitive polymer coatings.

Dissolution or diffusion-controlled release can be achieved by appropriate coating of a tablet, capsule, pellet, or granulate formulation of the compounds described herein, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

The liquid forms in which the compounds and compositions of the present invention can be incorporated for administration orally include aqueous solutions, suitably flavored syrups, aqueous or oil suspensions, and flavored emulsions with edible oils, e.g., cottonseed oil, sesame oil, coconut oil, or peanut oil, as well as elixirs and similar pharmaceutical vehicles.

Formulations for Parenteral Administration

The compounds described herein can be administered in a pharmaceutically acceptable parenteral (e.g., intravenous or intramuscular) formulation as described herein. The pharmaceutical formulation may also be administered parenterally (intravenous, intramuscular, subcutaneous or the like) in dosage forms or formulations containing conventional, non-toxic pharmaceutically acceptable carriers and adjuvants. In particular, formulations suitable for parenteral administration include aqueous and non-aqueous sterile injection solutions which may contain anti-oxidants, buffers, bacteriostats and solutes which render the formulation isotonic with the blood of the intended recipient, and aqueous and non-aqueous sterile suspensions which may include suspending agents and thickening agents. For example, to prepare such a composition, the compounds may be dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution and isotonic sodium chloride solution. The aqueous formulation may also contain one or more preservatives, for example, methyl, ethyl, or n-propyl p-hydroxybenzoate. Additional information regarding parenteral formulations can be found, for example, in the United States Pharmacopeia-National Formulary (USP-NF), herein incorporated by reference.

Exemplary formulations for parenteral administration include solutions of the compound prepared in water suitably mixed with a surfactant, e.g., hydroxypropylcellulose. Dispersions can also be prepared in glycerol, liquid polyethylene glycols, DMSO and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in Remington: The Science and Practice of Pharmacy, 22nd Ed., Allen, Ed. (2012) and in The United States Pharmacopeia: The National Formulary (USP 36 NF31), published in 2013.

Formulations for parenteral administration may, for example, contain excipients, sterile water, or saline, polyalkylene glycols, e.g., polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for the compounds described herein include ethylene-vinyl acetate copolymer particles, osmotic pumps, implantable infusion systems, and liposomes.

Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel. The parenteral formulation can be formulated for prompt release or for sustained/extended release of the compound. Exemplary formulations for parenteral release of the compound include aqueous solutions, powders for reconstitution, cosolvent solutions, oil/water emulsions, suspensions, oil-based solutions, liposomes, microspheres, and polymeric gels.

Kits

In another aspect, provided herein are kits including a first container comprising a compound as described herein (e.g., the compounds of any one of Formulas (I)-(III); e.g., the compounds of Table 1) and instructions for use. The kits may further comprise a container (e.g., a vial, ampule, bottle, syringe, and/or dispenser package, or other suitable container). In some embodiments, provided kits may optionally further include a second container comprising an excipient for dilution or suspension of a composition or polymer described herein. In some embodiments, the composition described herein provided in the first container and the second container are combined to form one unit dosage form.

Synthesis

Compound 5 is prepared as described in Example 1. Other compounds described herein (e.g., the compounds of any one of Formulas (I)-(III); e.g., the compounds of Table 1) are prepared analogously, using methods and reagents known to those of skill in the art of organic synthesis. Single enantiomer compounds may be prepared using stereoselective syntheses, or may be obtained using chiral separations, e.g., crystallization with chiral co-crystal formers, kinetic resolution, or chromatographic separation using a chiral stationary phase.

EXAMPLES

Example 1. Materials and Methods

Synthesis of 3-aminocyclohex-1-enecarboxylic acid hydrochloride (5)

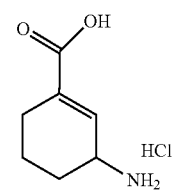

1.86 g of 5 was prepared in 6 steps (23.4% overall yield). The final overall synthesis is summarised in Scheme 1.

Scheme 1. Synthesis of 3-aminocyclohex-1-enecarboxylic acid hydrochloride (5)

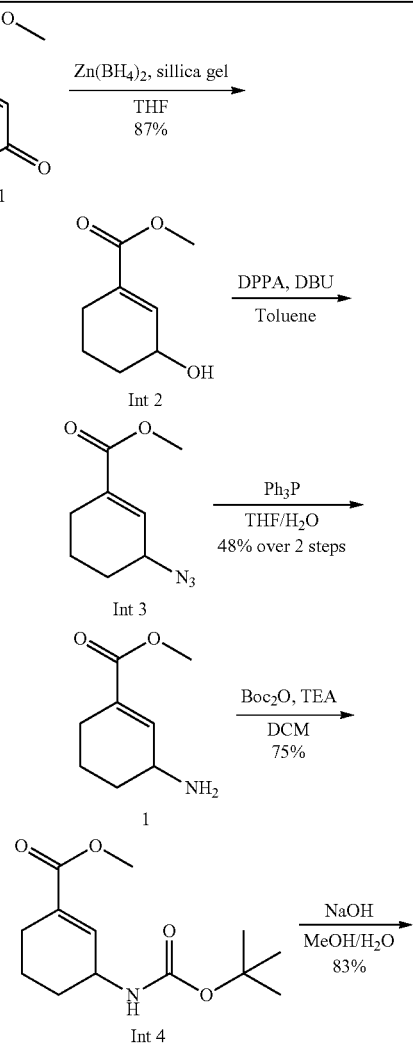

-continued

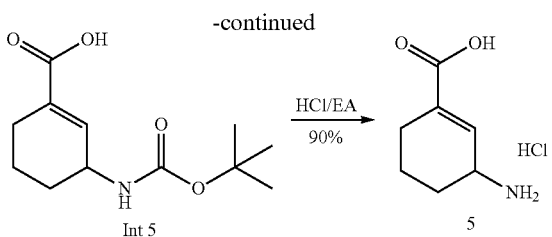

Synthesis of methyl 3-hydroxycyclohex-1-enecarboxylate (Int 2)

Synthesis of methyl 3-hydroxycyclohex-1-enecarboxylate (Int 2)

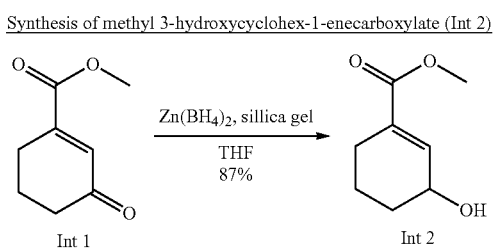

To a solution of $Zn(BH_4)_2$ (11.4 g, 120.0 mmol, 3.0 eq.) in THF (150 mL) was added silica gel (22.0 g, 100-200 mesh) in portions. The mixture was stirred at 5° C. for 3 hours. Methyl 3-oxocyclohex-1-enecarboxylate (1, 6.2 g, 40.0 mmol, 1.0 eq.) was added to the mixture dropwise at 5° C., the reaction mixture was stirred at 5° C. for 1 hour. Monitored with TLC, after the reaction was completed, the reaction mixture was poured into ice-cold sat. $NaHCO_3$ (150 mL) in portions, then the mixture was extracted with MTBE (200 mL), the combined organic phase was washed with brine (200 mL), dried over $Na_2SO_4$, filtered and concentrated to give methyl 3-hydroxycyclohex-1-enecarboxylate (2) as a colorless oil (5.4 g, 87%). $^1$H NMR (400 MHz, $CDCl_3$) δ 6.88 (t, J=2.8 Hz, 1H), 4.36 (s, 1H), 3.75 (s, 3H), 2.28-2.23 (m, 2H), 1.96-1.91 (m, 1H), 1.85-1.77 (m, 2H), 1.65-1.56 (m, 2H).

Synthesis of methyl 3-azidocyclohex-1-enecarboxylate (Int 3)

Synthesis of methyl 3-azidocyclohex-1-enecarboxylate (Int 3)

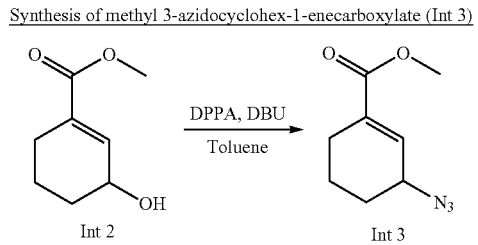

To a solution of methyl 3-hydroxycyclohex-1-enecarboxylate (Int 2, 5.2 g, 33.3 mmol, 1 eq.) and DBU (9.1 g, 60.0 mmol, 1.8 eq.) in toluene (60 mL) was added DPPA (13.8 g, 50.0 mmol, 1.5 eq.) dropwise under Nitrogen atmosphere at 5° C., then the reaction mixture was stirred at 5° C. overnight. The reaction mixture was diluted with MTBE (100 mL), washed with water (100 mL) and brine (100 mL), dried over $Na_2SO_4$, filtered and concentrated to give crude methyl 3-azidocyclohex-1-enecarboxylate (3) as a yellow oil, which was used for the next step directly.

Synthesis of methyl 3-aminocyclohex-1-enecarboxylate (5)

Synthesis of methyl 3-amonicyclohex-1-enecarboxylate (5)

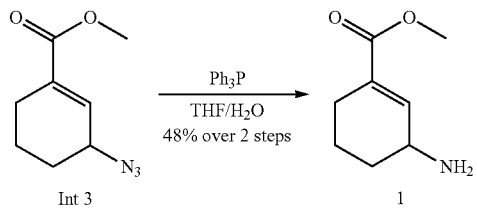

A solution of crude methyl 3-azidocyclohex-1-enecarboxylate (Int 3, 33.3 mmol, 1.0 eq.) and TPP (10.5 g, 40.0 mmol, 1.2 eq.) in THF (60 mL) and water (6 mL) was stirred at 85° C. for 10 h. The reaction mixture was diluted with toluene (120 mL), extracted with 2 N HCl (50 mL). The water phase was basified with $Na_2CO_3$ to pH>8, then extracted with DCM (100 mL×5), the combined organic phase was dried over $Na_2SO_4$, filtered and concentrated to give methyl 3-aminocyclohex-1-enecarboxylate (1) as a yellow oil (2.91 g, 56%). $^1$H NMR (400 MHz, $CDCl_3$) δ 6.82 (d, J=1.6 Hz, 1H), 3.74 (s, 3H), 3.49-3.45 (m, 1H), 2.30-2.17 (m, 2H), 1.98-1.91 (m, 1H), 1.83-1.77 (m, 1H), 1.62-1.56 (m, 1H), 1.36-1.28 (m, 3H). MS (ESI) m/z 156.2 $[M+H]^+$.

Synthesis of methyl 3-((tert-butoxycarbonyl)amino)cyclohex-1-enecarboxylate (Int 4)

Synthesis of methyl 3-((tert-butoxycarbonyl)amino)cyclohex-1-enecarboxylate (Int 4)

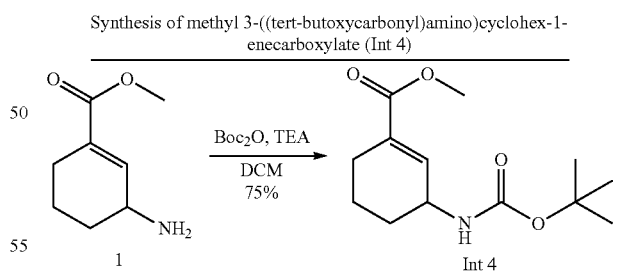

To a solution of methyl 3-aminocyclohex-1-enecarboxylate (1, 2.91 g, 18.8 mmol, 1.0 eq.) and TEA (2.85 g, 28.2 mmol, 1.5 eq.) in DCM (60 mL) was added $Boc_2O$ (4.92 g, 22.6 mmol, 1.2 eq) in DCM (15 mL) dropwise at 5° C., then the reaction mixture was stirred at 5° C. for 1 h. The reaction mixture was washed with water (50 mL) and brine (50 mL), dried over $Na_2SO_4$, filtered and concentrated to give methyl 3-((tert-butoxycarbonyl)amino)cyclohex-1-enecarboxylate (Int 4) as a white solid (3.58 g, 75%).

Synthesis of 3-((tert-butoxycarbonyl)amino)cyclohex-1-enecarboxylic acid (Int 5)

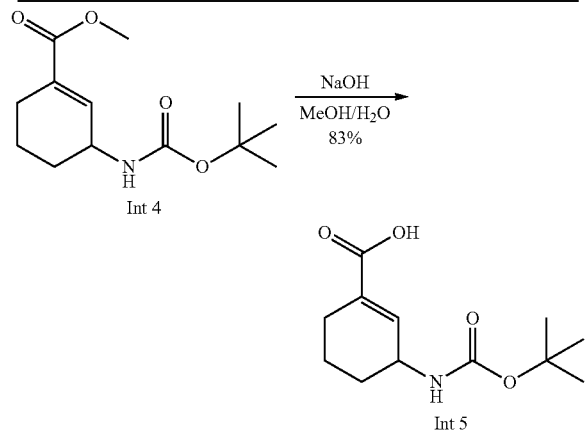

A solution of methyl 3-((tert-butoxycarbonyl)amino)cyclohex-1-enecarboxylate (Int 4, 3.58 g, 14.0 mmol, 1.0 eq.) and NaOH (2.24 g, 56.0 mmol, 4 eq) in MeOH (20 mL) and water (4 mL) was stirred at 30° C. for 2 h. The reaction mixture was concentrated to remove most of MeOH, the residue was diluted with water (10 mL) and acidified with 2 N HCl to pH<3, then filtered to give 3-((tert-butoxycarbonyl)amino)cyclohex-1-enecarboxylic acid (Int 5) as a white solid (2.8 g, 83%). $^1$H NMR (400 MHz, DMSO-d6) δ 12.33 (s, 1H), 7.07 (d, J=7.6 Hz, 1H), 6.57 (s, 1H), 4.07 (d, J=2.4 Hz, 1H), 2.15-2.05 (m, 2H), 1.76-1.72 (m, 2H), 1.54-1.47 (m, 1H), 1.36-1.30 (m, 10H). MS (ESI) m/z 240.1 [M−H]−.

Synthesis of 3-aminocyclohex-1-enecarboxylic acid hydrochloride (5)

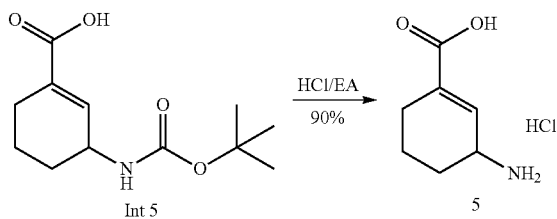

To a solution of 3-((tert-butoxycarbonyl)amino)cyclohex-1-enecarboxylic acid (Int 5, 2.8 g, 11.6 mmol, 1.0 eq.) in EtOAc (10 mL) was added HCl/EtOAc (2 N, 50 mL) at 25° C., the reaction mixture was stirred at 25° C. for 4 h. The white precipitate was collected by filtration, washed with EtOAc (10 mL) and PE (30 mL), dried to give 3-aminocyclohex-1-enecarboxylic acid hydrochloride (5) as a white solid (1.86 g, 90%). $^1$H NMR (400 MHz, DMSO-d6) δ 12.66 (s, 1H), 8.48 (s, 3H), 6.75 (s, 1H), 3.86 (s, 1H), 2.21-2.06 (m, 2H), 1.99-1.93 (m, 1H), 1.85-1.79 (m, 1H), 1.59-1.47 (m, 2H). MS (ESI) m/z 142.0 [M+1-1]+.

Figure 4:
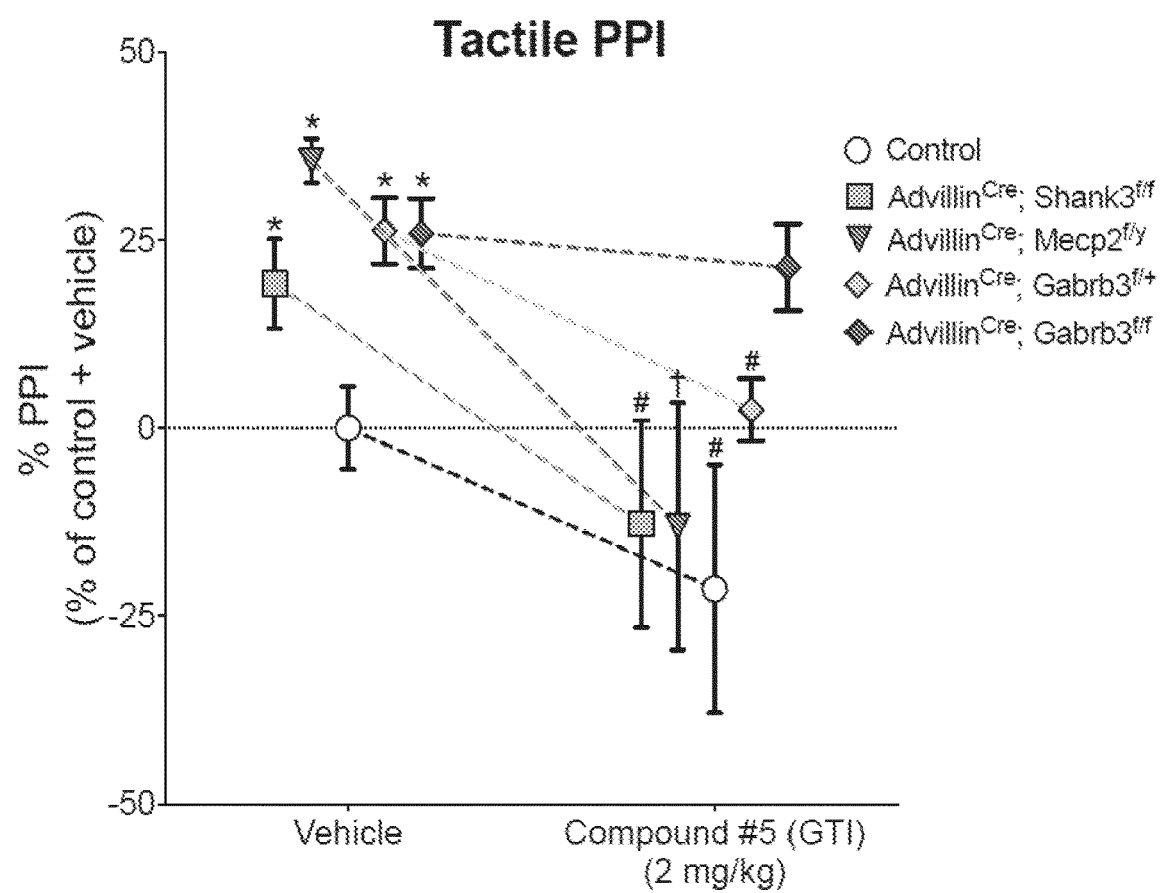
FIG. 4 is a graph showing the percent inhibition of an acoustic startle response (PPI) to a 125-dB noise (pulse), when the startle noise was preceded by a light air puff (prepulse, 0.9 PSI, 50 ms) at an interstimulus interval of 250 ms. Values were expressed as percent of control littermates' performance. Experiments were performed in mutant mice (Advillin$^{Cre}$; Mecp2$^{f/y}$, Advillin$^{Cre}$; Shank3$^{f/f}$, Advillin$^{Cre}$; Gabrb3$^{f/+}$, Advillin$^{Cre}$; Gabrb3$^{f/f}$) and control littermates, 30 minutes after an intraperitoneal injection of either saline (vehicle) or Compound 5 at 2 mg/kg. While saline-treated Advillin$^{Cre}$; Mecp2$^{f/y}$, Advillin$^{Cre}$; Shank3$^{f/f}$, and Advillin$^{Cre}$; Gabrb3$^{f/+}$ exhibit enhanced tactile PPI performance compared to control littermates, mutant mice treated with Compound 5 show reduced tactile PPI performance. Notably, mice with a complete loss of GABA-A receptors on peripheral somatosensory neurons (AdvillinCre; Gabrb3f/f), do not show a reduction in tactile sensitivity when administered Compound 5, indicating that GABA-A receptors on peripheral sensory neurons are necessary for Compound 5 to improve hairy skin hypersensitivity. Two-way ANOVA, with post-hoc Holm-Sidak's test, *, $p<0.05$, when comparing mutants to control within same treatment; t, $p<0.05$, or #, $p<0.10$, when comparing the same genotype across different treatments.
Figure 5:
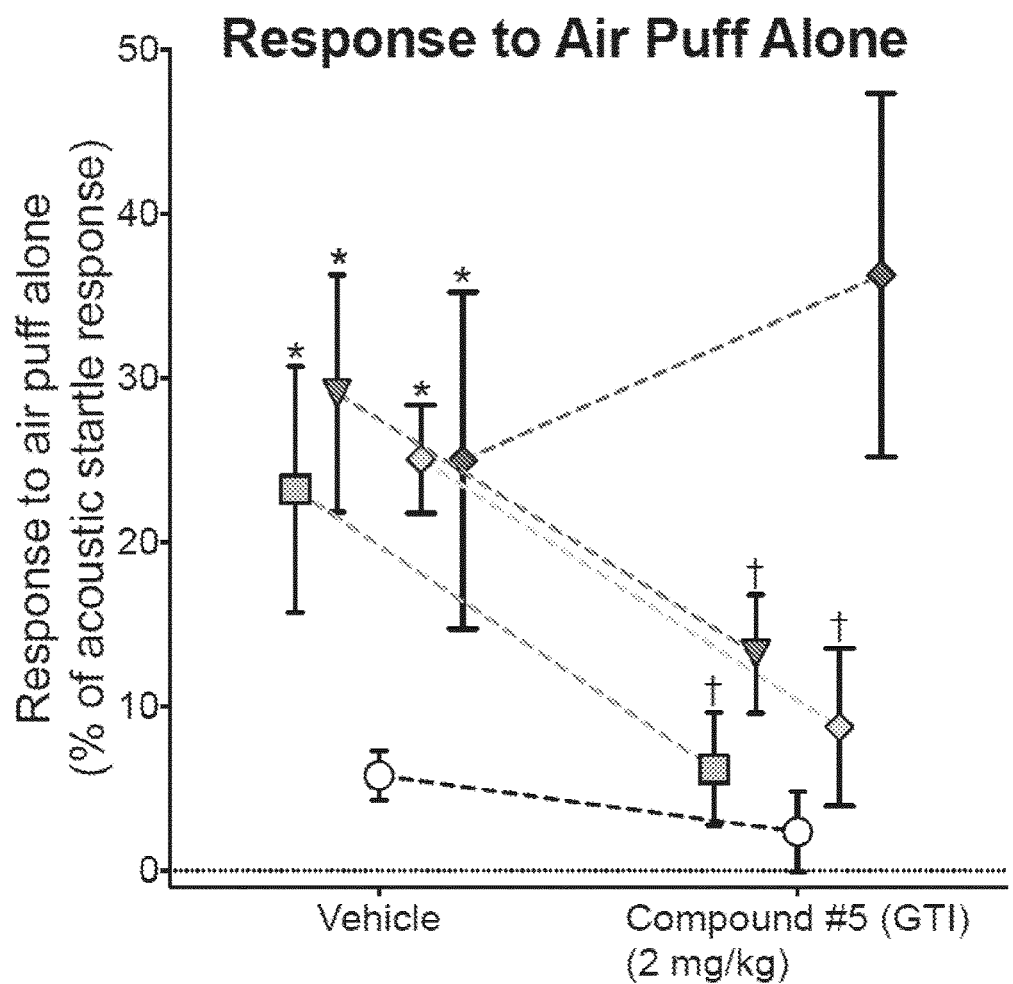
FIG. 5 is a graph showing the response to a light air puff stimulus alone (0.9 PSI, 50 ms). Responses were expressed as a percent of startle response to a 125-B noise. Experiments were performed in mutant mice (Advillin$^{Cre}$; Mecp2$^{f/y}$, Advillin$^{Cre}$; Shank3$^{f/f}$, Advillin$^{Cre}$; Gabrb3$^{f/+}$, Advillin$^{Cre}$; Gabrb3$^{f/f}$) and control littermates, 30 minutes after an intraperitoneal injection of either saline (vehicle) or Compound 5 at 2 mg/kg. While saline-treated Advillin$^{Cre}$; Mebp2$^{f/y}$, Advillin$^{Cre}$; Shank3$^{f/f}$ and Advillin$^{Cre}$; Gabrb3$^{f/+}$ exhibit enhanced responsivity to an air puff stimulus compared to control littermates, mutant mice treated with Compound 5 show reduced responsivity to an air puff stimulus. Importantly, animals with complete loss of GABA-A receptors on peripheral sensory neurons (Advillin$^{Cre}$; Gabrb3$^{f/f}$) did not show any improvements in hairy skin sensitivity, indicating that GABA-A receptors on peripheral sensory neurons are necessary for Compound 5 to improve hairy skin hypersensitivity. Two-way ANOVA, with post-hoc Holm-Sidak's test, *, p<0.05, when comparing mutants to control within same treatment; f, p<0.05, when comparing the same genotype across different treatments.

Example 2. Compound 5 Reduced Hairy Skin Hypersensitivity in Mecp2, and Shank3 and Gabrb3 Mutant Mice A novel derivative of isoguvacine, termed Compound 5, was synthesized. In order to test its effect on tactile sensation, a tactile prepulse inhibition (PPI) assay was performed in mutant mice. When administered via intraperitoneal injection, Compound 5 significantly reduced hairy skin hypersensitivity in both Mecp2 hemizygous null, Shank3 homozygous, and Gabrb3 heterozygous conditional mutant mice, as measured by the tactile PPI assay and response to air puff stimulus alone (FIGS. 1-2, FIGS. 4-5). Importantly, mice with a complete loss of GABA-A receptors on peripheral somatosensory neurons (Advillin$^{Cre}$; Gabrb3$^{f/f}$), do not show a reduction in tactile sensitivity when administered Compound 5, indicating that GABA-A receptors on peripheral sensory neurons are necessary for Compound 5 to improve hairy skin hypersensitivity (FIGS. 4-5).

Figure 1:
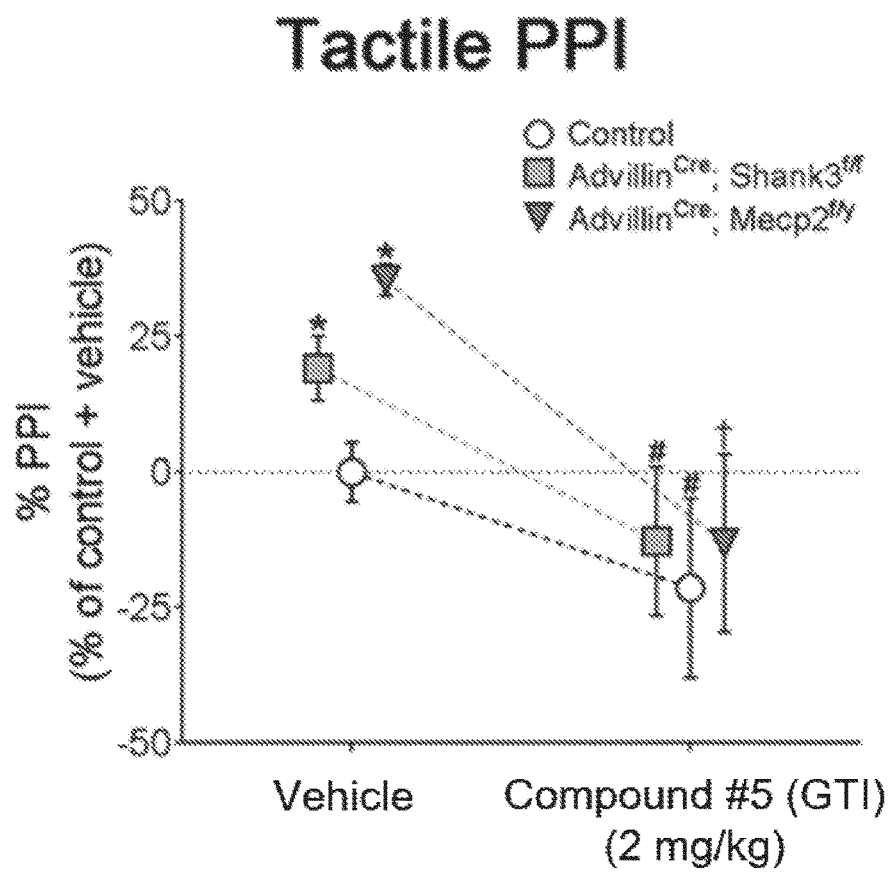
FIG. 1 is a graph showing percent inhibition of an acoustic startle response (PPI) to a 125-dB noise (pulse), when the startle noise was preceded by a light air puff (prepulse, 0.9 PSI, 50 ms) at an interstimulus interval of 250 ms. Values are expressed as percent of control littermates' performance. Experiments were performed in mutant mice (Advillin$^{Cre}$; Mecp2$^{f/y}$, Advillin$^{Cre}$; Shank3$^{f/f}$) and control littermates, 30 minutes after an intraperitoneal injection of either saline (vehicle) the peripherally restricted Compound 5 (2 mg/kg). Two-way ANOVA, with post-hoc Holm-Sidak's test, *, $p<0.05$, when comparing mutants to control within same treatment; I, $p<0.05$, or $p<0.10$, when comparing the same genotype across different treatments.

FIGS. 1 and 4 show the percent inhibition of an acoustic startle response (PPI) to a 125-dB noise (pulse), when the startle noise was preceded by a light aft puff (prepulse, 0.9 PSI, 50 ms) at an interstimulus interval of 250 ms. Values were expressed as percent of control littermates' performance. Experiments were performed in mutant mice (Advillin$^{Cre}$; Mecp2$^{f/y}$, Advillin$^{Cre}$; Shank3$^{f/f}$, Advillin$^{Cre}$; Gabrb3$^{f/+}$, Advillin$^{Cre}$; Gabrb3$^{f/f}$) and control littermates, 30 minutes after an intraperitoneal injection of either saline (vehicle) or Compound 5 at 2 mg/kg.

Figure 2:
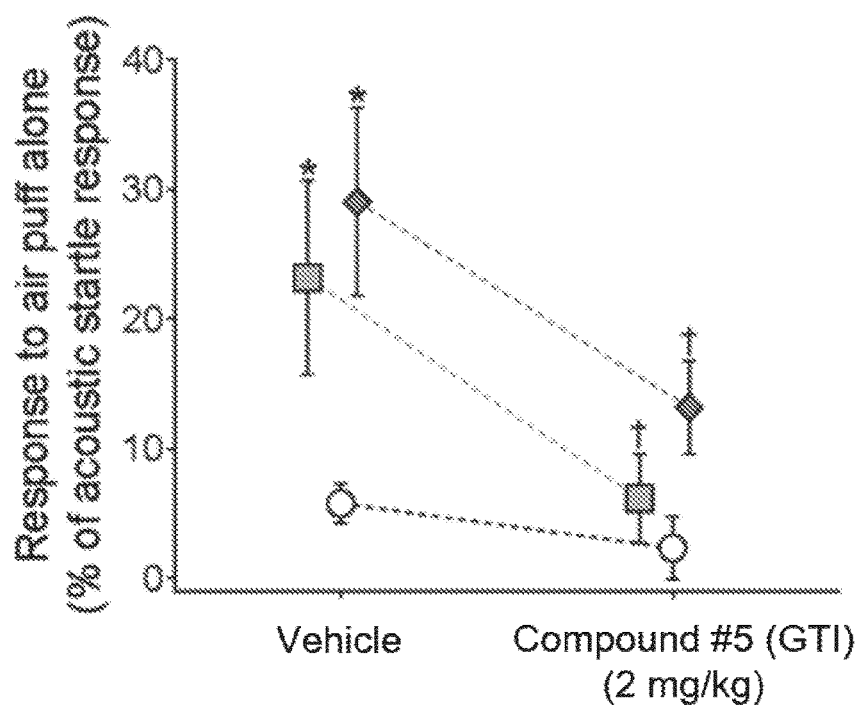
FIG. 2 is a graph showing response to a light air puff stimulus alone (0.9 PSI, 50 ms). Responses are expressed as a percent of startle response to a 125-B noise. Experiments were performed in mutant mice (Advillin$^{Cre}$; Mecp2$^{f/y}$, Advillin$^{Cre}$; Shank3$^{f/f}$) and control littermates, 30 minutes after an intraperitoneal injection of either saline (vehicle) the peripherally restricted Compound 5 (2 mg/kg). Two-way ANOVA, with post-hoc Holm-Sidak's test, *, $p<0.05$, when comparing mutants to control within same treatment; I, $p<0.05$, when comparing the same genotype across different treatments.

FIG. 2 shows the response to a light aft puff stimulus alone (0.9 PSI, 50 ms). Responses were expressed as a percent of startle response to a 125-B noise. Experiments were performed in mutant mice (Advillin$^{Cre}$; Mecp2$^{f/y}$, Advillin$^{Cre}$; Shank3$^{f/f}$, Advillin$^{Cre}$; Gabrb3$^{f/+}$, Advillin$^{Cre}$; Gabrb3$^{f/f}$) and control littermates, 30 minutes after an intraperitoneal injection of either saline (vehicle) or Compound 5 at 2 mg/kg.

Figure 3:
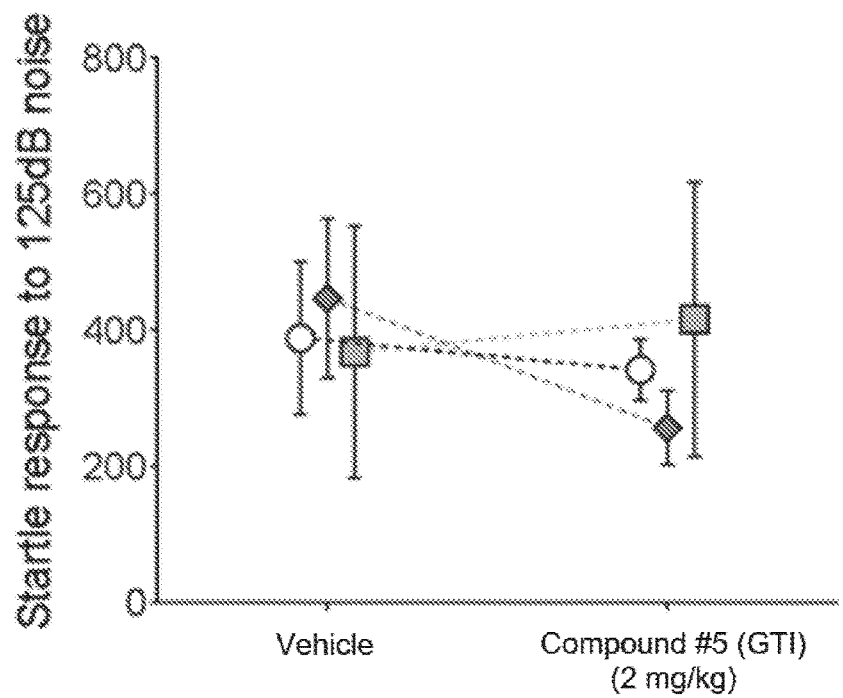
FIG. 3 is a graph showing magnitude of startle response to a 125-dB noise. Experiments were performed in mutant mice (Advillin$^{Cre}$; Mecp2$^{f/y}$, Advillin$^{Cre}$; Shank3$^{f/f}$) and control littermates, 30 minutes after an intraperitoneal injection of either saline (vehicle) the peripherally restricted Compound 5 (2 mg/kg). Two-way ANOVA, no significant differences between any genotypes or treatment groups.
Figure 6:
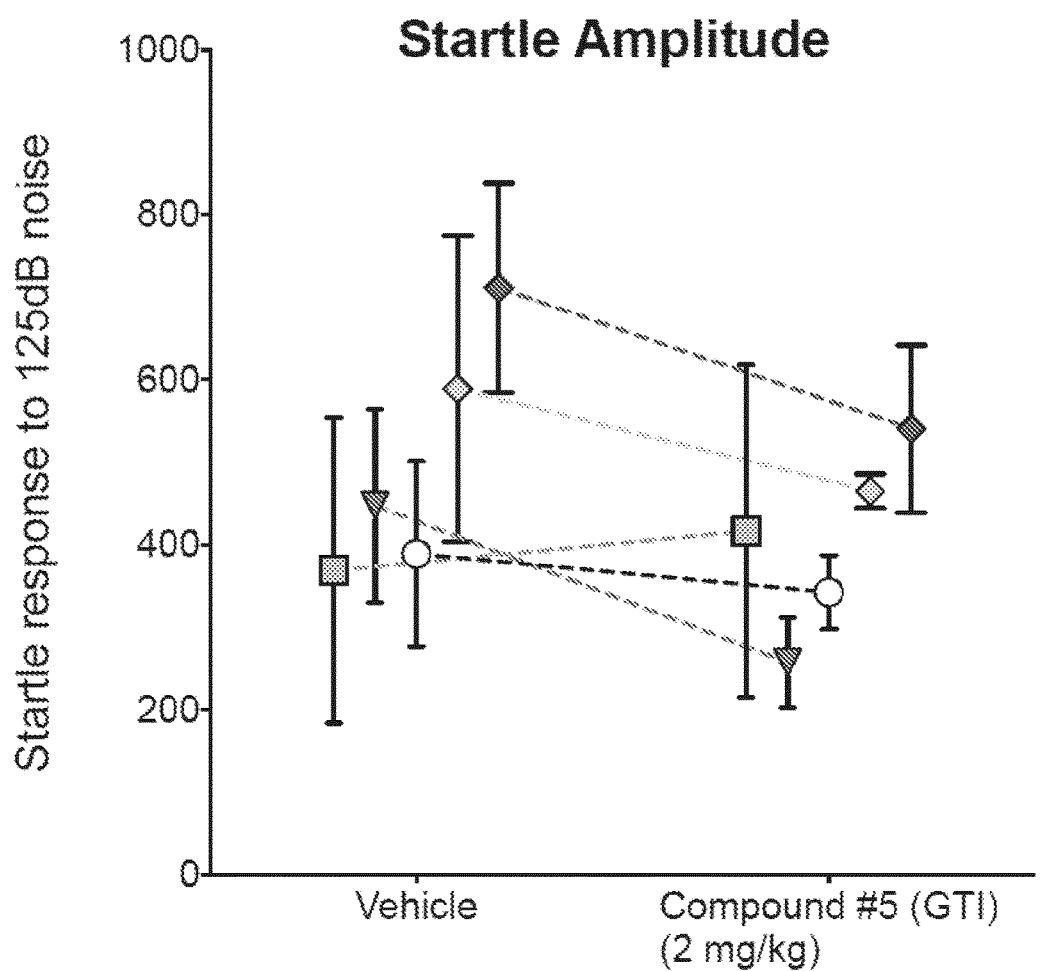
FIG. 6 is a graph showing Compound 5 did not have negative effects on motor behaviors or sedation, as measured by the average startle amplitude elicited by a 125-dB noise during the PPI trials. Experiments were performed in mutant mice (Advillin$^{Cre}$; Mecp2$^{f/y}$, Advillin$^{Cre}$; Shank3$^{f/f}$, Advillin$^{Cre}$; Gabrb3$^{f/+}$, Advillin$^{Cre}$; Gabrb3$^{f/f}$) and control littermates, 30 minutes after an intraperitoneal injection of either saline (vehicle) or Compound 5 at 2 mg/kg. Two-way ANOVA, no significant differences between any genotypes or treatment groups.
Figure 7:
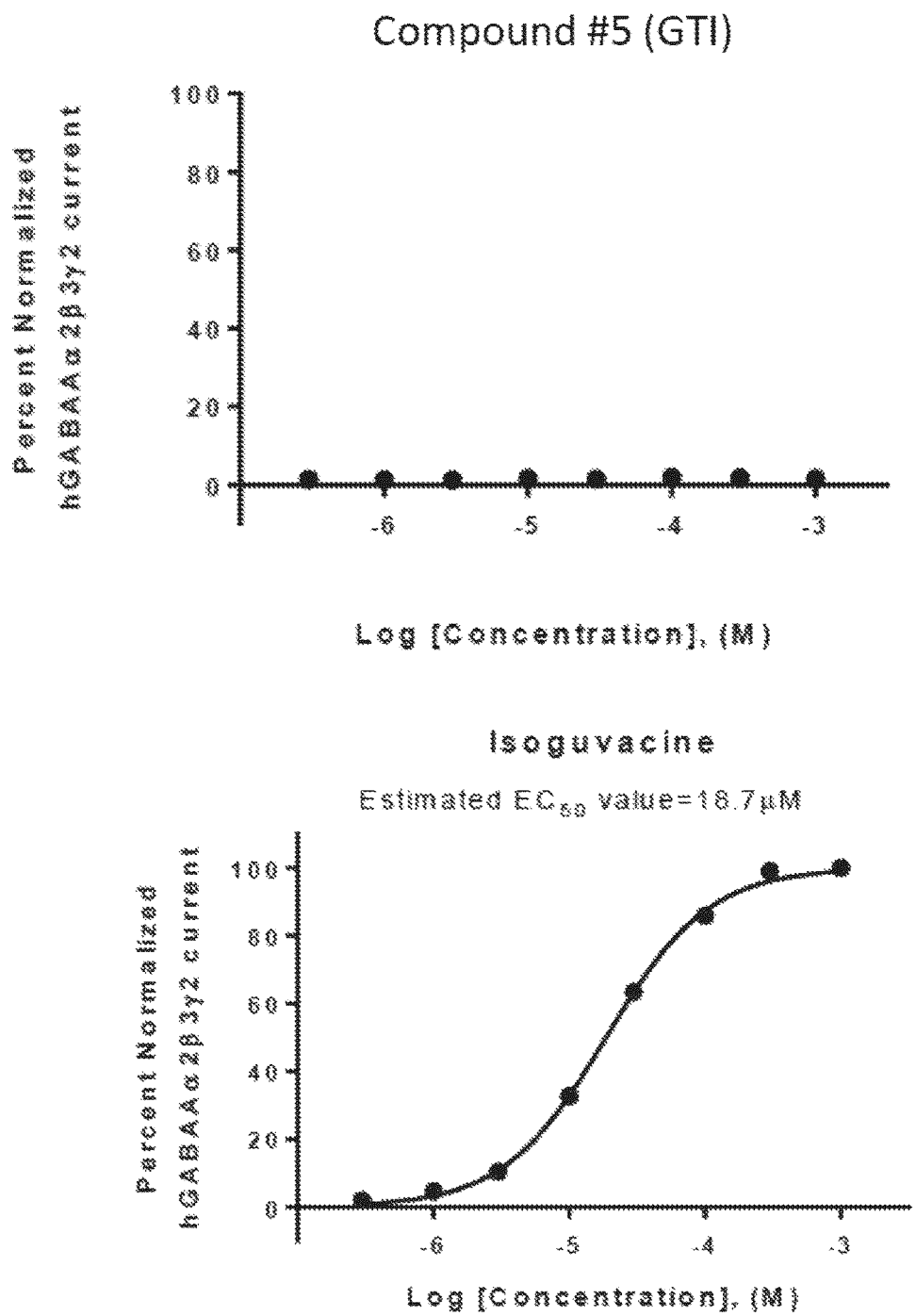
FIG. 7 is two graphs showing the effects of Compound 5 on the human GABA-A α2β3γ2 receptor and GABA transporter function. Compound 5 had no agonism for the alpha2, beta3, gamma 2-containing GABA-A receptor subunit composition, based on an in vitro chloride flux assay. This is in comparison to a known GABA-A receptor agonist, isoguvacine.

Importantly, Compound 5 did not have negative effects on motor behaviors or sedation, as measured by the average startle amplitude elicited by a 125-dB noise during the PPI trials (FIGS. 3 and 6). Experiments were performed in mutant mice (Advillin$^{Cre}$; Mecp2$^{f/y}$, Advillin$^{Cre}$; Shank3$^{f/f}$, Advillin$^{Cre}$; Gabrb3$^{f/+}$, Gabrb3$^{f/f}$) and control littermates, 30 minutes after an intraperitoneal injection of either saline (vehicle) or Compound 5 at 2 mg/kg.

Example 3. Efficacy of Isoguvacine and Compound 5 in the Rat Spinal Nerve Ligation (SNL) Pain Rats Model of Neuropathic Pain

TABLE 2

| Test Article(s) | | |
|---|---|---|
| Name: | Isoguvacine | Compound 5 |
| Storage Conditions: | 2-8° C., away from light | 2-8° C., away from light |

TABLE 3

| Vehicle | |
|---|---|
| Name: | Saline |
| Supplier: | WuXi |
| Physical State: | Clear |
| Storage Conditions: | 2-8° C. |

TABLE 4

Animal Use

| | |
|---|---|
| Species | SD Rat |
| Body Weight Range | ~140 g |
| Age (Study started) | 5-6 weeks old |
| Arrive Date | 2019 Mar. 12 |
| Sex | Male |
| Source | SLAC, ShangHai, China |
| Address of Supplier | NO. 1696 Day Rd. Fengxian, Shanghai, P.R. China |
| Method of Identification | Tail markers |
| Number of Animals for Acclimation | 24 |
| Number of Animals for Dosing | 50 rats |
| Justification for number of Animals | 3 groups, animal number per dose group is 8 |

TABLE 5

Group and Dose Protocol

| Group | Administration | Dose | Vehicle | Route of Admin | Dosing volume | N |
|---|---|---|---|---|---|---|
| 1 | Vehicle | — | Saline | IP | 5 ml/kg | 8 |
| 2 | Isoguvacine | 5 mpk | Saline | IP | 5 ml/kg | 8 |
| 3 | Compound 5 | 5 mpk | Saline | IP | 5 ml/kg | 8 |

Chung surgery were conducted on anesthetized rats. Rats were habituated in the testing environment for 15 minutes before allodynia measurement (2-3 times). Pre-dose baseline were taken on day 9 post surgery. Rats that don't show allodynic response at this point were excluded. SNL rats with a paw withdrawal threshold >4 g. The animals were grouped according to 50% paw withdrawal threshold (g) and weight. The animals were dosed test articles and vehicle according to the dose protocol. On the testing day (Day 9), rats were dosed with testing articles with 16 min interval between groups. Rats were measured for allodynic response at 0.75, 1.5, 3 h time point post dosing. All values will be expressed as mean±S.E.M. The significance of the differences among groups will be evaluated by two-way ANOVA followed by Dunnett's test using graphpad Prism 6 software. A p value of less than 0.05 is considered statistically significant.

TABLE 6

Body Weight

| Animal ID | Group | Body weight (g) | Dose volume (mL) |
|---|---|---|---|
| 5 | Vehicle | 239.6 | 1.20 |
| 2 | Vehicle | 241.7 | 1.21 |
| 4 | Vehicle | 218.5 | 1.09 |
| 30 | Vehicle | 233.3 | 1.17 |
| 26 | Vehicle | 215.7 | 1.08 |
| 34 | Vehicle | 225.4 | 1.13 |
| 24 | Vehicle | 227.6 | 1.14 |
| 16 | Vehicle | 233.4 | 1.17 |
| | Mean | 229.40 | 1.15 |
| | SEM | 3.31 | 0.02 |
| 7 | Isoguvacine | 236.3 | 1.18 |
| 3 | Isoguvacine | 243.6 | 1.22 |
| 35 | Isoguvacine | 237.0 | 1.19 |
| 53 | Isoguvacine | 214.4 | 1.07 |
| 18 | Isoguvacine | 237.9 | 1.19 |
| 19 | Isoguvacine | 243.5 | 1.22 |
| 21 | Isoguvacine | 233.2 | 1.17 |
| 36 | Isoguvacine | 221.9 | 1.11 |
| | Mean | 233.48 | 1.17 |
| | SEM | 3.64 | 0.02 |
| 13 | Compound 5 | 233.4 | 1.17 |
| 6 | Compound 5 | 225.4 | 1.13 |
| 37 | Compound 5 | 228.2 | 1.14 |
| 50 | Compound 5 | 227.4 | 1.14 |
| 20 | Compound 5 | 232.6 | 1.16 |
| 29 | Compound 5 | 228.2 | 1.14 |
| 32 | Compound 5 | 231.3 | 1.16 |
| 38 | Compound 5 | 219.6 | 1.10 |
| | Mean | 228.26 | 1.14 |
| | SEM | 1.57 | 0.01 |

TABLE 7

50% g Threshold

| Animal ID | Group | 0 Hour | 0.75 Hour | 1.5 Hour | 3 Hour |
|---|---|---|---|---|---|
| 5 | Vehicle | 0.64 | 1.85 | 2.20 | 1.85 |
| 2 | Vehicle | 1.56 | 0.51 | 0.51 | 0.99 |
| 4 | Vehicle | 1.85 | 0.82 | 0.99 | 1.56 |
| 30 | Vehicle | 2.20 | 1.85 | 1.85 | 2.59 |
| 26 | Vehicle | 2.81 | 2.20 | 2.20 | 2.81 |
| 34 | Vehicle | 2.81 | 0.82 | 0.99 | 1.31 |
| 24 | Vehicle | 3.12 | 2.20 | 1.56 | 1.56 |
| 16 | Vehicle | 3.72 | 0.99 | 0.67 | 1.56 |
| | Mean | | 2.34 | 1.40 | 1.37 |
| | SEM | | 0.35 | 0.24 | 0.24 |
| 7 | Isoguvacine | 0.99 | 1.31 | 1.85 | 2.81 |
| 3 | Isoguvacine | 1.10 | 2.37 | 2.37 | 6.74 |
| 35 | Isoguvacine | 1.85 | 1.31 | 0.82 | 7.91 |
| 53 | Isoguvacine | 2.23 | 2.81 | 1.85 | 3.33 |
| 18 | Isoguvacine | 2.81 | 1.56 | 2.81 | 5.15 |
| 19 | Isoguvacine | 3.00 | 0.99 | 1.85 | 4.34 |
| 21 | Isoguvacine | 3.31 | 1.56 | 1.56 | 5.77 |
| 36 | Isoguvacine | 3.31 | 2.37 | 2.64 | 3.31 |
| | Mean | | 2.32 | 1.78 | 1.97 |
| | SEM | | 0.33 | 0.23 | 0.23 |
| 13 | Compound 5 | 0.99 | 3.33 | 6.74 | 6.42 |
| 6 | Compound 5 | 1.10 | 4.12 | 5.10 | 3.33 |
| 37 | Compound 5 | 1.56 | 2.81 | 1.85 | 2.81 |
| 50 | Compound 5 | 2.64 | 1.85 | 3.71 | 2.61 |
| 20 | Compound 5 | 2.81 | 4.34 | 3.31 | 3.71 |
| 29 | Compound 5 | 2.81 | 3.31 | 3.71 | 4.34 |
| 32 | Compound 5 | 3.31 | 2.37 | 1.56 | 0.82 |
| 38 | Compound 5 | 3.31 | 6.74 | 6.74 | 7.91 |
| | Mean | | 2.31 | 3.61 | 4.09 |
| | SEM | | 0.34 | 0.54 | 0.70 |

TABLE 8

Von frey test (MEAN ± S.E.M.) (g)

| Group | 0 Hour | 0.75 Hour | 1.5 Hour | 3 Hour |
|---|---|---|---|---|
| Vehicle | 2.3 ± 0.35 | 1.4 ± 0.24 | 1.4 ± 0.24 | 1.8 ± 0.22 |
| Isoguvacine | 2.3 ± 0.33 | 1.8 ± 0.23 | 2.0 ± 0.23 | 4.9 ± 0.64 |
| Compound 5 | 2.3 ± 0.34 | 3.6 ± 0.54 | 4.1 ± 0.70 | 4.0 ± 0.79 |

TABLE 9

Statistical analysis-Von frey test (vs. Vehicle)
(Two way ANOVA followed by Dunn)

| Group | 0 Hour | 0.75 Hour | 1.5 Hour | 3 Hour |
|---|---|---|---|---|
| Isoguvacine | P > 0.05 | P > 0.05 | P > 0.05 | P < 0.0001 |
| Compound 5 | P > 0.05 | P < 0.01 | P < 0.001 | P < 0.01 |

Chung surgery rats showed tactile allodynia 9 days after surgery. Isoguvacine showed significant analgesia effect at the 3 hour time point dose.

Example 4. Assessment of Compound 5 for GABA Transporter Inhibition

The activity of compound Compound 5 was evaluated in Radioligand Binding assays. Methods employed herein have been adapted from the scientific literature to maximize reliability and reproducibility. Reference standards were run as an integral part of each assay to ensure the validity of the results obtained. Where presented, $IC_{50}$ values were determined by a non-linear, least squares regression analysis using MathIQ™ (ID Business Solutions Ltd., UK). Where inhibition constants (K) are presented, the $K_i$ values were calculated using the equation of Cheng and Prusoff (Cheng, Y., Prusoff, W. H., Biochem. Pharmacol. 22:3099-3108, 1973) using the observed $IC_{50}$ of the tested compound, the concentration of radioligand employed in the assay, and the historical values for the $K_D$ of the ligand (obtained experimentally at Eurofins Panlabs, Inc.). Where presented, the Hill coefficient ($n_H$), defining the slope of the competitive binding curve, was calculated using MathIQ™. Hill coefficients significantly different than 1.0 may suggest that the binding displacement does not follow the laws of mass action with a single binding site. Where $IC_{50}$, $K_i$ and/or $n_H$ data are presented without Standard Error of the Mean (SEM), data are insufficient to be quantitative.

Biochemical assay results are presented as the percent inhibition of specific binding or activity. All other results are expressed in terms of the quantitation method of that assay. For primary assays, only the lowest concentration with a significant response, judged by the criteria of the assay, is shown in this summary. Where applicable, either the secondary assay results with the lowest dose/concentration meeting the significance criteria or, if inactive, the highest dose/concentration that did not meet the significance criteria is shown. Unless otherwise requested, primary screening in duplicate with quantitative data (e.g., IC50±SEM, Ki ±SEM and $n_H$) are shown where applicable for individual requested assays. In screening packages, primary screening in duplicate with semi-quantitative data (e.g., estimated IC50, $K_i$ and $n_H$) are shown where applicable (concentration range of 4 log units); available secondary functional assays are carried out (30 mM) and MEC or MIC determined only if active in primary assays >50% at 1 log unit below initial test concentration. Significant responses 50% inhibition or stimulation for Biochemical assays) were noted in the primary assays listed below:

TABLE 10

| Cat # | Assay Name | Species | Conc. | % Inh. | $IC_{50}$* | $K_I$ | $n_H$ |
|---|---|---|---|---|---|---|---|
| 226400 | Transporter, GABA | rat | 30 μM | 52 | 28.1 μM | 27.5 μM | 1.47 |

*A standard error of the mean is presented where results are based on multiple, independent determinations.

TABLE 11

| Cat # | Assay Name | Batch* | Spec. | Rep. | Conc. | % Inh. | $IC_{50}$* | $K_I$ | $n_H$ |
|---|---|---|---|---|---|---|---|---|---|
| 226400 | Transporter, GABA | 424211 | rat | 2 | 1 mM | 104 | 28.1 μM | 27.5 μM | 1.47 |
| | | | rat | 2 | 300 μM | 97 | | | |
| | | | rat | 2 | 100 μM | 86 | | | |
| | | | rat | 2 | 30 μM | 52 | | | |
| | | | rat | 2 | 10 μM | 19 | | | |
| | | | rat | 2 | 3 μM | 2 | | | |
| | | | rat | 2 | 1 μM | -1 | | | |
| | | | rat | 2 | 0.3 μM | 3 | | | |
| | | | rat | 2 | 0.1 μM | -10 | | | |

Note:
Items meeting criteria for significance (≥50% stimulation or inhibition) are highlighted.
*Batch: Represents compounds tested concurrently in the same assay(s).

TABLE 12

226400 Transporter, GABA

| | | | |
|---|---|---|---|
| Source: | Wistar Rat cerebral cortex | Ligand: | 6.0 nM [³H] GABA |
| Vehicle: | 1.00% DMSO | Non-Specific Ligand: | 10.0 μM NO-711 |
| Incubation Time/Temp: | 20 minutes @ 25° C. | Specific Binding: | 80%* |
| Incubation Buffer: | 10 mM HEPES, pH 7.5, 120 mM NaCl, 4 mM Ca(CH₃COO)₂, 10 μM Isoguvacine, 10 μM S(−)-Baclofen | Quantitation Method: | Radioligand Binding |

TABLE 12-continued

| 226400 Transporter, GABA | | | |
|---|---|---|---|
| Kd: | 0.30 µM* | Significance Criteria: | ≥50% of max stimulation or inhibition |
| | | Bmax: | 60.0 pmole/mg Protein* |

*Historical Values

Shank R P, Baldy W J, Mattucci L C and Villani F J Jr (1990) Ion and temperature effects on the binding of gamma-aminobutyrate to its receptors and the high-affinity transport system. J Neurochem. 54:2007-2015.

TABLE 13

| | | Reference Compounds | | | | | |
|---|---|---|---|---|---|---|---|
| | | Reference | Historical | | | Concurrent | |
| Cat # | Assay Name | Compound | $IC_{50}$* | $K_I$ | $n_H$ | Batch* | $IC_{50}$* |
| 226400 | Transporter, GABA | NO-711 | 0.20 µM | 0.20 µM | 1.10 | 424211 | 0.17 µM |

*Batch: Represents compounds tested concurrently in the same assay(s).

Figure 11A:
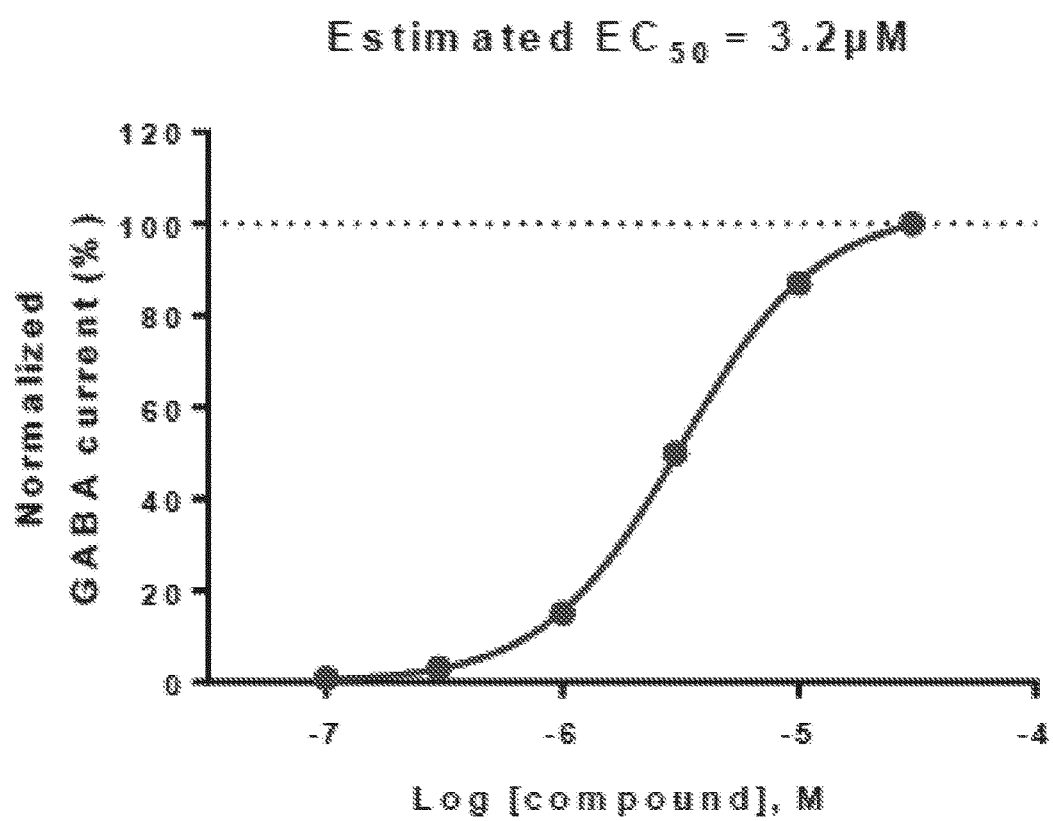
FIG. 11A is a graph showing six point concentration response of GABA, tested to serve as an agonist control for the GABA-A receptor agonist, Cl-flux assay.
Figure 11B:
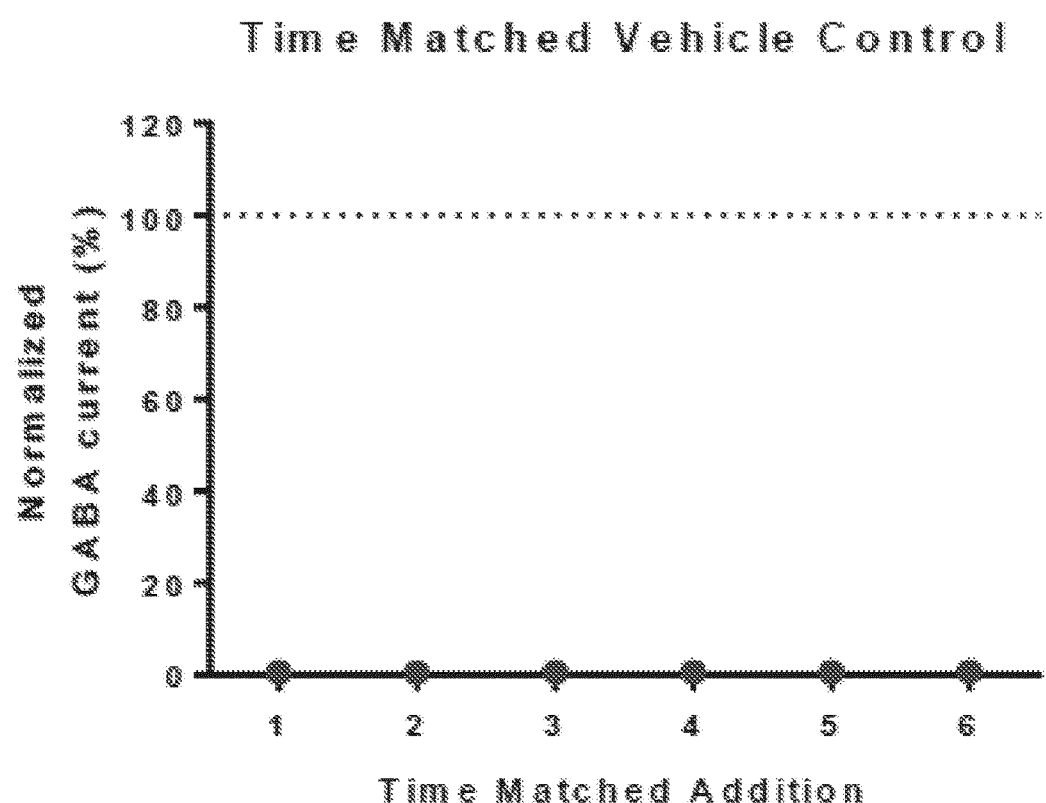
FIG. 11B is a graph showing data for six additions of 0.33% DMSO for 2 seconds introduced to the cells to act as a time matched vehicle control for the agonist during the GABA-A receptor agonist, Cl-flux assay.

Example 5. Assessment for Agonism Activity of Isoguvacine and Compound 5 for GABA-A Receptors of the Human α1β3γ2 Subunit Composition The effects of two compounds on human GABA-A α1β3γ2 ion channels are shown in FIG. 8. All compound response data has been normalized to the baseline peak current induced by addition of $EC_{100}$ GABA for 2 seconds illustrated by the dotted line (FIG. 10). Six-point concentration response of GABA was tested to serve as an agonist control. GABA evoked human GABA-A α1β3γ2 ion channel currents in a concentration dependent manner (FIG. 11A). Six additions of 0.33% DMSO for 2 seconds were introduced to the cells to act as a time matched vehicle control for the agonist. Data are shown in FIG. 11B. Note: The test compound was applied over two 'experimental patterns' in increasing concentrations. Table 14 shows the normalized peak current values for the two test compounds assayed at seven concentrations against human GABA-A α1β3γ2 ion channels (FIGS. 10A and 10B). Time-matched negative and reference compound data are included for comparison.

TABLE 14

| | Summary Data. | | | |
|---|---|---|---|---|
| | | Normalized Peak hGABAA α1β3γ2 Current (%) Agonist | | |
| | Concentration | | | |
| Compound ID | (µM) | Mean | SEM | n |
| Isoguvacine | 0.1 | 0.55 | 0.08 | 8 |
| | 0.3 | 1.02 | 0.14 | 8 |
| | 1 | 1.92 | 0.16 | 8 |
| | 3 | 4.94 | 0.33 | 8 |
| | 10 | 21.18 | 1.07 | 8 |
| | 30 | 53.29 | 2.17 | 8 |
| | 100 | 79.91 | 0.86 | 8 |
| Compound 5 | 0.1 | 0.58 | 0.17 | 8 |
| | 0.3 | 0.56 | 0.14 | 8 |
| | 1 | 0.58 | 0.08 | 8 |
| | 3 | 0.62 | 0.15 | 8 |
| | 10 | 0.79 | 0.22 | 8 |

TABLE 14-continued

| | Summary Data. | | | |
|---|---|---|---|---|
| | | Normalized Peak hGABAA α1β3γ2 Current (%) Agonist | | |
| | Concentration | | | |
| Compound ID | (µM) | Mean | SEM | n |
| | 30 | 0.57 | 0.06 | 8 |
| | 100 | 0.49 | 0.10 | 8 |
| Time-matched Vehicle | Addition 1 | 0.70 | 0.25 | 8 |
| | Addition 2 | 0.57 | 0.14 | 8 |
| | Addition 3 | 0.70 | 0.28 | 8 |
| | Addition 4 | 0.70 | 0.27 | 8 |
| | Addition 5 | 0.67 | 0.21 | 8 |
| | Addition 6 | 0.76 | 0.17 | 8 |
| GABA | 0.1 | 0.85 | 0.11 | 8 |
| | 0.3 | 3.05 | 0.32 | 8 |
| | 1 | 15.02 | 1.28 | 8 |
| | 3 | 49.97 | 2.35 | 8 |
| | 10 | 86.91 | 1.16 | 8 |
| | 30 | 100.00 | 0.00 | 8 |

Figure 12A:
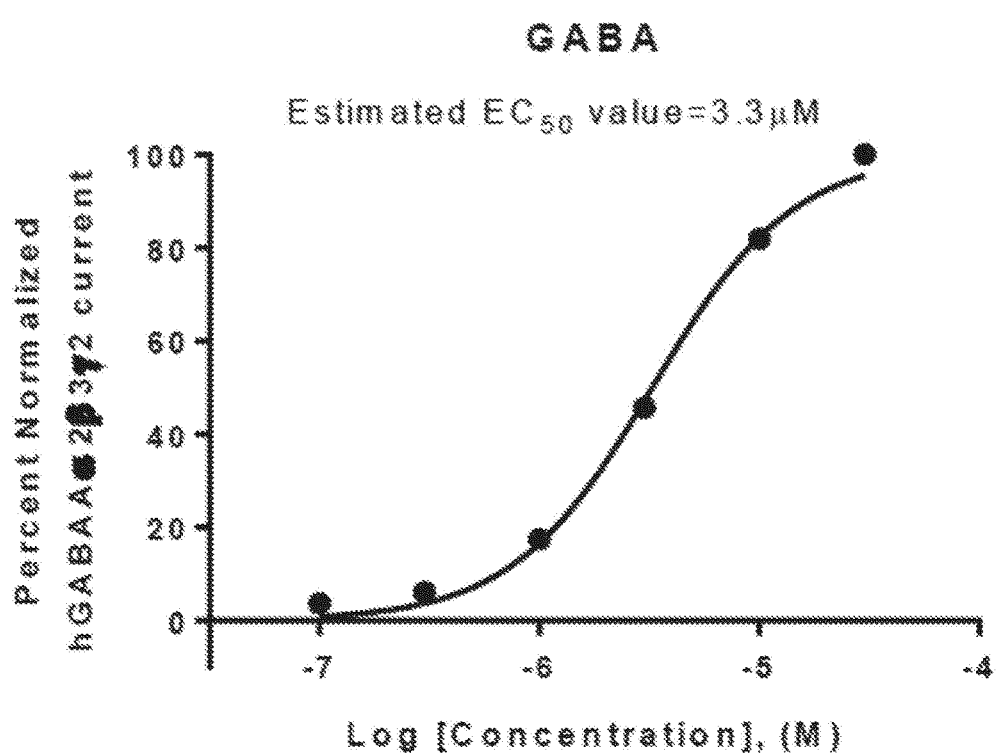
FIG. 12A shows six point concentration response of GABA, tested to serve as an agonist control.
Figure 12B:
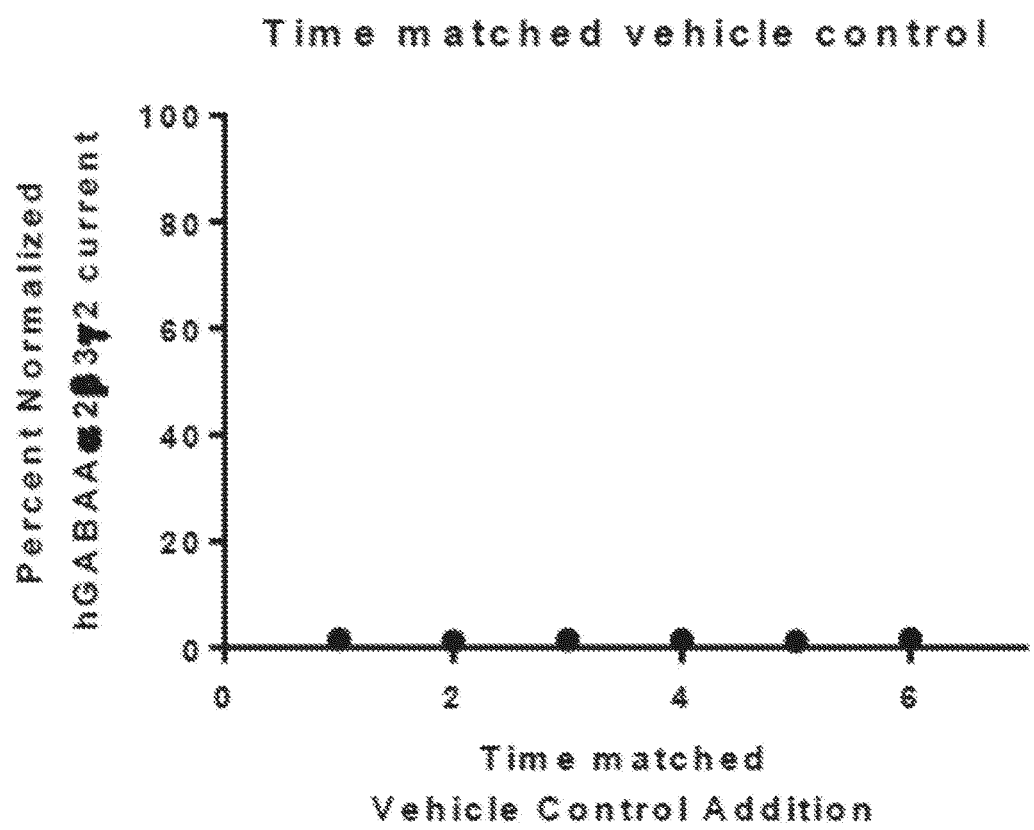
FIG. 12B shows data for six additions of vehicle control for 2 seconds, introduced to the cells to act as a time matched control for agonist assay. Note: The test compounds were applied over two 'experimental patterns' in increasing concentrations.
Figure 13:
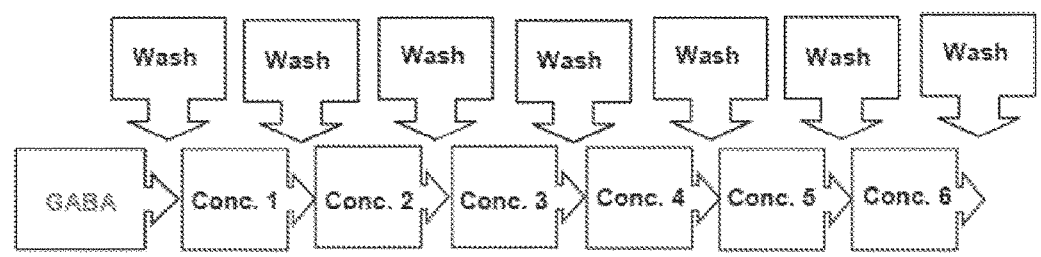
FIG. 13 is a schematic showing the human GABA-A receptor IonFlux HT agonist assay.
Figure 13:
Figure 13:
Figure 13:

Example 5a. Assessment for Agonism Activity of Isoguvacine and Compound 5 for GABA-A Receptors of the Human α2β3γ2 Subunit Composition The effects of two compounds on human GABA-A α2β3γ2 ion channels are shown in FIG. 8. All compound response data has been normalized to the baseline peak current induced by addition of $EC_{100}$ GABA for 2 seconds illustrated by the dotted line (FIGS. 10C and 10D). Six-point concentration response of GABA was tested to serve as an agonist control. GABA evoked human GABA-A α2β3γ2 ion channel currents in a concentration dependent manner. (FIG. 12A) Six additions of 0.33% DMSO for 2 seconds were introduced to the cells to act as a time matched vehicle control for the agonist. (FIG. 12B) Note: The test compound was applied over two 'experimental patterns' in increasing concentrations. Table 14a shows the normalized peak current values for the two test compounds assayed at seven concentrations against human GABA-A α2β3γ2 ion channels. Time-matched negative and reference compound data are included for comparison.

TABLE 14a

Summary Data.

| Compound ID | Concentration (µM) | Estimated EC$_{50}$ (µM) | Normalized Percentage Activation | | |
|---|---|---|---|---|---|
| | | | Mean | SEM | n |
| Compound 5 | 0.3 | >1000 | 1.42 | 0.17 | 8 |
| Compound 5 | 1 | | 1.28 | 0.11 | 8 |
| Compound 5 | 3 | | 1.23 | 0.12 | 8 |
| Compound 5 | 10 | | 1.56 | 0.22 | 8 |
| Compound 5 | 30 | | 1.48 | 0.13 | 8 |
| Compound 5 | 100 | | 1.96 | 0.28 | 8 |
| Compound 5 | 300 | | 1.77 | 0.16 | 8 |
| Compound 5 | 1000 | | 1.64 | 0.12 | 8 |
| Isoguvacine | 0.3 | 18.7 | 2.09 | 0.25 | 8 |
| Isoguvacine | 1 | | 4.69 | 0.33 | 8 |
| Isoguvacine | 3 | | 10.43 | 0.60 | 8 |
| Isoguvacine | 10 | | 32.71 | 1.46 | 8 |
| Isoguvacine | 30 | | 63.48 | 2.19 | 8 |
| Isoguvacine | 100 | | 85.91 | 1.61 | 8 |
| Isoguvacine | 300 | | 99.01 | 0.68 | 8 |
| Isoguvacine | 1000 | | 100.05 | 0.95 | 8 |
| GABA | 0.1 | 3.30 | 3.68 | 0.45 | 8 |
| GABA | 0.3 | | 6.13 | 0.58 | 8 |
| GABA | 1 | | 17.45 | 1.39 | 8 |
| GABA | 3 | | 45.68 | 2.03 | 8 |
| GABA | 10 | | 81.94 | 1.31 | 8 |
| GABA | 30 | | 100.00 | 0.00 | 8 |
| Time-matched vehicle control | Vehicle 1 | | 1.54 | 0.19 | 8 |
| Time-matched vehicle control | Vehicle 2 | | 1.24 | 0.06 | 8 |
| Time-matched vehicle control | Vehicle 3 | | 1.45 | 0.11 | 8 |
| Time-matched vehicle control | Vehicle 4 | | 1.47 | 0.13 | 8 |
| Time-matched vehicle control | Vehicle 5 | | 1.23 | 0.13 | 8 |
| Time-matched vehicle control | Vehicle 6 | | 1.59 | 0.15 | 8 |

Compound Plate Preparation

The supplied compounds were prepared in DMSO to concentrations that were 300× the final assay concentrations of 0.1, 0.3, 1, 3, 10, 30 and 100 µM. Aliquots were taken out and diluted 300× into external buffer to give the final assay concentration. All wells included a final DMSO concentration of 0.33% including all control wells.

TABLE 15

| Ion Channel | EC$_{100}$ Control & Concentration |
|---|---|
| hGABAA α1β3γ2 | 30 µM GABA |
| Ion Channel | Positive Control (Reference Agonist) |
| hGABAA α1β3γ2 | 0.1, 0.3, 1, 3, 10, and 30 µM GABA |

TABLE 16

Electrophysiological Recording Solutions. The solutions for recording hGABAA α1β3γ2 currents on the IonFlux HT were:

| External Recording Solution [mM] | | Internal Recording Solution [mM] | |
|---|---|---|---|
| NaCl | 137 | KF | 70 |
| KCl | 4 | KCl | 60 |
| MgCl$_2$ | 1 | NaCl | 15 |
| CaCl$_2$ | 1.8 | HEPES | 5 |

TABLE 16-continued

Electrophysiological Recording Solutions. The solutions for recording hGABAA α1β3γ2 currents on the IonFlux HT were:

| External Recording Solution [mM] | | Internal Recording Solution [mM] | |
|---|---|---|---|
| HEPES | 10 | EGTA | 5 |
| Glucose | 10 | MgATP | 4 |
| pH 7.35 (titrated with NaOH) | | pH 7.3 (titrated with KOH) | |

Experimental Protocols & Data Analysis

Human GABA-A receptor IonFlux HT Agonist Assay Schematic

All recordings were obtained from a holding potential of −60 mV. The compound addition sequence that was used for all additions was the same for all assays. One addition of the EC$_{100}$ concentration of GABA was added to establish baseline response. Each test concentration of compound was applied for 2 seconds followed by 30 seconds wash. The process was repeated with the next ascending concentration of test compound up to a maximum of six concentrations per well (FIG. 14).

Human GABA-A receptor IonFlux HT Agonist Assay Data Analysis

Peak inward currents in response to the additions of compound were measured. All compound data have been normalized to the baseline peak current induced by addition of EC100 GABA for 2 seconds:

Normalized Peak Current=$(I^{Compound}/I^{GABA})$ where $I^{Compound}$ is the peak current induced by addition of test compound, $I^{GABA}$ is the baseline peak current induced by addition of EC$_{100}$ GABA. All data were first exported to an Excel compatible data file and then analyzed using Graph Pad Prism software.

TABLE 17

| IonChannelProfiler Data Filters. | | |
|---|---|---|
| Data Filter | Platform | Criteria |
| Rm | IonFlux HT | >60 MΩ |
| Current Amplitude | IonFlux HT | >1000 pA |

Example 6

Touch over-reactivity is common in patients with autism spectrum disorders (ASDs), and peripheral mechanosensory neuron dysfunction underlies tactile and related behavioral abnormalities in Mecp2 and Gabrb3 mouse models of ASD. Here, it is report that the ASD-associated gene Shank3 functions cell-autonomously in peripheral sensory neurons for normal mechanosensation and some ASD-related behaviors, indicating PNS dysfunction in disparate ASD models. Developmental loss of Shank3 or Mecp2 in mechanosensory neurons leads to region-specific cortical abnormalities, revealing a link between developmental sensory over-reactivity and the genesis of aberrant behavior. Acute treatment with a peripherally-restricted GABA$_A$ receptor agonist acts directly on mechanosensory neurons to normalize tactile over-reactivity in six distinct ASD models, whereas chronic treatment of Mecp2 and Shank3 mutant mice beginning neonatally improves body condition, cortical abnormalities, anxiety-like behaviors, and some social impairments. These findings enable a novel therapeutic strategy targeting mechanosensory neurons for treatment of tactile over-reactivity and related behaviors in ASD.

Autism spectrum disorders (ASDs) are a heterogeneous group of complex neurodevelopmental disorders characterized by impairments in social communication and interactions, as well as restricted and repetitive behaviors (RRPs). Although rates of ASD diagnosis are increasing, with approximately 1 in 59 people in the U.S. reported to be living with ASD, there are no FDA-approved treatments for core ASD symptoms (Baio et al., 2018). Indeed, a majority of adults with ASD (60%) exhibit concerns about current medication options aimed at alleviating co-morbid ASD symptoms due to a lack of efficacy and adverse side effects, including fatigue and sedation (Howes et al., 2018). Antipsychotic medications risperidone and aripiprazole are approved for treatment of irritability associated with ASD, however routine use is not recommended due to potential adverse effects (Howes et al., 2018). Selective serotonin reuptake inhibitors (SSRIs) may be beneficial for some ASD patients, but these drugs are poorly tolerated in children and evidence is lacking for their ability to improve RRPs, depression, and anxiety in the ASD population (Coury et al., 2012; King et al., 2009). Oxytocin is being investigated as a potential treatment for ASD, yet there are inconsistencies in efficacy with a lack of clear benefits across different trials (Anagnostou et al., 2012; Guastella et al., 2015; Howes et al., 2018; Yatawara et al., 2016). Pharmacological modulators of GABA receptor signaling have gained attention for possible therapeutic utility in patients with ASD. Bumetanide (a selective chloride importer NKCC1 antagonist) and arbaclofen (a $GABA_B$ receptor agonist) are being explored as means of restoring GABAergic inhibition to neural circuits and may show promise in recent clinical trials with regards to improving social behaviors in children with ASD (Erickson et al., 2014; Hadjikhani et al., 2018; Lemonnier et al., 2017; Veenstra-VanderWeele et al., 2017). Clearly, new therapeutic strategies are needed to treat symptoms observed in patients with syndromic and non-syndromic ASD.

A major hurdle in developing effective treatments for ASD patients is that ASD symptoms and severity are highly heterogeneous across individuals. In addition, identifying neurobiological underpinnings of behavioral and cognitive abnormalities in ASD, which is needed for rational drug design, has been challenging. The finding that sensory processing impairments are a key feature of ASD is intriguing, and sensory over-reactivity is now recognized as a core diagnostic symptom of ASD (DSM-V, 2013). Indeed, sensory over-reactivity across multiple sensory domains is predictive of RRPs and, perhaps surprisingly, ASD diagnosis adds no predictive value beyond sensory hypersensitivity (Schulz and Stevenson, 2018). Furthermore, linear regression modeling indicates that sensory over-responsivity is strongly correlated with anxiety and gastrointestinal dysfunction in people with ASD (Mazurek et al., 2013). Of particular interest is an emerging body of literature indicating that abnormal responses to touch are tightly correlated with, and predictive of, ASD severity. Young children with ASD exhibit greater sensitivity to light touch than children with other developmental disorders (Wiggins et al., 2009), and touch avoidance during infancy predicts deficits in social development and ASD diagnosis in young children (Mammen et al., 2015).

Recent work aimed at identifying the neurobiological basis of abnormal tactile sensitivity in ASD revealed that peripheral mechanosensory neurons, called low-threshold mechanoreceptor neurons (LTMRs), and their connections within the spinal cord, are dysfunctional in Mecp2 and Gabrb3 ASD mouse models (Orefice et al., 2016). Moreover, aberrant tactile reactivity observed in Mecp2 and Gabrb3 mutant mice contributes to a subset of ASD-associated behavioral phenotypes, including social impairments and anxiety-like behaviors (Orefice et al., 2016).

The present study employs conditional mouse genetics, and behavioral, electrophysiological, synaptic and biochemical analyses to identify mechanosensory neuron abnormalities that underlie tactile over-reactivity in genetically distinct mouse models of ASD and its relationship to brain development, cognitive function and behavior. It was observed that distinct somatosensory neuron pathophysiological mechanisms account for tactile over-reactivity in different genetic models of ASD. Moreover, altered somatosensory neuron function in distinct ASD models leads to region-specific alterations in brain development and cortical microcircuit function. Regardless of the pathophysiological mechanism of somatosensory neuron abnormality, tactile over-reactivity can be attenuated in a range of genetic and environmental models of ASD by acute treatment with a peripherally-restricted $GABA_A$ receptor agonist, isoguvacine. Isoguvacine acts directly on mechanosensory neurons to reduce their activation by mechanical stimuli acting on the skin but, importantly, it does not enter the brain nor does it cause sedation. Moreover, chronic postnatal treatment with isoguvacine improved tactile over-reactivity, as well as altered body weight, somatosensory cortex E/I balance, anxiety-like behaviors, and some social impairments in adulthood, in both Mecp2 and Shank3 mouse models. Thus, tactile over-reactivity in different ASD models can result from disparate molecular and pathophysiological mechanisms, aberrant tactile reactivity leads to region-specific abnormal brain development, and a peripherally-restricted pharmacological approach to suppress tactile over-reactivity during early postnatal development has the potential to improve some behavioral abnormalities associated with ASD.

Shank3 Functions in Peripheral Sensory Neurons for Normal Touch Behaviors and Some ASD-Related Behaviors.

Figure 15A:
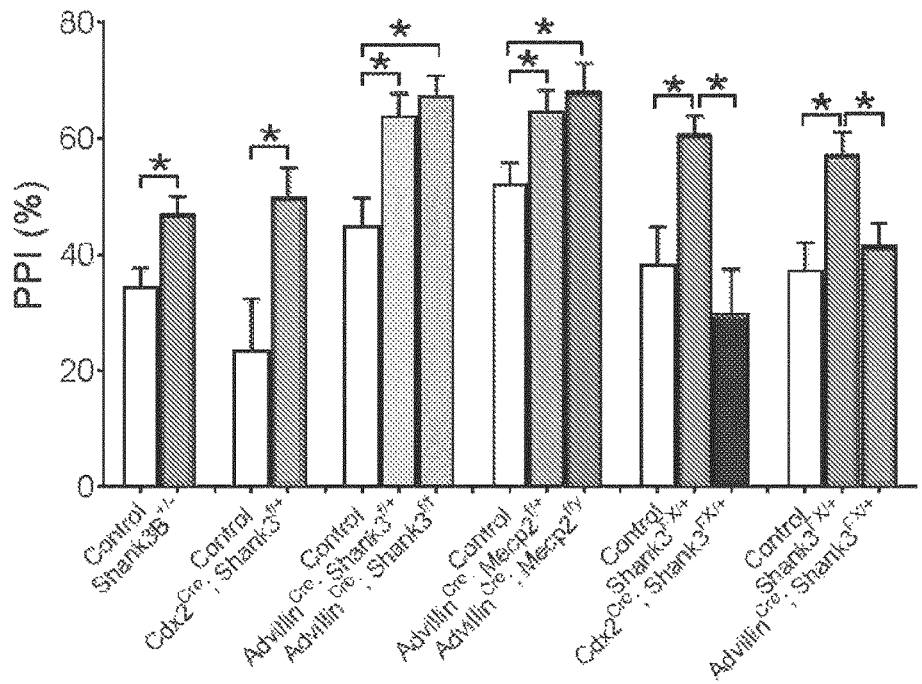
FIGS. 15A-15N show Shank3 functions cell-autonomously in peripheral somatosensory neurons for normal innocuous touch behaviors.
Figure 15B:
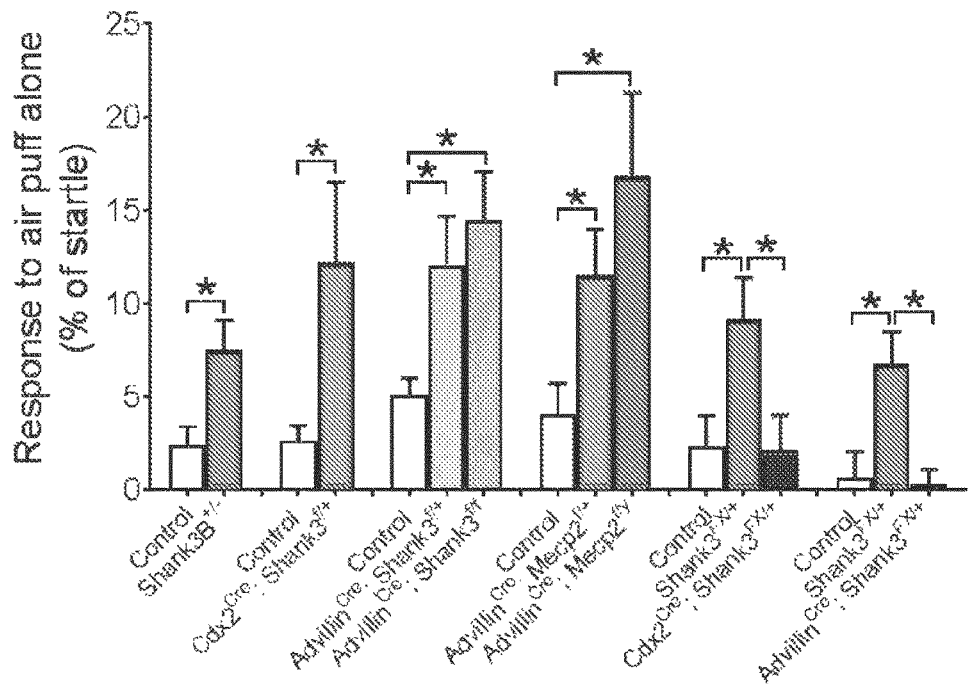
FIG. 15B: Response to a light air puff stimulus alone directed to the back hairy skin. Responses are expressed as percent of startle response to a 125 dB noise. Student's unpaired t-test or one-way ANOVA with post-hoc Tukey's test, *, p<0.05.
Figure 15C:
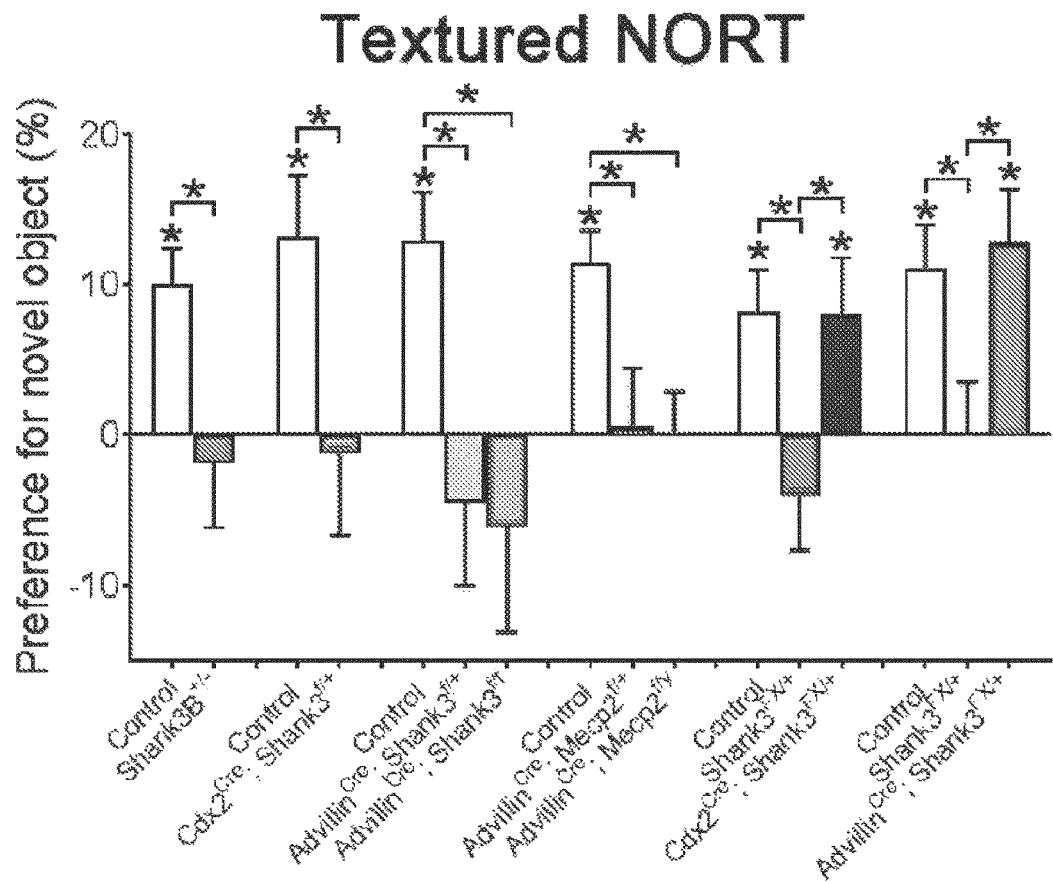
FIG. 15C: Texture discrimination was measured using the textured NORT behavioral assay. A positive value indicates preference for the novel object, compared to the familiar object. Student's unpaired t-test or one-way ANOVA with post-hoc Tukey's test, *, p<0.05.
Figure 15D:
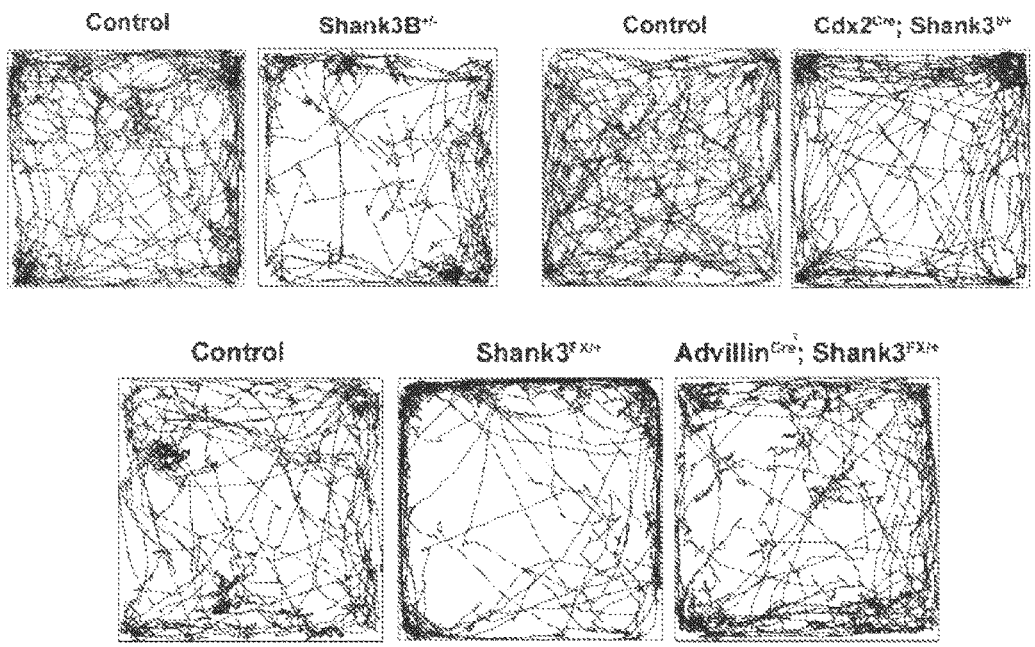
FIG. 15D: Open field (OF) test was used as a general measure of exploration and anxiety-like behavior. Shown are representative activity traces in the OF test for mutant mice and control littermates.
Figure 15E:
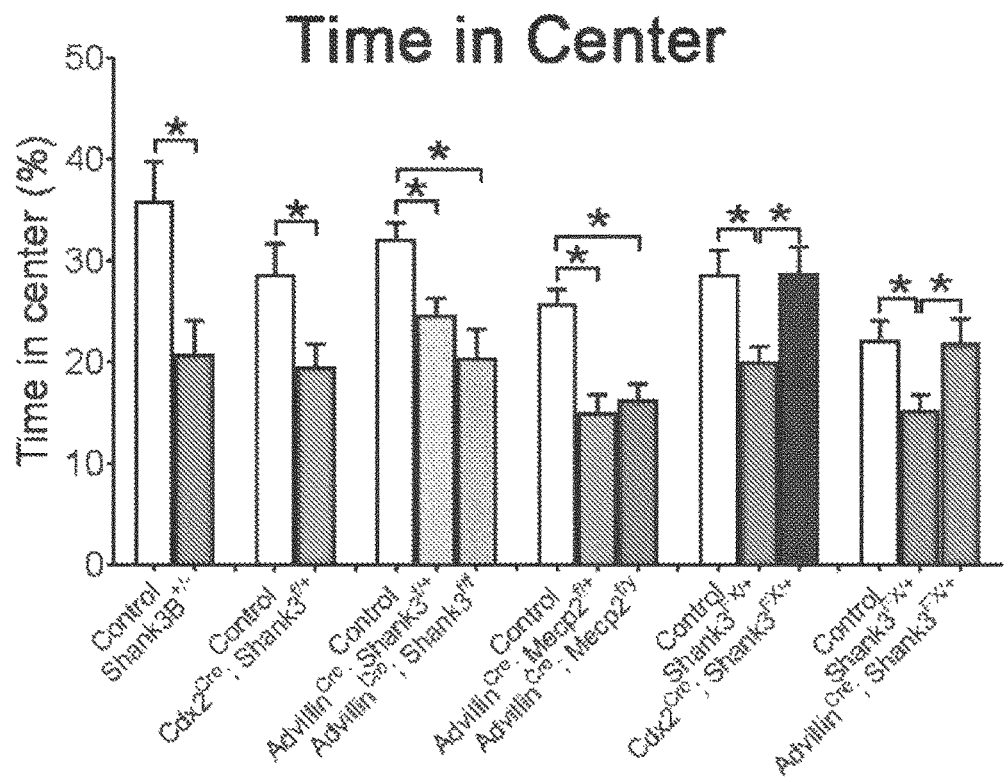
FIG. 15E: Percent time spent in the center of the OF chamber. Student's unpaired t-test or one-way ANOVA with post-hoc Tukey's test, *, p<0.05.
Figure 15F:
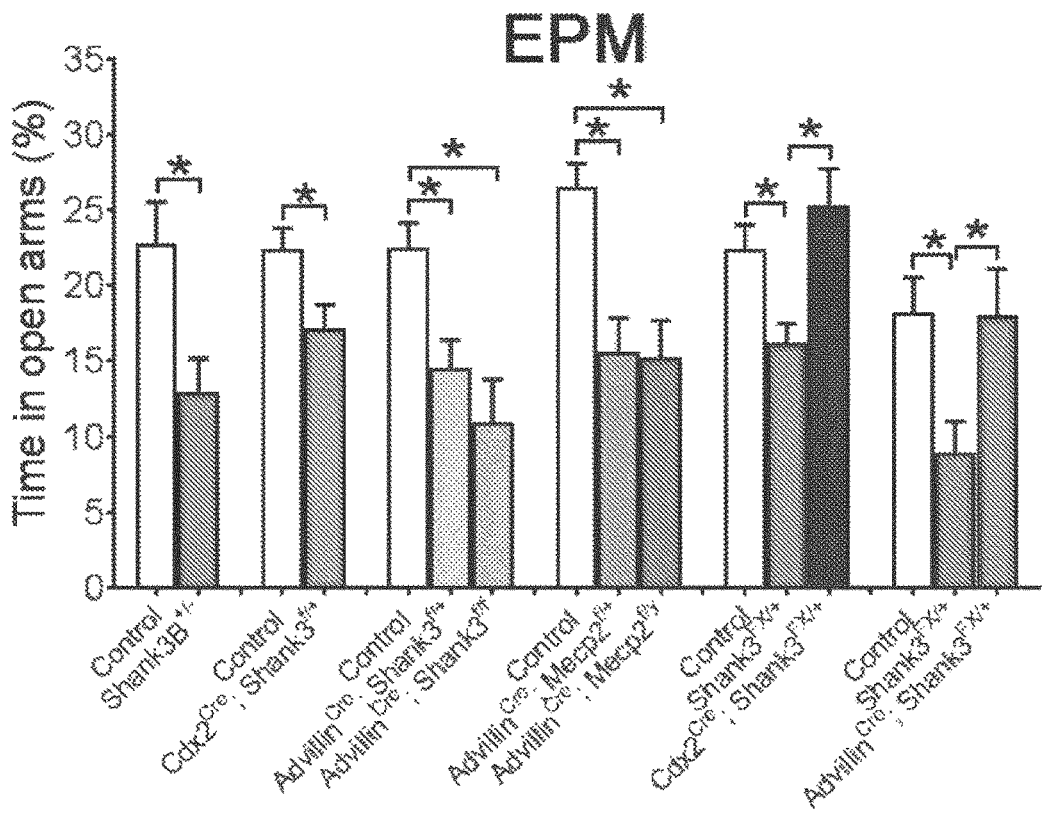
FIG. 15F: Percent time spent in the open arms of the EPM. Student's unpaired t-test or one-way ANOVA with post-hoc Tukey's test, *, p<0.05.
Figure 15G:
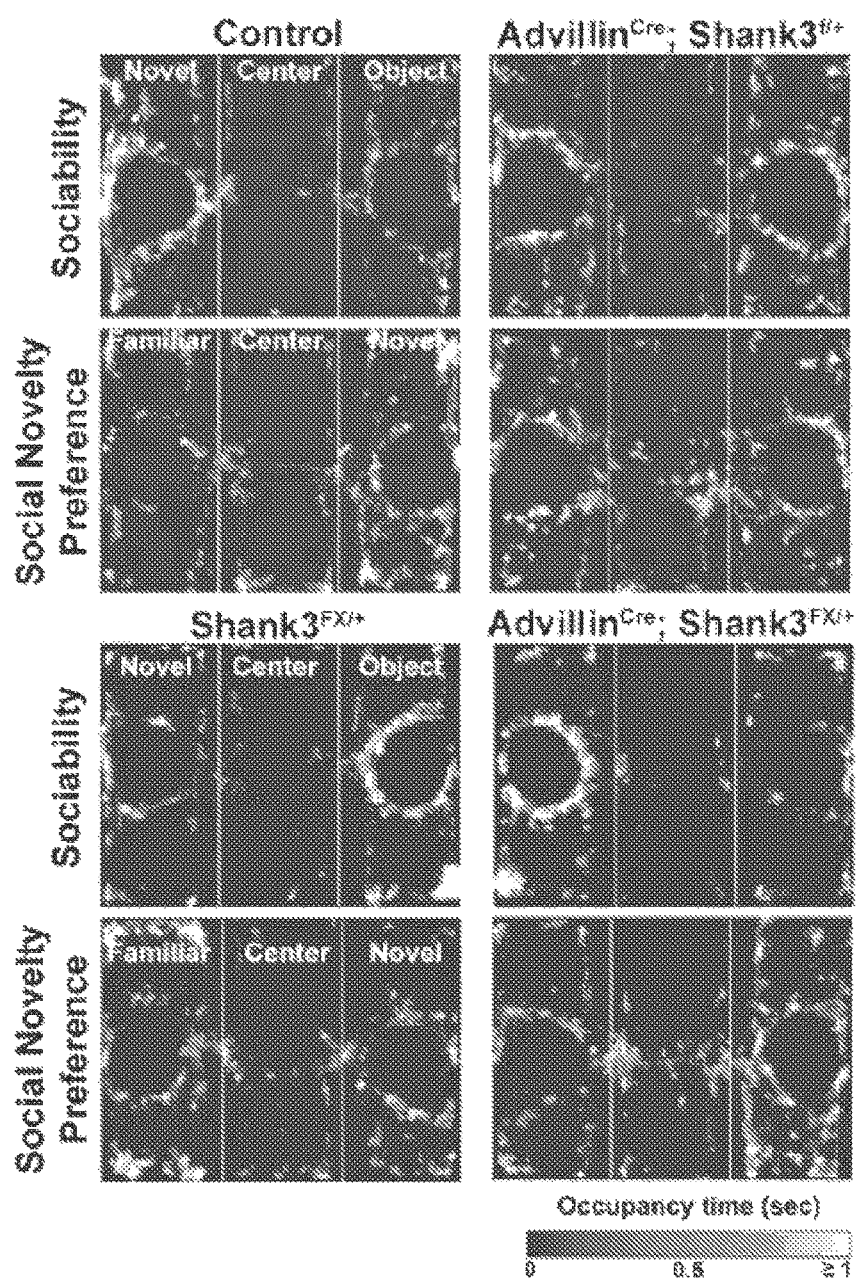
FIG. 15G: Representative heat maps of activity in the 3-chamber social interaction test during the "Sociability" (top panels) and "Social Novelty Preference" (bottom panels) portions of the assay, for mutant mice and control littermates.
Figure 15H:
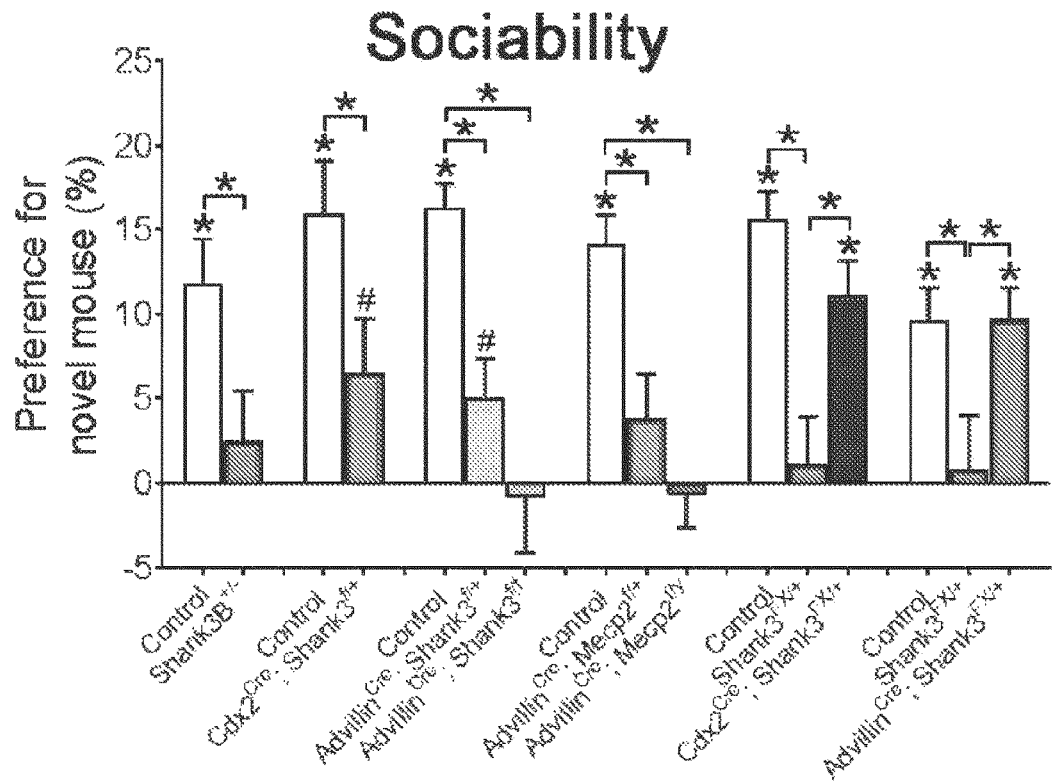
FIG. 15H: Preference index for the percentage of time spent investigating the novel mouse in the "Sociability" portion of the 3-chamber social interaction test. Student's unpaired t-test or one-way ANOVA with post-hoc Tukey's test, *, p<0.05.
Figure 15I:
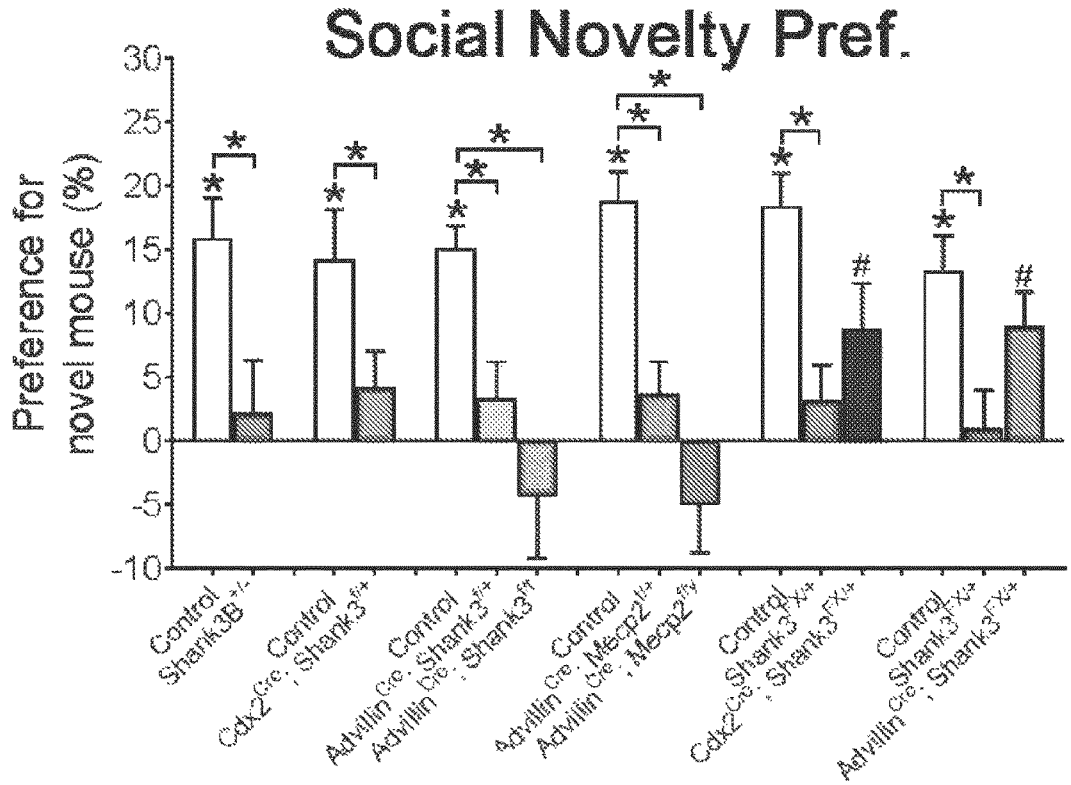
FIG. 15I: Preference index for the percentage of time spent investigating a novel mouse in the "Social Novelty Recognition" portion of the 3-chamber social interaction test. Student's unpaired t-test or one-way ANOVA with post-hoc Tukey's test, *, p<0.05.
Figure 15J:
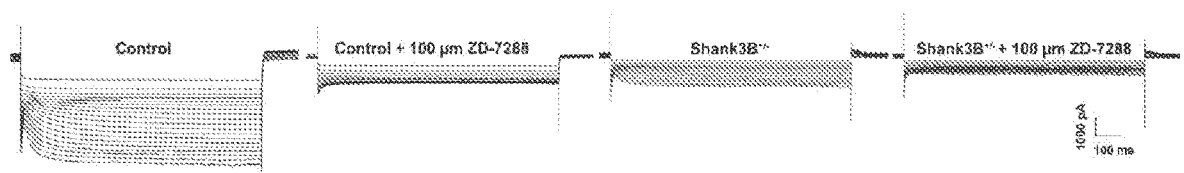
FIG. 15J: Representative electrophysiological traces showing I$_h$ during a hyperpolarizing voltage step protocol in large diameter DRG neurons cultured control and Shank3B$^{+/-}$ mutant mice, with and without a selective HCN-channel blocker, ZD-7288.
Figure 15K:
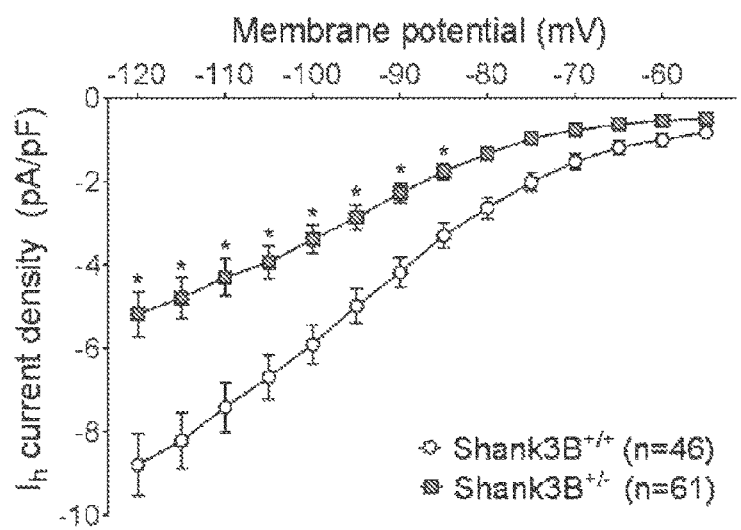
FIG. 15K: Quantification of I$_h$ density at each voltage step for large diameter neurons cultured from DRGs of control and mutant mice. Two-way ANOVA with post-hoc Sidak's test, *, p<0.05.
Figure 15L:
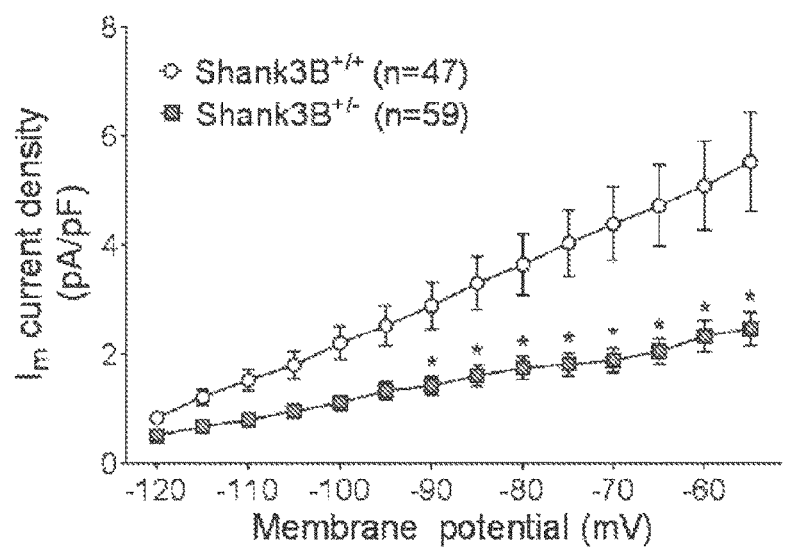
FIG. 15L: Quantification of I$_m$ density at each voltage step for large diameter neurons cultured from DRGs of control and mutant mice. Two-way ANOVA with post-hoc Sidak's test, *, p<0.05.
Figure 15M:
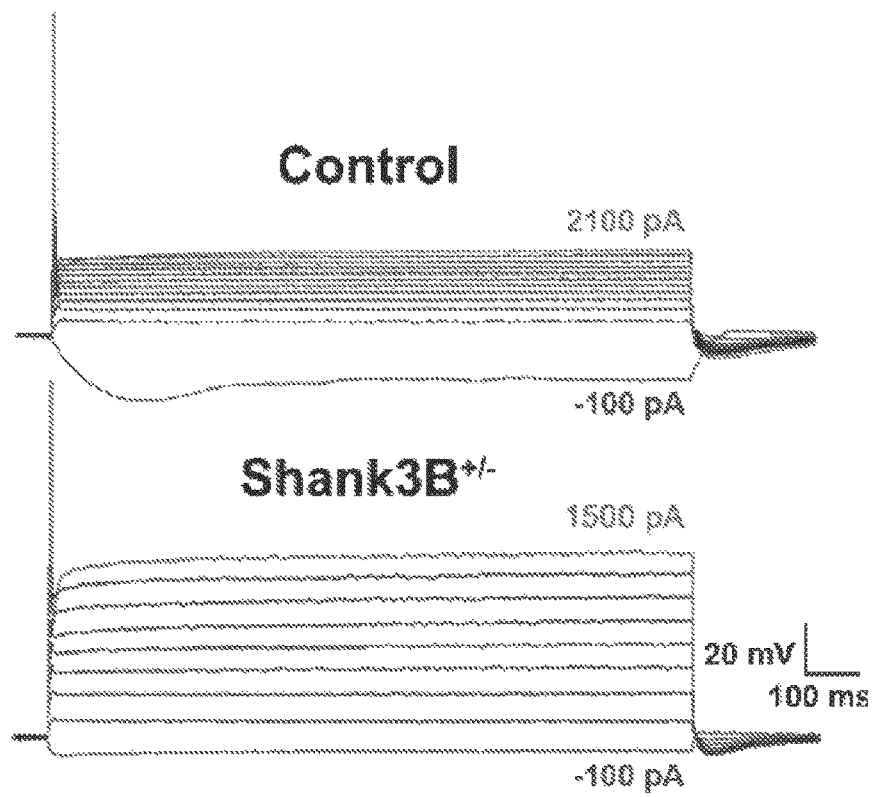
FIG. 15M: Representative traces from large diameter DRG neurons cultured from control and Shank3B$^{+/-}$ mutant mice during whole cell current clamp recordings, in which the minimal amount of current required to elicit an action potential in each neuron (rheobase, $R_h$), was determined.
Figure 15N:
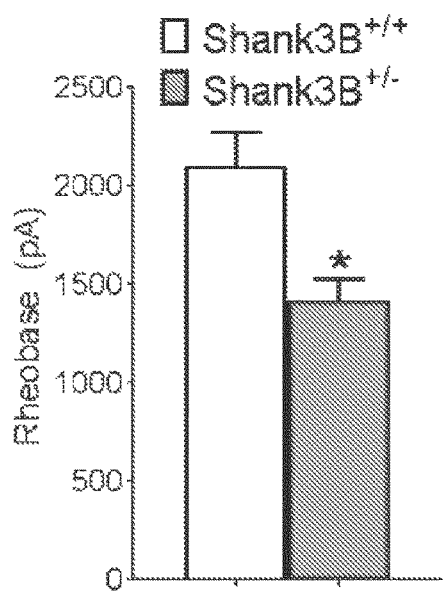
Figure 22A:
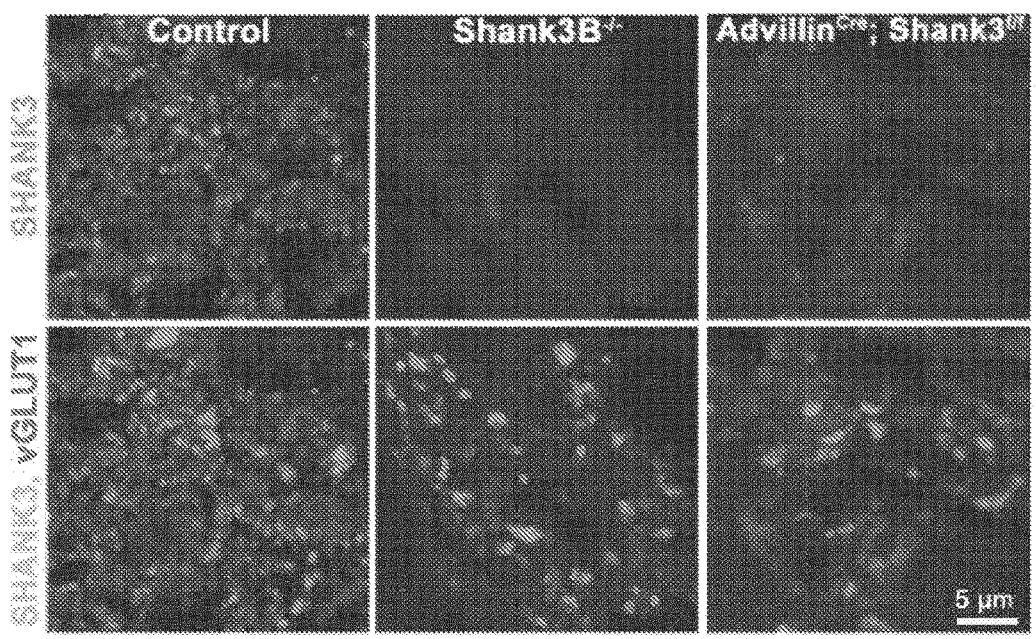
FIGS. 22A-22R are related to FIGS. 15A-15N.
Figure 22B:
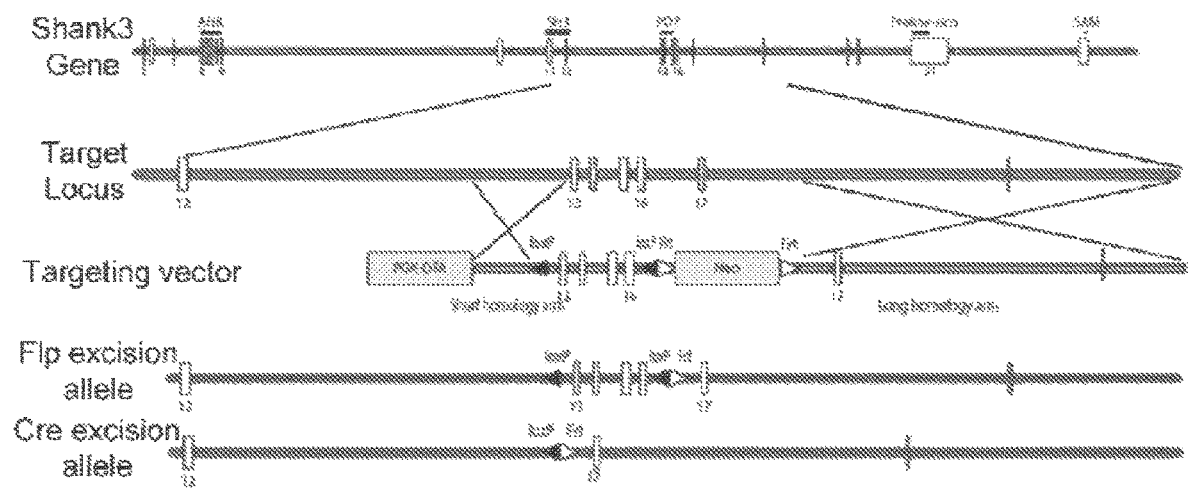
FIG. 22B: Schematic describing strategy to create Shank3B conditional knockout (Shank3$^f$) mouse. Mice containing targeted allele were crossed to Flp mice to remove the Neo cassette and β-Actin$^{Cre}$ mice to excise Exons 13-16.
Figure 22C:
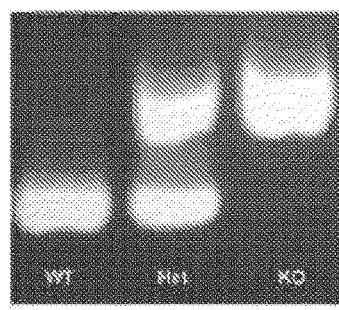
FIG. 22C: PCR genotyping confirms successful deletion of Exons 13-16 from genome of Shank3$^f$.
Figure 22D:
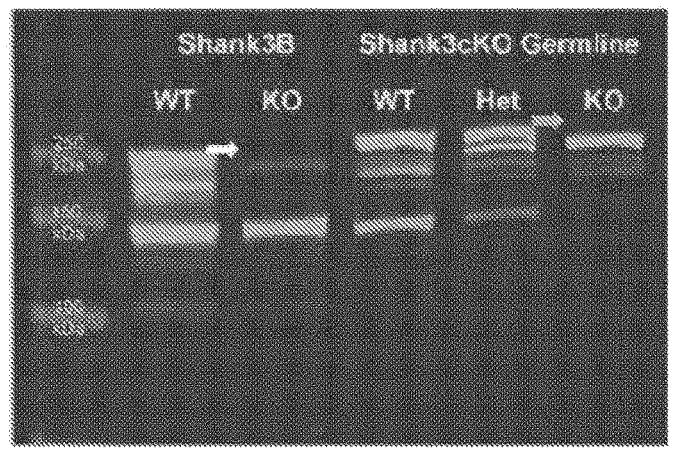
FIG. 22D: Western blot of whole brain lysates from Shank3B$^{-/-}$ and β-Actin$^{Cre}$; Shank3$^f$ mice shows deletion of protein products from full-length isoform (white arrows).
Figure 22E:
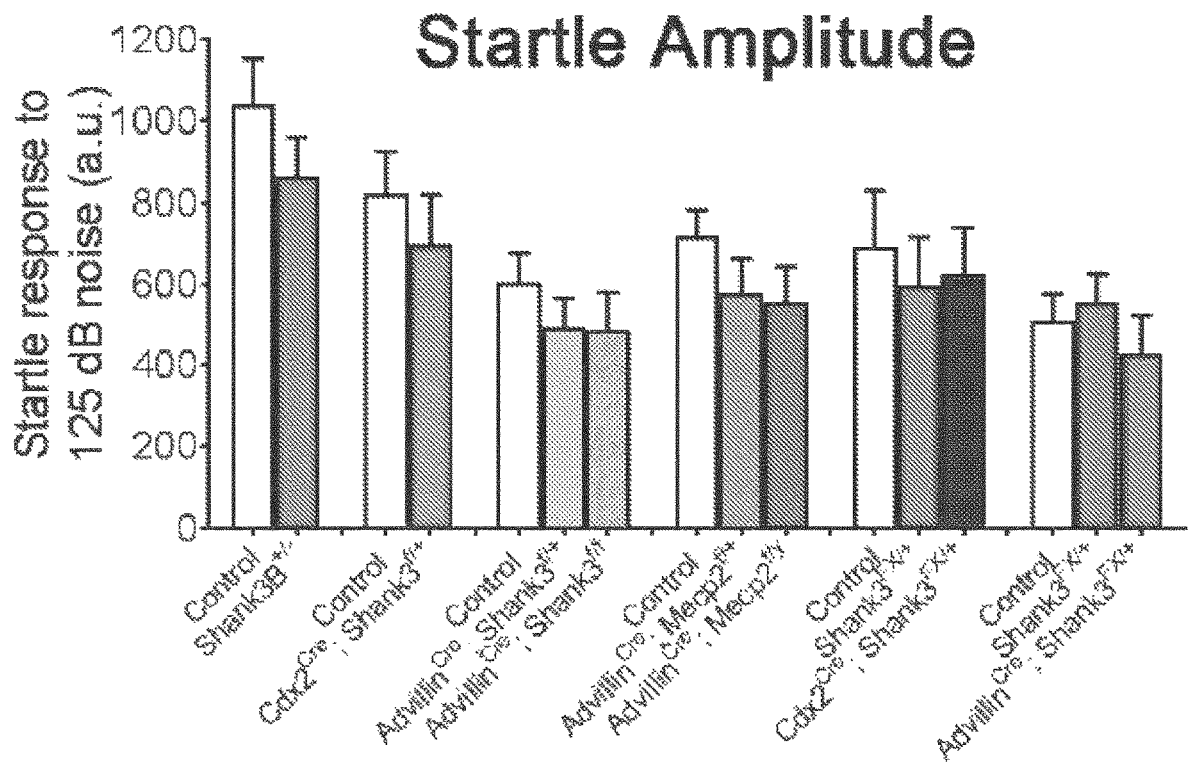
FIG. 22E: Magnitude of startle response to a 125 dB noise in mutant mice and control littermates.
Figure 22F:
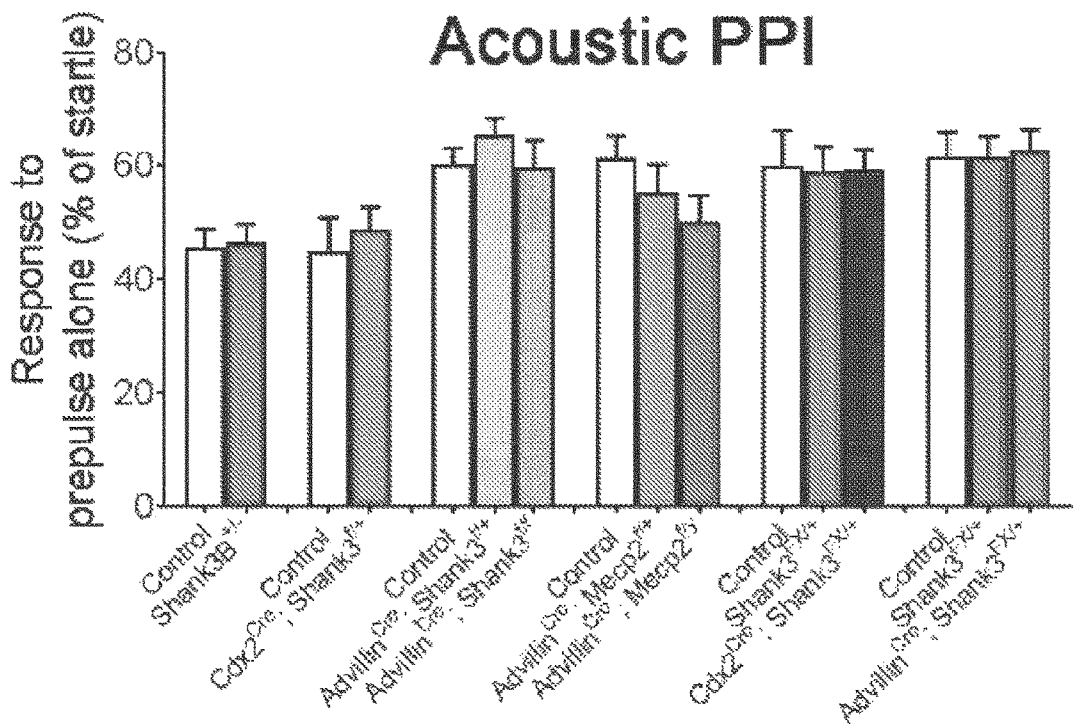
FIG. 22F: Percent inhibition of the startle response to a 125 dB noise (pulse), when the startle noise is preceded by tone prepulse (80 dB, 'acoustic PPI') in mutant mice and control littermates.
Figure 22G:
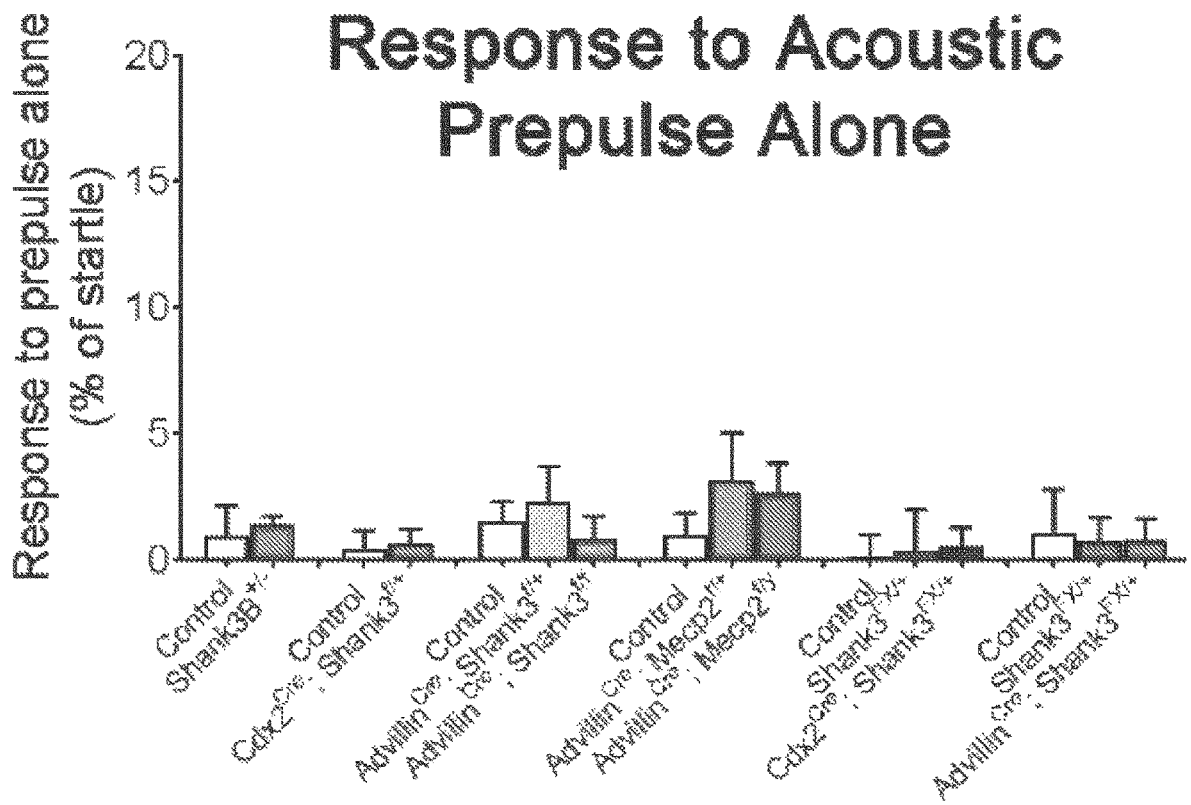
FIG. 22G: Response to a non-startling acoustic noise (80 dB, 20 ms), mutant mice and their control littermates. Responses are expressed as percent of startle response to a 125 dB startle noise.
Figure 22H:
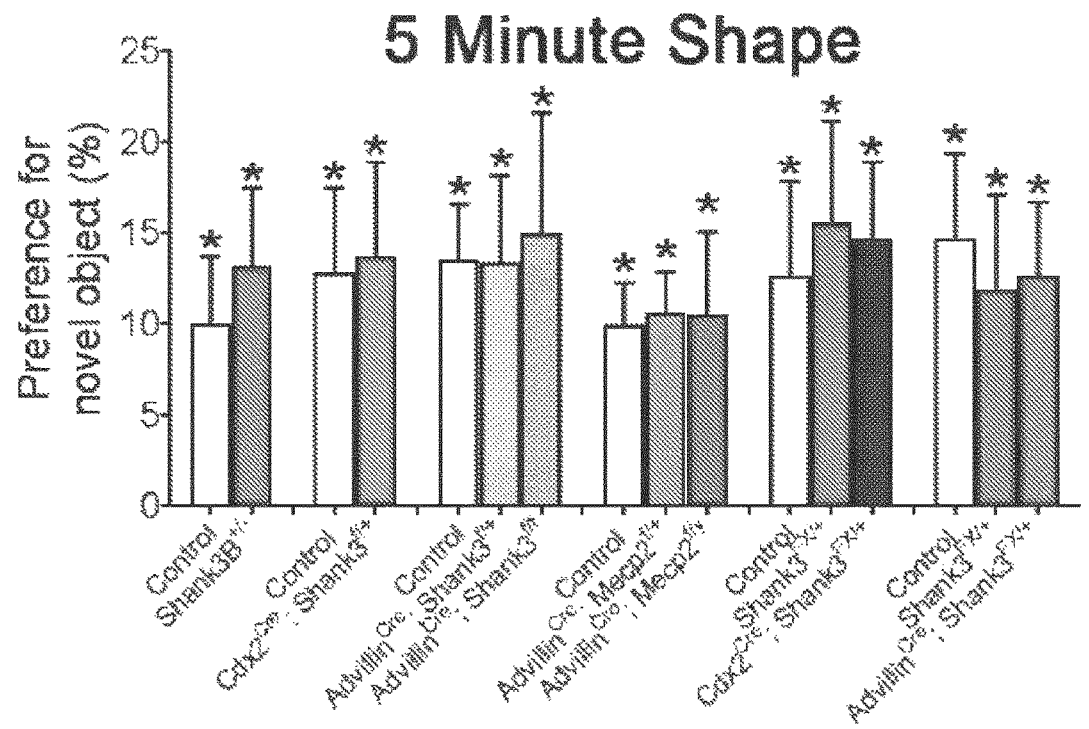
FIG. 22H: Discrimination index for 5-minute NORT.

It was previously found that Mecp2 and Gabrb3 function in peripheral somatosensory neurons for normal tactile behaviors (Orefice et al., 2016), however the extent to which dysfunction of PNS neurons contributes to altered somatosensation in other genetic models of ASD is not known. Mice with a germline loss-of-function mutation in Shank3 ($Shank3B^{+/-}$), which in humans causes Phelan-McDermid syndrome (Phelan and McDermid, 2012), a disorder characterized by severe intellectual disability and often accompanied by autism, also exhibit tactile over-reactivity (Orefice et al., 2016). SHANK5 is a synaptic protein that is expressed in both mouse and human DRG neurons (Ray et al., 2018; Usoskin et al., 2015), including at the presynaptic terminals of LTMRs responsible for transmitting light touch information to the spinal cord dorsal horn (FIG. 22A). Therefore, it was asked whether peripheral mechanosensory neuron dysfunction in Shank3 mutant mice underlies abnormal innocuous touch behaviors. To address this, a mouse line harboring a Shank3 floxed ($Shank3^{floxed}$) allele was generated (FIGS. 22A-22D) to enable selective ablation of Shank3 in cells expressing Cre recombinase. $Shank3^f$ mice were crossed with mice expressing Cre recombinase below cervical level 2 [$Cdx2^{Cre}$; $Shank3^{f/+}$; (Akyol et al., 2008)] or all DRG, trigeminal and sympathetic ganglia neurons [$Advillin^{Cre}$; $Shank3^{f/+ \text{ or } f/f}$; (Hasegawa et al., 2007) FIG. 22A]. $Cdx2^{Cre}$; $Shank3^{f/+}$, $Advillin^{Cre}$; $Shank3^{f/+}$, or $Advillin^{Cre}$; $Shank3^{f/+}$ conditional mutants as well as mice with heterozygous germline Shank3 deletion ($Shank3B^{+/-}$) and, for comparison, sensory-neuron specific deletion of Mecp2 ($Advillin^{Cre}$; $Mecp2^{f/+ \text{ or } f/y}$) and control littermates, were subjected to a battery of behavioral assays to assess tactile sensitivity and ASD-related behaviors. Consistent with previous findings, Shank3B$^{+/-}$, Advillin$^{Cre}$; Mecp2$^{f/+}$, and Advillin$^{Cre}$; Mecp2$^{f/y}$ mutant mice all exhibited hairy skin hypersensitivity as measured by a tactile PPI assay and responsivity to an air puff stimulus alone delivered to back hairy skin [FIGS. 15A-15B; (Orefice et al., 2016)]. Shank3B$^{+/-}$, Advillin$^{Cre}$; Mecp2$^{f/+}$, and Advillin$^{Cre}$; Mecp2$^{f/y}$ mutant mice also displayed deficits in texture discrimination, assessed using a paw, glabrous skin textured novel object recognition test ["textured NORT", FIG. 15C, (Orefice et al., 2016)]. Interestingly, loss of Shank3 in cells below the neck (Cdx2$^{Cre}$; Shank3$^{f/+}$) or in peripheral sensory neurons (Advillin$^{Cre}$; Shank3$^{f/+}$ or Advillin$^{Cre}$; Shank3$^{f/f}$) also led to an increase in tactile PPI performance, increased responsivity to an air puff stimulus, and deficits in textured discrimination (FIGS. 15A-15C). Cdx2$^{Cre}$; Shank3$^{f/+}$, Advillin$^{Cre}$; Shank3$^{f/+}$ and Advillin$^{Cre}$; Shank3$^{f/f}$ mutant mice were grossly normal, however, as no differences in gross motor behaviors, acoustic PPI, novelty seeking behavior, memory retention or exploratory drive were observed among any of the groups (FIGS. 22E-22J).

Figure 22I:
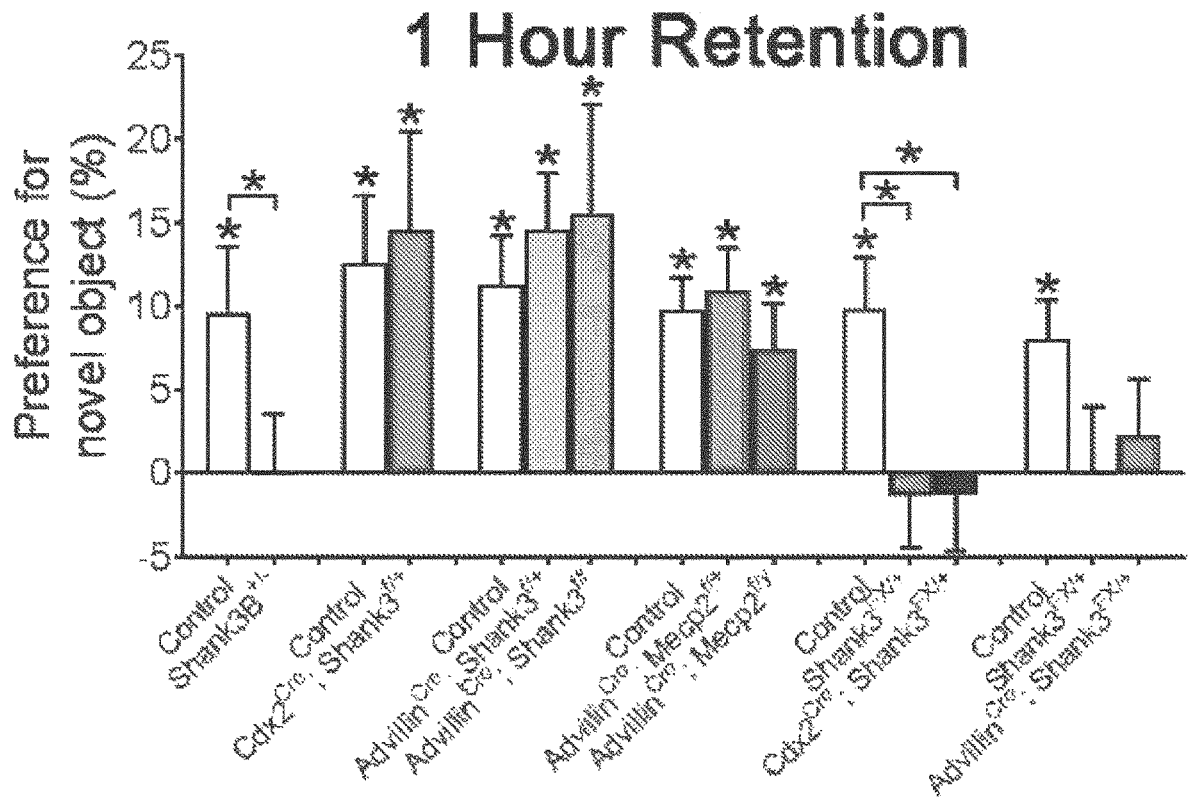
FIG. 22I: Discrimination index for 1-hour NORT. Student's unpaired t-test or one-way ANOVA with post-hoc Tukey's test, *, p<0.05.
Figure 22J:
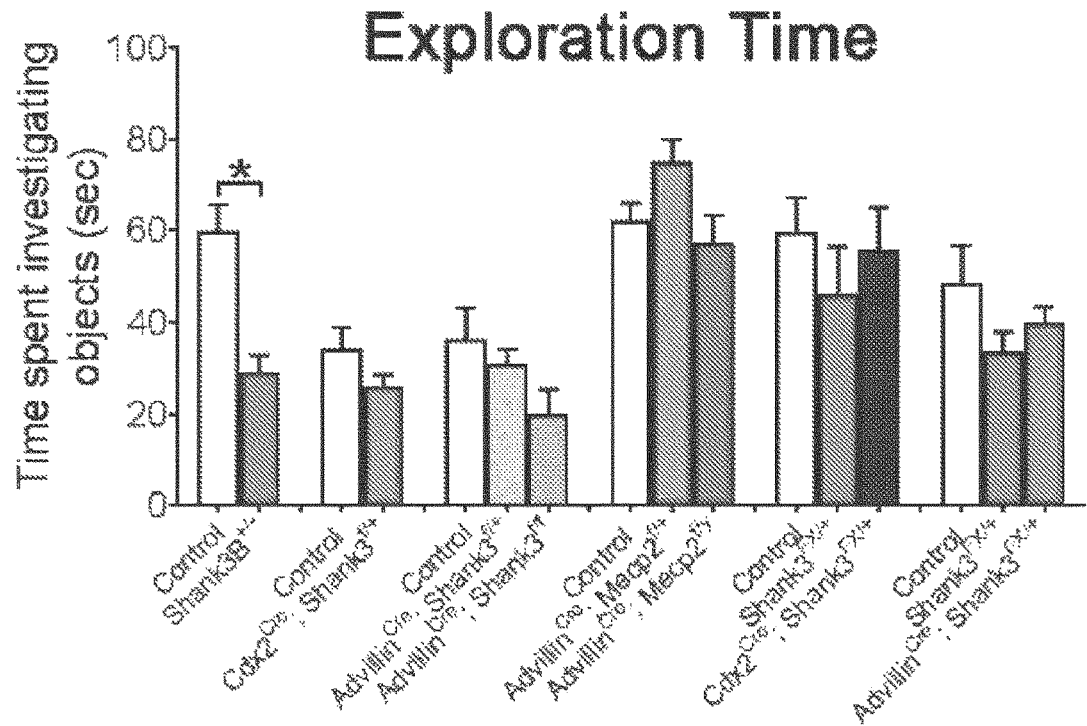
FIG. 22J: Average amount of time (seconds) spent physically interacting with both the familiar and novel object in the NOR tests in mutant mice and their control littermates.
Figure 22K:
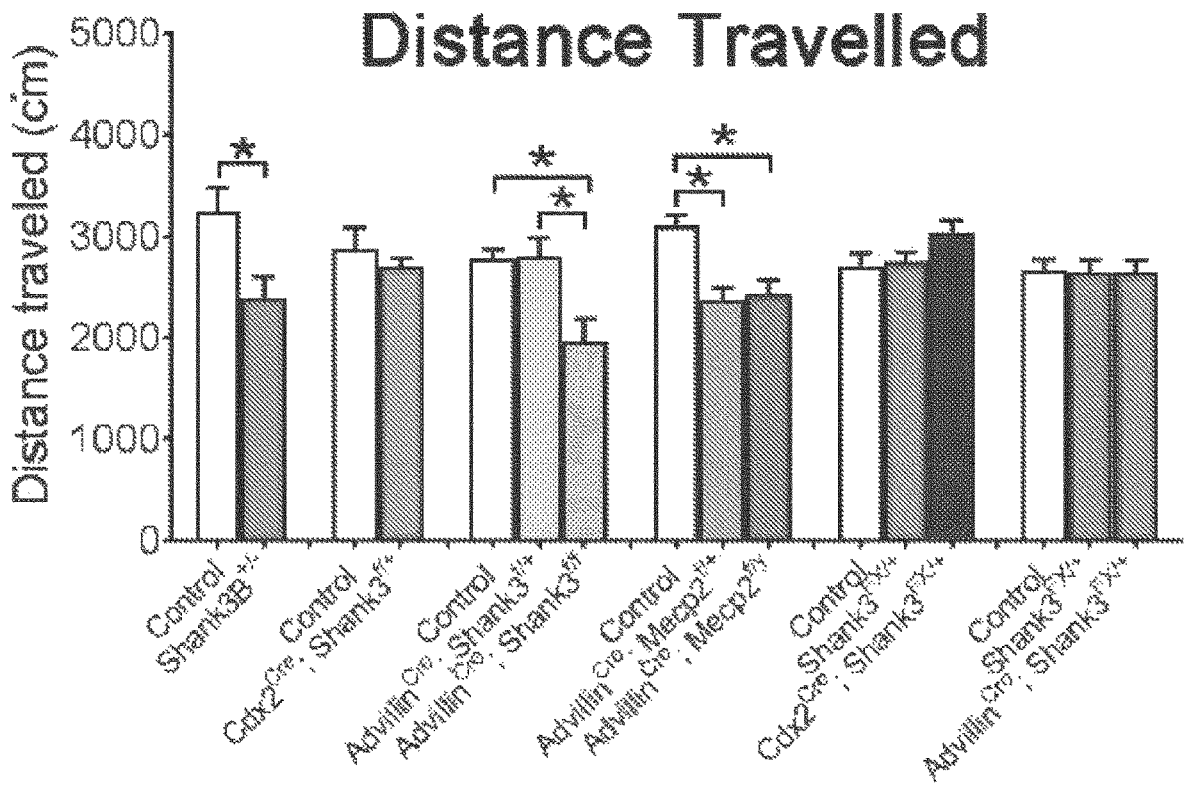
FIG. 22K: Average total distance traveled in the open field chamber for mutant mice and their control littermates. Student's unpaired t-test or one-way ANOVA with post-hoc Tukey's test, *, p<0.05.
Figure 22L:
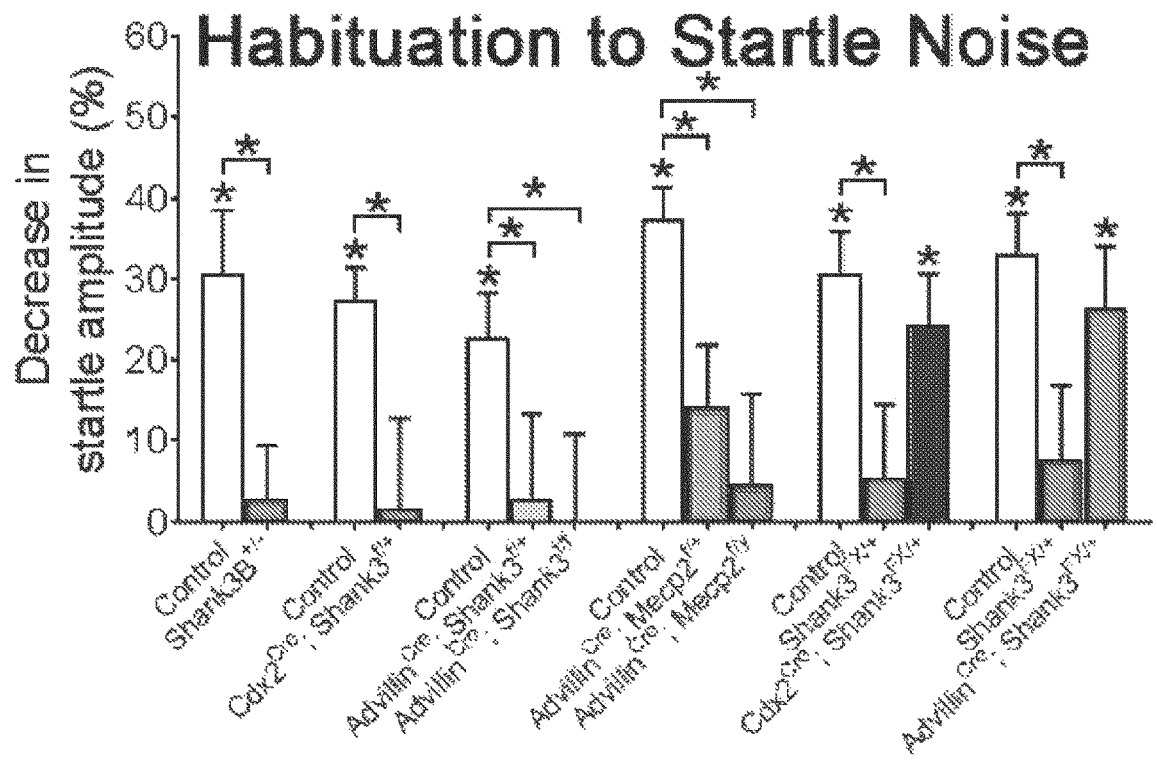
FIG. 22L: Percent decrease in startle response to a 125 dB noise during a 30-minute tactile PPI session, when comparing the first five startle responses to the last five responses to a 125 dB noise for mutant mice and their control littermates. Student's unpaired t-test or one-way ANOVA with post-hoc Tukey's test, *, p<0.05.
Figure 22M:
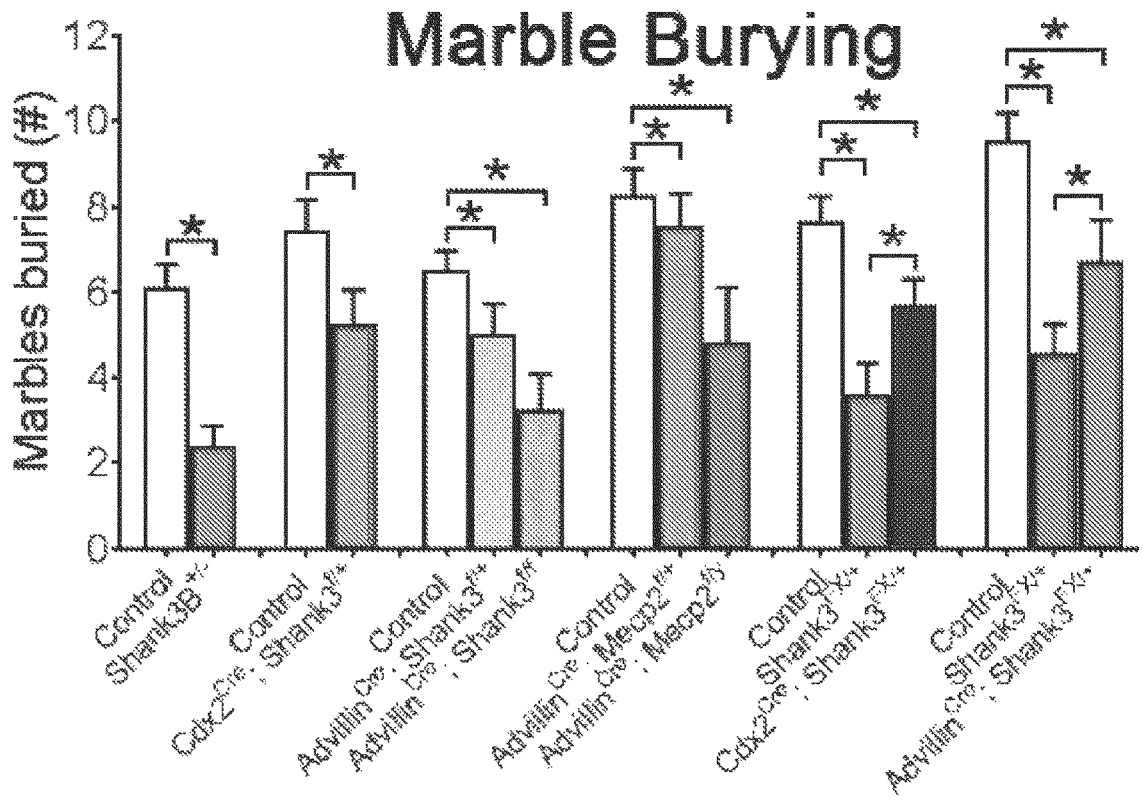
FIG. 22M: Average number of marbles buried (out of 12) during a twenty-minute assay for mutant mice and their control littermates. Student's unpaired t-test or one-way ANOVA with post-hoc Tukey's test, *, p<0.05.
Figure 22N:
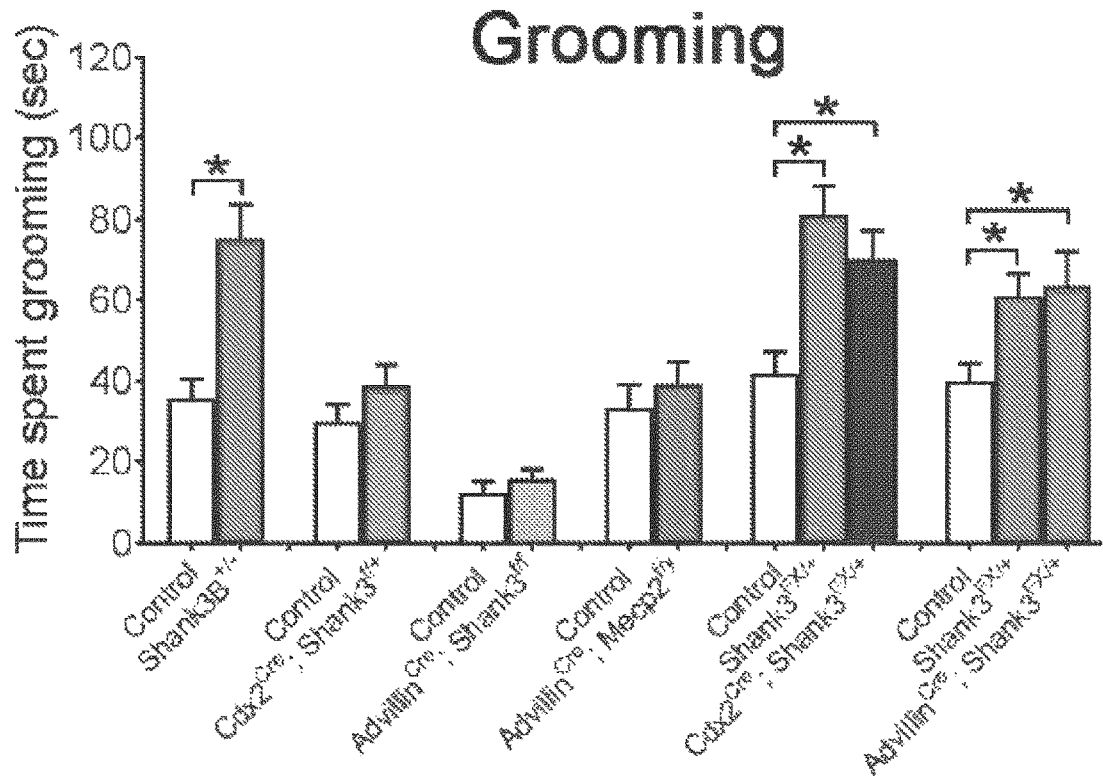
FIG. 22N: Average amount of time spent grooming during a 10-minute open field assessment for mutant mice and their control littermates. Student's unpaired t-test or one-way ANOVA with post-hoc Tukey's test, *, p<0.05.

Concomitant with altered reactivity to tactile stimuli, mice in which either Mecp2 or Gabrb3 was ablated in peripheral somatosensory neurons during embryonic development exhibited increased anxiety-like behaviors and abnormal social behaviors in adulthood [FIGS. 15D-15F, 22K, 22L; (Orefice et al., 2016)]. Therefore, it was hypothesized that altered tactile processing due to loss of Shank3 in peripheral sensory neurons during development may also contribute to anxiety-like behaviors and abnormal social behaviors in adult mice. Consistent with prior findings, Shank3B$^{+/-}$ mice displayed anxiety-like behaviors in the open field test, elevated plus maze (EPM) and lack of habituation to an acoustic startle noise (Peca et al., 2011), (FIGS. 15F-15H, 22K, 22L). Similarly, Cdx2$^{Cre}$; Shank3$^{f/+}$, Advillin$^{Cre}$ Shank3$^{f/+}$ and Advillin$^{Cre}$ Shank3$^{f/f}$ mutant mice also exhibited a decreased amount of time spent in the center of an open field chamber, less time in the open arms of the EPM, and did not habituate to an acoustic startle noise over 30 minutes (FIGS. 15D-15F, 22L). Advillin$^{Cre}$; Shank3$^{f/f}$ mice also showed a decrease in the total distance traveled in the open field chamber (FIG. 22K). Abnormal social interactions, neophobia, and overgrooming behaviors are additional characteristic features of Shank3B$^{+/-}$ mutant mice (Peca et al., 2011) (Jaramillo et al., 2017) and therefore these behaviors were also assessed in Shank3 conditional mutants. The three-chamber social interaction test was implemented to assess sociability and social novelty recognition preference in the conditional mutants (Silverman et al., 2010). Similar to Shank3B$^{+/-}$ mice, Cdx2$^{Cre}$; Shank3$^{f/+}$, Advillin$^{Cre}$ Shank3$^{f/+}$ and Advillin$^{Cre}$ Shank3$^{f/f}$ mice did not show a preference for a novel mouse in either the sociability or social novelty recognition portion of the test, although Cdx2$^{Cre}$; Shank3$^{f/+}$ and Advillin$^{Cre}$; Shank3$^{f/+}$ (heterozygous) mutants did exhibit a trend towards preference in the sociability assay (FIGS. 15G-15I, 29). Neophobia was assessed using a marble burying task. Shank3$^{+/-}$ mice exhibited severe neophobia, evidenced by a decreased number of marbles buried compared to controls, as previously reported (Jaramillo et al., 2017), (FIG. 22M). A modest decrease in the number of marbles buried was observed in Cdx2$^{Cre}$; Shank3$^{f/}$, Advillin$^{Cre}$; Shank3$^{f/+}$ and Advillin$^{Cre}$; Shank3$^{f/f}$ mutant mice (FIG. 22M) compared to control littermates. Finally, while Shank3B$^{+/-}$ mutants display a profound overgrooming behavior, grooming behavior was normal in Cdx2$^{Cre}$; Shank3$^{f/+}$, Advillin$^{Cre}$; Shank3$^{f/+}$, and Advillin$^{Cre}$; Shank3$^{f/f}$ mice (FIG. 22N). These findings indicate that a subset of behavioral abnormalities observed in Shank3B$^{+/-}$ mice are also observed in mice lacking one or both Shank3 alleles in primary somatosensory neurons.

Figure 22O:
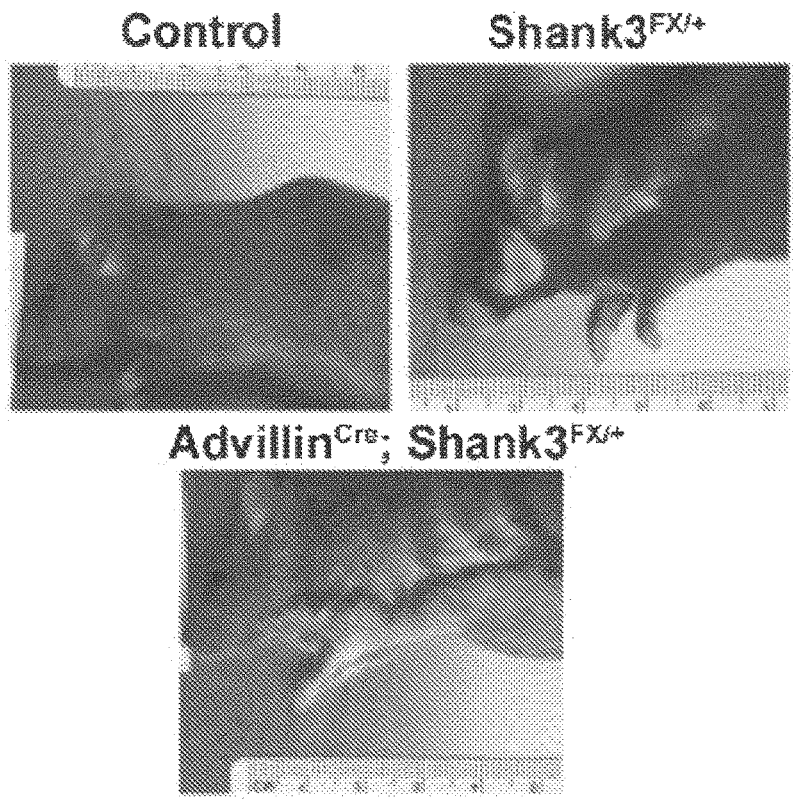
FIG. 22O: Representative images of control, Shank3$^{FX/+}$ and Advillin$^{Cre}$; Shank3$^{FX}$ mice, showing excessive overgrooming and loss of fur in the Shank3$^{FX/+}$ and Advillin$^{Cre}$; Shank3$^{FX}$ mice.
Figure 22P:
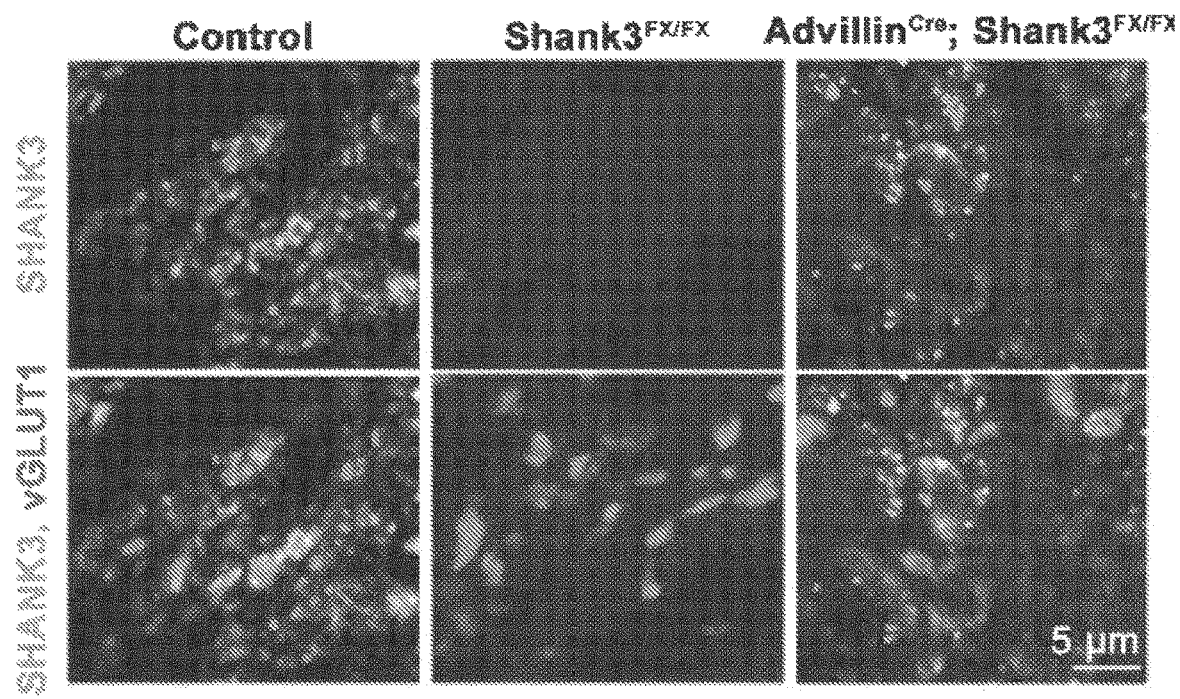
FIG. 22P: IHC images of SC dorsal horn lamina III/IV from control, Shank3B$^{FX/FX}$ or Advillin$^{Cre}$; Shank3$^{FX/+}$ mice, showing SHANKS expression at vGLUT1+ presynaptic terminals.
Figure 22Q:
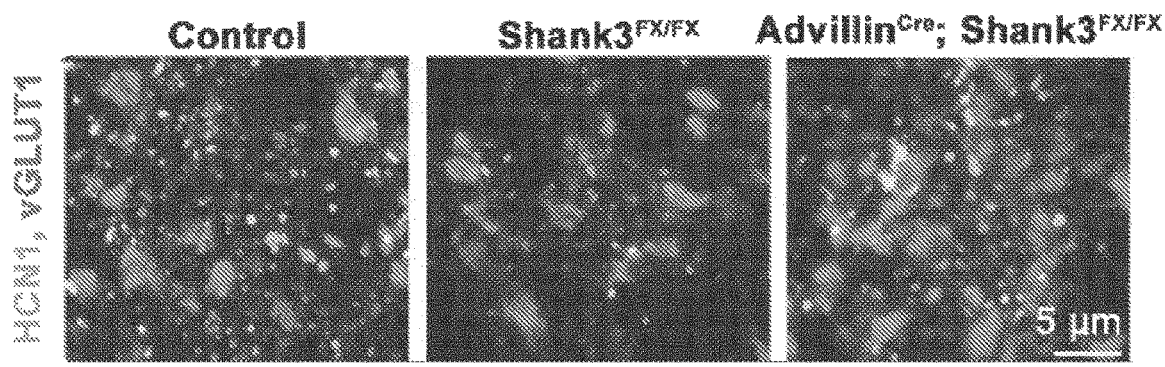
FIG. 22Q: IHC images of SC dorsal horn lamina III/IV from control, Shank3B$^{FX/FX}$ or Advillin$^{Cre}$; Shank3$^{FX/+}$ mice, showing HCN1 expression at vGLUT1+ presynaptic terminals.
Figure 22R:
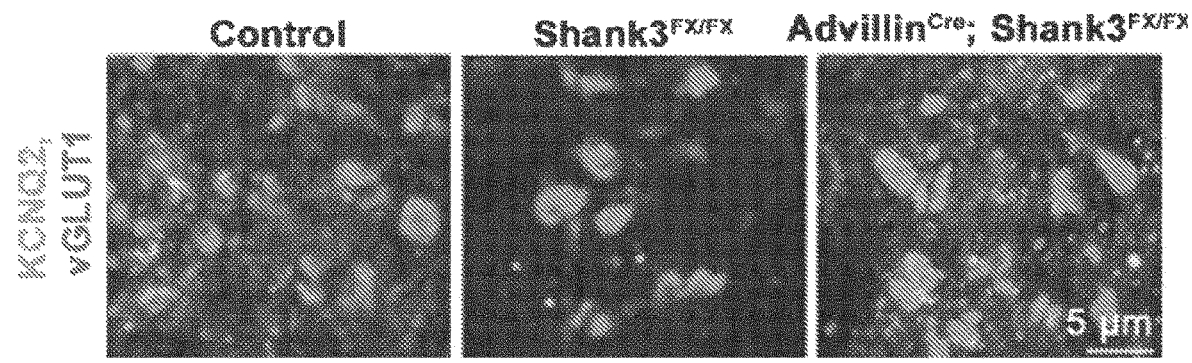
Figure 23A:
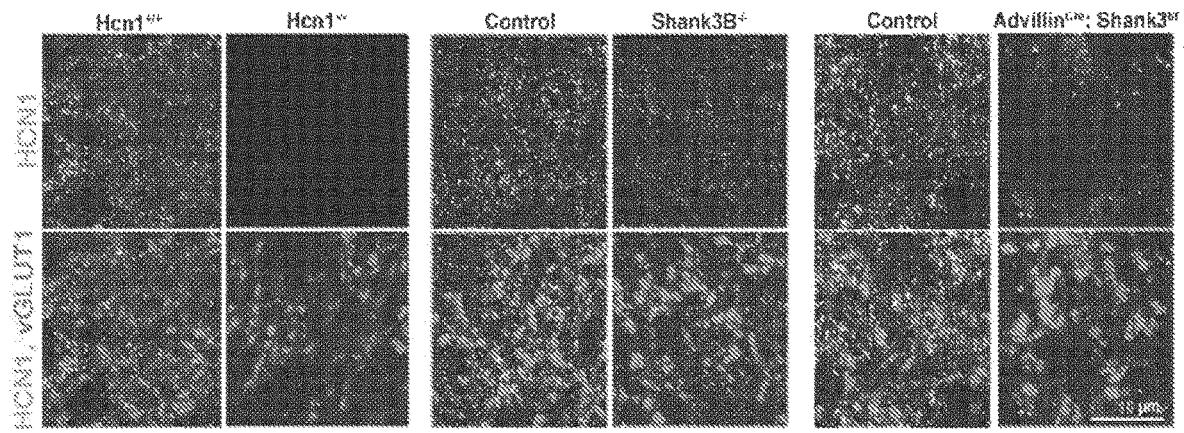
FIGS. 23A-23Z are related to FIGS. 15A-15N.
Figure 23B:
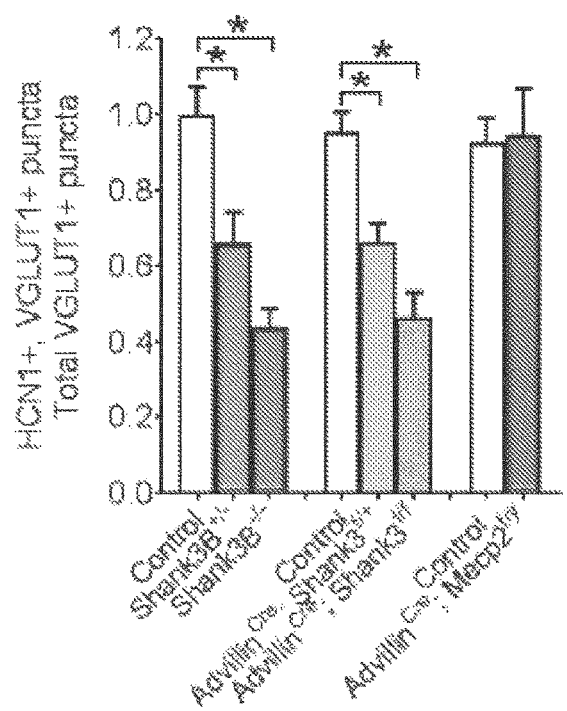
FIG. 23B: Quantification for the number of HCN1 puncta that co-localize with vGLUT1+ puncta in lamina III/IV of the spinal cord dorsal horn of mutants and control littermates. Student's unpaired t-test or one-way ANOVA with post-hoc Tukey's test, *, p<0.05.
Figure 23C:
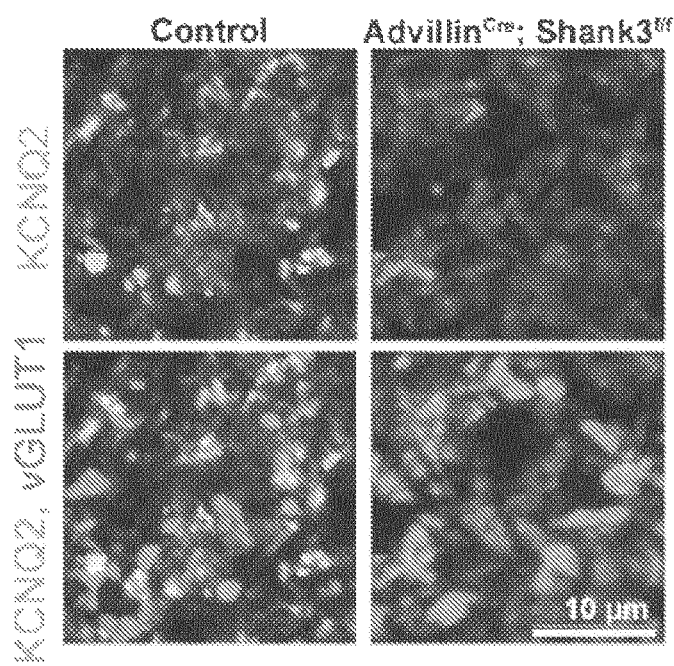
FIG. 23C: IHC images of spinal cord (SC) dorsal horn lamina III/IV from Advillin$^{Cre}$; Shank3$^{f/f}$ mice and their control littermates, showing KCNQ2 expression at vGLUT1+ presynaptic terminals.
Figure 23D:
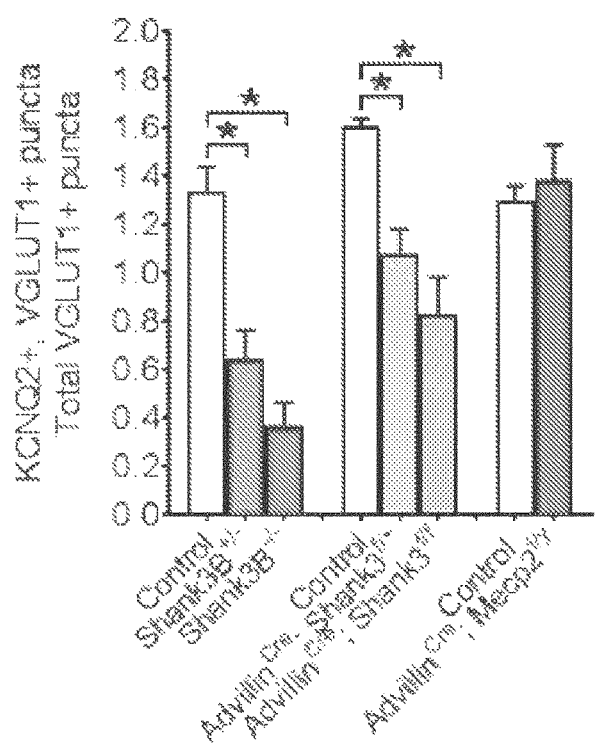
FIG. 23D: Quantification for the number of KCNQ2 puncta that co-localize with vGLUT1+ puncta in lamina III/IV of the spinal cord dorsal horn of mutants and control littermates. Student's unpaired t-test or one-way ANOVA with post-hoc Tukey's test, *, p<0.05.
Figure 23E:
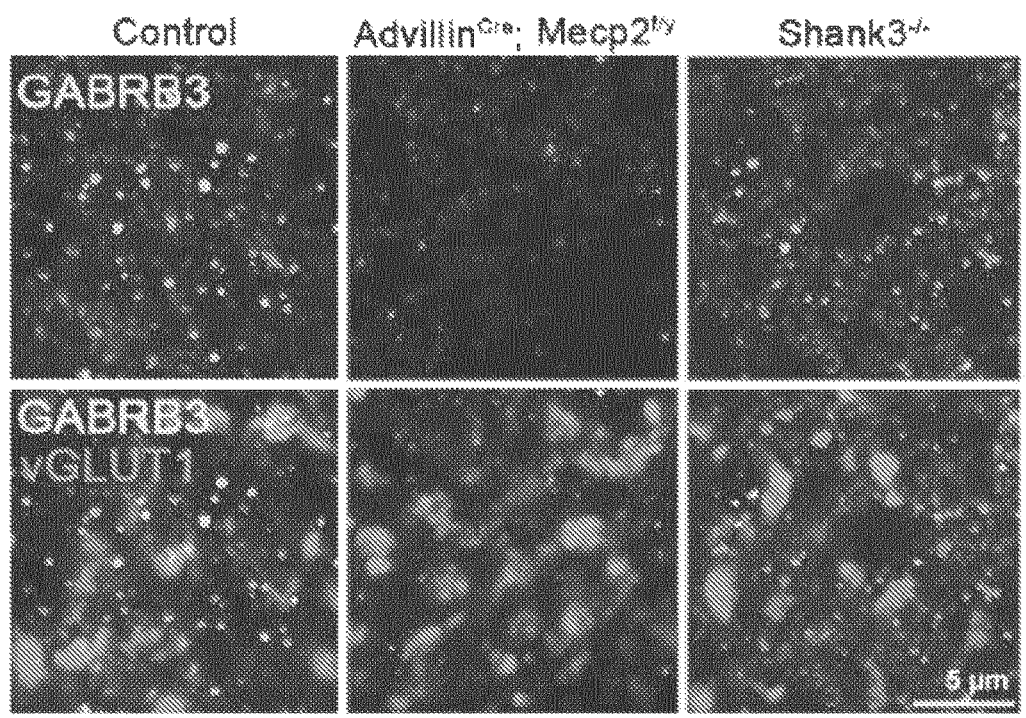
FIG. 23E: IHC images of spinal cord (SC) dorsal horn lamina III/IV from Advillin$^{Cre}$; Mecp2$^{f/y}$ and Shank3$^{-/-}$ mice and their control littermates, showing GABRB3 expression at vGLUT1+ presynaptic terminals.
Figure 23F:
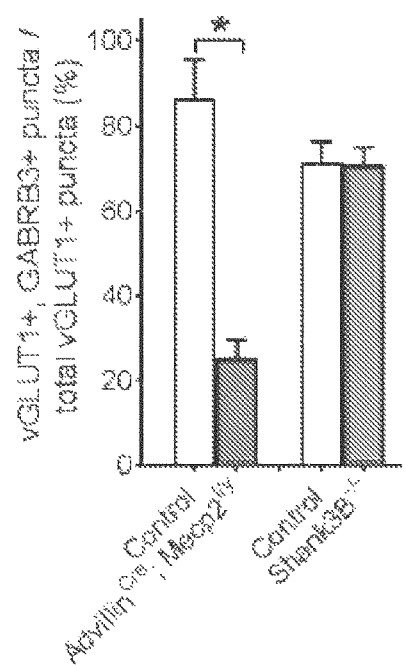
FIG. 23F: Quantification for the number of GABRB3 puncta that co-localize with vGLUT1+ puncta in lamina III/IV of the spinal cord dorsal horn of mutants and control littermates. Student's unpaired t-test, *, p<0.05.
Figure 23G:
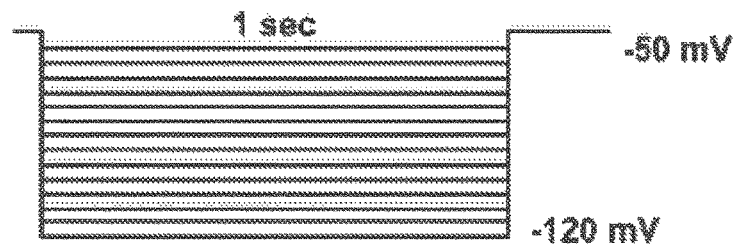
FIG. 23G: Voltage step protocol used to activate HCN channels and elicit $I_h$ during whole-cell voltage clamp recordings.
Figure 23H:
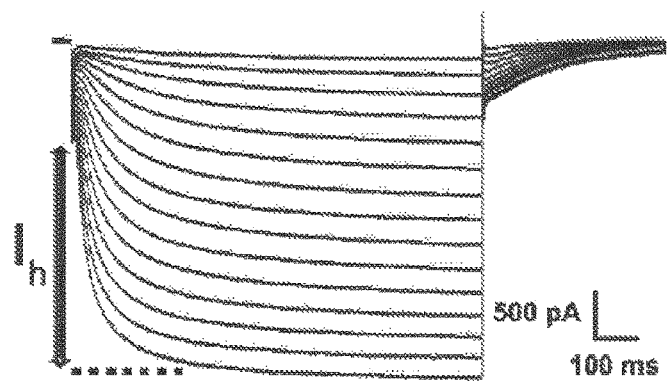
FIG. 23H: Whole-cell voltage clamp trace showing $I_h$ during a hyperpolarizing voltage step protocol in a large diameter neuron cultured from a mouse DRGs, which is blocked following application of 5 mM CsCl$_2$.
Figure 23I:
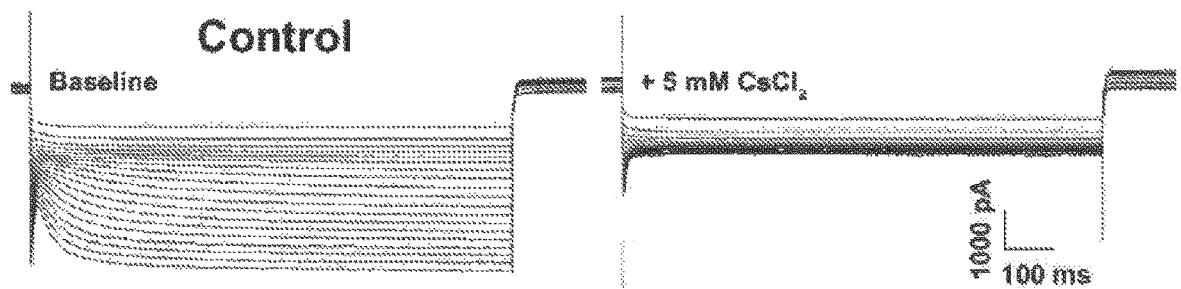
FIGS. 23I-23J: Representative traces from large diameter DRG neurons cultured from a control (FIG. 23I) and Shank3B$^{+/-}$ (FIG. 23J) mice, showing $I_h$ during a hyperpolarizing voltage step protocol.
Figure 23J:
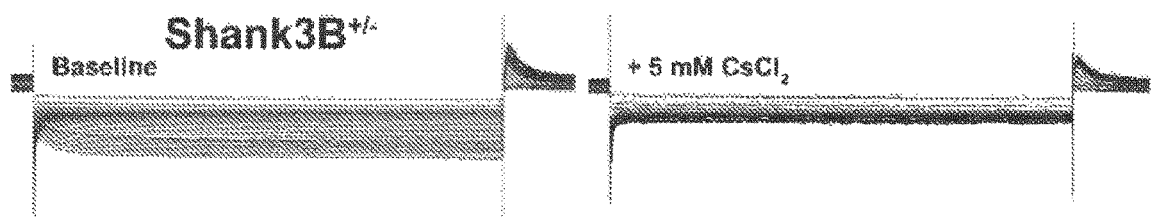
Figure 23K:
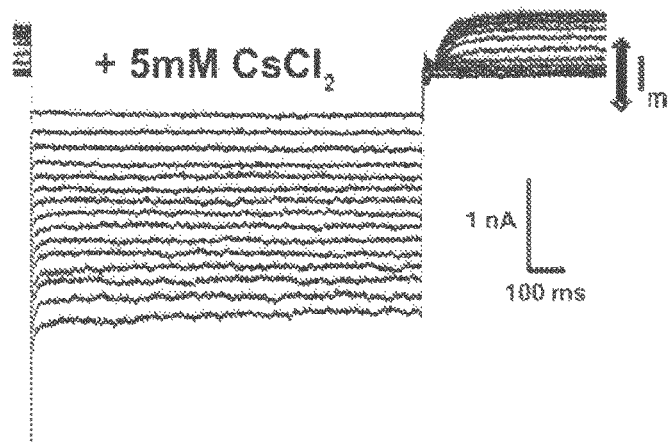
FIG. 23K: Whole-cell voltage clamp trace showing $I_m$ during a hyperpolarizing voltage step protocol in a large diameter neuron cultured from a mouse DRGs, which is evident following application of 5 mM CsCl$_2$.
Figure 23L:
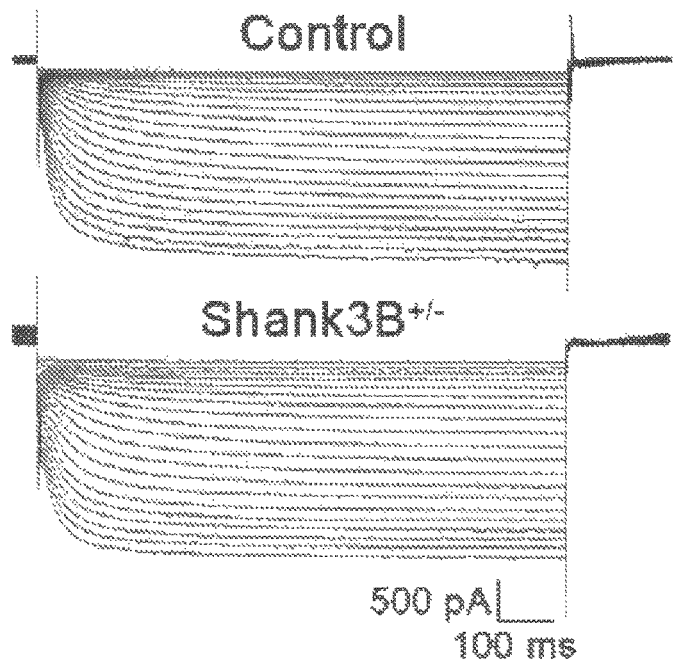
FIG. 23L: Representative traces from small diameter DRG neurons cultured from a control and Shank3B$^{+/-}$ mice, showing $I_h$ during a hyperpolarizing voltage step protocol.
Figure 23M:
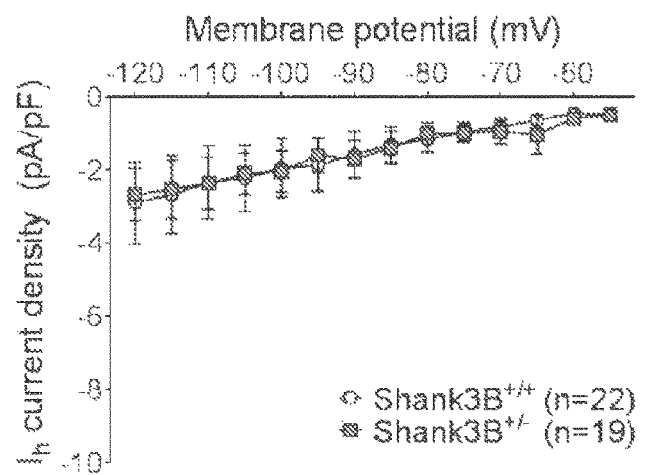
FIG. 23M: Quantification of total $I_h$ density at each hyperpolarizing voltage step for small diameter neurons cultured from DRGs of control and Shank3B$^{+/-}$ mutant mice. Repeated measures two-way ANOVA, not significant.
Figure 23N:
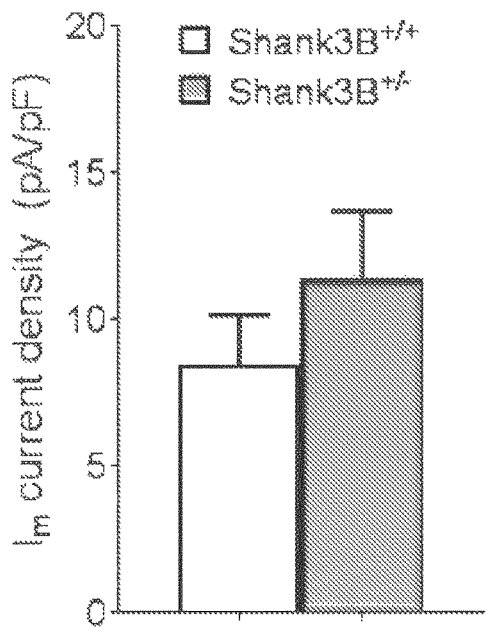
FIG. 23N: Quantification of maximum $I_m$ density during hyperpolarizing voltage step protocol with $CsCl_2$ application for small diameter neurons cultured from DRGs of control and Shank3B$^{+/-}$ mutant mice. Student's t-test, not significant.
Figure 23O:
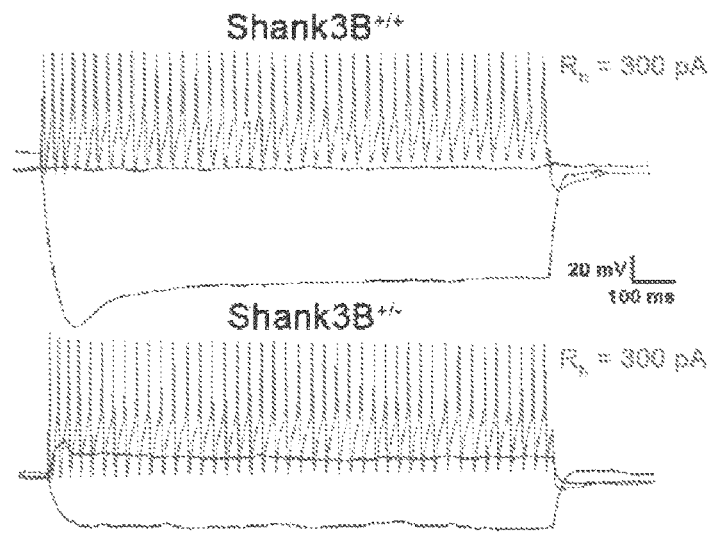
FIG. 23O: Representative traces from small diameter neurons cultured from DRGs of control and Shank3B$^{+/-}$ mice during whole cell current clamp recordings, in which the minimal amount of current required to elicit an action potential in each neuron (rheobase, $R_h$), was determined.
Figure 23P:
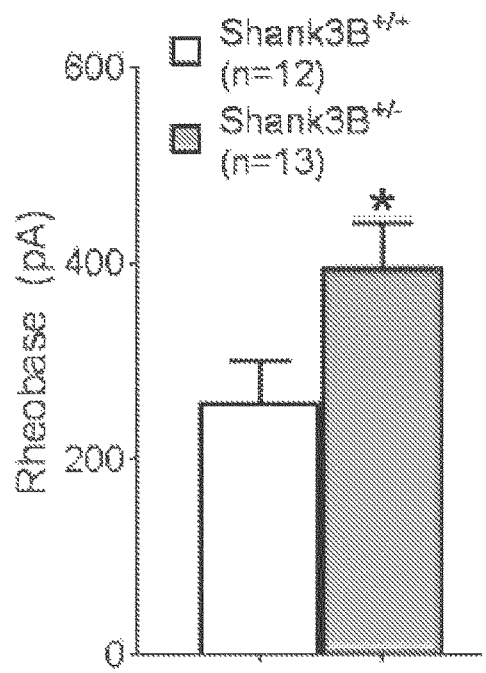
FIG. 23P: Average $R_h$ in small diameter neurons cultured from DRGs of control and Shank3B$^{+/-}$ mice during whole-cell current clamp recordings. Student's t-test, p<0.05.
Figure 23Q:
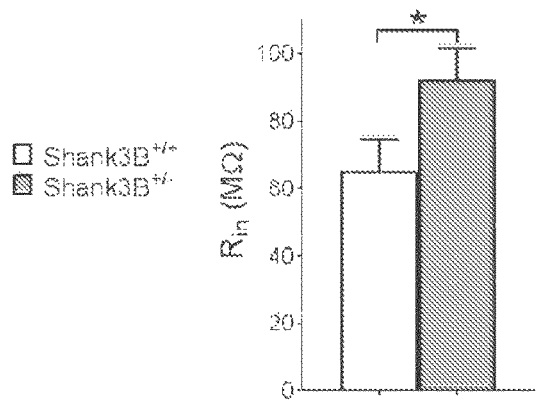
FIG. 23Q: Average input resistance ($R_{in}$) of large diameter neurons cultured from DRGs of control and Shank3B$^{+/-}$ mice during whole-cell patch clamp recordings. Student's t-test, p<0.05.
Figure 23R:
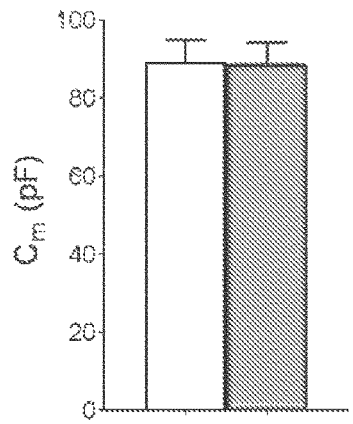
FIG. 23R: Average capacitance ($C_m$) of large diameter neurons cultured from DRGs of control and Shank3B$^{+/-}$ mice during whole-cell patch clamp recordings. Student's t-test, not significant.
Figure 23S:
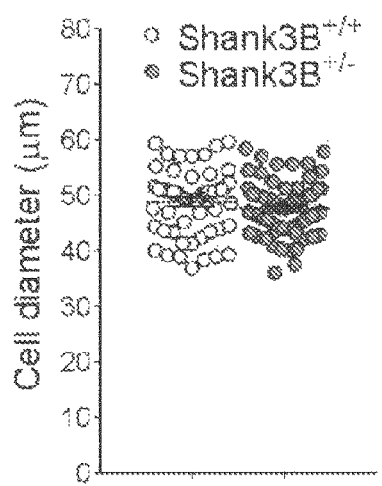
FIG. 23S: Average cell body size of large diameter neurons cultured from DRGs of control and Shank3B$^{+/-}$ mice during whole-cell patch clamp recordings. Student's t-test, not significant.
Figure 23T:
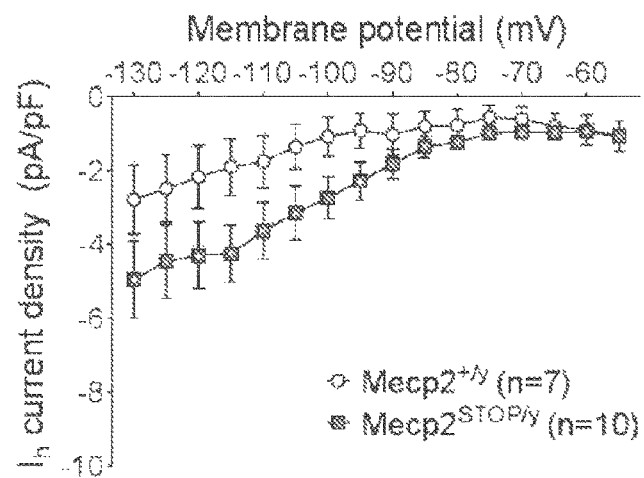
FIG. 23T: Quantification of total $I_h$ density at each hyperpolarizing voltage step for small diameter neurons cultured from DRGs of control and Mecp2$^{STOP/y}$ mutant mice. Repeated measures two-way ANOVA, not significant.
Figure 23U:
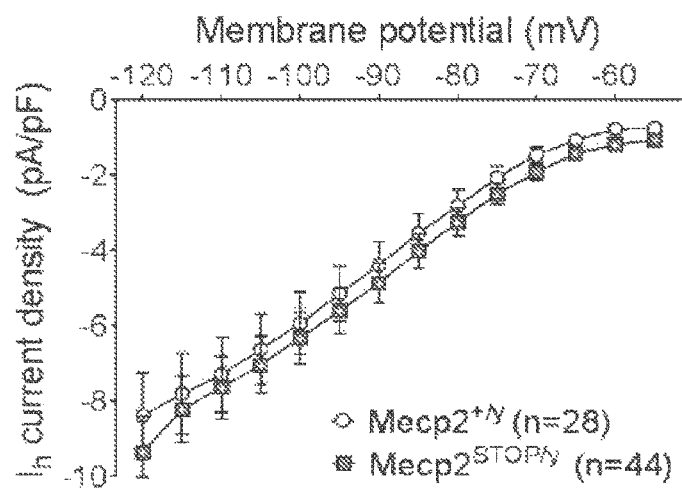
FIG. 23U: Quantification of total $I_h$ density at each hyperpolarizing voltage step for large diameter neurons cultured from DRGs of control and Mecp2$^{STOP/y}$ mutant mice. Repeated measures two-way ANOVA, not significant.
Figure 23V:
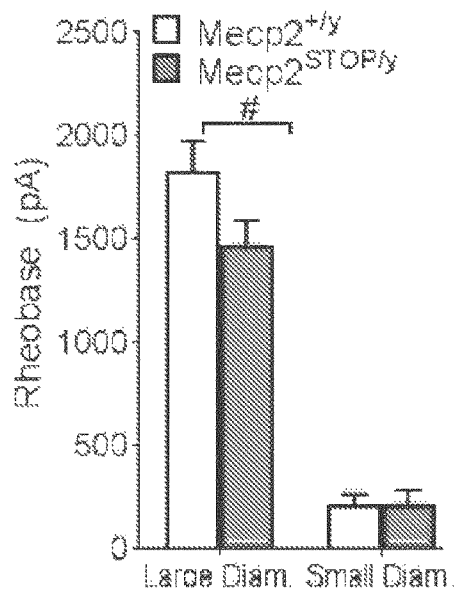
FIG. 23V: Average $R_h$ in large and small diameter neurons cultured from DRGs of control and Mecp2$^{STOP/y}$ mice during whole-cell current clamp recordings. Student's t-test, p<0.05.
Figure 23W:
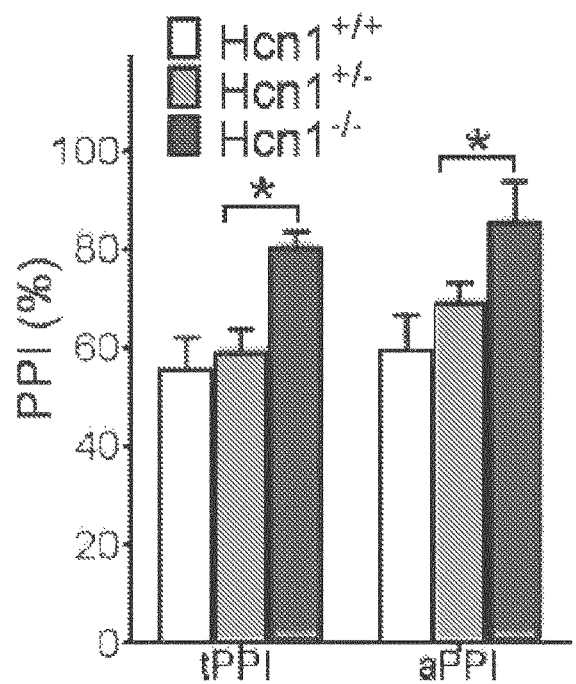
FIG. 23W: Percent inhibition of the startle response to a 125 dB noise, when the startle noise is preceded by a light air puff ('tactile PPI') tone prepulse ('acoustic PPI') in mutant mice and control littermates. One-way ANOVA with post-hoc Tukey's test, *, p<0.05.
Figure 23X:
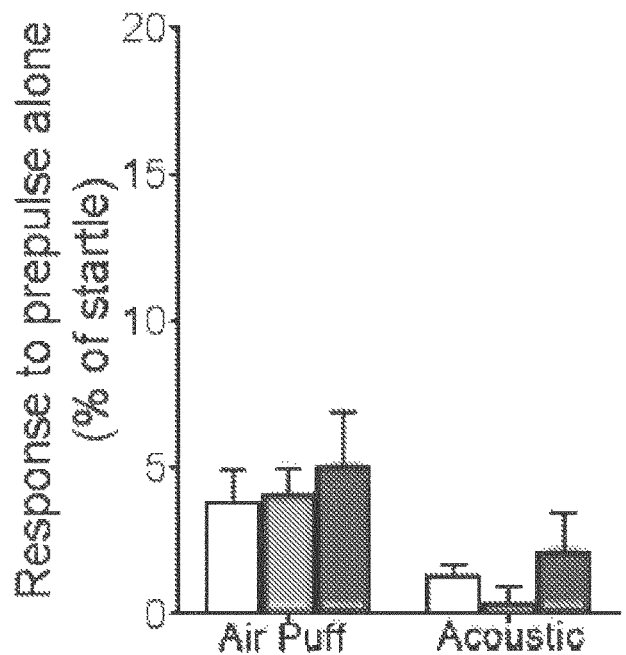
FIG. 23X: Response to a light air puff stimulus (0.9PSI, 50 ms) or non-startling tone prepulse (80 dB, 20 ms) alone. Responses are expressed as percent of startle response to a 125 dB noise. One-way ANOVA with post-hoc Tukey's test, *, p<0.05.
Figure 23Y:
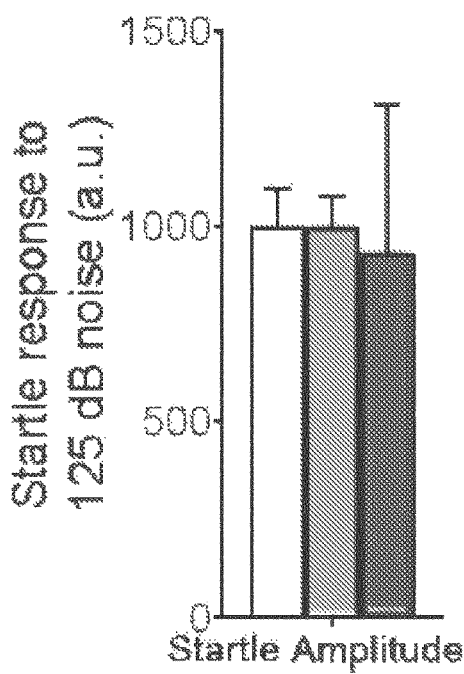
FIG. 23Y: Magnitude of startle response to a 125 dB noise in mutant mice and control littermates.
Figure 23Z:
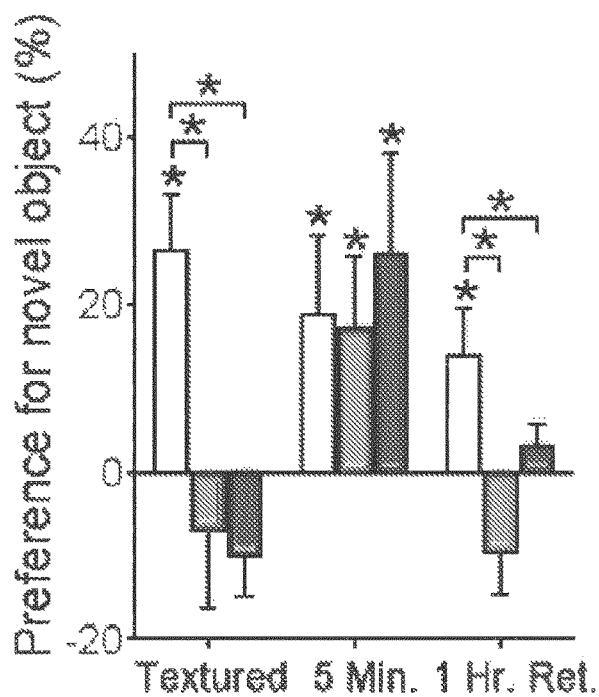

Next it was asked whether restoration of Shank3 expression selectively in peripheral somatosensory neurons might improve tactile deficits and other ASD-related phenotypes observed in Shank3 germline mutant mice. A Cre-dependent genetic switch (FLEx) knock-in mouse was employed, which enables conditional expression of Shank3 from its endogenous genomic locus. In the absence of Cre recombinase, the Shank3$^{FX}$ allele is non-functional and thus fails to express most Shank3 isoforms (Mei et al., 2016) (FIG. 22P). Selective restoration of Shank3 expression in cells below the neck (Cdx2$^{Cre}$; Shank3$^{FX/+}$) or in peripheral somatosensory neurons (Advillin$^{Cre}$; Shank3$^{FX/+}$, FIG. 22P) normalized hairy skin hypersensitivity and textured discrimination deficits, as these "rescue" mice behaved similar to control littermates in the tactile PPI and textured NORT assays (FIGS. 15A-15C). Moreover, Cdx2$^{Cre}$; Shank3$^{FX/+}$ and Advillin$^{Cre}$; Shank3$^{FX/+}$ mice did not exhibit anxiety-like behaviors during the open field test, EPM or habituation to a startle noise (FIGS. 15D-15F, 22K, 22L). Furthermore, while Shank3$^{FX/+}$ mice did not show a preference for a novel mouse in either portion of the 3-chamber social interaction test, both Cdx2$^{Cre}$; Shank3$^{FX/+}$ and Advillin$^{Cre}$; Shank3$^{FX/+}$ rescue mice exhibited preference for the novel mouse in the sociability assay, and they exhibited a trend towards preference for the novel mouse in the social novelty recognition preference assay (FIGS. 15G-15I, 29). An intermediate phenotype in the marble burying test was also observed: Cdx2$^{Cre}$; Shank3$^{FX/+}$ and Advillin$^{Cre}$; Shank3$^{FX/+}$ rescue mice buried more marbles than their Shank3$^{FX/+}$ littermates, but fewer than control littermates (FIG. 22M). On the other hand, no improvements in memory deficits or overgrooming behaviors were observed in either Cdx2$^{Cre}$; Shank3$^{FX/+}$ or Advillin$^{Cre}$; Shank3$^{FX/+}$ rescue mice (FIGS. 22I, 22N, 22O). Therefore, as observed for Mecp2 and Gabrb3 (Orefice et al., 2016), Shank3 function is required in cell-autonomously in peripheral somatosensory neurons for normal tactile sensitivity and texture discrimination as well as a subset of ASD-related behaviors, including anxiety-like behaviors and some social behaviors. These findings support the idea that dysfunction of peripheral mechanosensory neurons is a common feature of ASD mouse models, despite the disparate molecular functions and properties of ASD-associated genes.

Figure 16A:
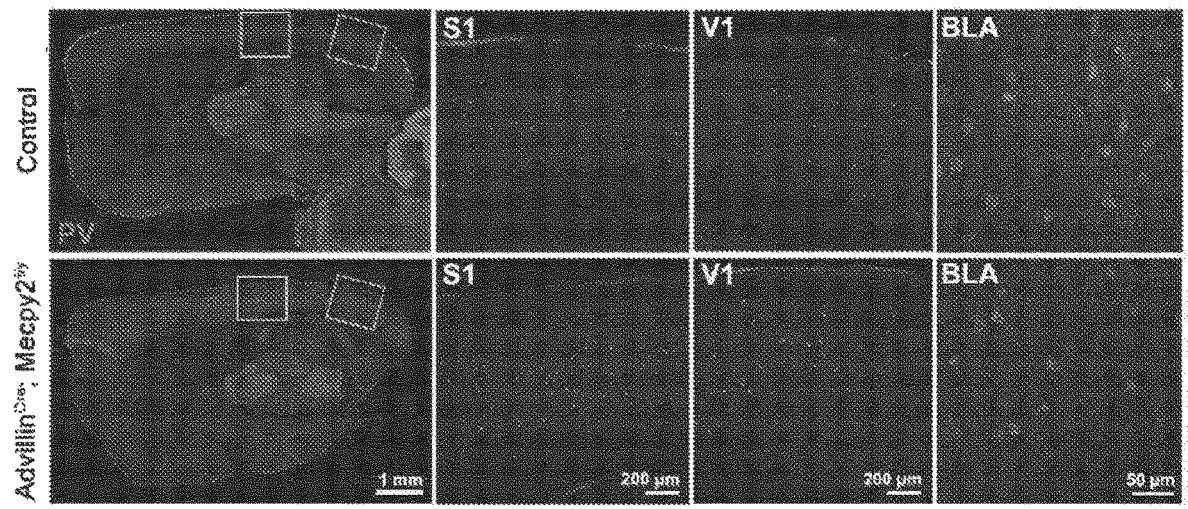
Figures 16B, 16C:
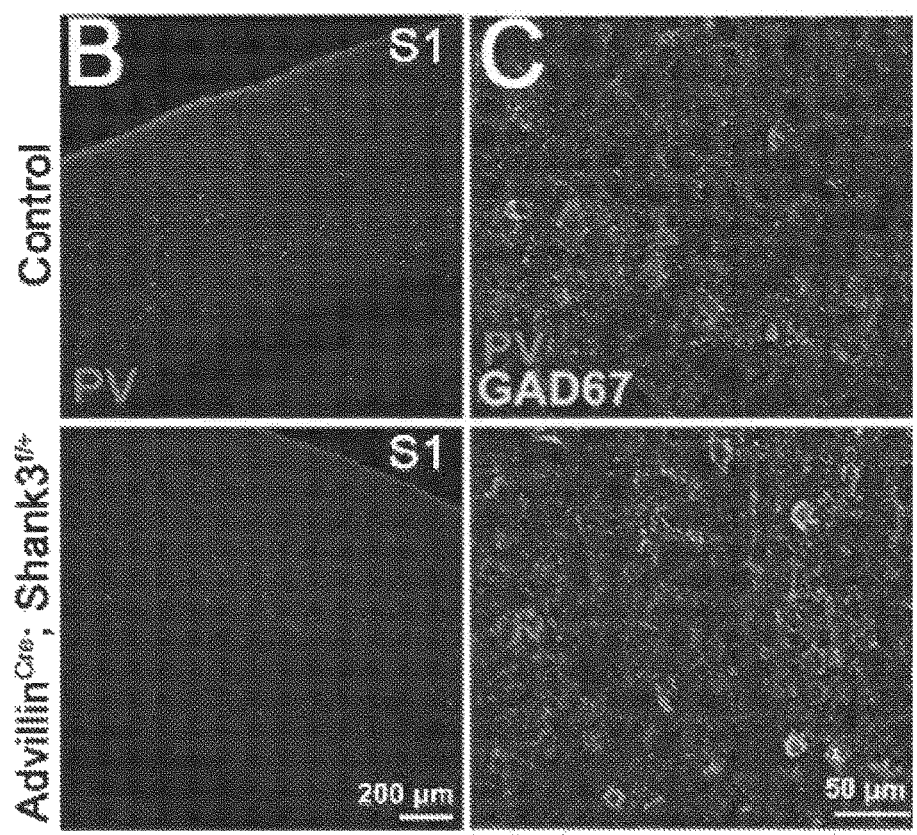
FIG. 16B: Representative IHC images of transverse brain sections, showing PV immunoreactivity in control or Advillin$^{Cre}$; Shank3$^{f/+}$ mutant mice.
FIG. 16C: Representative IHC images of transverse S1 brain sections, showing PV and GAD67 immunoreactivity in control or Advillin$^{Cre}$; Shank3$^{f/+}$ mutant mice.
Figures 16I, 16J, 16K:
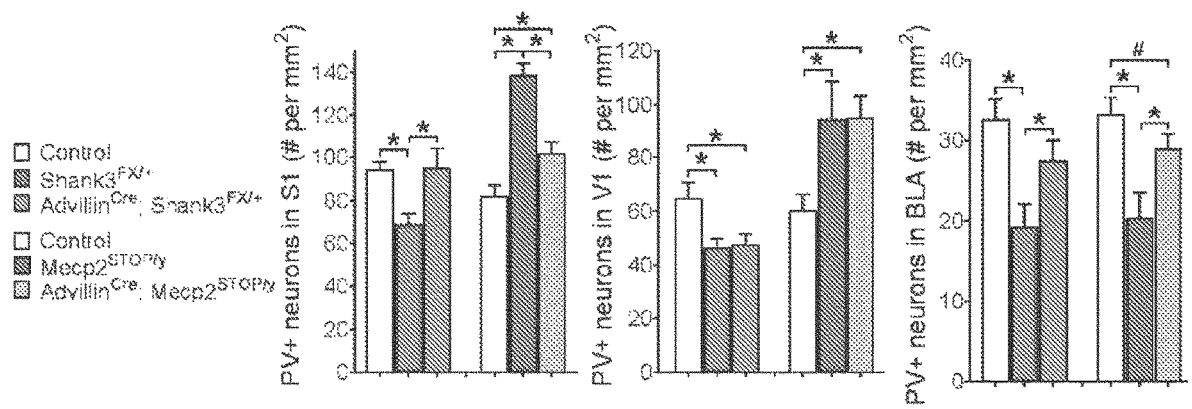
FIGS. 16I-16K: Quantification of the number of PV$^+$ neurons in S1 (FIG. 16I), V1 (FIG. 16J), and BLA (FIG. 16K) in mutant mice and their control littermates. One-way ANOVA with post-hoc Tukey's test, *, p<0.05.

ASD-Related Gene Mutations in Peripheral Somatosensory Neurons Lead to Region-Specific Alterations in Brain Inhibitory Interneurons and Cortical Microcircuit Properties The findings that aberrant peripheral somatosensory neuron function in Mecp2, Gabrb3, and Shank3 mutants leads to anxiety-like behaviors and deficits in social behaviors, which are naturally attributed to brain-specific circuits and function (Amaral, 2003; Amaral et al., 2003; Janak and Tye, 2015), was intriguing. Therefore, the relationship between aberrant tactile reactivity, caused by ablation of Mecp2 and Shank3 in peripheral somatosensory neurons, and brain development and cortical microcircuit properties was next explored. One clue that may help to explain this relationship stems from decades of research indicating that sensory experience guides development of neocortical areas that represent features of external stimuli (Hubei and Wiesel, 1970; Simons and Land, 1987; Wiesel and Hubei, 1965). For example, sensory experience governs the maturation of cortical microcircuits and aberrant sensory stimuli adversely affect the development of cortical inhibitory interneurons during critical periods of development (Dorrn et al., 2010; Jiao et al., 2011). In line with this, postmortem analysis of brains from patients with ASD as well as animal models of ASD revealed abnormalities in parvalbumin-positive (PV+) inhibitory interneurons in multiple brain regions (Hashemi et al., 2017; Marin, 2012; Nelson and Valakh, 2015; Zikopoulos and Barbas, 2013). Indeed, Mecp2 mutations lead to abnormalities in forebrain inhibitory network development (Fukuda et al., 2005; Tomassy et al., 2014), and $Mecp2^{-/y}$ and $Mecp24^{+/-}$ germline mutant mice exhibit an increased density of PV+ interneurons in primary sensory cortices (Fukuda et al., 2005) (Krishnan et al., 2015). Conversely, Shank3 germline mutants display decreased expression of PV in inhibitory interneurons of primary somatosensory cortex (S1) (Filice et al., 2016). PV+ cortical interneurons are fast-spiking interneurons that play roles in feed-forward and feedback inhibition and modulate sensory responsiveness (Konig et al., 1996; Sohal et al., 2009; Womelsdorf et al., 2014), and thus it was hypothesized that aberrant sensory input caused by peripheral somatosensory neuron dysfunction in ASD models may affect properties of PV+ inhibitory interneurons in brain circuits that process somatosensory inputs. In agreement with this idea, it was observed that loss of Mecp2 in peripheral sensory neurons, in $Adviffin^{Cre}$; $Mecp2^{f/+}$ mice, caused an increased number of PV+ interneurons in S1, but not V1, of adult mice compared to controls (FIGS. 16A, 16C, 16D). On the other hand, loss of Shank3 in peripheral sensory neurons, in $Adviffin^{Cre}$; $Shank3^{f/+}$ mice, led to a reduction in PV+ neurons in S1, but not primary visual cortex (V1), of adult mice compared to control littermates (FIGS. 16B-16D). These region-specific alterations in PV+ neurons in the Shank3 and Mecp2 conditional mutants are in contrast to the more widespread alterations observed in the germline mutants: $Mecp2^{-/y}$, $Mecp24^{+/-}$ and $Shank3^{+/-}$ germline mutant mice exhibited alterations in PV+ neurons in both S1 and V1. Also observed was a decrease in the number of PV+ neurons in the basolateral amygdala (BLA), a region of the brain that plays critical roles in anxiety and social behaviors, in both Shank3 and Mecp2 conditional mutants (FIGS. 16A, 16E). Conversely, developmental restoration of either Shank3 or Mecp2 selectively in peripheral somatosensory neurons, in $Advillin^{Cre}$; $Shank3^{FX/+}$ and $Advillin^{Cre2}$; $Mecp2^{STOP/y}$ mice, respectively, significantly improved the PV+ neuron abnormalities observed in $Shank3^{FX/+}$ and $Mecp2^{STOP/y}$ mice in both S1 and BLA, but not in V1 (FIGS. 16F-16J).

Figure 16L:
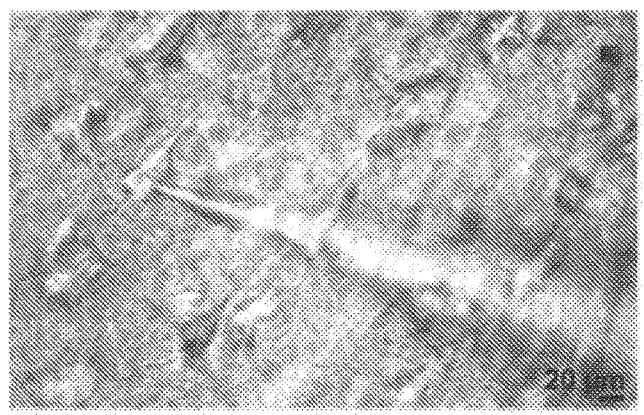
FIG. 16L: Example image of a transverse S1 slice with a layer 2/3 pyramidal neuron in whole cell patch clamp recording configuration.
Figure 16M:
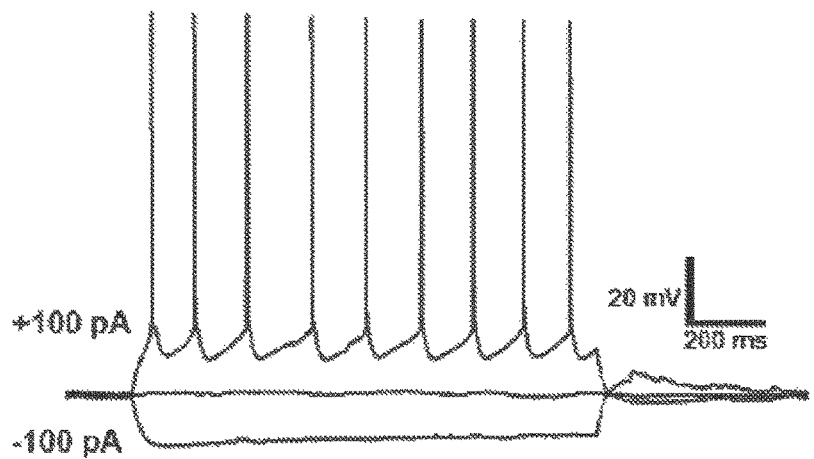
FIG. 16M: Example firing pattern of a layer 2/3 pyramidal neuron in whole cell patch clamp recording configuration during current injection steps.
Figure 16N:
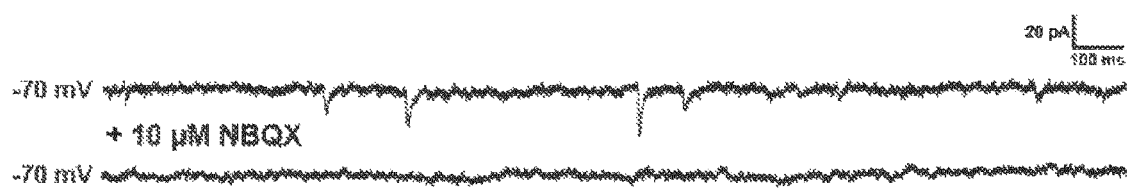
FIG. 16N: Example traces from a layer 2/3 pyramidal neuron showing spontaneous excitatory postsynaptic currents (ePSCs) in normal bath solution or following NBQX (10 μm).
Figure 16O:
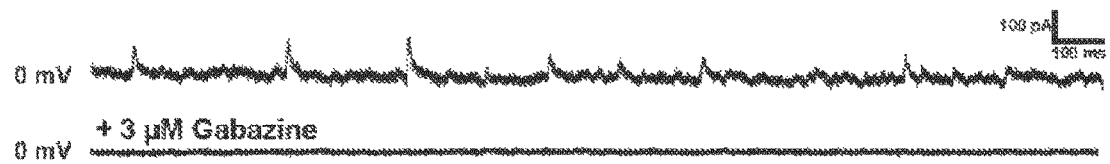
FIG. 16O: Example traces from a layer 2/3 pyramidal neuron showing spontaneous inhibitory postsynaptic currents (iPSCs) in normal bath solution or following gabazine (3 μm).
Figure 16P:
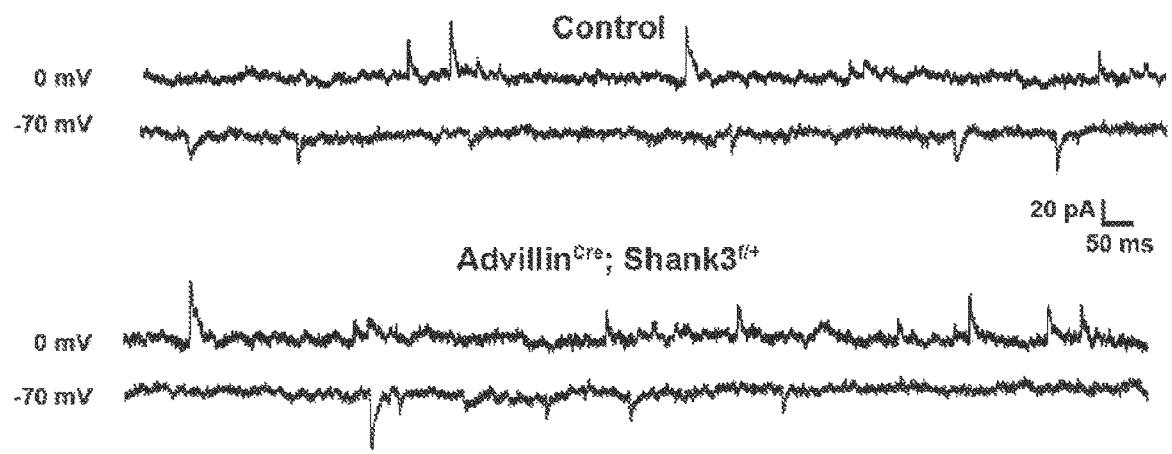
FIGS. 16P-16Q: Representative traces showing ePSCS (-70 my hold) and iPSCs (0 mV hold) from S1 slices of control or Advillin$^{Cre}$; Shank3$^{f/+}$ mutant mice.
Figure 16Q:
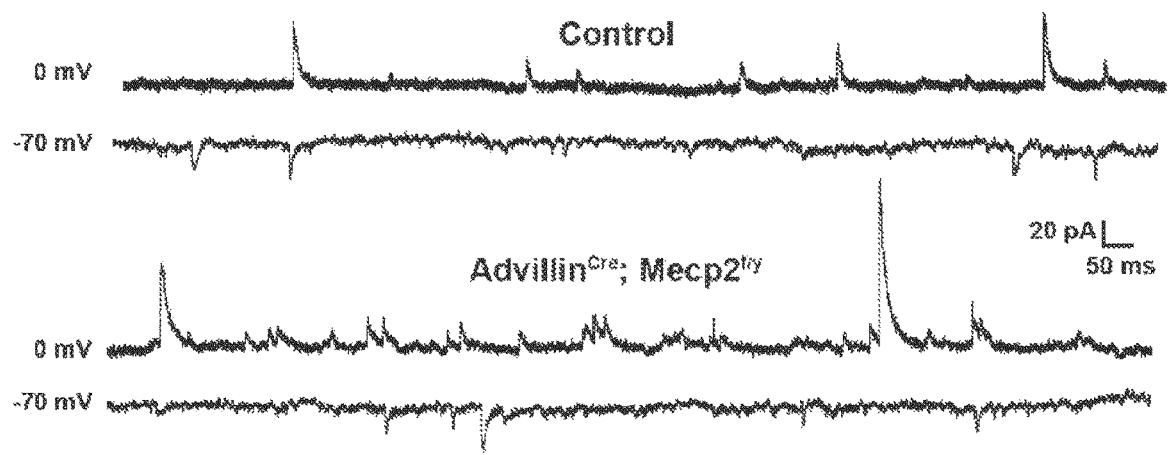

Alterations in S1 and BLA PV+ interneurons observed in Shank3 and Mecp2 conditional mutant mice suggested that peripheral somatosensory neuron dysfunction in ASD mouse models causes alterations in cortical microcircuits. Therefore, it was also asked whether loss of either Mecp2 or Shank3 in peripheral sensory neurons leads to changes in S1 microcircuit physiological properties. To address this, the spontaneous excitatory and inhibitory postsynaptic currents (EPSCs, IPSCs) in layer 2/3 pyramidal neurons in S1 and V1 slices from 8-10 week old mice with peripheral somatosensory neuron deletion of Mecp2 or Shank3 (FIGS. 16K-16M) was assessed. It was found that loss of either Mecp2 or Shank3 in peripheral somatosensory neurons led to decreased excitatory/inhibitory (E/I) ratios in S1, but not V1, compared to control littermates (FIGS. 16N-16P). However, as with the PV+ interneuron abnormalities noted by IHC, distinctions between the altered physiological properties of S1 microcircuits in Shank3 and Mecp2 mutant mice were apparent. Layer 2/3 pyramidal neurons from S1 slices of $Advillin^{Cre2}$; $Mecp2^{f/y}$ mice exhibited an increase in IPSO frequency, with no differences observed in EPSC or IPSO amplitude (FIGS. 16Q, 16R). On the other hand, while layer 2/3 pyramidal neurons from S1 slices of $Adviffin^{Cre}$; $Shank3^{f/+}$ mice showed no significant differences in the overall frequency of IPSCs, an increase in EPSC amplitudes and a decrease in IPSO amplitudes were observed in these mutants (FIGS. 16Q, 16R). No differences in either the amplitude or frequency of events was observed in V1 in any of the conditional mutants analyzed (FIGS. 16S, 16T). These analyses indicate that physiological dysfunction of peripheral somatosensory neurons caused by distinct ASD-associated gene mutations and the resultant aberrant reactivity to tactile stimuli lead to functional changes in cortical microcircuit properties in a region-specific manner. Therefore, changes in sensory cortex E/I ratios observed in ASD models may reflect adaptations to aberrant sensory input from the periphery.

A Critical Window During which Somatosensory Neuron Dysfunction Influences Cognitive and Social Behaviors These findings reveal a causal relationship between embryonic deletion or rescue of either Shank3 or Mecp2 in peripheral sensory neurons, LTMR physiological properties and tactile reactivity, cortical microcircuit properties, and anxiety-like behaviors and social interactions in adult mice (FIGS. 15, 16). This raises the question of when during development ASD-associated genes function in peripheral somatosensory neurons to govern tactile reactivity, brain microcircuit development, and behavior. To address this, conditional mouse genetics to either delete or rescue either Shank3 or Mecp2 during different postnatal developmental stages was used, followed by assessment of tactile reactivity, texture discrimination, PV+ interneurons in S1, V1 and BLA, as well as cognitive and social behaviors in young adult mice. Using the tamoxifen-sensitive $Adviffin^{CreERT2}$ mouse line (Lau et al., 2011), either Shank3 or Mecp2 was selectively ablated in peripheral somatosensory neurons at various time points during postnatal development. A five-day tamoxifen dosing regimen resulted in recombination of target genes in >90% of DRG neurons, while Shank3 and Mecp2 gene expression was unaltered in the brains or spinal cords of these mice (FIGS. 24A-24D).

Figure 24A:
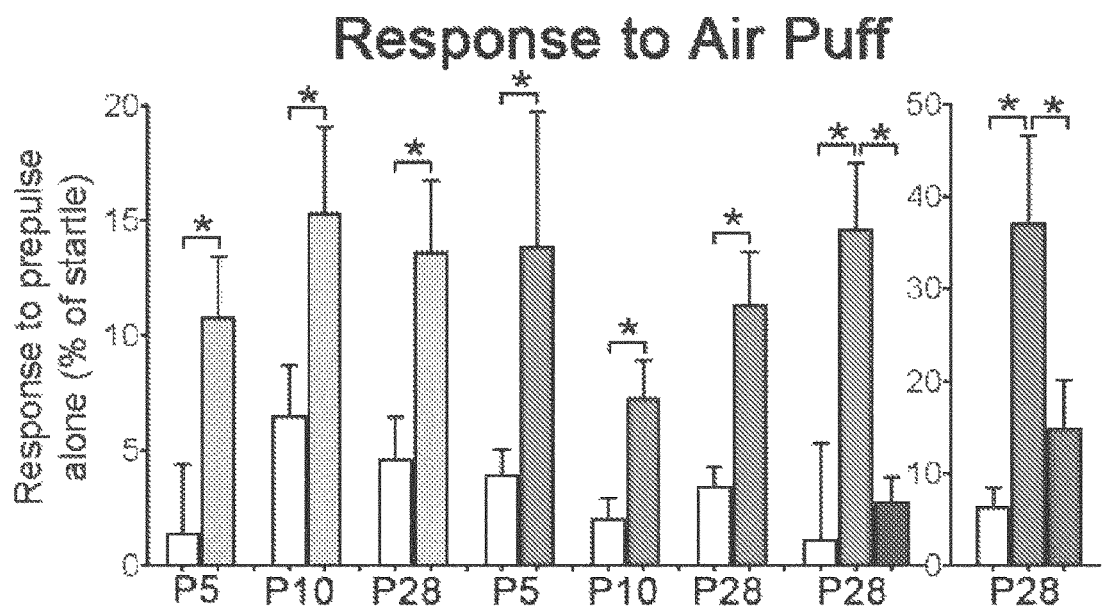
FIGS. 24A-24L are related to FIGS. 17A-17J.
Figure 25A:
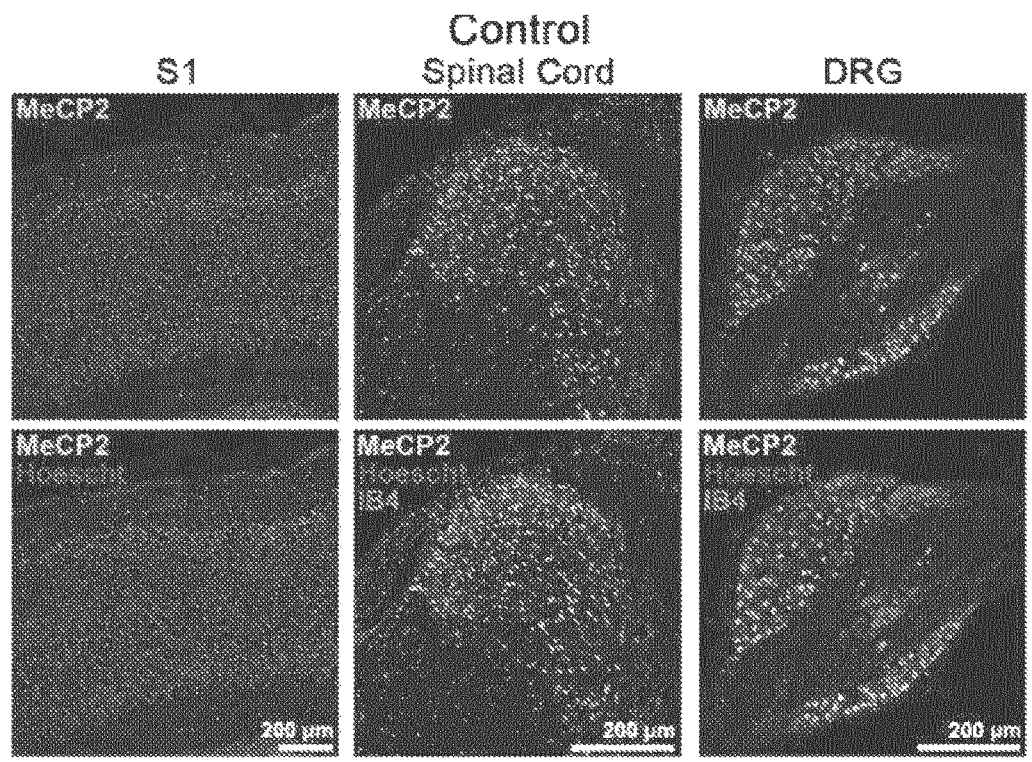
FIGS. 25A-25M are related to FIGS. 17A-17J.
Figure 25B:
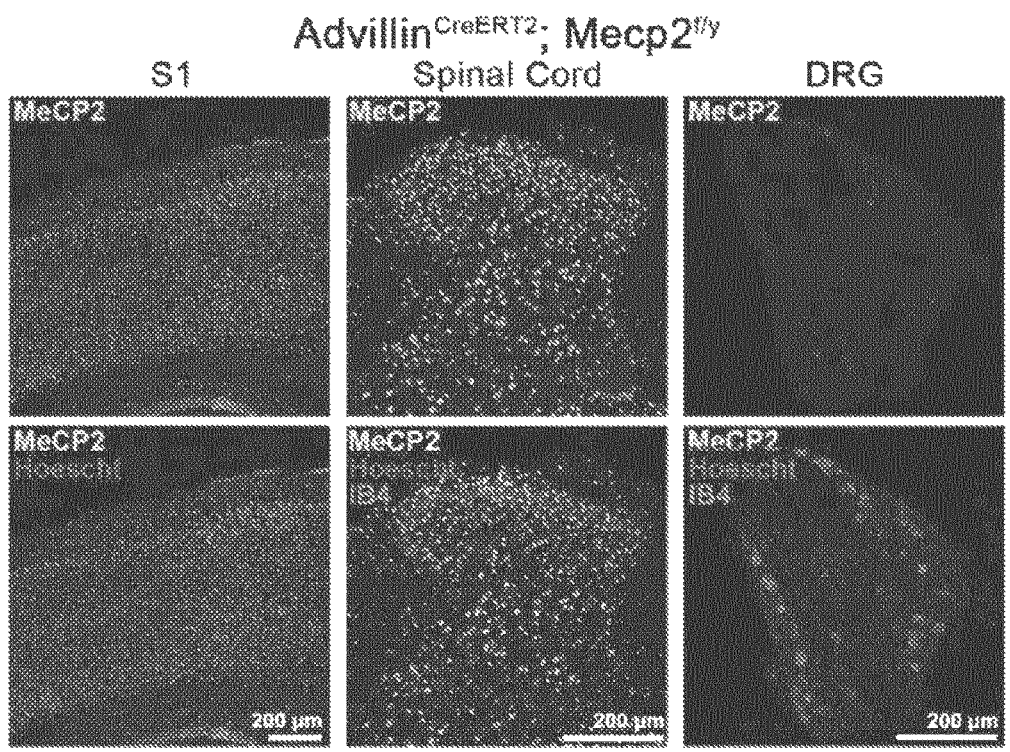
Figure 25C:
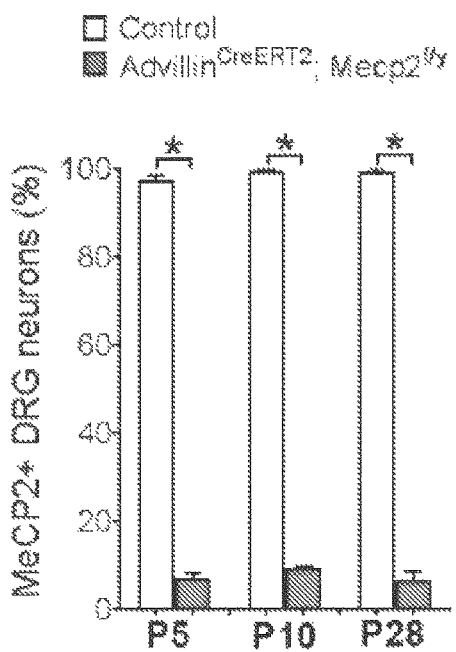
Figure 25D:
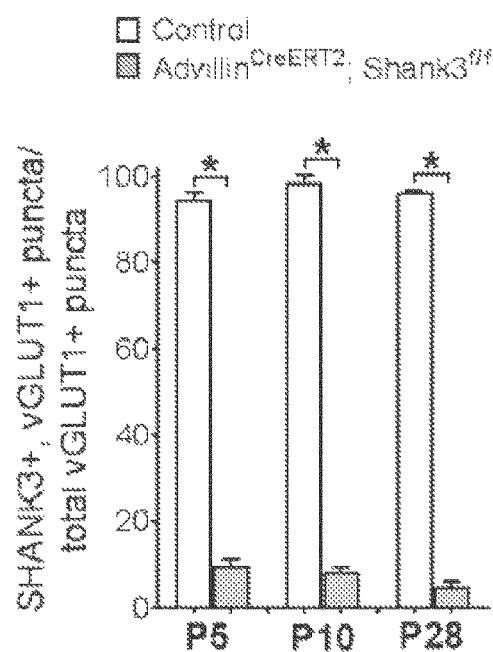
Figure 25E:
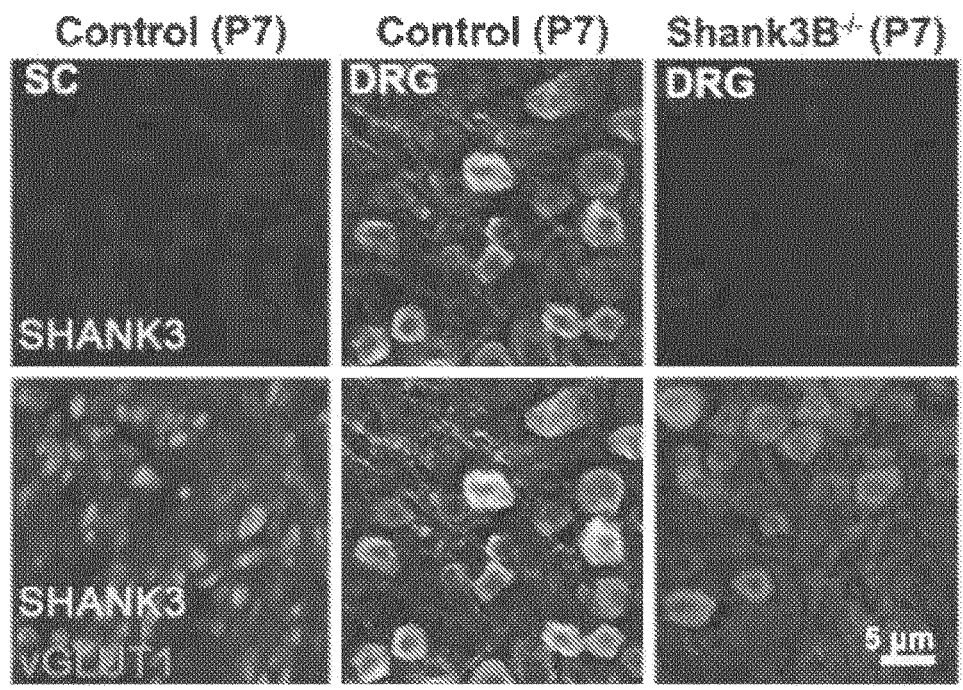
Figure 25F:
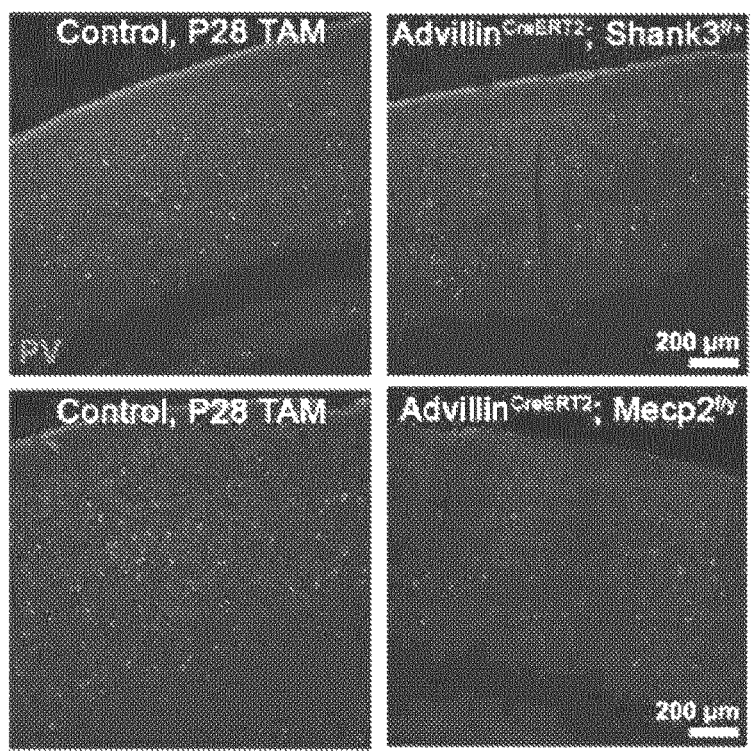
Figure 25G:
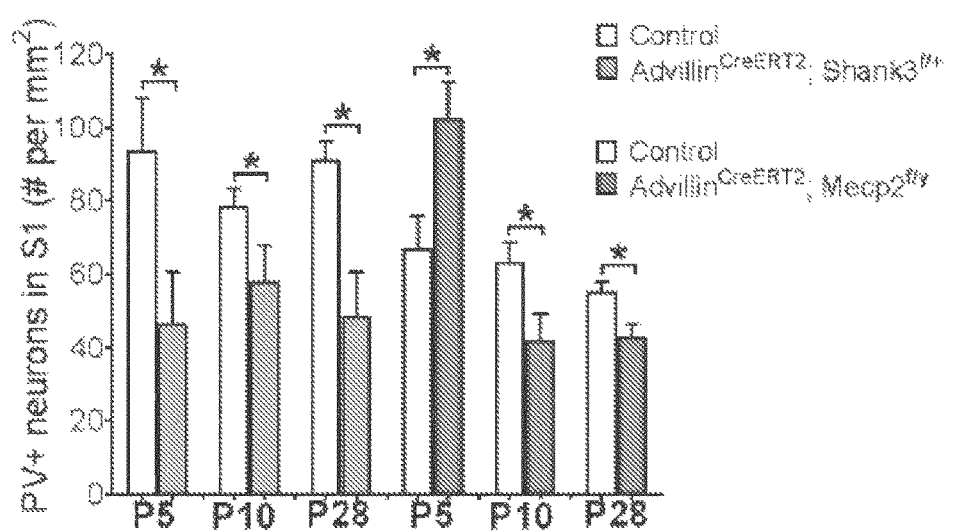
Figure 25H:
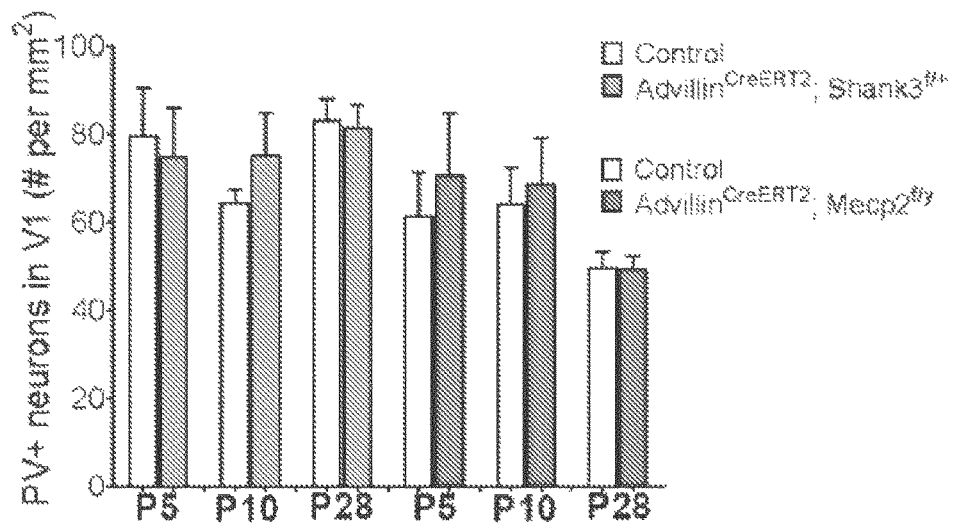
Figure 25I:
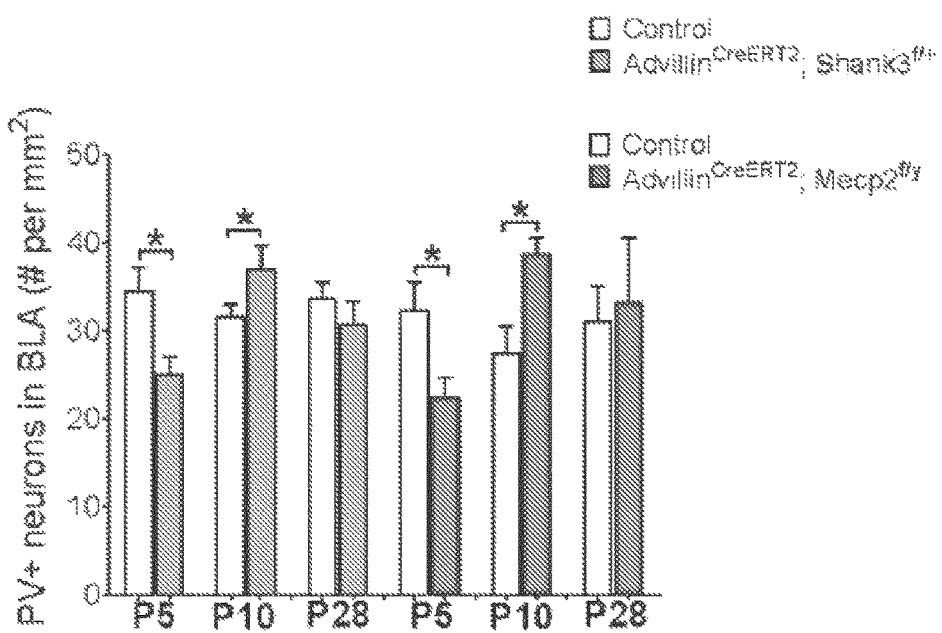

Early postnatal deletion of either Shank3 or Mecp2, beginning at P5 ($Advillin^{CreERT2}$; $Shank3^{f/+}$ or $Advillin^{CreERT2}$; $Mecp2^{f/y}$), z recapitulated the behavioral phenotypes observed in $Advillin^{Cre}$; $Shank3^{f/+}$ and $Advillin^{Cre}$; $Mecp2^{f/y}$ mice: P5-deletion mutant mice exhibited deficits in texture discrimination, hairy skin hypersensitivity, decreased marble burying, anxiety-like behaviors, as well as sociability and social novelty recognition preference impairments (FIGS. 17, 25B, 24A, 24H-24L, Table 2). Moreover, similar to $Advillin^{Cre}$; $Mecp2^{f/y}$ mice, $Advillin^{CreERT2}$; $Mecp2^{f/y}$ mutant mice receiving P5 tamoxifen treatment exhibited more PV+ neurons in S1 (FIG. 25G). Likewise, $Advillin^{CreERT2}$; $Shank3^{f/+}$ mutant mice displayed fewer PV+ neurons S1, compared to their control littermates, which was similar to that observed in $Advillin^{Cre}$; $Shank3^{f/+}$ mice (FIG. 25G). Decreased density of PV+ neurons in BLA was also observed in both $Advillin^{CreERT2}$; $Shank3^{f/+}$ and $Advillin^{CreERT2}$; $Mecp2^{f/y}$ mutant mice receiving the P5 tamoxifen treatment (FIG. 25I). On the other hand, while deletion of either Mecp2 or Shank3 in peripheral sensory neurons ($Advillin^{creERT2}$; $Mecp2^{floxed}$ or $Advillin^{CreERT2}$; $Shank3^{floxed}$) at P28 led to abnormalities in tactile behaviors and PV+ neuron density in S1, these mice did not exhibit anxiety-like behaviors or neophobia, and their social impairments were less severe than mice with embryonic or P5 deletion of either gene in peripheral sensory neurons (FIGS. 17, 24A, 24H-24L, 25F, 25G, Table 2). Mice with P28 deletion also displayed no abnormalities in BLA PV$^+$ neuron density (FIG. 25I). Interestingly, when either Mecp2 or Shank3 was ablated in peripheral somatosensory neurons beginning at an intermediate developmental time point, P10, mice exhibited a distinct set of behavioral alterations. In P10 deletions, tactile and social behavior abnormalities were observed, similar to embryonic deletions, but this was accompanied by hyperactivity and reduced anxiety-like behaviors (FIGS. 17, 24A, 24H-24L, Table 2). Moreover, P10 ablations of Shank3 and Mecp2 in peripheral somatosensory neurons led to similar differences in the PV$^+$ neuron morphological correlates observed in the embryonic ablations in S1, but increased density of PV$^+$ neurons in the BLA (FIGS. 25G-25I).

Figure 17B:
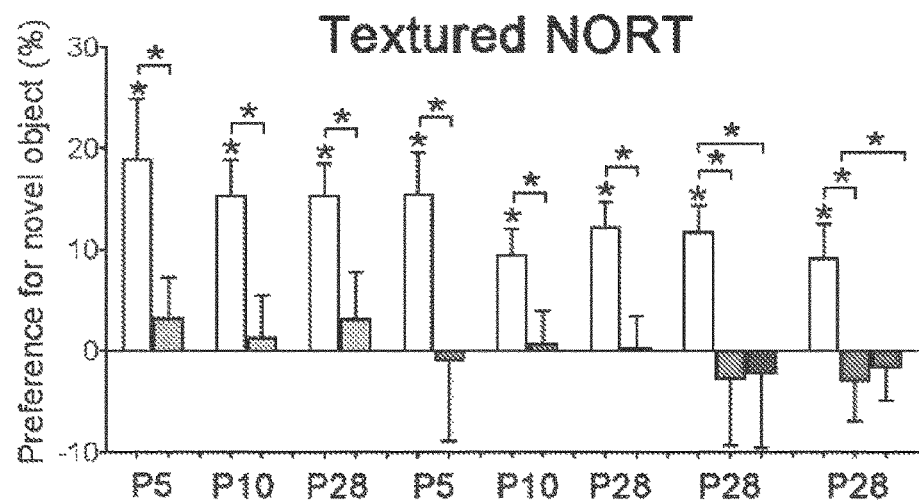
Figure 17C:
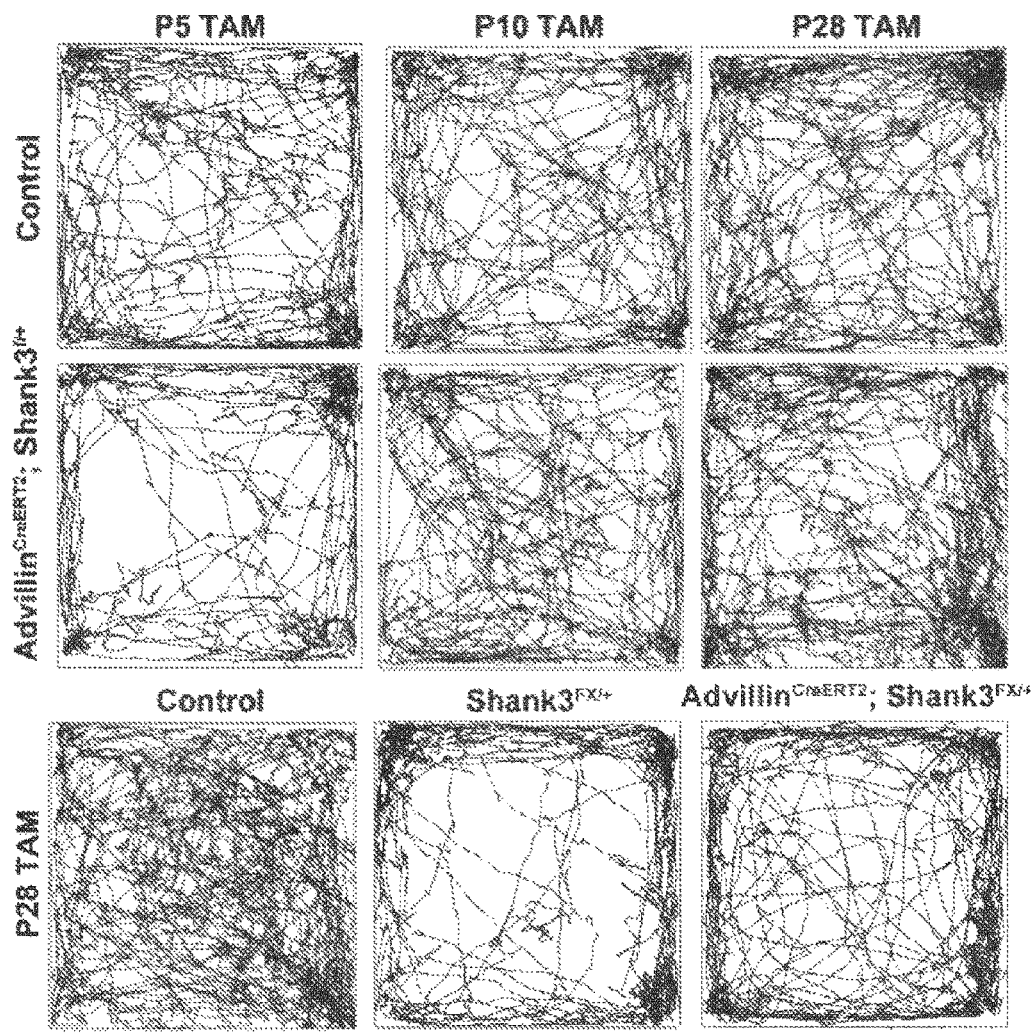
Figure 17D:
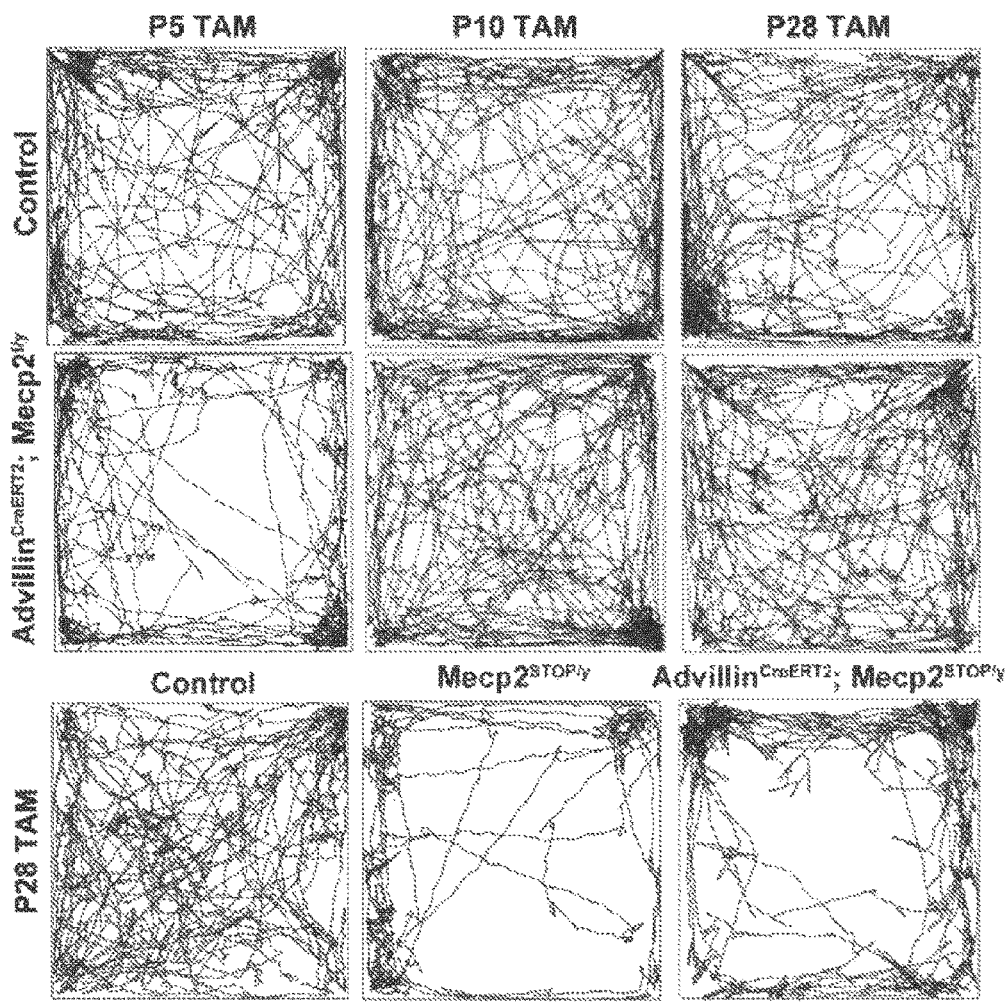
Figure 17E:
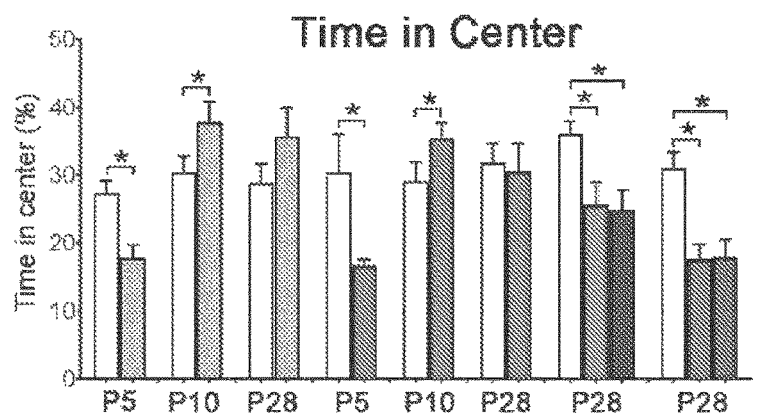
Figure 17F:
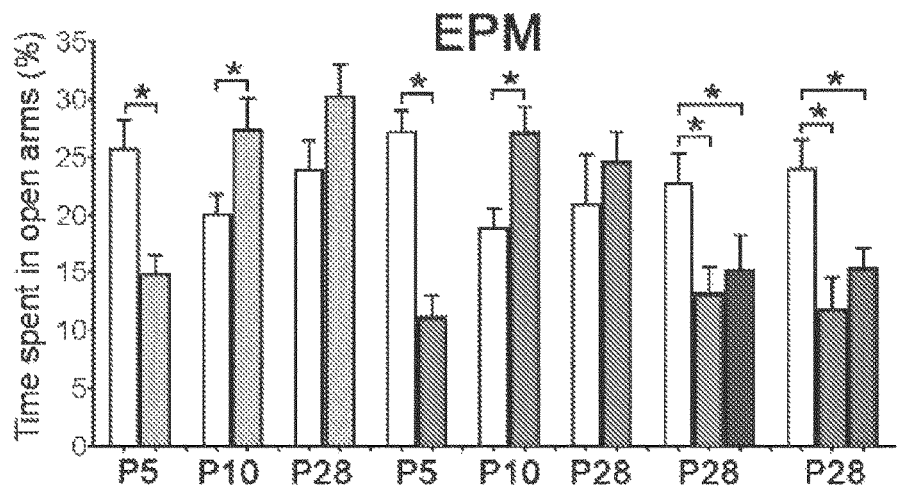
Figure 17G:
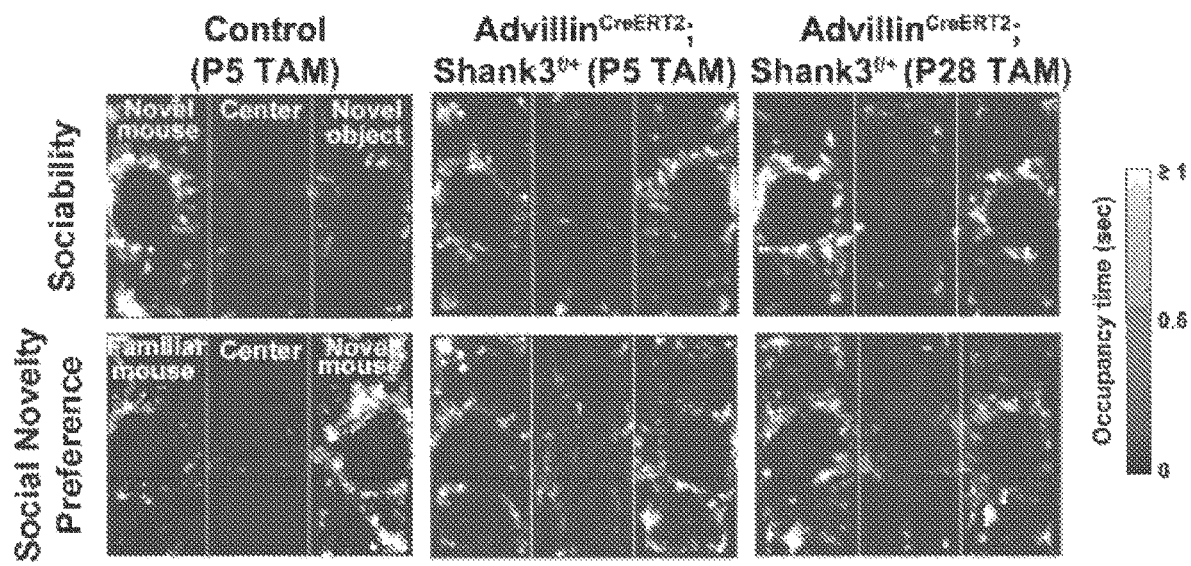
Figure 17H:
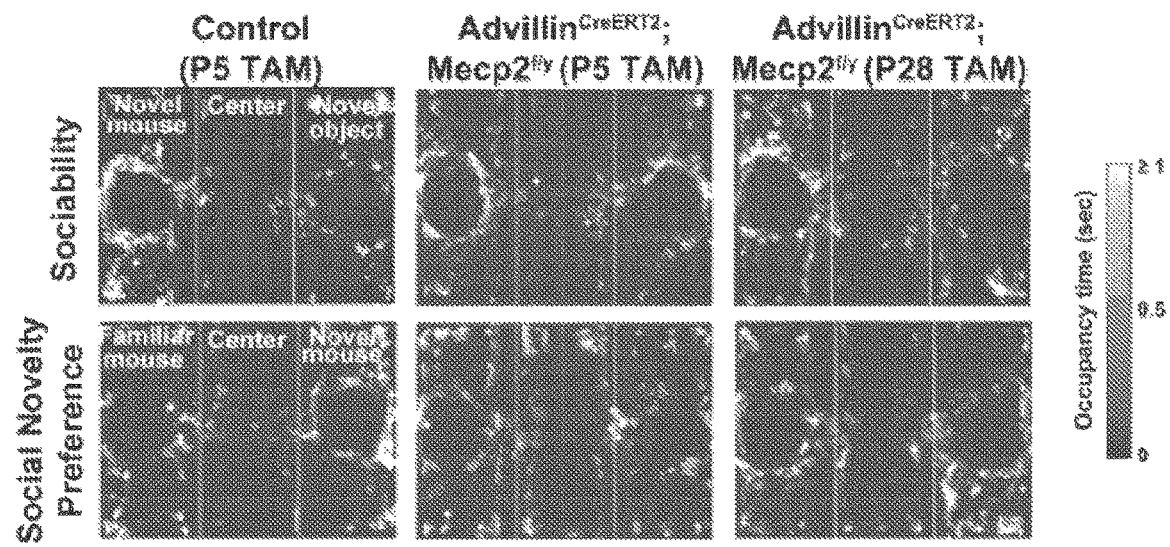
Figure 17I:
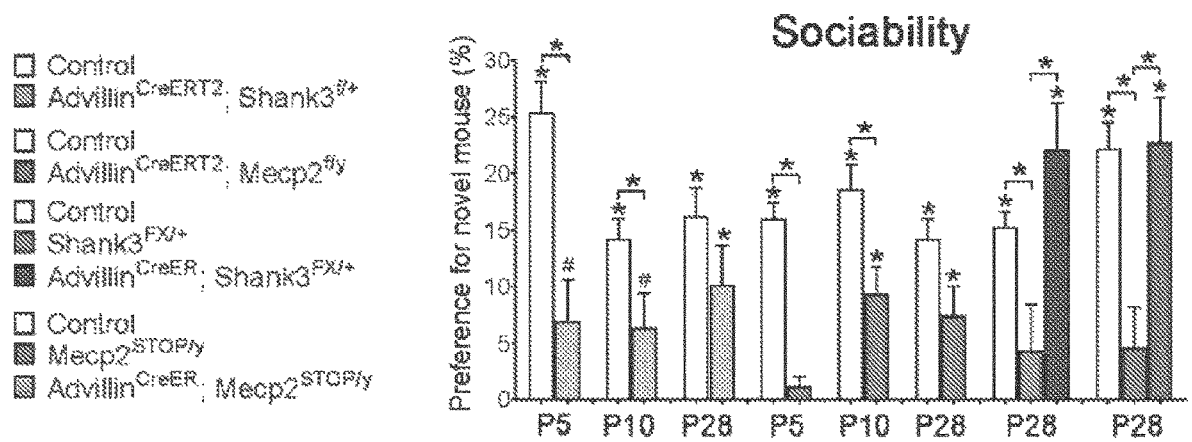
Figure 17J:
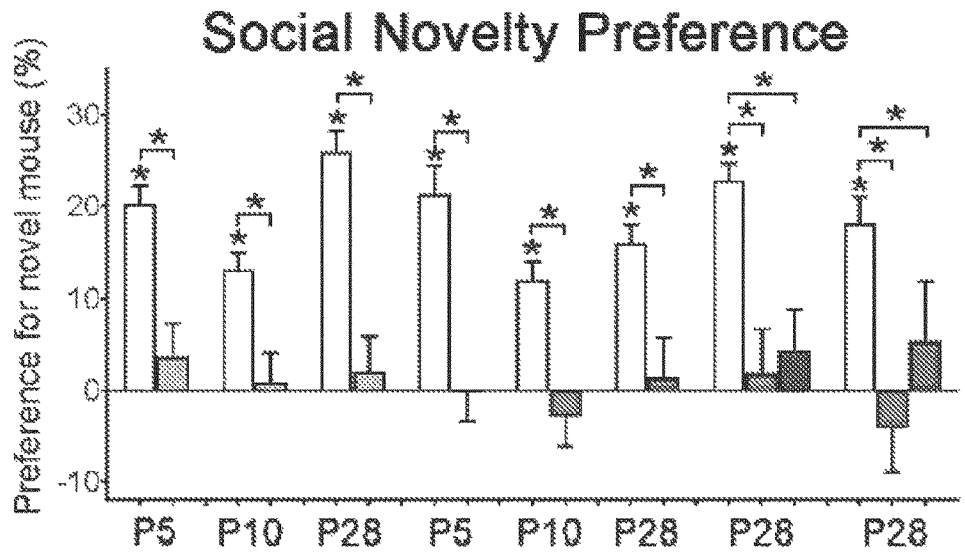
Figure 24B:
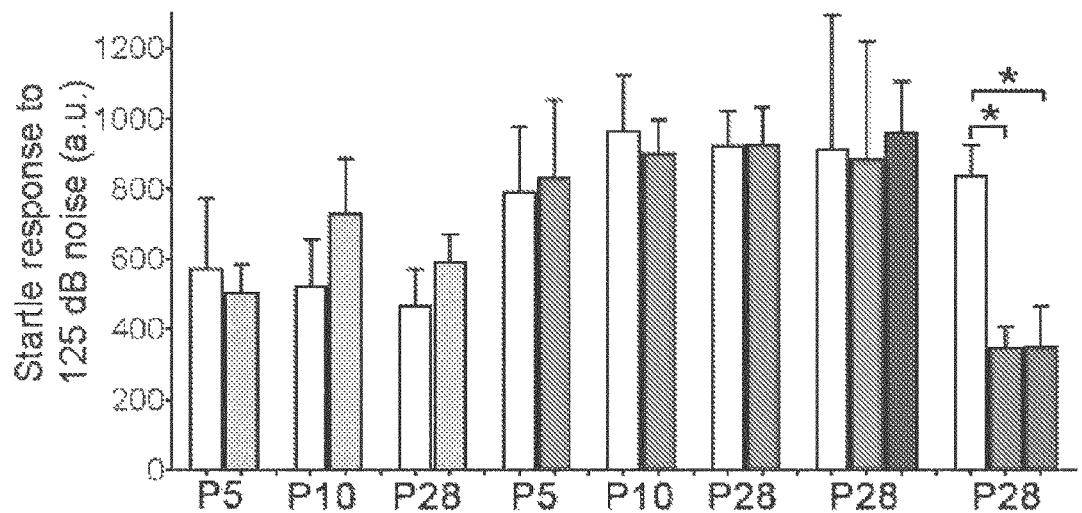
Figure 24C:
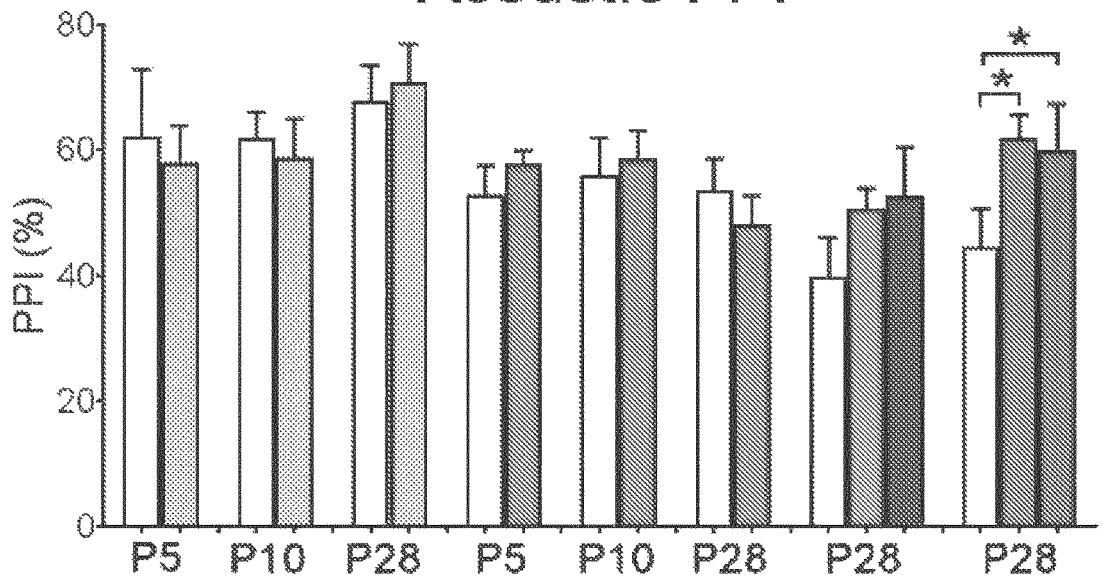
Figure 24D:
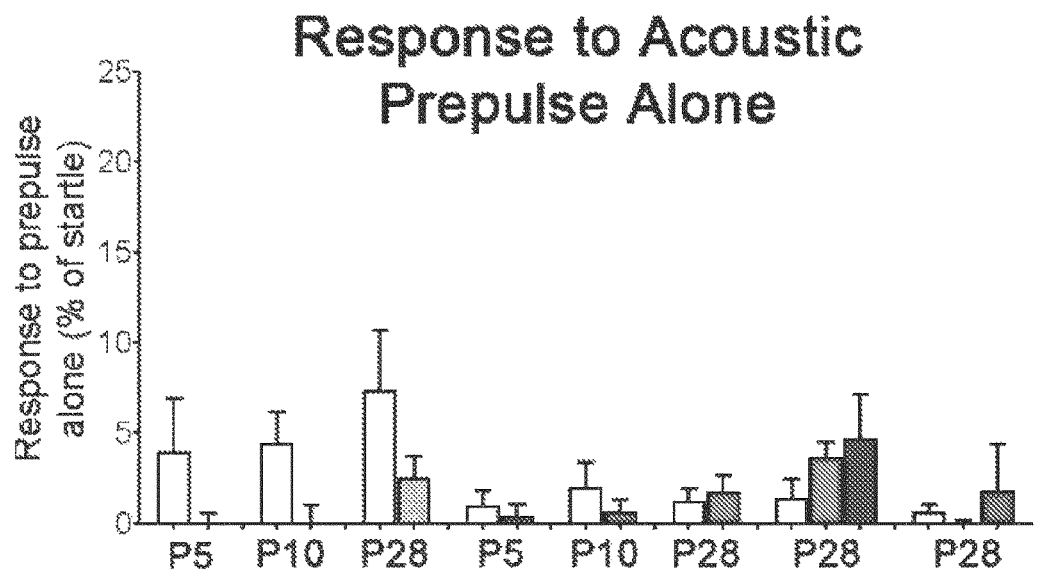
Figure 24E:
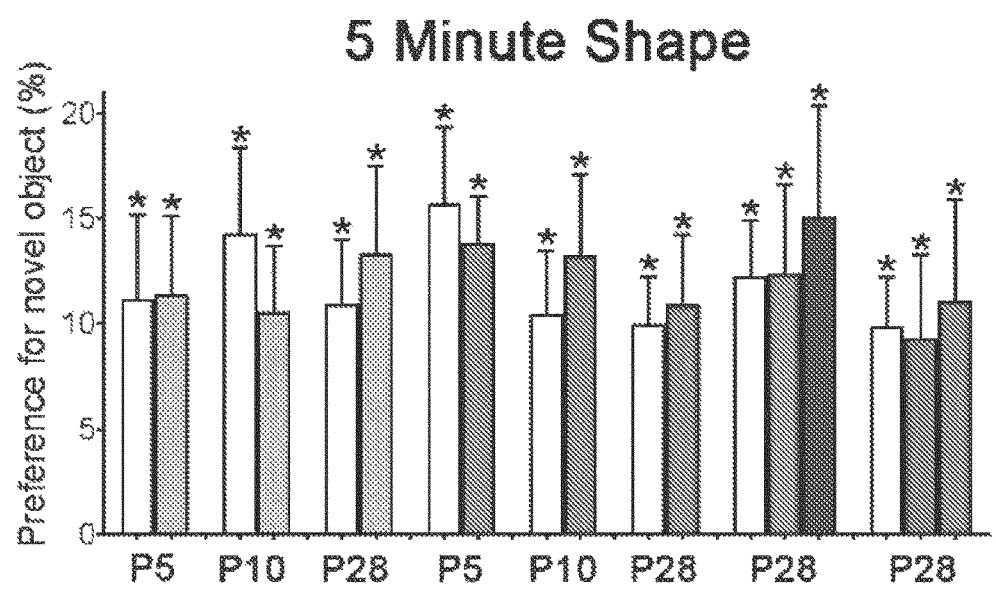
Figure 24F:
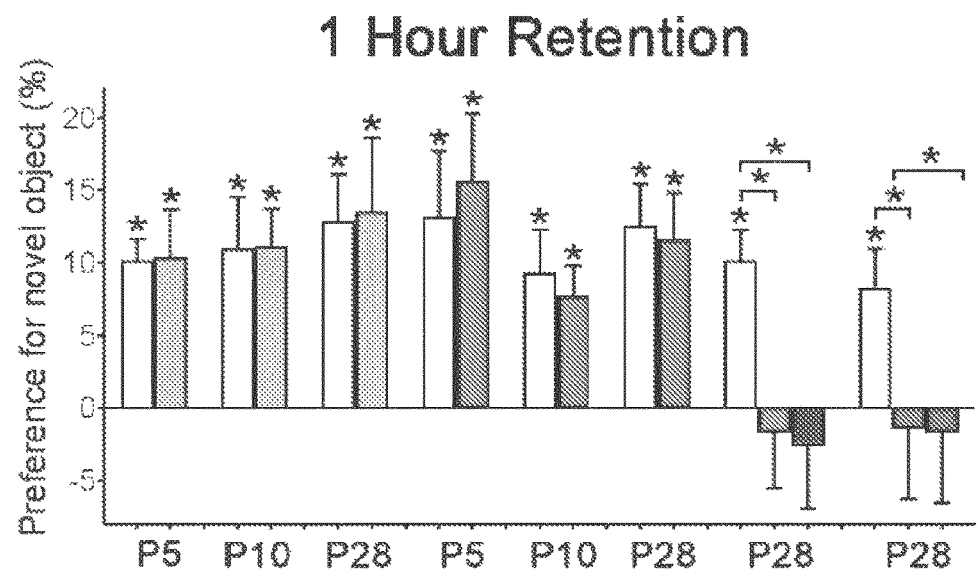
Figure 24G:
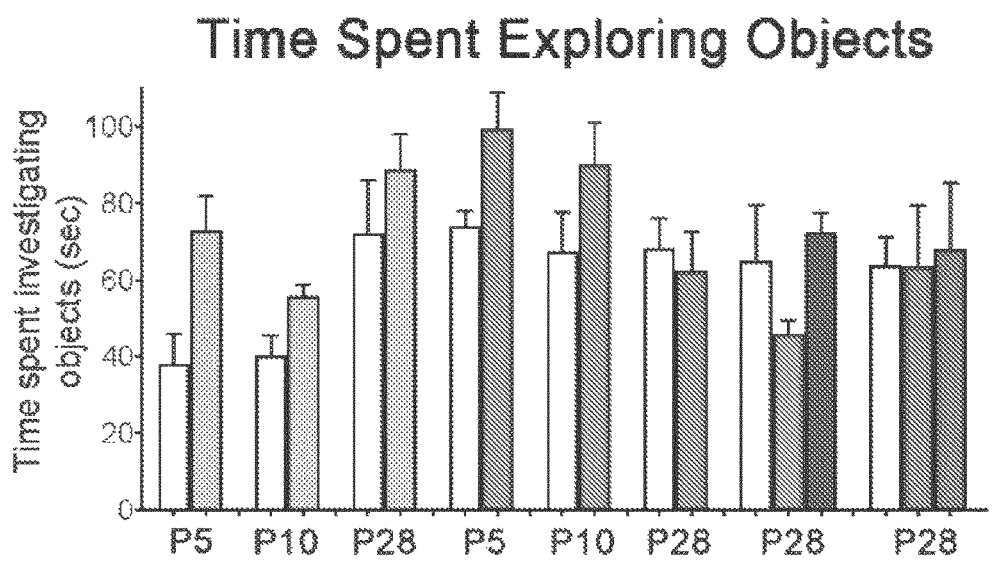
Figure 24H:
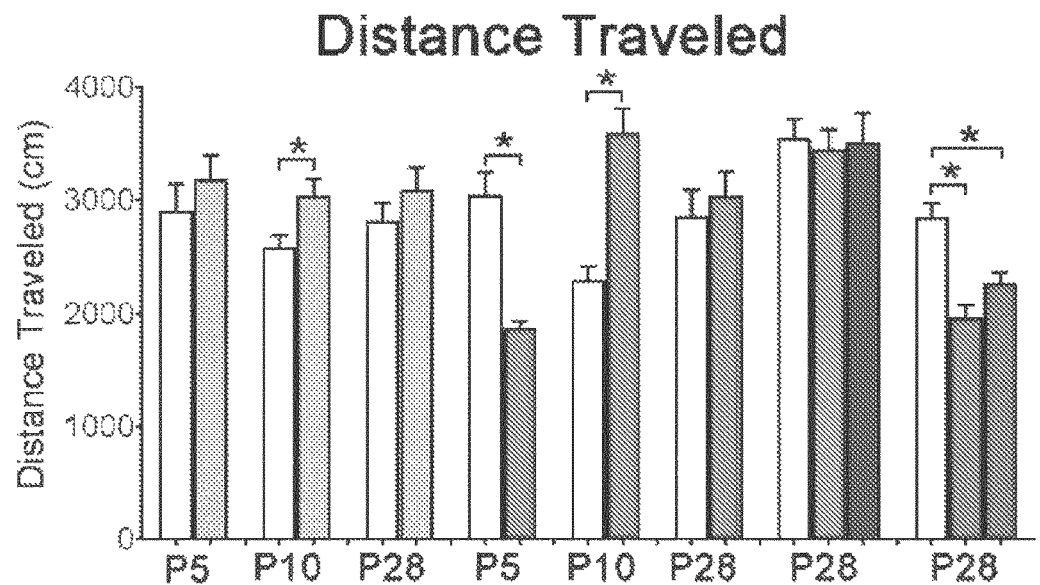
Figure 24I:
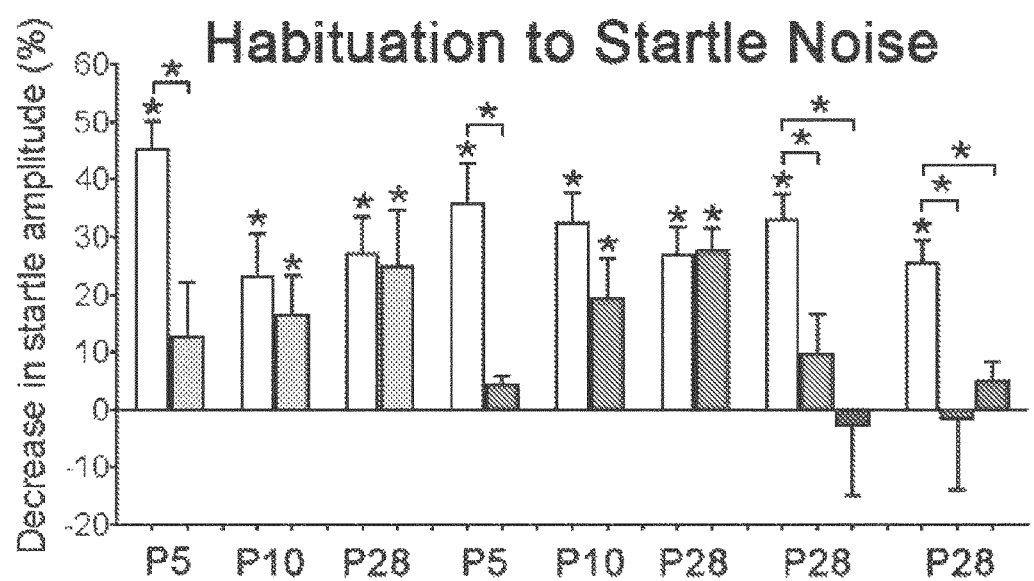
Figure 24J:
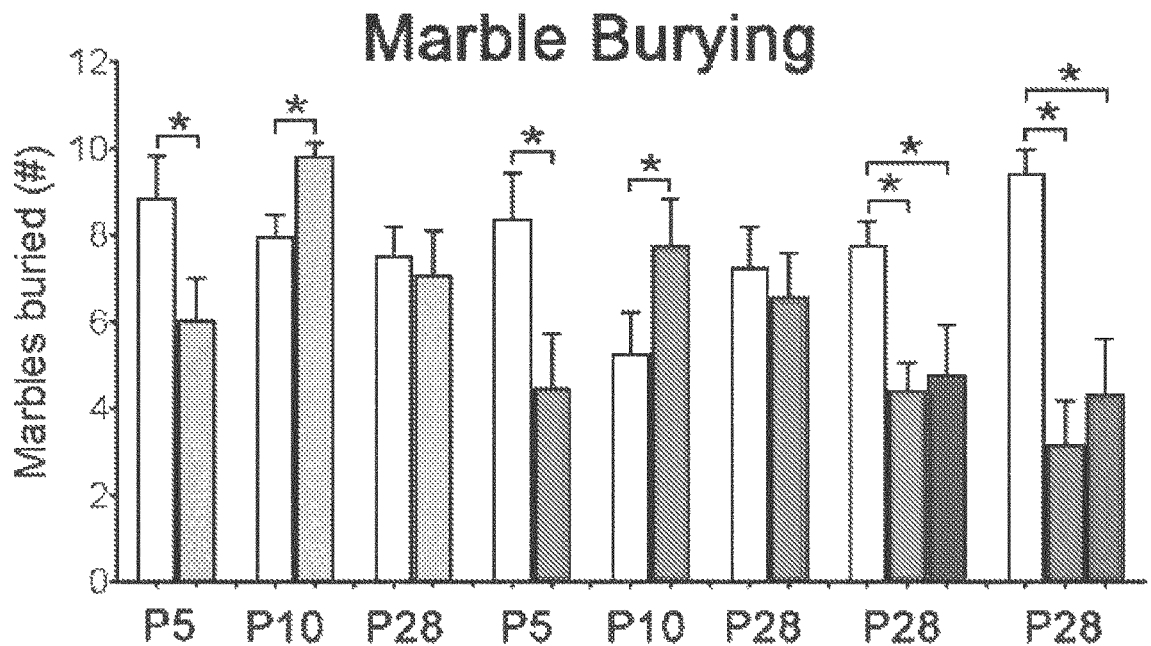
Figure 24K:
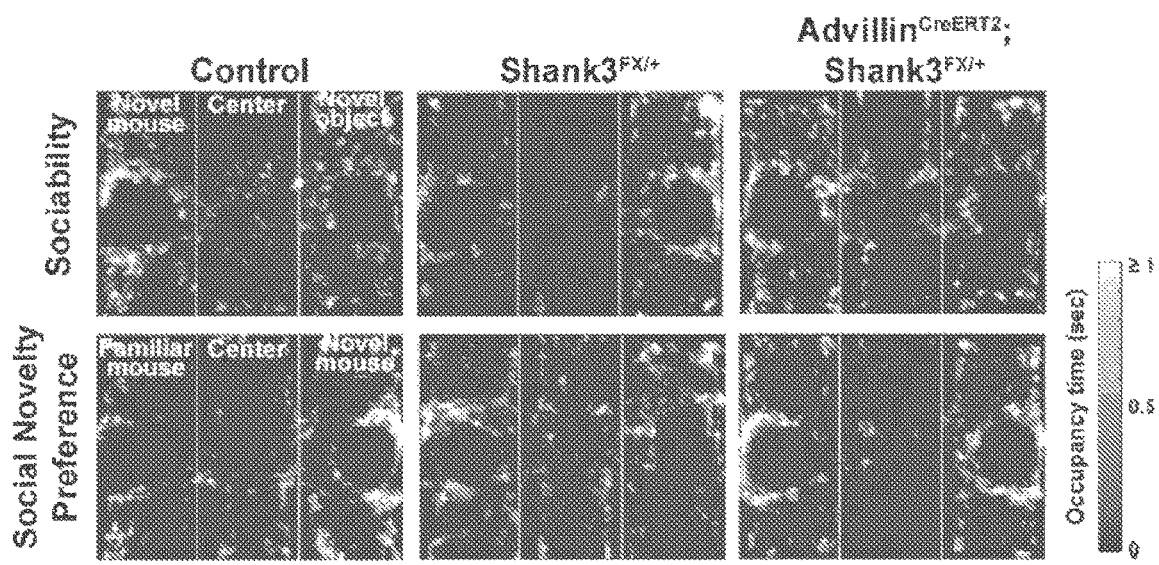
Figure 24L:
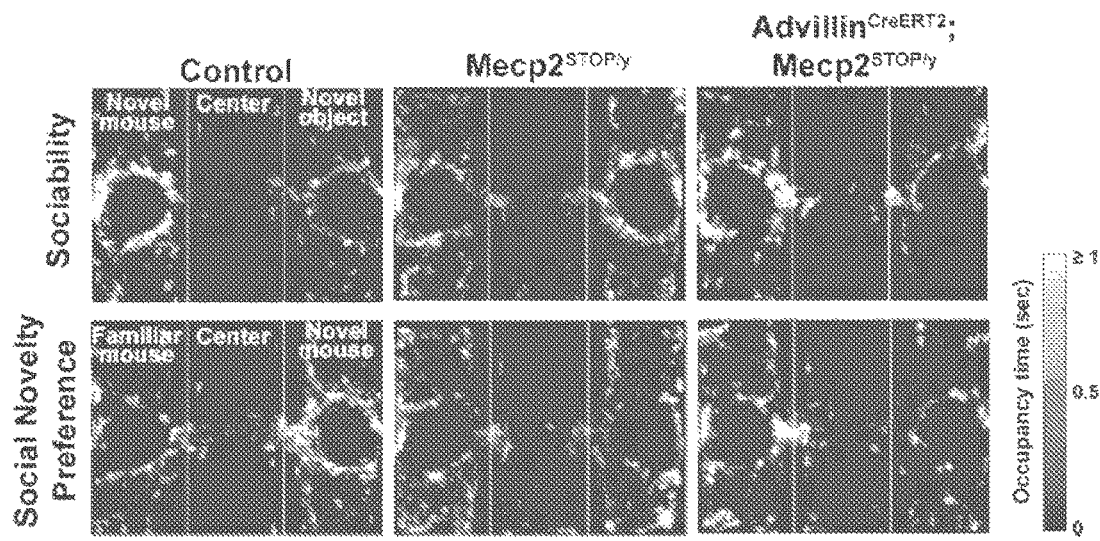
Figure 25J:
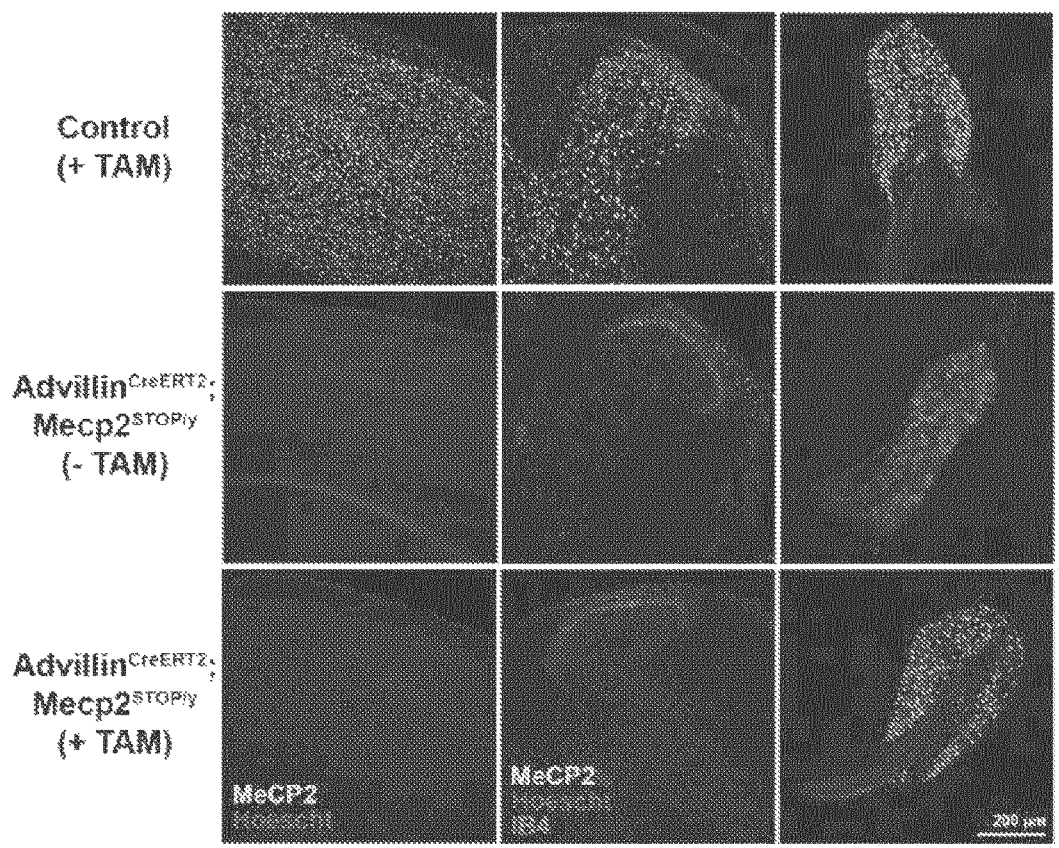
Figure 25K:
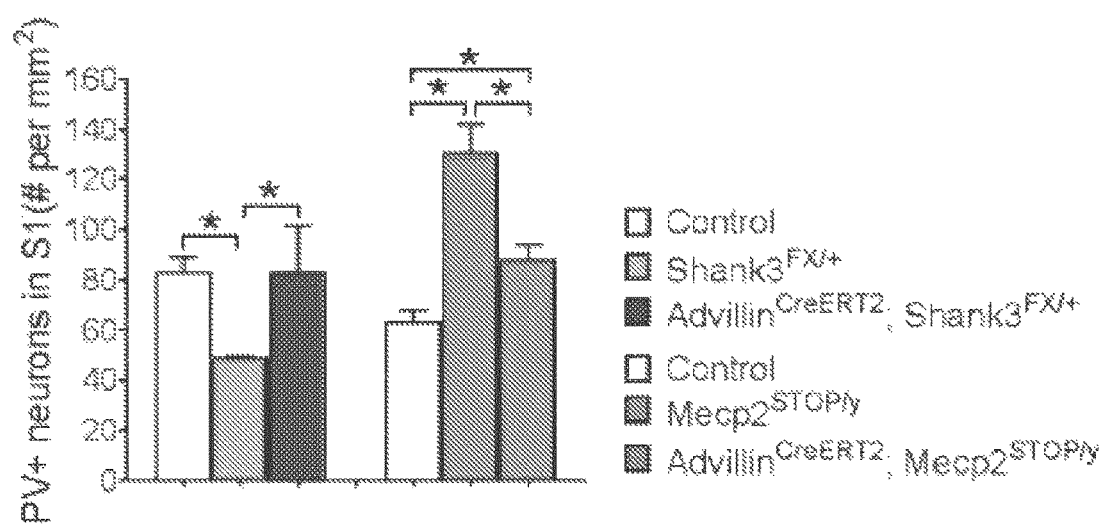
Figure 25L:
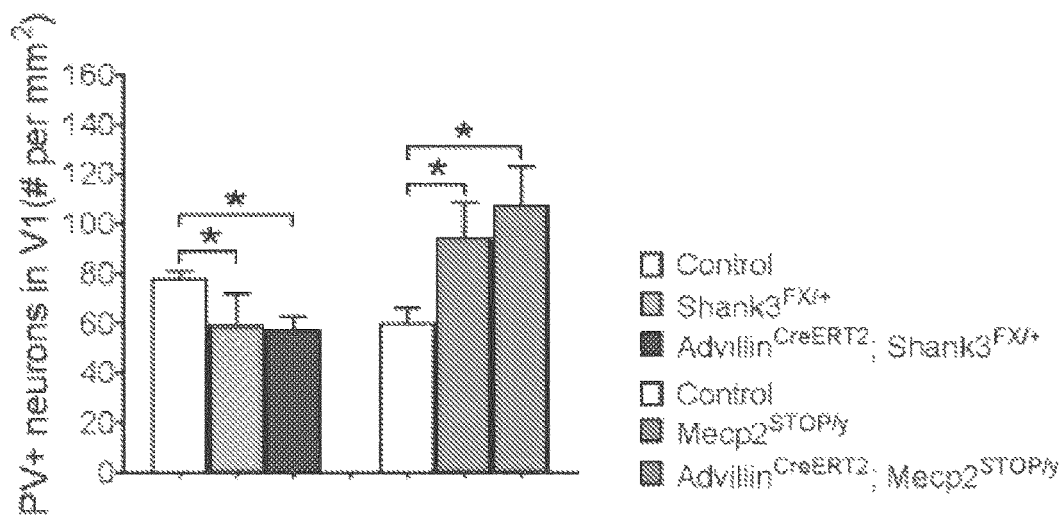
Figure 25M:
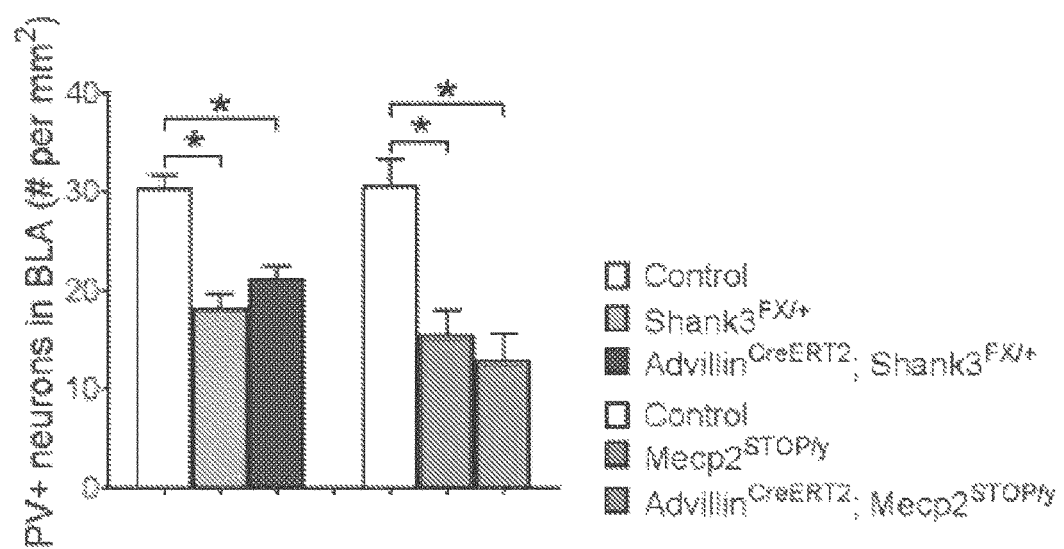

In related experiments, it was asked whether postnatal restoration of Mecp2 or Shank3 function in somatosensory neurons might improve ASD-related phenotypes in mice. For this, Advillin$^{CreERT2}$ mice crossed to either Shank3$^{FX/+}$ or Mecp2$^{STOP/+}$ mice were used to restore Shank3 or Mecp2 expression, respectively, in peripheral sensory neurons following 5 days of tamoxifen administration beginning at P28 (FIG. 25J). Consistent with results from the conditional ablation experiments, described above, restoration of either Shank3 or Mecp2 in peripheral sensory neurons, beginning at P28, was sufficient to normalize the hairy skin hypersensitivity observed in Shank3$^{FX/+}$ or Mecp2$^{STOP/y}$ littermates (FIGS. 17A, 17B, 24A). However, memory deficits were not improved in either Advillin$^{CreERT2}$; Shank3$^{FX/+}$ or Advillin$^{CreERT2}$; Mecp2$^{STOP/y}$ P28 rescue mice (FIG. 24F), and the motor impairments typically observed in Mecp2 germline mutant mice were also not improved in Advillin$^{CreERT2}$; Mecp2$^{STOP/y}$ mice (FIG. 24B). Furthermore, Advillin$^{CreERT2}$; Shank3$^{FX/+}$ and Advillin$^{CreERT2}$; Mecp2$^{STOP/y}$ mice treated with tamoxifen beginning at P28 did not show improvements in texture discrimination deficits, anxiety-like behaviors or neophobia (FIGS. 17B-17F, 24H, 24I, 24J). Advillin$^{CreERT2}$; Shank3$^{FX/+}$ and Advillin$^{CreERT2}$; Mecp2$^{STOP/y}$ rescue mice showed modest improvements in social behaviors, with a significant preference for a novel mouse in the sociability assay, but not in the social novelty recognition preference test (FIGS. 17I, 17J, 24K, 24L, Table 2). Together, these findings indicate that normal tactile reactivity is necessary during postnatal development for the acquisition of normal brain microcircuit properties and cognitive behaviors. This suggests that targeting the peripheral nervous system may provide a novel opportunity for therapeutic intervention in ASD, with optimal intervention occurring early during postnatal life.

Postnatal Viral Restoration of GABRB3 Improves Behavioral Deficits in an Mecp2 Mouse Model of RTT/ASD The genetic deletion and rescue experiments raised the exciting possibility that improving sensory neuron function during early postnatal development may lead to improved tactile reactivity, anxiety-like and social behaviors in adult mice. Targeting the GABA$_A$ receptor in primary sensory neurons provides a means of attenuating tactile over-reactivity in ASD models and, in doing so, improves anxiety-like behaviors and potentially other ASD-associated behaviors. The rationale stems from the finding that Mecp2 mutant mice exhibit decreased expression of the GABA$_A$ receptor obligatory subunit GABRB3 at presynaptic terminals of LTMRs in the spinal cord, leading to functional deficits in presynaptic inhibition of mechanosensory neuron input to the spinal cord and altered tactile processing (Orefice et al., 2016). Moreover, GABA receptor agonists effectively attenuate DRG sensory neuron excitability (Carlton et al., 1999; Enna and McCarson, 2006; Levy and Anderson, 1972; Page and Blackshaw, 1999). Thus, it was hypothesized that GABA, GABA mimetics, GABA reuptake inhibitors, or GABA$_A$ receptor modulators acting directly on peripheral LTMRs may attenuate tactile over-reactivity and improve brain microcircuit function and behaviors observed in different ASD mouse models, despite the finding that the mode of physiological dysfunction in primary mechanosensory neurons varies among the different ASD models. To begin to test this "LTMR GABA$_A$ receptor hypothesis for treating genetically distinct forms of ASD", first used was a genetic approach to ask whether selective restoration of GABRB3 expression in peripheral somatosensory neurons of Mecp2 mutant mice, at an early postnatal age, may augment GABA$_A$ receptor expression in LTMRs and improve tactile over-reactivity, brain development, and ASD-associated behavioral alterations observed in these mice.

Figure 18A:
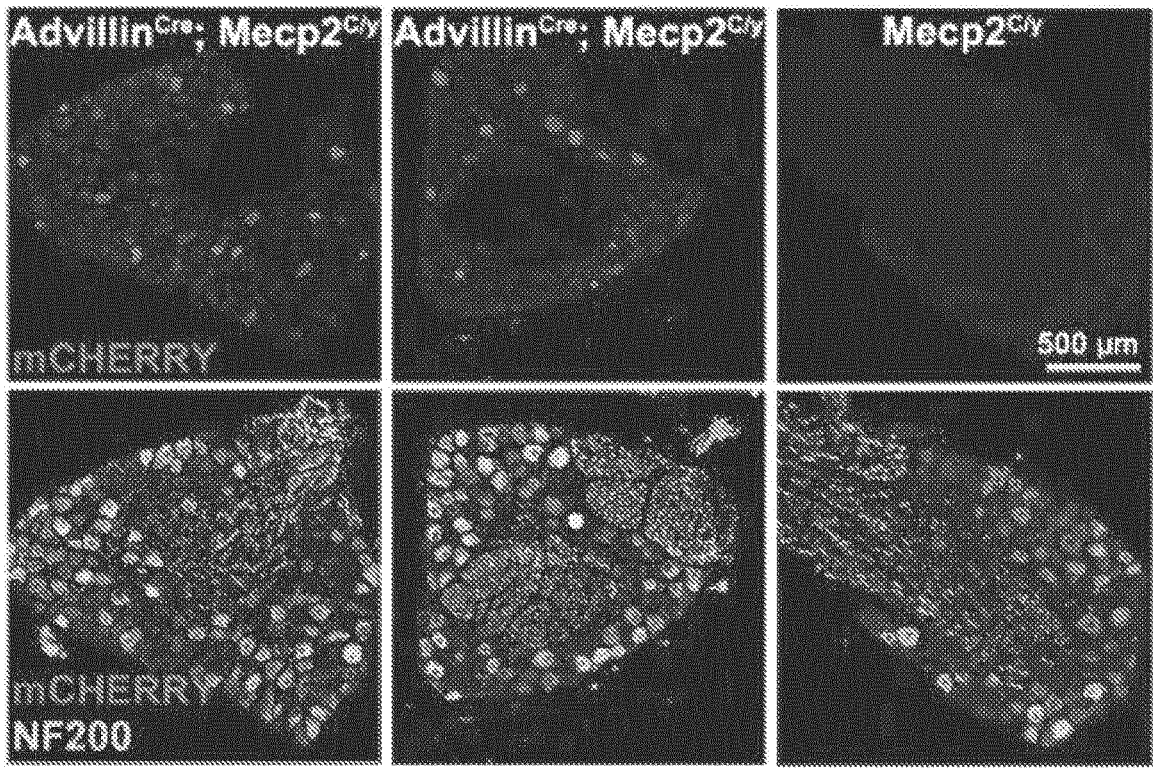
FIGS. 18A-18O show viral expression of GABRB3 in peripheral sensory neurons, beginning at P5, improves some tactile, brain and behavioral deficits observed in Mecp2$^{R306C}$ mutant mice.
Figure 18B:
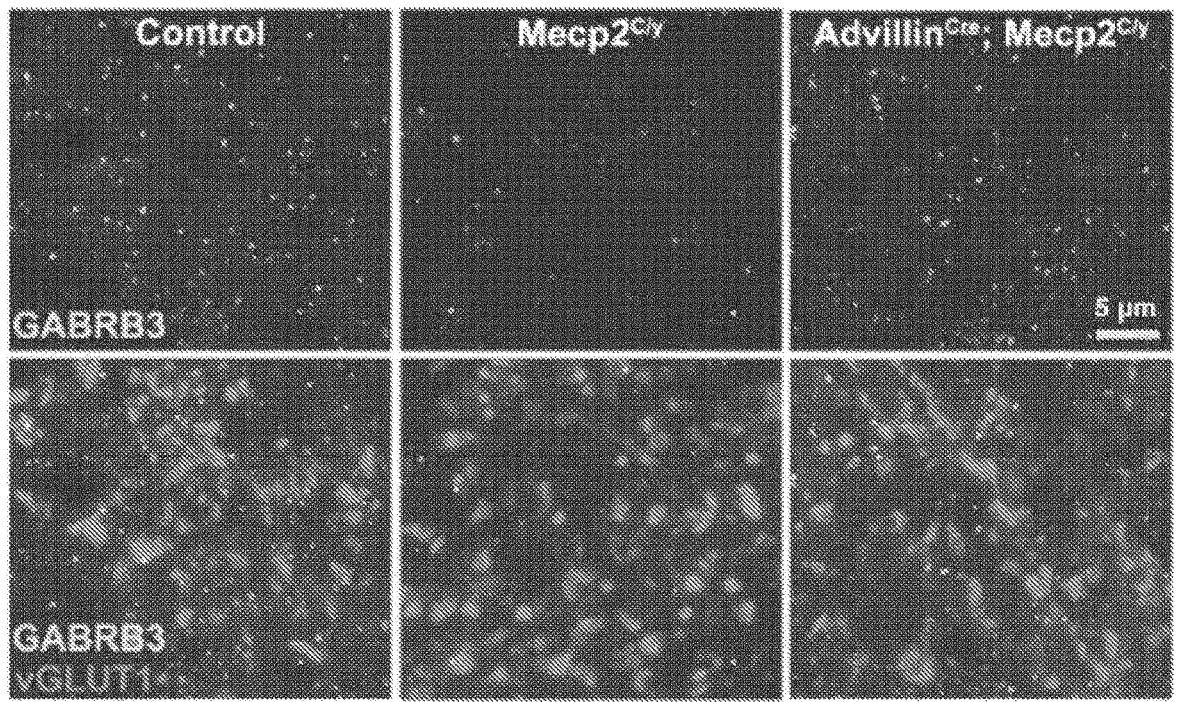
FIG. 18B: IHC images of spinal cord (SC) dorsal horn lamina III/IV from control, Mecp2$^{C/y}$ or Advillin$^{Cre}$; Mecp2$^{C/y}$ mice, showing GABRB3 puncta at vGLUT1+ presynaptic terminals for Aβ and Aδ LTMRs.
Figure 18C:
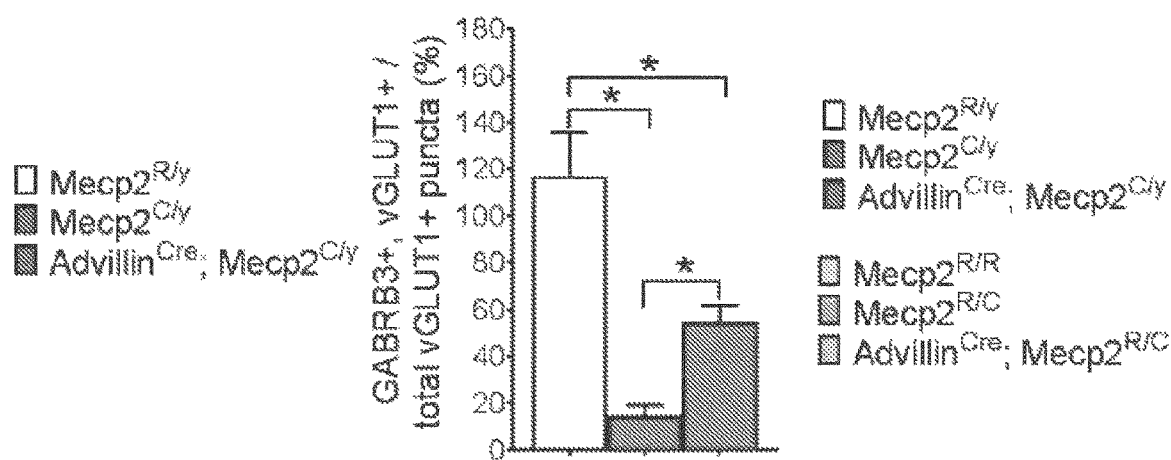
FIG. 18C: Quantification of vGLUT1+ puncta co-labeled with GABRB3, relative to the total number of vGLUT1+ puncta visualized per image of SC dorsal horn. One-way ANOVA with post-hoc Tukey's test, *, p<0.01.
Figure 18D:
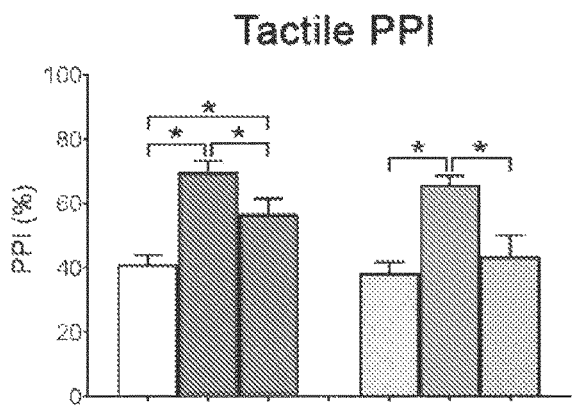
FIG. 18D: Percent inhibition of the startle response to a 125 dB noise, when the startle noise is preceded by a light air puff in male control, Mecp2$^{C/y}$, Advillin$^{Cre}$; Mecp2$^{C/y}$ or female control Mecp2$^{R/C}$, Advillin$^{Cre}$; Mecp2$^{R/C}$ mice. One-way ANOVA with post-hoc Tukey's test, *, p<0.05.
Figure 18E:
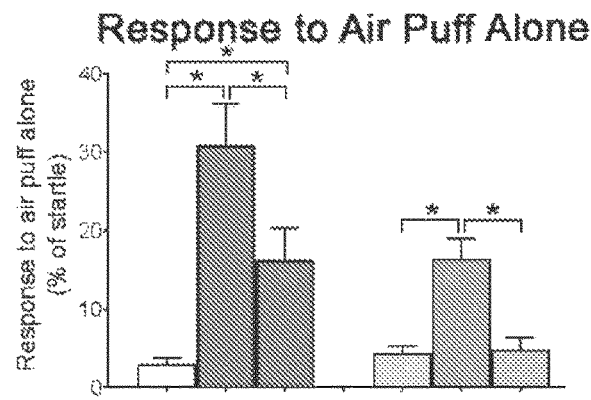
FIG. 18E: Response to a light air puff stimulus alone. Responses are expressed as percent of startle response to a 125 dB noise. One-way ANOVA with post-hoc Tukey's test, *, p<0.05.
Figure 18F:
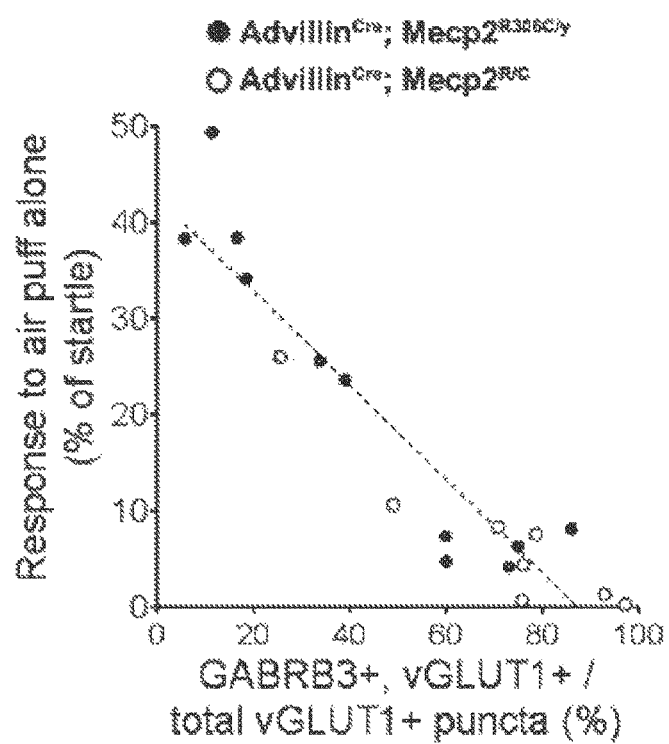
FIG. 18F: The percentage of vGLUT1+ puncta co-labeled with GABRB3, relative to the total number of vGLUT1+ puncta is negatively correlated with hairy skin sensitivity. Comparison of individual animals' expression levels of GABRB3 at vGLUT1+ terminals, to their responses to a light air puff stimulus (50 ms, 0.9 PSI). Linear regression analysis, $R^2$=0.8792.
Figure 18G:
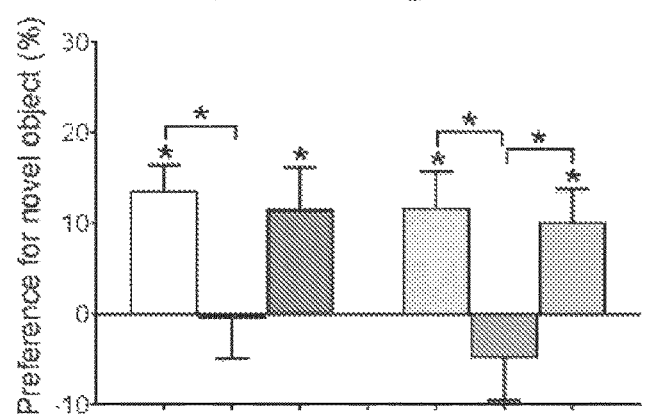
FIG. 18G: Discrimination index for textured NORT. Student's unpaired t-test or one-way ANOVA with post-hoc Tukey's test, *, p<0.05.
Figure 18H:
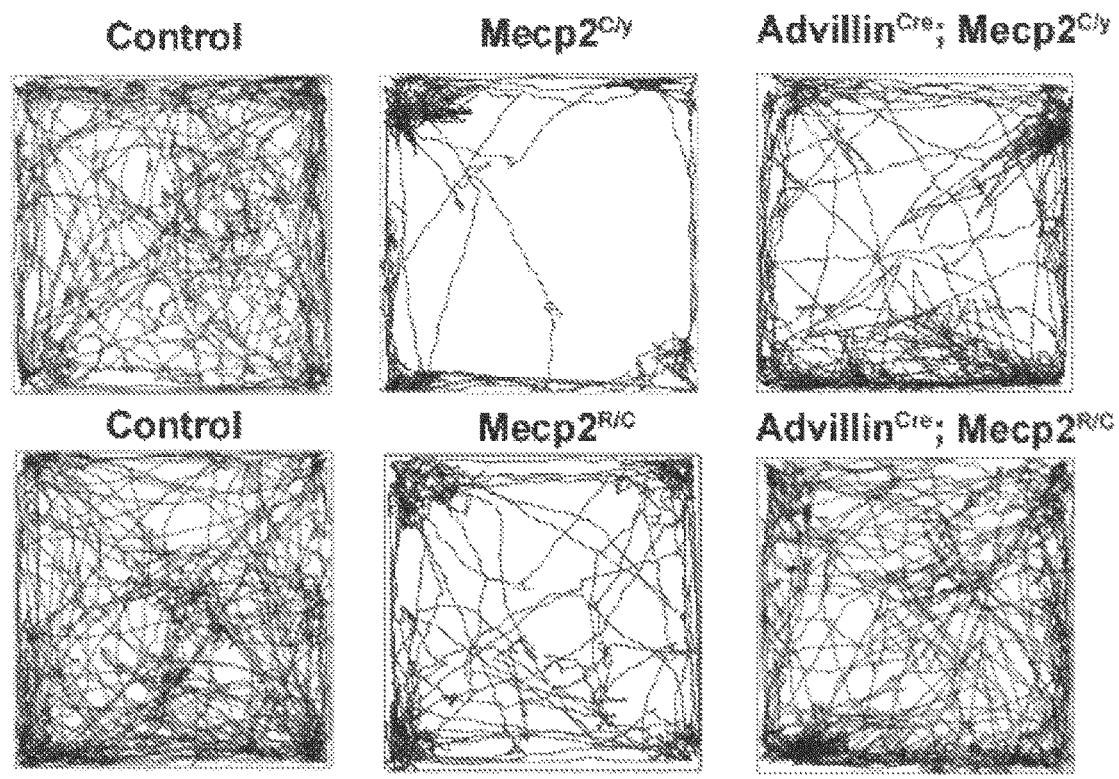
FIG. 18H: Representative activity traces in the OF test.
Figure 18I:
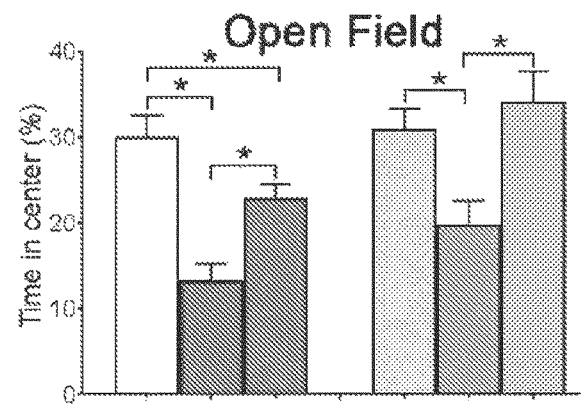
FIG. 18I: Percent time spent in the center of the OF chamber. One-way ANOVA with post-hoc Tukey's test, *, p<0.05.
Figure 18J:
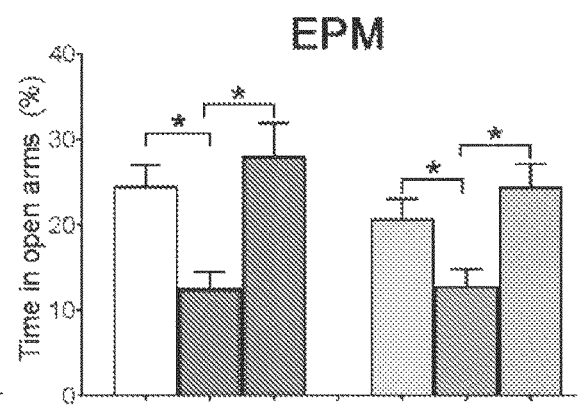
FIG. 18J: Percent time spent in the open arms of the EPM. One-way ANOVA with post-hoc Tukey's test, *, p<0.05.
Figure 18K:
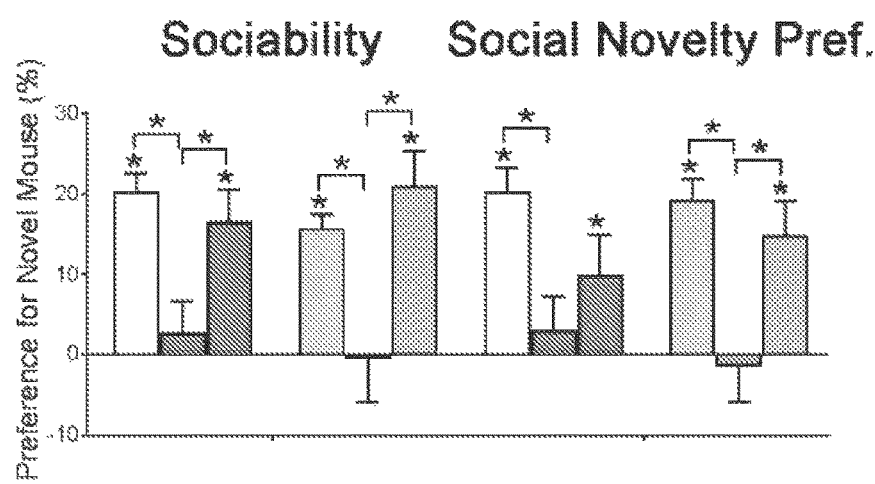
FIG. 18K: Preference index for the percentage of time spent investigating the novel mouse in the "Sociability" or "Social Novelty Recognition Preference" portion of the 3-chamber social interaction test. One-way ANOVA with post-hoc Tukey's test, *, p<0.05.
Figure 18L:
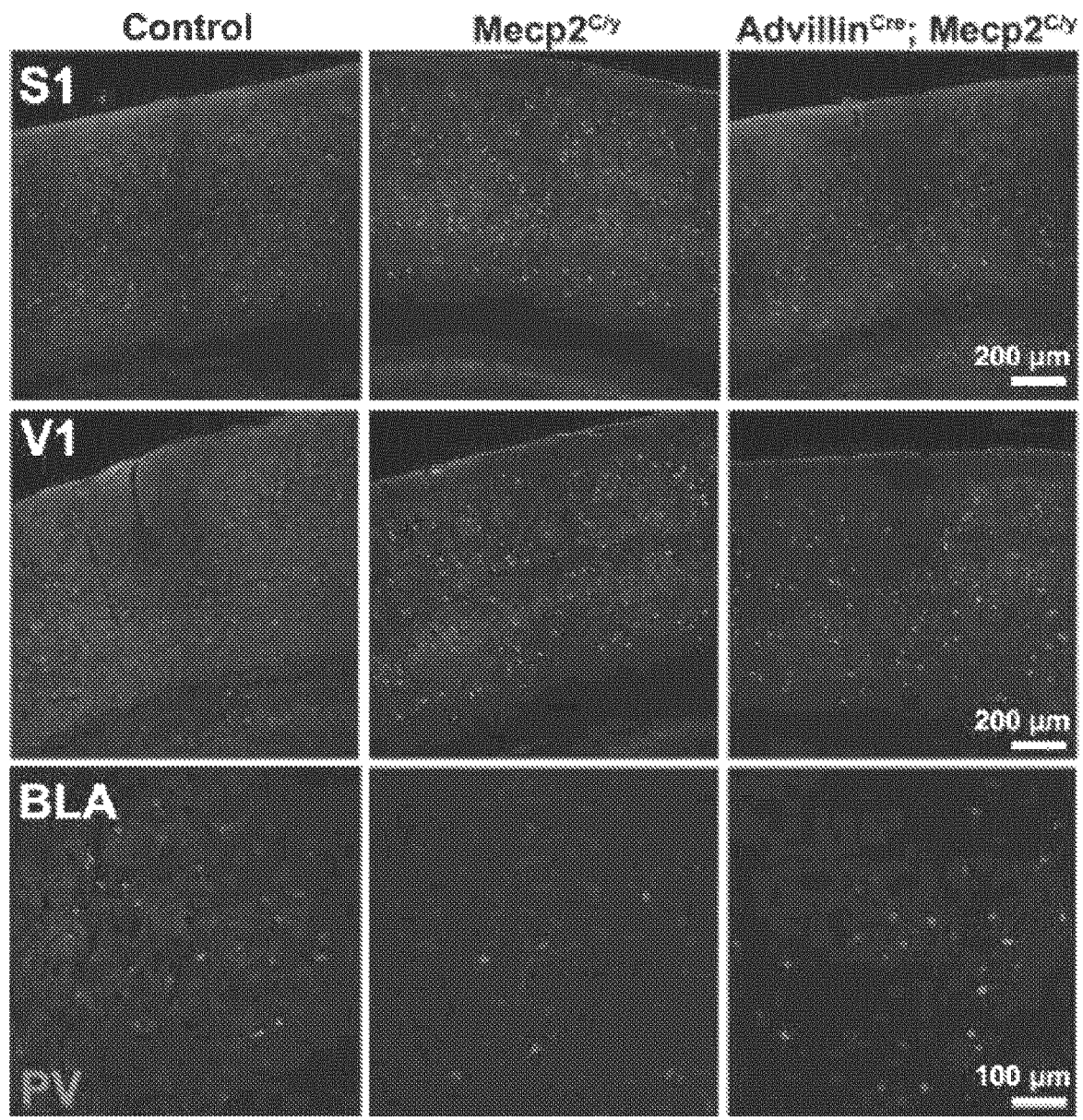
FIG. 18L: Representative IHC images of transverse S1, V1 and BLA brain sections, showing PV immunoreactivity in control, Mecp2$^{C/y}$ or Adv-iffin$^{Cre}$; Mecp2$^{C/y}$ mice.
Figure 18M:
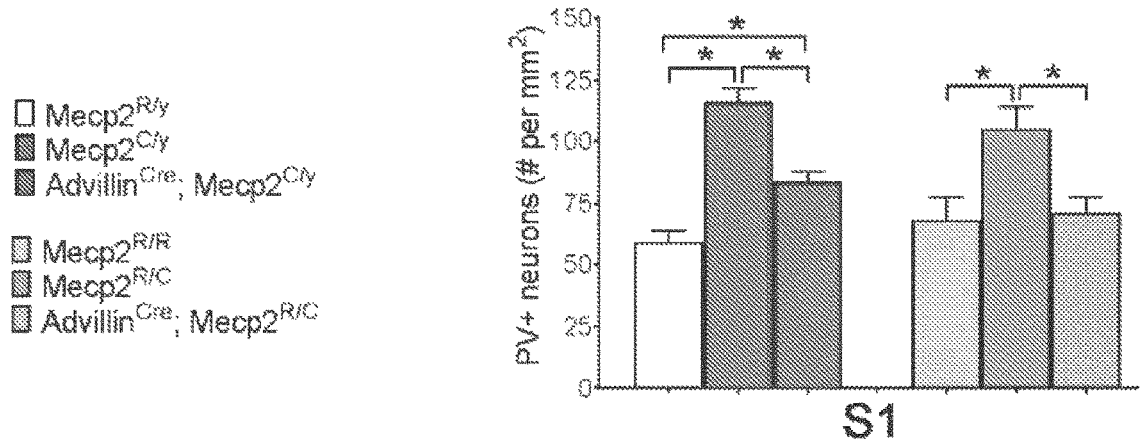
Figure 18N:
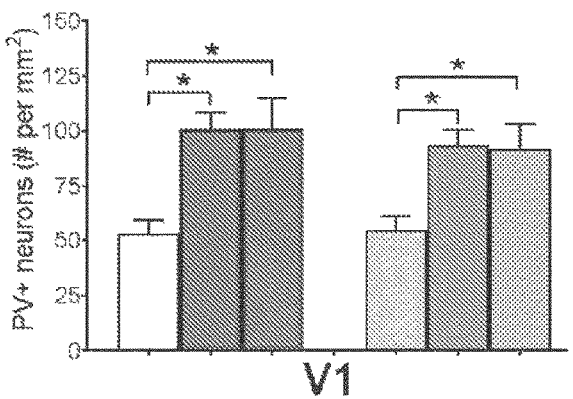
Figure 18O:
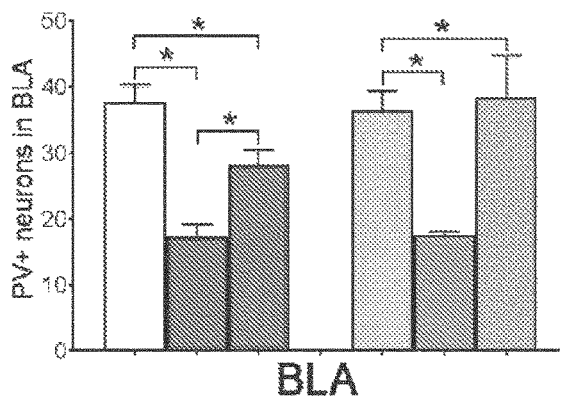
Figure 26A:
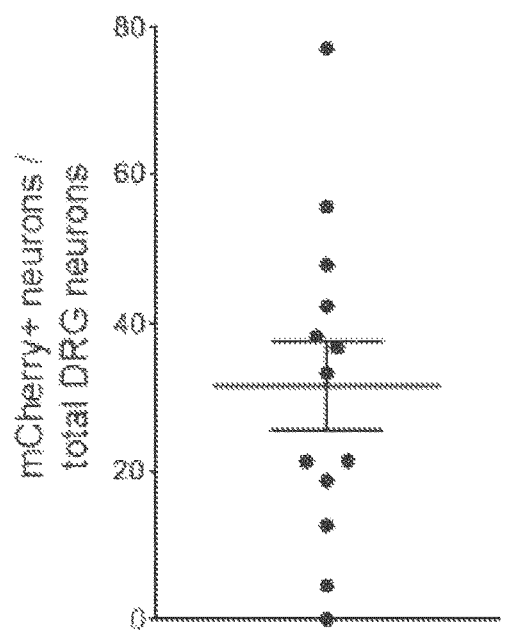
FIGS. 26A-26N are related to FIGS. 18A-18O.
Figure 26B:
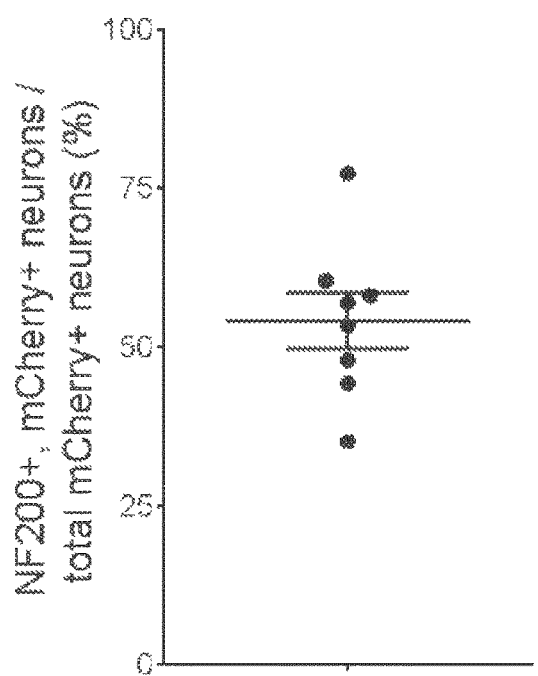
FIG. 26B: Percentage of mCherry⁺ DRG neurons that are NF200+ neurons in mice that received P5 i.p. injection of AAV.FLEX.GABRB3.
Figure 26C:
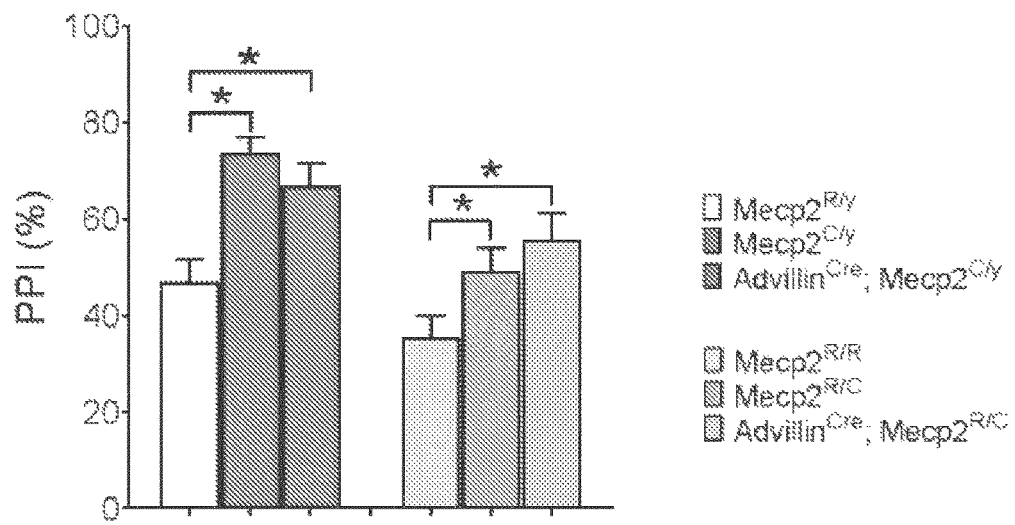
FIG. 26C: Percent inhibition of the startle response to a 125 dB noise (pulse), when the startle noise is preceded by tone prepulse in male and female control, mutant and mutant rescue mice. All littermates received an i.p. injection of AAV.FLEX.GABRB3 at P5. One-way ANOVA with post-hoc Tukey's test, *, p<0.05.
Figure 26D:
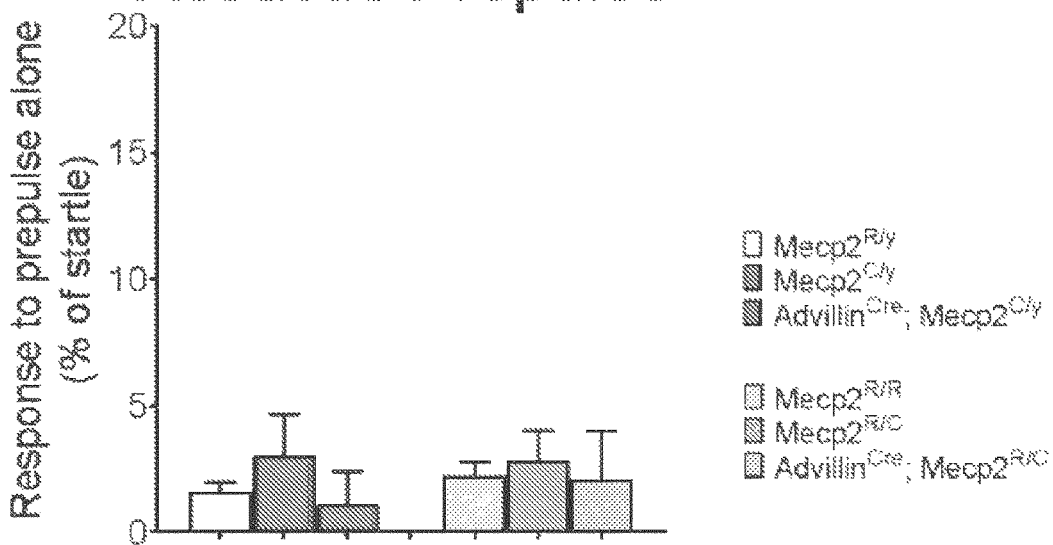
FIG. 26D: Response to a non-startling acoustic noise (80 dB, 20 ms) in male and female control, mutant and mutant rescue mice. Responses are expressed as percent of startle response to a 125 dB startle noise.
Figure 26E:
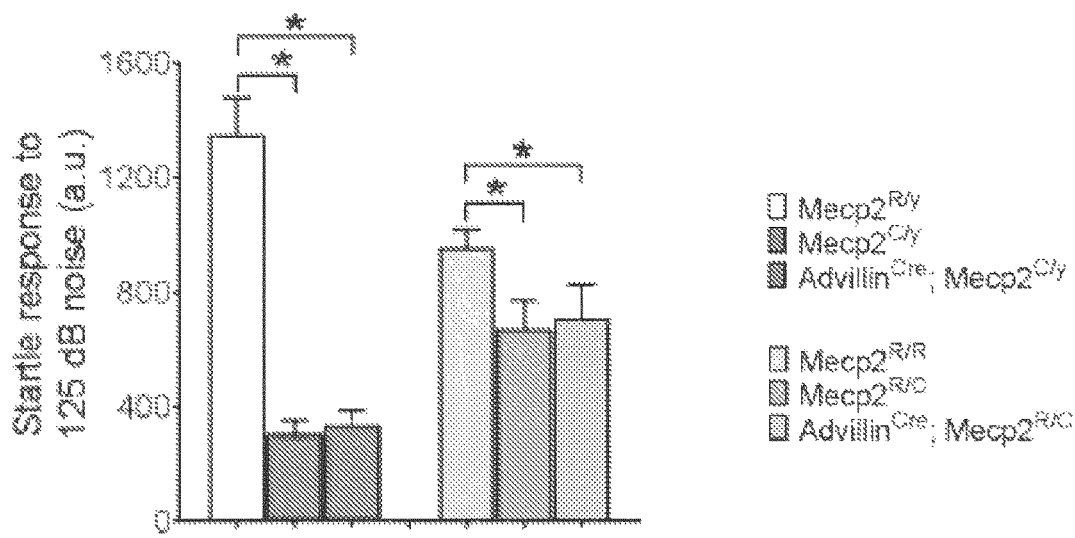
FIG. 26E: Magnitude of startle response to a 125 dB noise in male and female control, mutant and mutant rescue mice. One-way ANOVA with post-hoc Tukey's test, *, p<0.05.
Figure 26F:
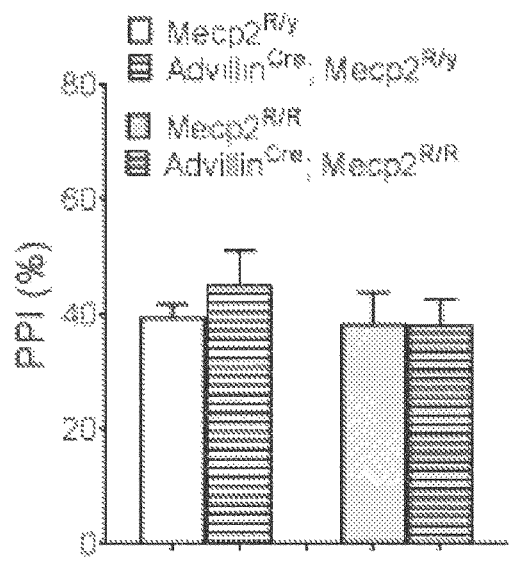
FIG. 26F: Percent inhibition of the startle response to a 125 dB noise, when the startle noise is preceded by a light air puff in Mecp2$^{R/y}$ and Adviffin$^{Cre}$; Mecp2$^{R/y}$ control mice. One-way ANOVA, not significant.
Figure 26G:
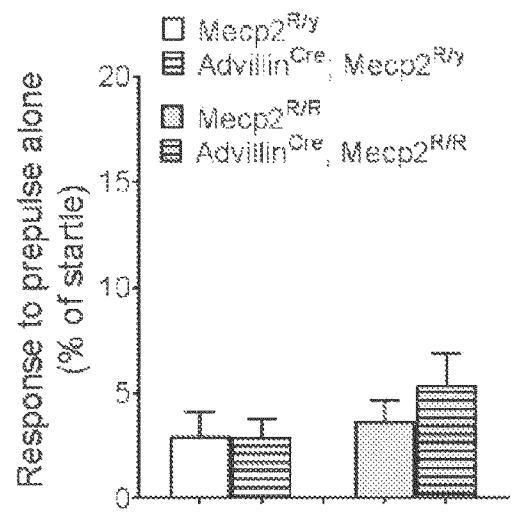
FIG. 26G: Response to a light air puff stimulus alone in Mecp2$^{R/y}$ and Adviffin$^{Cre}$; Mecp2$^{R/y}$ control mice. Responses are expressed as percent of startle response to a 125 dB noise. One-way ANOVA, not significant.
Figure 26H:
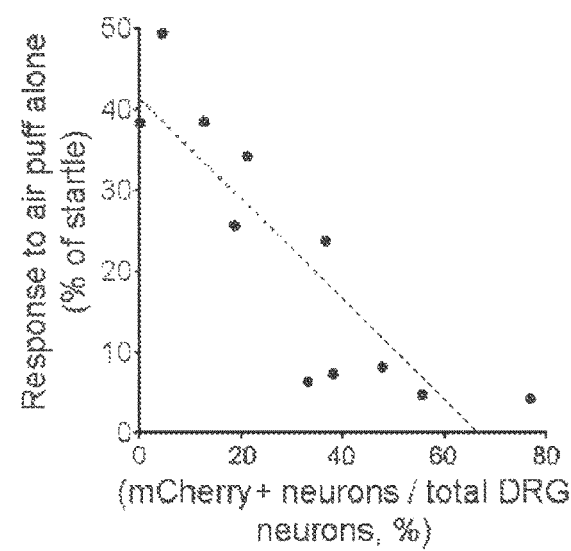
FIG. 26H: Percent of DRG neurons transduced with AAV.FLEX.GABRB3, plotted against response to a light air puff stimulus alone for Adviffin$^{Cre}$; Mecp2$^{C/y}$ mice.
Figure 26I:
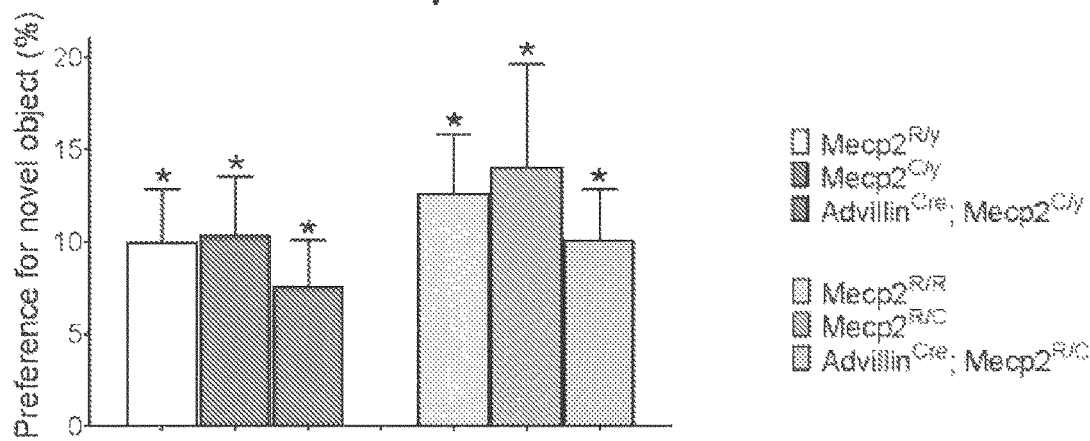
FIG. 26I: Discrimination index for 5-minute NORT.
Figure 26J:
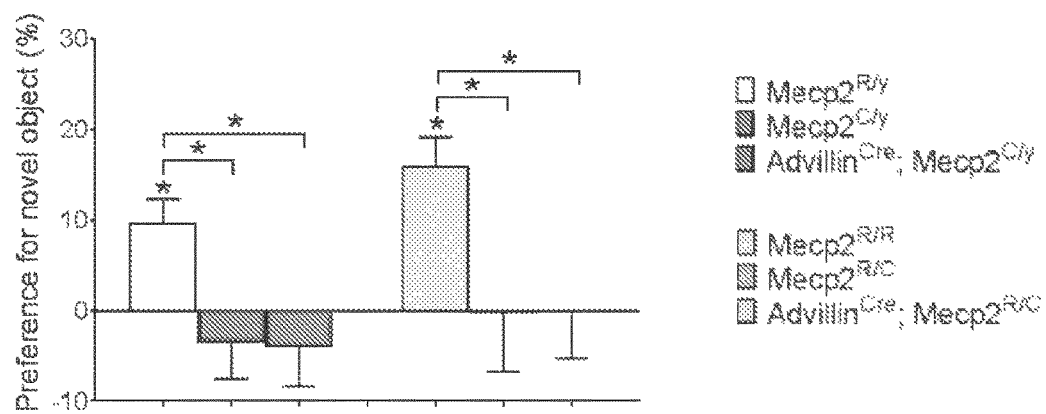
FIG. 26J: Discrimination index for 1-hour NORT. Student's unpaired t-test or one-way ANOVA with post-hoc Tukey's test, *, p<0.05.
Figure 26K:
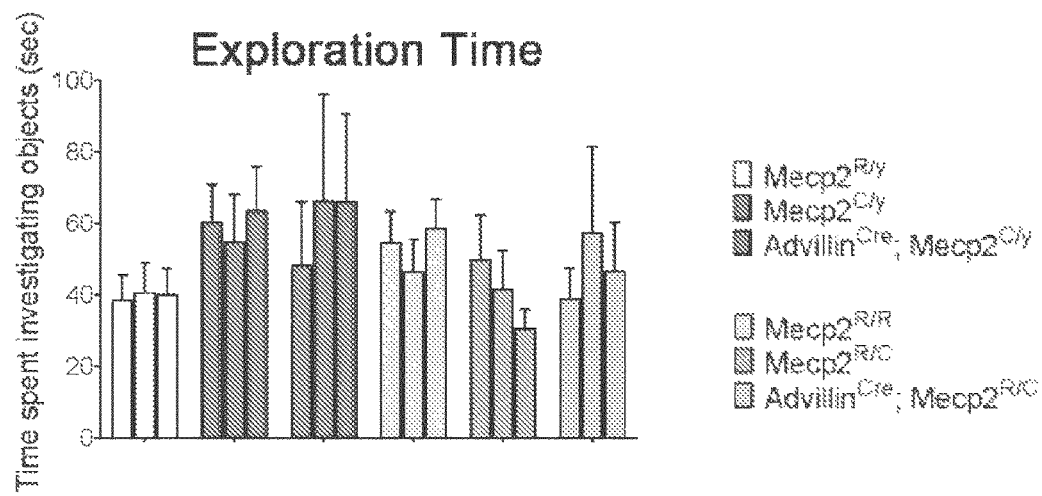
FIG. 26K: Average amount of time (seconds) spent physically interacting with both the familiar and novel object in the NOR tests in mutant mice and their control littermates.
Figure 26L:
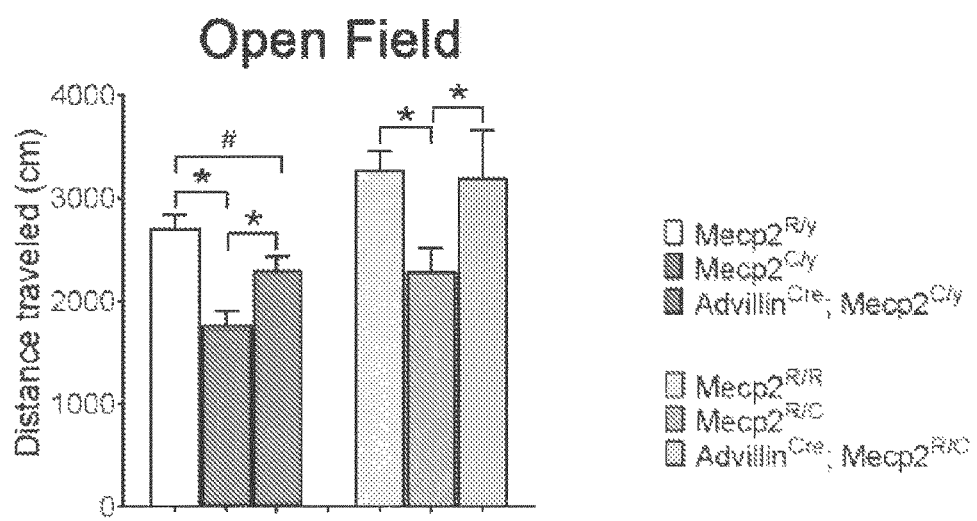
FIG. 26L: Average total distance traveled in the open field chamber for mutant, mutant rescue mice and their control littermates. One-way ANOVA with post-hoc Tukey's test, *, p<0.05.
Figure 26M:
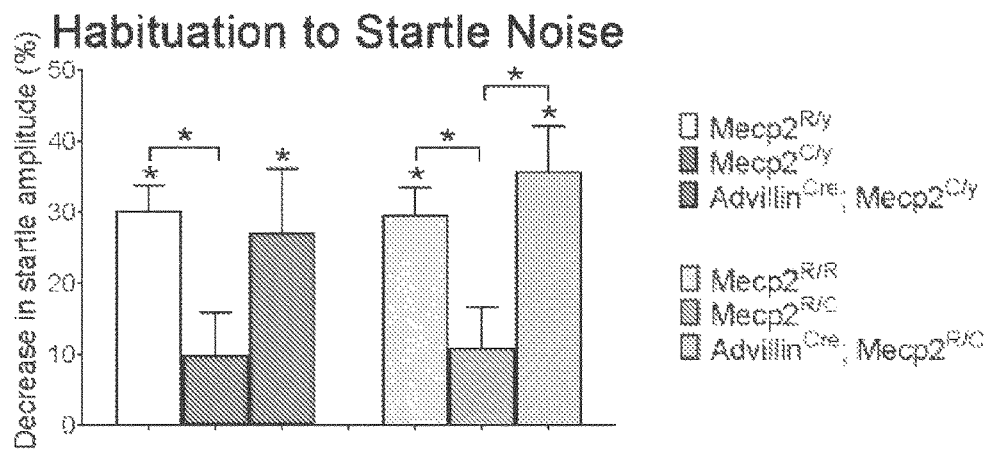
FIG. 26M: Percent decrease in startle response to a 125 dB noise during a 30-minute tactile PPI session, when comparing the first five startle responses to the last five responses to a 125 dB noise for mutant, mutant rescue mice and their control littermates. One-way ANOVA with post-hoc Tukey's test, *, p<0.05.
Figure 26N:
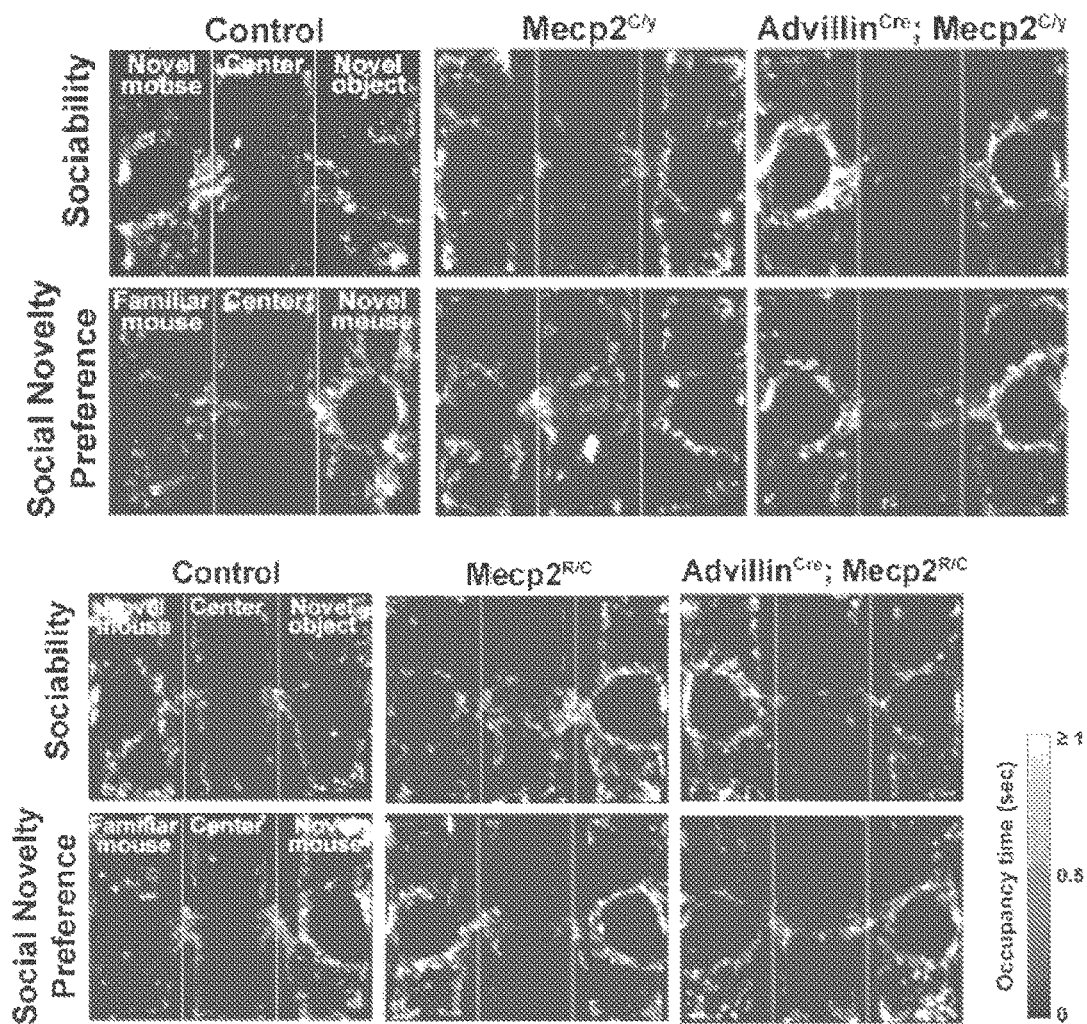
Figure 26O:
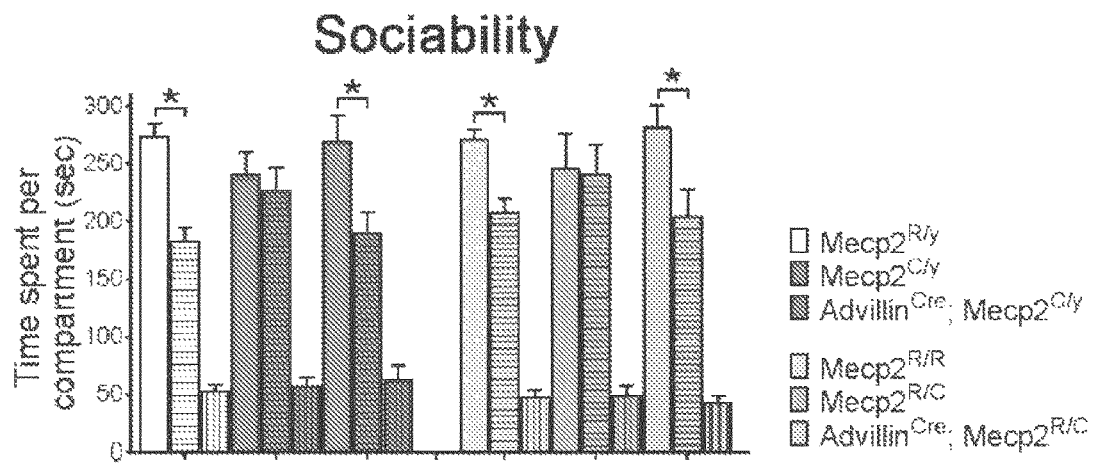
Figure 26P:
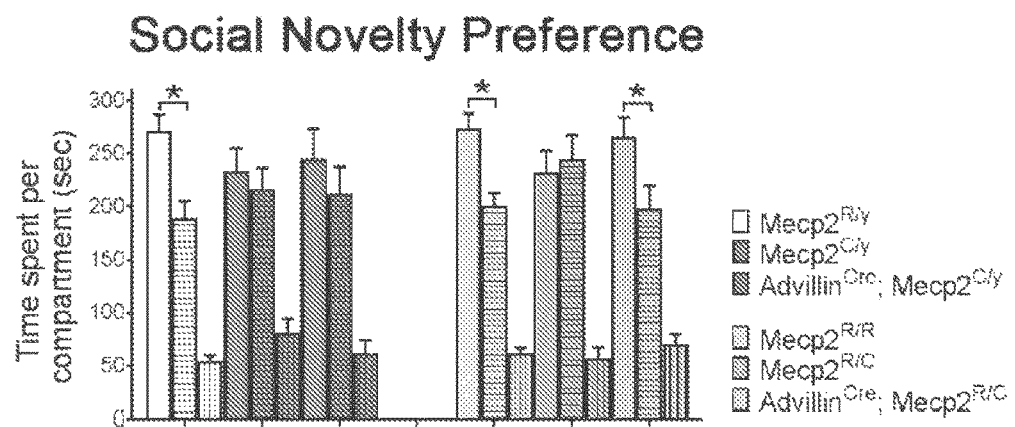

Using conditional mouse genetics and a flexed AAV delivery strategy, it was possible to selectively restore GABRB3 expression in peripheral somatosensory neurons of Mecp2 mutant mice in a temporally precise manner. Mecp2 mutant mice with an arginine-to-cysteine missense mutation in Mecp2, (Mecp2$^{R306C}$) a common allele found in human RTT patients (Lyst et al., 2013), were used in these studies because Mecp2$^{R306C}$ mutant mice live longer than mice harboring the Mecp2 null allele. Advillin$^{Cre}$ mice and intraperitoneal injection of an AAV.FLEX.GABRB3.t2A.mCherry virus, under control of the human Synapsin promoter, at P5, were used to selectively express GABRB3 in peripheral sensory neurons. Thus, DRG neurons in mice harboring both the Mecp2$^{R306C}$ and Advillin$^{Cre}$ alleles expressed functional GABRB3 following I.P. injection of P5 pups with AAV.FLEX.GABRB3.t2A.mCherry. Mecp2$^{R306C}$ mice lacking the Advillin$^{Cre}$ allele and injected with AAV.FLEX.GABRB3.t2A.mCherry served as a control. It was found that I.P. injection of Advillin$^{Cre}$; Mecp2$^{R306C}$ mice, but not Mecp2$^{R306C}$ mice lacking the Advillin$^{Cre}$ allele, with AAV.FLEX.GABRB3.t2A.mCherry led to transduction of all types of DRG sensory neurons, a large fraction of which are LTMRs, and a dramatic increase in the amount of GABRB3 puncta at presynaptic terminals of Aδ-LTMRs and Aβ-LTMRs in the spinal cord dorsal horn (FIGS. 18A-18C, 26A, 26B). Strikingly, increased expression of GABRB3 in peripheral somatosensory neurons of Advillin$^{Cre}$; Mecp2$^{R306C}$ improved tactile behavior abnormalities in a dose-dependent manner: Advillin$^{Cre}$; Mecp2$^{C/y}$ mice displayed significant improvements in hairy skin hypersensitivity and texture discrimination, compared to Mecp2$^{C/y}$ mice (FIGS. 18D-18F). Female 'GABRB3 rescue' mice, which are heterozygous for the Mecp2 mutation (Advillin$^{Cre}$; Mecp2$^{R/C}$), showed a complete normalization of somatosensory phenotypes, and were not different than control littermates (FIGS. 18D-18F). In line with this, it was found a significant correlation between both the number of DRG neurons transduced and the number of GABRB3 puncta in the dorsal horn and reduced responsivity to an air puff stimulus in Mecp2 mutant mice (FIGS. 18G and 26H). Strikingly, restoration of GABRB3 expression in peripheral somatosensory neurons also improved anxiety-like behaviors and social impairments in both male and female mutant mice, with male mice exhibiting an improvement and female mice displaying normalization of these behavioral parameters (FIGS. 18H-18K, 26L-26P). Viral restoration of GABRB3 expression beginning at P5 also ameliorated PV$^+$ neuron abnormalities in S1 and BLA, but not V1, of both male and female rescue mice, with female Advillin$^{Cre}$; Mecp2$^{R/C}$ mice exhibiting values similar to those of control littermates (FIGS. 18L-18O). Viral restoration of GABRB3 expression, however, did not improve memory deficits, motor impairments and heightened acoustic PPI performance in mutant animals (FIGS. 26C-26E, 26I). This proof-of-concept genetic restoration experiment suggests that increasing $GABA_A$ receptor function in primary somatosensory neurons during early postnatal development ameliorates tactile over-reactivity, altered S1 and BLA microcircuits, and at least some behavioral deficits observed in germline Mecp2 mutants.

Figure 19A:
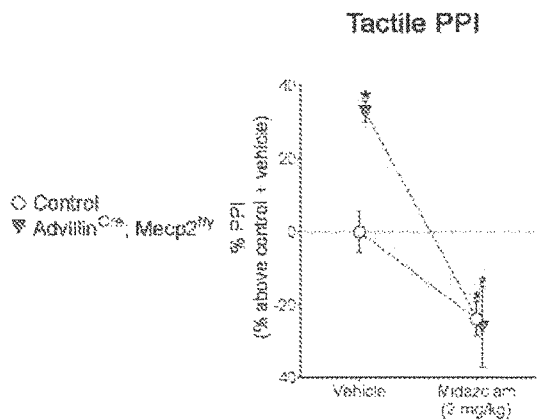
FIGS. 19A-19N show acute administration of the peripherally-restricted GABA$_A$ receptor agonist isoguvacine improves tactile hypersensitivity in five genetic and one environmental model of ASD.
Figure 19B:
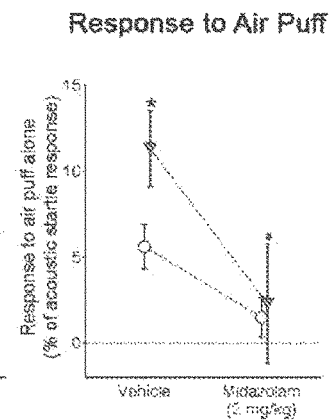
FIG. 19B: Response to a light air puff stimulus alone in mice following i.p. administration of either saline or 2 mg/kg midazolam treatment. Responses are expressed as percent of startle response to a 125 dB noise. Two-way ANOVA with post-hoc Sidak's test, *, p<0.05.
Figure 19C:
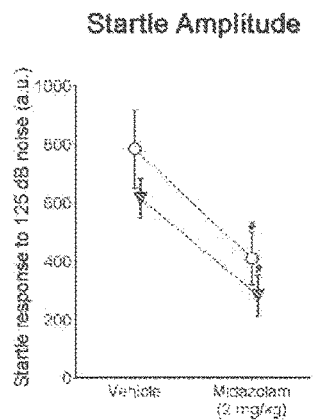
FIG. 19C: Magnitude of startle response to a 125 dB noise in mice following i.p. administration of either saline or 2 mg/kg midazolam treatment. Responses are expressed as percent of startle response to a 125 dB noise. Two-way ANOVA with post-hoc Sidak's test, *, p<0.05.

Acute Treatment with a Peripherally-Restricted $GABA_A$ Receptor Agonist Improves Hairy Skin Hypersensitivity in Six Distinct, Genetic and Environmental Models of ASD Results of the $GABA_A$ receptor restoration experiments raised the possibility that pharmacological treatment with a $GABA_A$ receptor agonist may improve tactile reactivity in Mecp2 mutant mice. It was therefore tested whether benzodiazepines, which are positive allosteric modulators (PAMs) of $GABA_A$ receptors, would attenuate hairy skin hypersensitivity in Mecp2 mutant mice. $Advillin^{Cre}$; $Mecp2^{f/y}$ mutant mice and their control littermates were administered either vehicle alone or the benzodiazepine midazolam (2 mg/kg, i.p.) in a pseudorandomized manner, and then subjected to tactile PPI. On the following day, treatment regimens were reversed, and tactile PPI was repeated. As expected, $Advillin^{Cre}$; $Mecp2^{f/y}$ mice receiving vehicle treatment showed tactile hypersensitivity compared to control littermates (FIGS. 19A, 19B). Treatment with midazolam significantly attenuated tactile sensitivity in both Mecp2 mutants and controls, with all mice exhibiting a decreased performance in tactile PPI (FIGS. 19A, 19B). However, although midazolam treatment reduced tactile sensitivity, this treatment also caused significant sedation in all mice, as evidenced by a ~50% reduction in their startle amplitude (FIG. 19C).

Figure 19D:
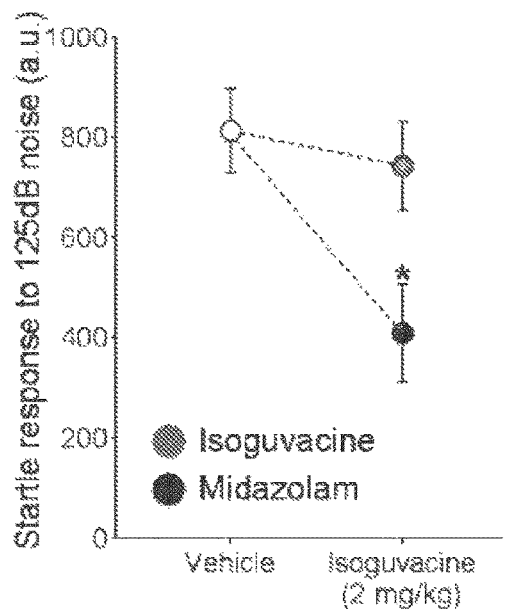
FIG. 19D: Magnitude of startle response to a 125 dB noise in mice following i.p. administration of saline, midazolam (2 mg/kg) or a peripherally-restricted GABA$_A$ receptor agonist, isoguvacine (2 mg/kg). Responses are expressed as percent of startle response to a 125 dB noise. Two-way ANOVA with post-hoc Sidak's test, *, p<0.05.
Figure 19E:
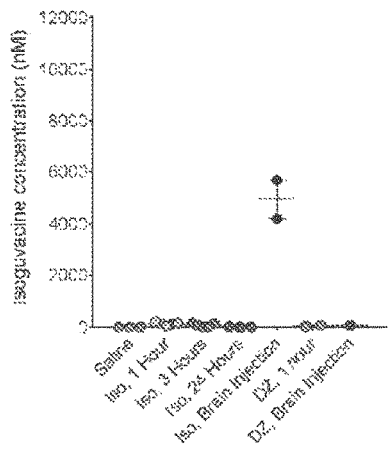
FIGS. 19E-19G: Liquid chromatography mass spectrometry (LC-MS) quantified isoguvacine concentrations in cerebrospinal fluid (CSF) (FIG. 19E), blood (FIG. 19F) or liver (FIG. 19G) samples of mice treated with: i.p. saline, i.p. isoguvacine ("Iso.", 20 mg/kg, samples collected 1, 3 or 24 hours post-injection), intracerebral injection isoguvacine (20 mg/kg, 1 hour post-injection), i.p. diazepam ("DZ", 20 mg/kg, 1 hour post injection) or intracerebral injection diazepam (20 mg/kg, 1 hour post injection).
Figure 19F:
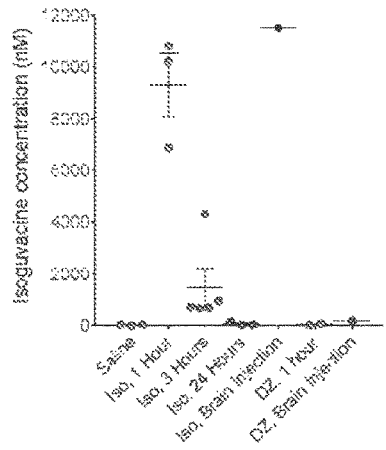
Figure 19G:
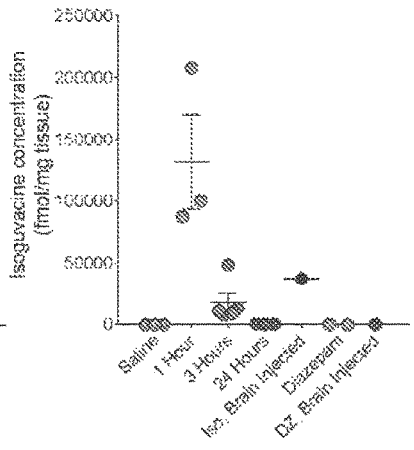

While traditional blood-brain barrier (BBB) penetrating benzodiazepines and non-benzodiazepine $GABA_A$ receptor PAMs are useful for treating some ASD-related symptoms in patients, including acute anxiety, significant adverse effects including sedation and addictive potential are common (Gudex, 1991). Furthermore, long-term benzodiazepine use is linked to cognitive impairment across multiple domains, including short-term verbal memory and attention (Golombok et al., 1988; Tata et al., 1994), leading to general reluctance within the medical community for prescribing benzodiazepines and other $GABA_A$ receptor PAMs to young children (Howes et al., 2018). The observation that peripheral nervous system restoration of $GABA_A$ receptor function during early postnatal life improves tactile over-reactivity and a subset of ASD-associated behaviors in $Mecp2^{R306C}$ mutant adult mice prompted the question of whether peripherally restricted $GABA_A$ receptor agonists could be administered beginning at a young age to ameliorate tactile hypersensitivity in ASD models. A peripherally restricted $GABA_A$ receptor agonist administered at early postnatal times may cause fewer adverse effects compared to brain-penetrating benzodiazepines, including sedation and cognitive impairment, which may be attributed to a central nervous system site of drug action. Isoguvacine is a potent and selective GABA mimetic that is an agonist for the $GABA_A$ receptor (Bowery et al., 1983; Hill and Bowery, 1981; Krogsgaard-Larsen and Johnston, 1978; Krogsgaard-Larsen et al., 1977). Due to its zwitterionic structure, isoguvacine is predicted to not cross the blood-brain barrier ('BBB') (Krogsgaard-Larsen et al., 1981). In agreement with this, it was found that isoguvacine administration (2 mg/kg, i.p.) did not cause sedation in mice, which is in contrast to treatment with the BBB-penetrating benzodiazepine midazolam (FIG. 19D).

Figure 19H:
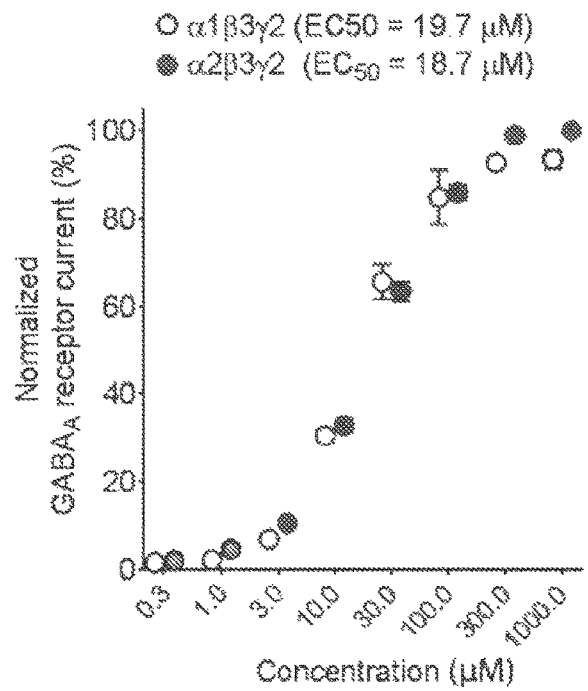
FIG. 19H: Normalized peak chloride flux through α1β3γ2- and α2β3γ2-containing GABA$_A$ receptors in response to isoguvacine application. Response data has been normalized to the baseline peak current induced by addition of EC$_{100}$ GABA (30 μM) for 2 seconds during the assay.

Moreover, a bio-distribution analysis indicated that following i.p. administration of isoguvacine (20 mg/kg) the drug was detected in the blood and liver, but undetectable in the brain or cerebrospinal fluid, confirming that isoguvacine does not cross the BBB (FIGS. 19E-19H). Also analyzed was transcriptome data obtained from RNA deep sequence analysis of genetically labeled DRG neuron subtypes (YZ and DDG, unpublished) to determine the expression level of each of the $GABA_A$ receptor alpha, beta and gamma subunits across sensory neuron subtypes. This analysis revealed that α1β3γ2- and α2β3γ2-containing $GABA_A$ receptors are the major holo-pentameric $GABA_A$ receptors expressed in LTMR subtypes, with lower levels of expression in nociceptors and proprioceptors (FIGS. 19I-19K, 27H). In addition, using a $GABA_A$ receptor chloride flux assay, it was found that isoguvacine potently activates both α1β3γ2- and α2β3γ2-containing $GABA_A$ receptors, with EC50 values of 19.7 μM and 18.7 μM, respectively (FIG. 19H).

Figure 19I:
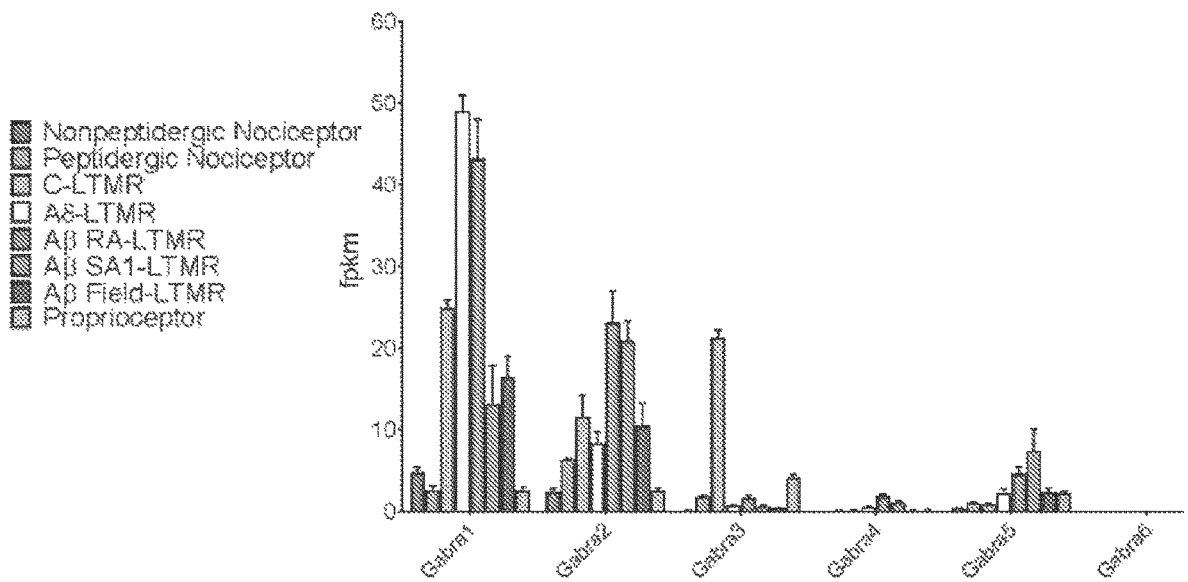
FIGS. 19I-19K: GABA$_A$ receptor subunit RNA expression levels across peripheral somatosensory neuron subtypes, for the alpha (FIG. 19I), beta (FIG. 19J), and gamma (FIG. 19K) subunit types.
Figure 19J:
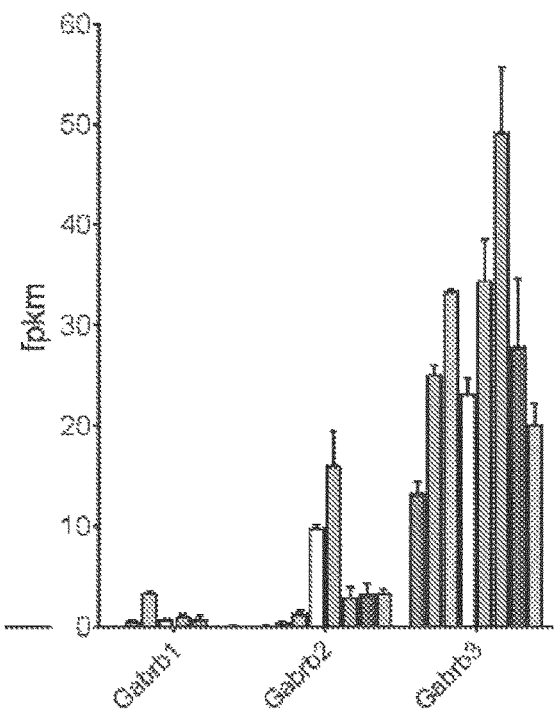
Figure 19K:
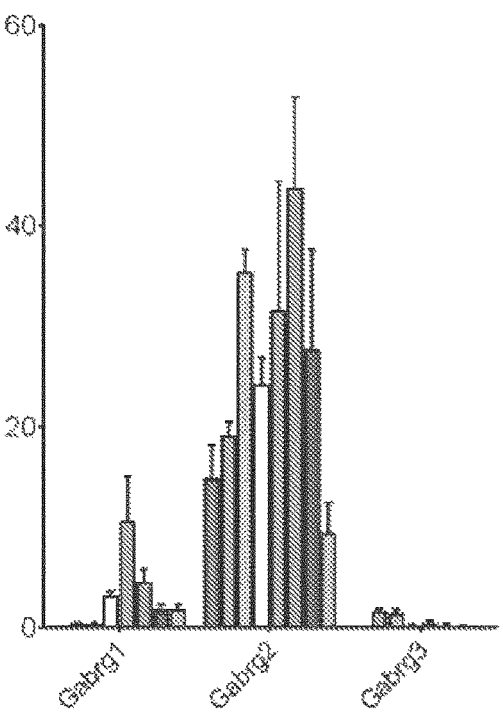
Figure 19L:
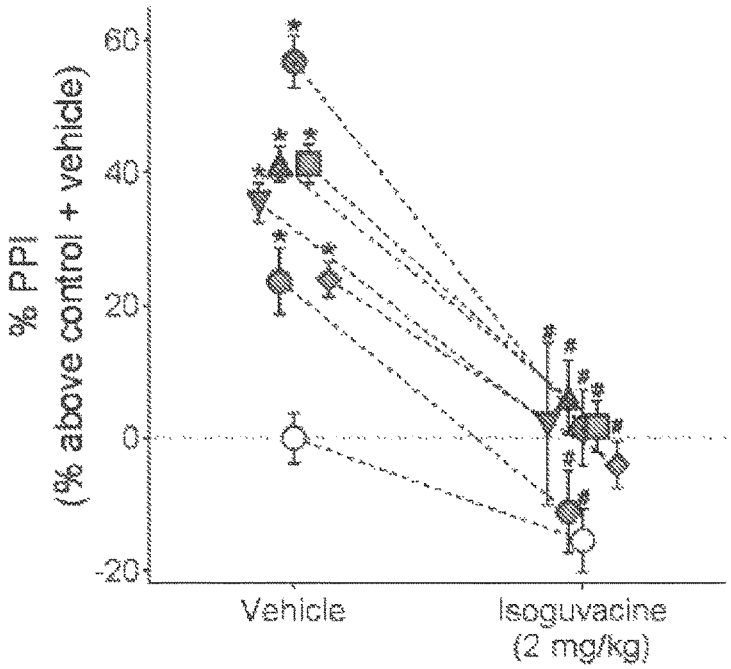
FIG. 19L: Percent inhibition of the startle response to a 125 dB noise, when the startle noise is preceded by a light air puff in mice following i.p. administration of 2 mg/kg isoguvacine (i.p., 2 mg/kg). Two-way ANOVA with post-hoc Sidak's test, *, p<0.05.
Figure 19M:
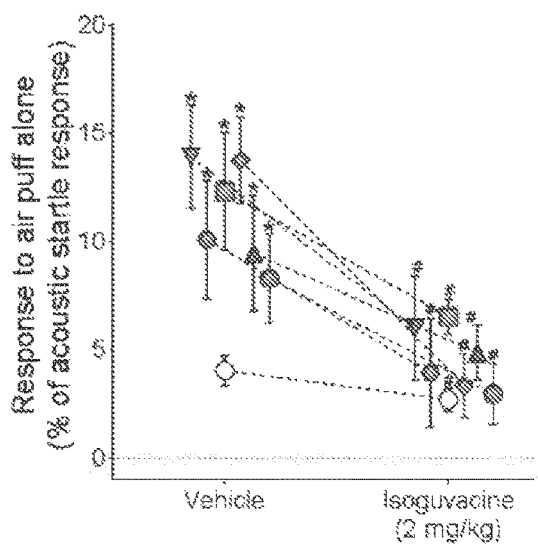
FIG. 19M: Response to a light air puff stimulus alone in mice following i.p. administration of either saline or 2 mg/kg isoguvacine treatment. Responses are expressed as percent of startle response to a 125 dB noise. Two-way ANOVA with post-hoc Sidak's test, *, p<0.05.
Figure 19N:
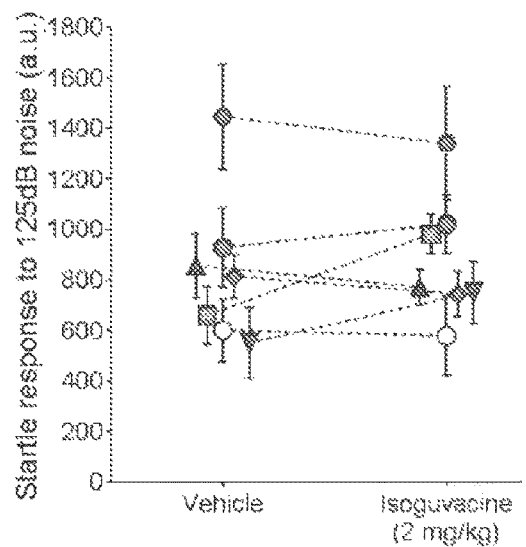

It was found that acute administration of isoguvacine (2 mg/kg, i.p.) significantly reduced tactile hypersensitivity in both $Advillin^{Cre}$; $Mecp2^{f/y}$ and $Advillin^{Cre}$; $Gabrb3^{f/+}$ mutant mice, demonstrated by reduced tactile PPI performance and responsivity to an air puff stimulus alone (FIGS. 19L, 19M). Because of the positive outcome of these experiments, it was next asked whether this peripherally restricted $GABA_A$ receptor agonist may attenuate tactile over-reactivity in other ASD mouse models. Although other ASD mouse models with tactile hypersensitivity have been identified in which the primary deficit is not in $GABA_A$ receptor-dependent presynaptic inhibition, i.e. Shank3 mutants, it is reasoned that because GABA acts directly on mechanosensory neurons to attenuate their firing that GABA receptor agonists will reduce tactile over-reactivity regardless of the pathophysiological mechanism of mechanosensory neuron dysfunction. Indeed, in addition to normalizing tactile over-reactivity in Mecp2 and heterozygous Gabrb3 mutant mice, acute administration of isoguvacine also attenuated hairy skin hypersensitivity in Shank3, Fmr1, and Cntnap2 mutant mice (FIGS. 19I, 19J). It was also observed an improvement in hairy skin hypersensitivity following isoguvacine treatment in mice exposed to polyinosinic:polycytidylic acid at E12.5 (FIGS. 19I, 19J), which is a model of maternal immune activation-induced ASD in rodents (Choi et al., 2016). Importantly, isoguvacine administration did not lead to sedation in any of animal cohorts tested, as startle amplitude was unchanged when compared within animal to vehicle-treated conditions, which is consistent with a peripheral site of action of this compound (FIG. 19N).

Figure 20A:
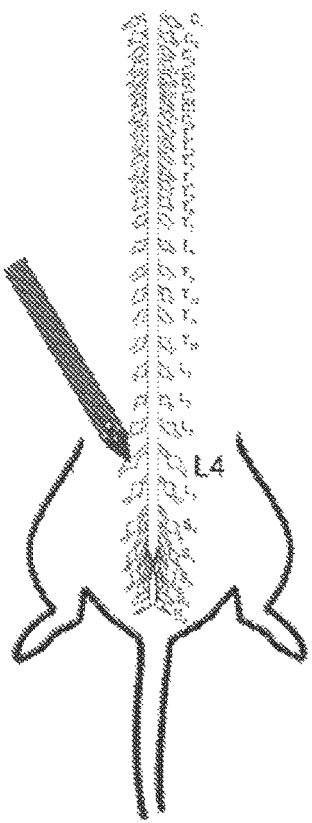
Figure 20B:
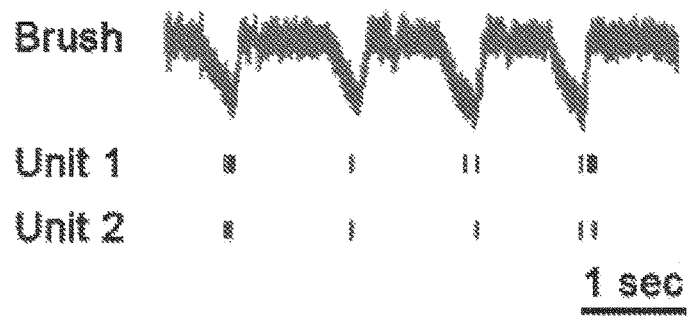
FIG. 20B: Activity traces of two putative neurons (units) in response to a brush stimulus.
Figure 20C:
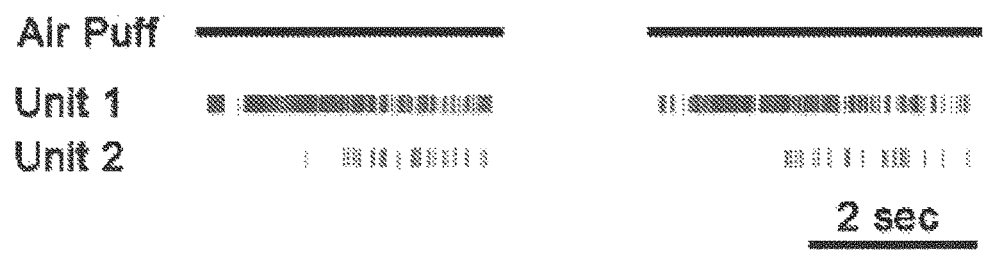
FIG. 20C: Activity traces of two putative neurons (units) in response to a light air puff stimulus (1 PSI).
Figure 20D:
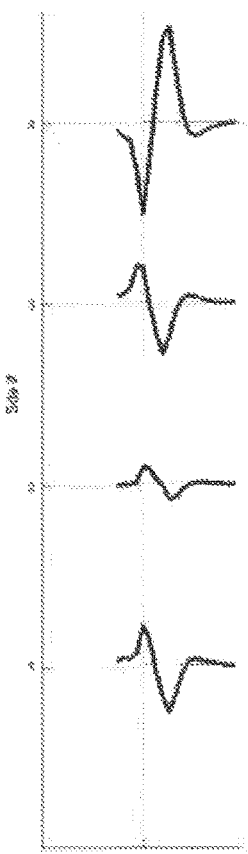
Figure 20H:
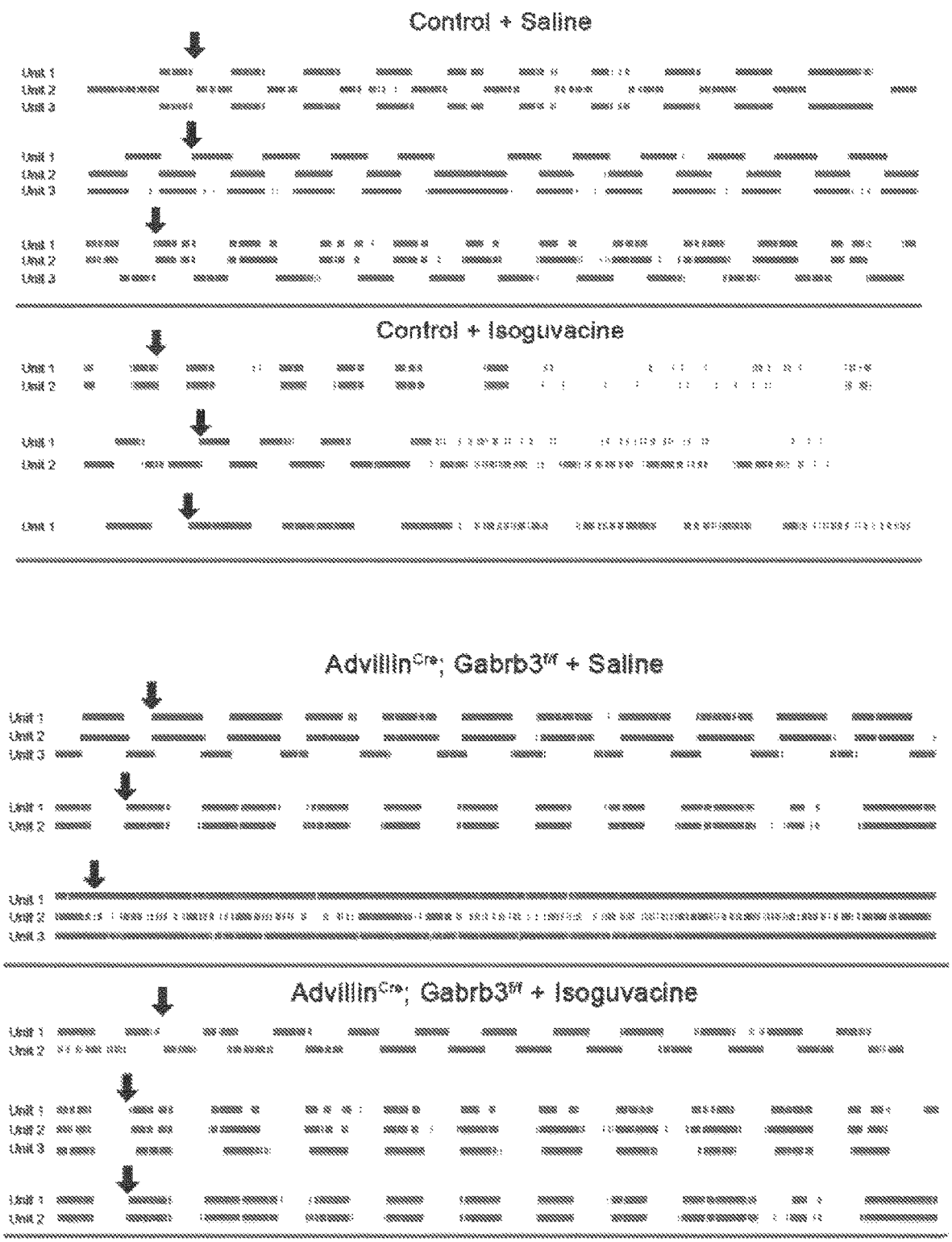
FIG. 20H: Representative activity raster plots for multiple putative LTMRs in multiple mice over the duration of a recording experiment in controls and Advillin$^{Cre}$; Gabrb3$^{f/f}$ mice. Mice received a subcutaneous injection of either saline or isoguvacine (2 mg/kg) during the experiment, and activity of light-touch responsive units in response to a light brush stimulus was assessed over a 90-minute period.
Figure 20I:
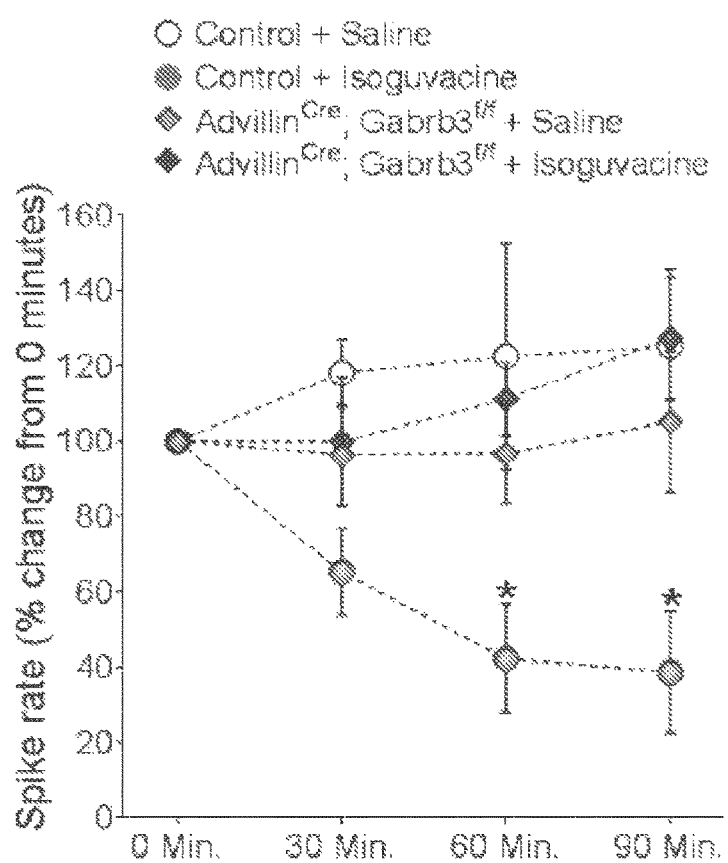
FIG. 20I: Average firing frequency of LTMRs over the duration of each recording experiment, following subcutaneous injection of either saline or isoguvacine (2 mg/kg). Repeated measures, two-way ANOVA with post-hoc Dunnett's test, *p<0.05.
Figure 27A:
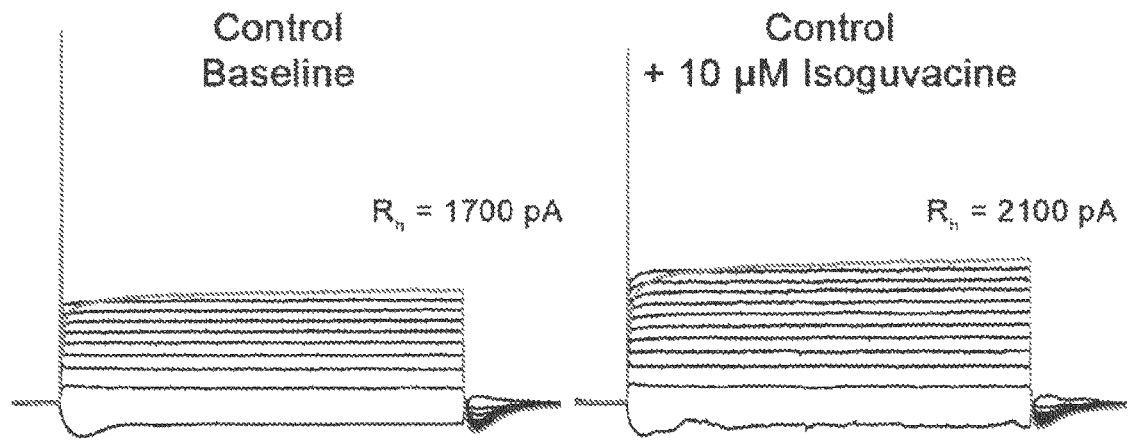
FIGS. 27A-27K are related to FIGS. 19A-19N.
Figure 27B:
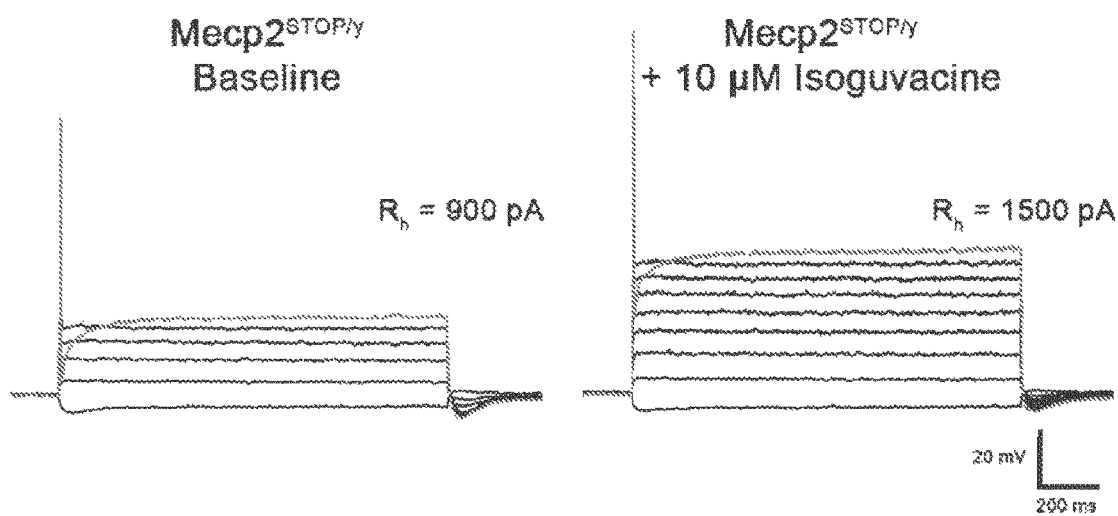
Figure 27C:
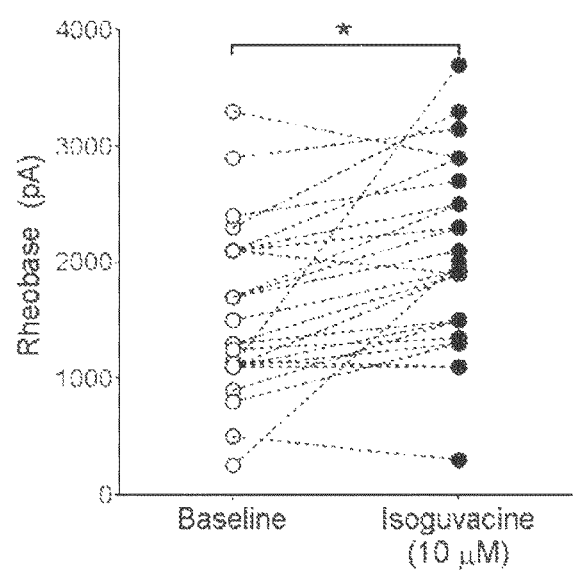
Figure 27D:
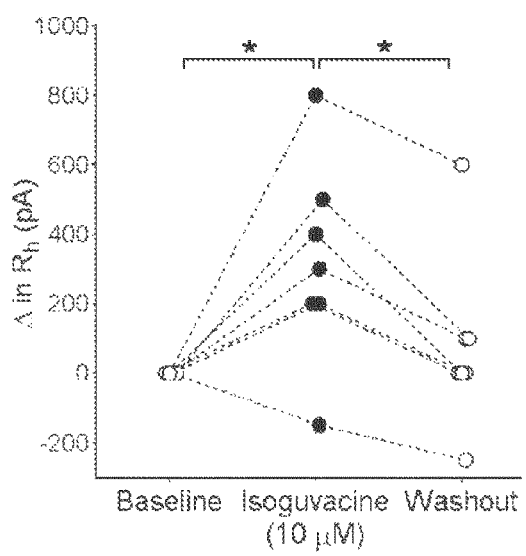
Figure 27E:
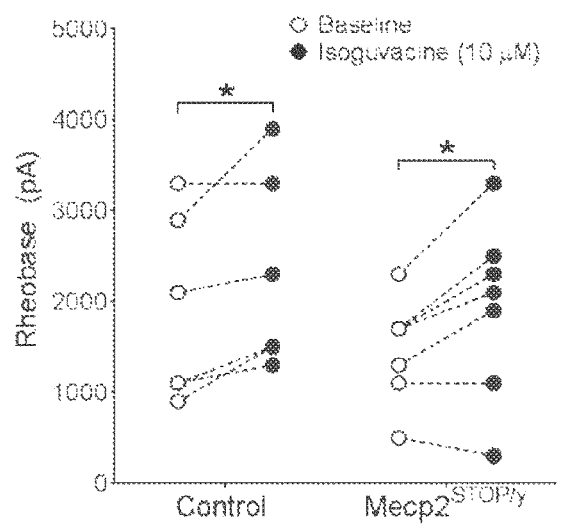
Figure 27F:
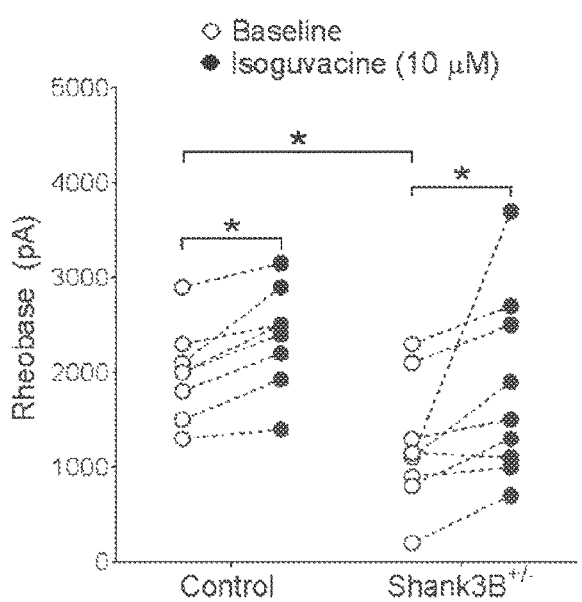
Figure 27G:
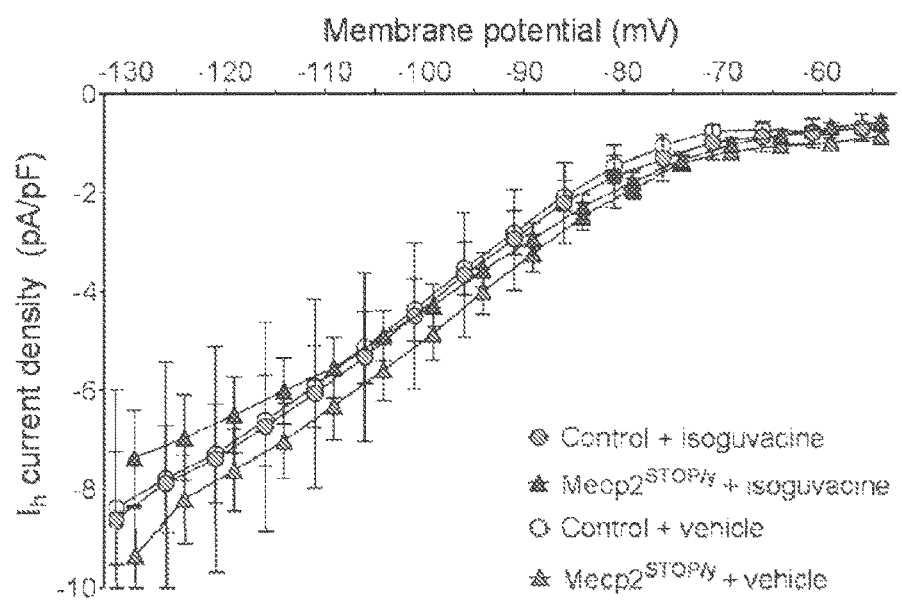
Figure 27H:
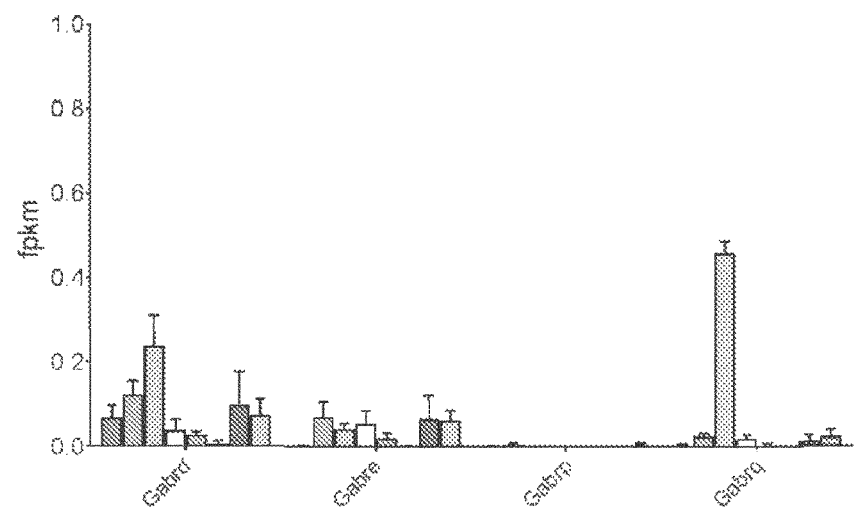
Figure 27I:
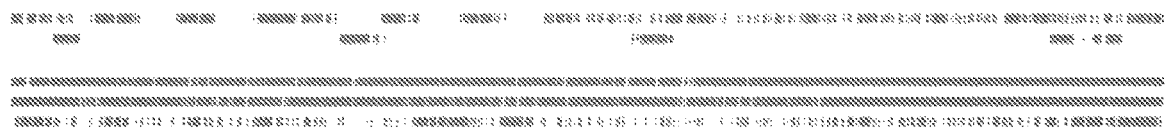
Figure 27I:
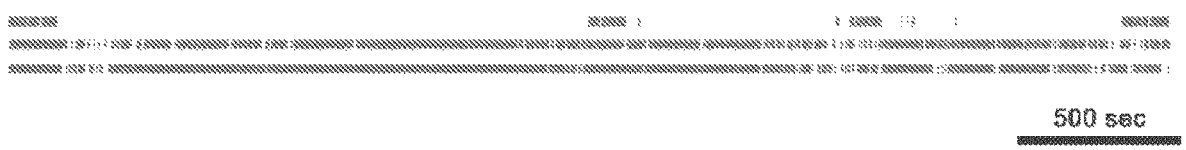
Figure 27J:
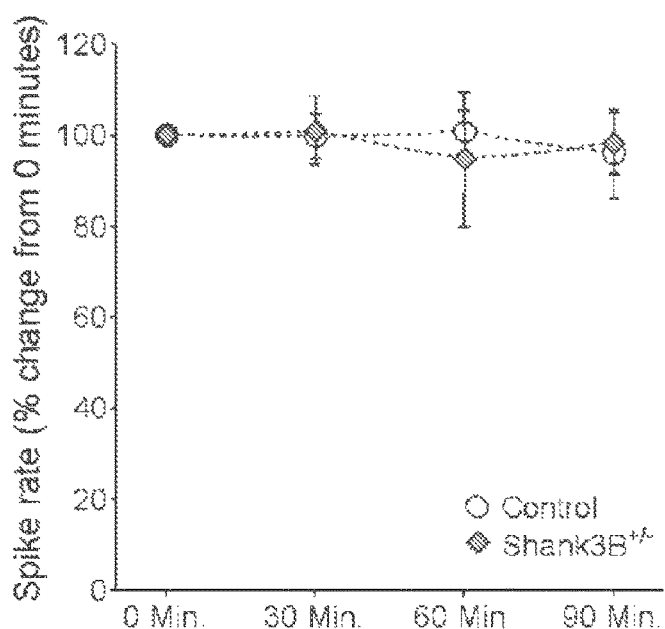
Figure 27K:
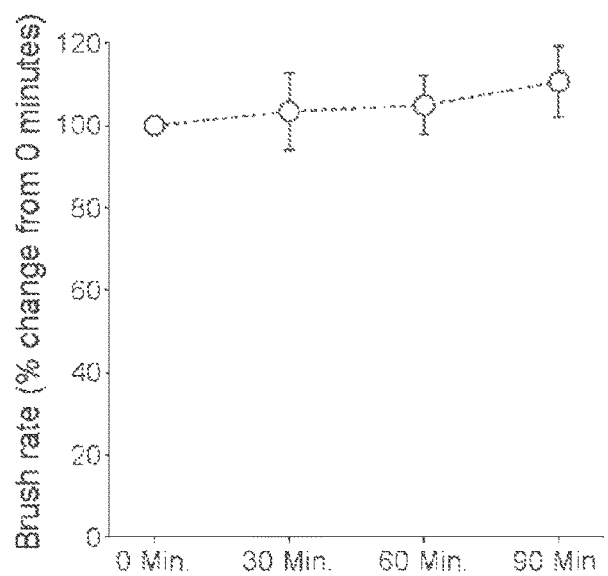

Isoguvacine Attenuates Tactile Sensitivity Through Reduced Excitability of Peripheral, Low-Threshold Mechanosensory Neurons These findings suggest that augmenting $GABA_A$ receptor signaling in cells outside the BBB can improve tactile hypersensitivity in a range of animal models of ASD. To test the hypothesis that isoguvacine exerts its effects by acting directly on primary somatosensory neurons, electrophysiological recordings were performed both in vitro and in vivo. DRG cultures from Mecp2 and Shank3 mutant and control littermates were first produced to assess excitability of these neurons in vitro using whole cell patch-clamp recordings. Application of isoguvacine reduced the hyperexcitability phenotype observed in large diameter neurons cultured from Mecp2 and Shank3 mutant mice, without affecting $I_h$ (FIGS. 27A-27G). It was next asked whether administration of isoguvacine would reduce mechanosensory neuron sensitivity in vivo by performing multiunit electrode recordings in the L4 DRG of urethane- and isoflurane-anesthetized mice (FIG. 20A). In this preparation, multiple neurons (2-12 units per experiment) whose receptive fields were either on the thigh or hind paw of a mouse could be identified following stimulation using innocuous mechanical stimuli. Units were characterized as glabrous or hairy skin innervating Aβ RA1-LTMRs, Aβ SA1-LTMRs or Aβ field-LTMRs, or proprioceptors, based on conduction velocity, firing rate, and optimal stimulus type (FIGS. 20B, 20C). Once LTMR units were identified, animals were administered a subcutaneous injection of either saline vehicle or isoguvacine (2 mg/kg) and then sensitivity and firing frequency in response to tactile stimuli were monitored over a 90-minute period for each identified unit. Units were sorted and classified using JRClust (Jun et al., 2017) (FIG. 20D). These findings indicate that while proprioceptor sensitivity and firing were unaffected, subcutaneous administration of isoguvacine increased response thresholds to light touch stimuli and reduced spiking in both glabrous- and hairy-skin innervating Aβ LTMRs in vivo (FIGS. 20E, 20F, 27I). These results are consistent with the finding that while LTMRs exhibit high expression levels of $GABA_A$ receptor subunits, including GABRB3, proprioceptors do not (FIGS. 19E-19G, 27H). To test the idea that the effects of isoguvacine on cutaneous LTMR firing properties and tactile sensitivity are mediated through its direct activation of $GABA_A$ receptors found on somatosensory neurons, next performed was a similar set of in vivo DRG recordings in mice with somatosensory neuron specific, homozygous deletion of Gabrb3 (Advillin$^{Cre}$; Gabrb3$^{f/f}$) and their control littermates (Gabrb3$^{f/f}$). Since Gabrb3 encodes the principal obligatory beta subunit of the $GABA_A$ receptor in DRG neurons (FIGS. 19E-19G, 27H), somatosensory neurons in Advillin$^{Cre}$; Gabrb3$^{f/f}$ mutant mice are virtually devoid of $GABA_A$ receptors (Orefice et al., 2016) (Zimmerman et al., in press). Sixty minutes following subcutaneous injection of isoguvacine (2 mg/kg), tactile stimulus-evoked (brush or air puff stimulus) responsivity of LTMRs was significantly decreased in control mice, while no change in tactile stimulus-evoked LTMR responses were observed in littermate control mice injected with saline (FIGS. 20E, 20F). Importantly, mice with somatosensory neuron specific homozygous deletion of Gabrb3 showed no changes in tactile stimulus-evoked LTMR sensitivity following administration of isoguvacine, indicating that isoguvacine exerts its effects in somatosensory neurons through acting on GABRB3-containing $GABA_A$ receptors (FIGS. 20E, 20F). The question asked next was whether isoguvacine treatment would attenuate LTMR sensitivity in a mouse model in which deficits in $GABA_A$ receptor signaling was not the primary pathophysiological deficit. For this, Shank3B and control littermates were subjected to the same in vivo DRG recording preparation. LTMRs from Shank3B$^{-/-}$ mutant injected with saline exhibited higher response rates to innocuous touch stimuli compared to LTMRs from control littermates injected with saline (FIGS. 20G-20I), and isoguvacine treatment attenuated firing in both Shank3B and control littermates (FIGS. 20G-20I).

Figure 20J:
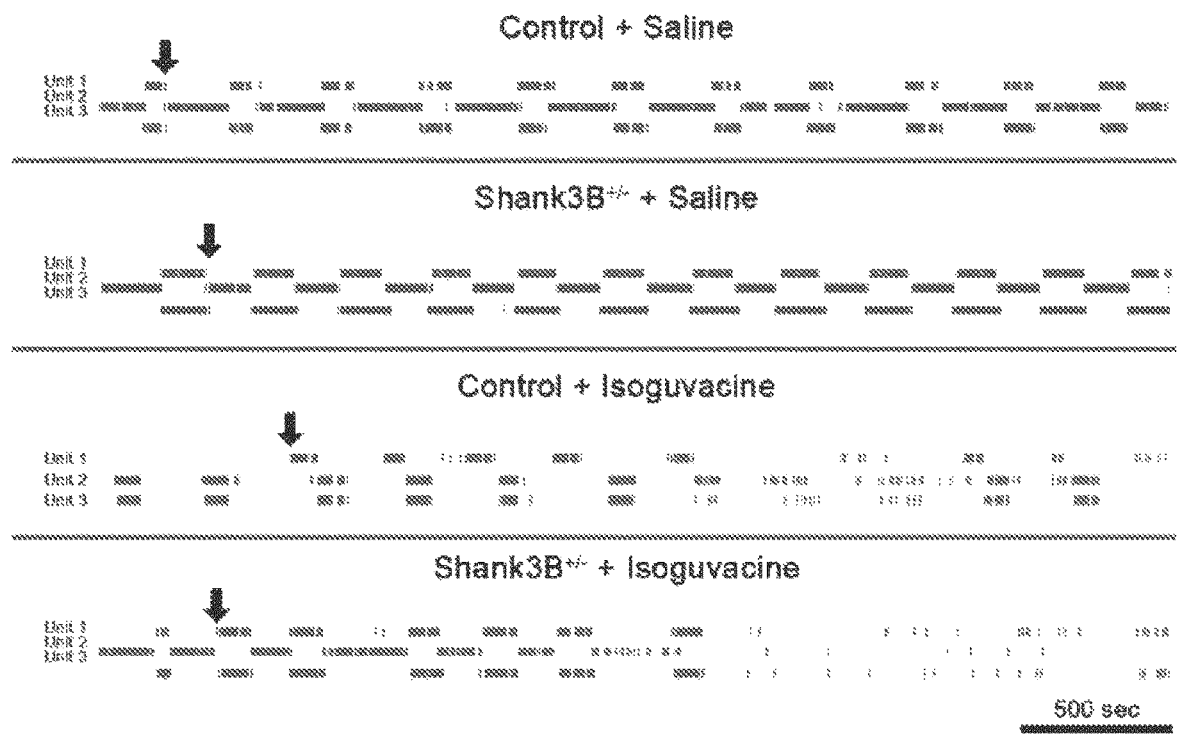
FIG. 20J: Representative activity raster plots for putative LTMRs in multiple mice over the duration of recordings in controls and Shank3B$^{+/-}$ mice. Mice received a subcutaneous injection of either saline or isoguvacine (2 mg/kg) during the experiment, and activity of light-touch responsive units was assessed over a 90-minute period.
Figure 20K:
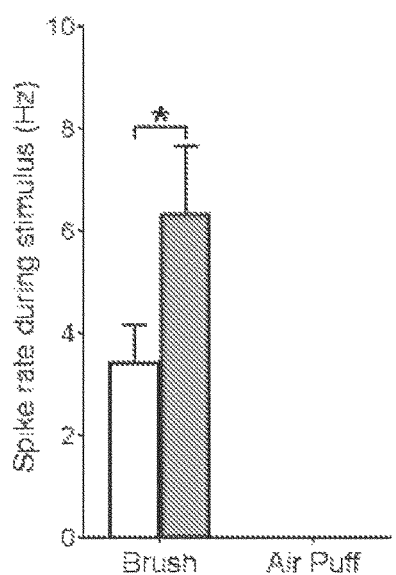
FIG. 20K: Average baseline spike rate of LTMRs in response to brush or air puff stimulus, in control and Shank3B$^{+/-}$ mice. Student's t-test, *p<0.05.
Figure 20L:
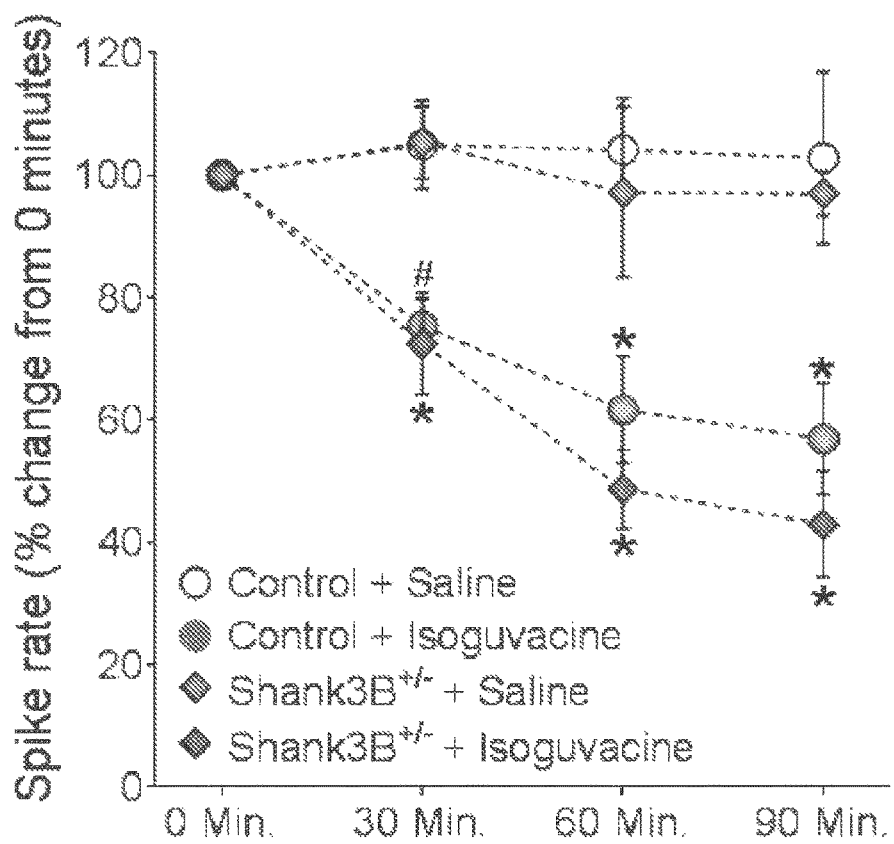
FIG. 20L: Average firing frequency of LTMRs over the duration of each recording experiment, following subcutaneous injection of either saline or isoguvacine (2 mg/kg). Repeated measures, two-way ANOVA with post-hoc Dunnett's test, *p<0.05.
Figure 20M:
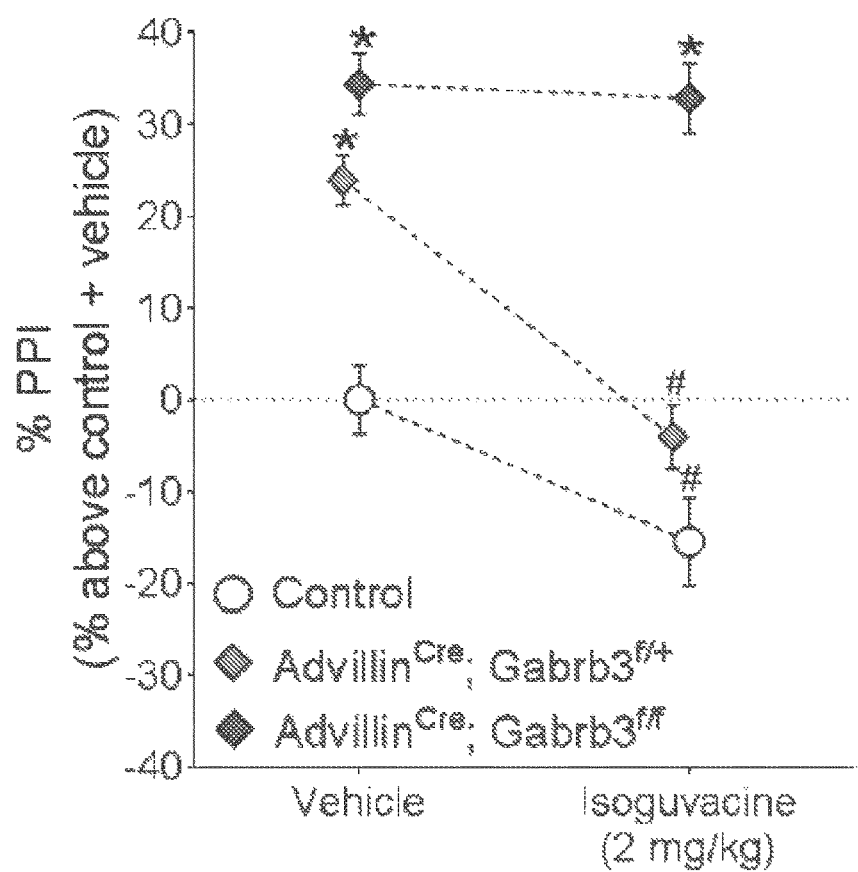
FIG. 20M: Percent inhibition of the startle response to a 125 dB noise, when the startle noise is preceded by a light air puff in control, Advillin$^{Cre}$; Gabrb3$^{f/+}$ and Advillin$^{Cre}$; Gabrb3$^{f/f}$ mice following i.p. administration of 2 mg/kg isoguvacine (i.p., 2 mg/kg). Two-way ANOVA with post-hoc Sidak's test, *, p<0.05.
Figure 20N:
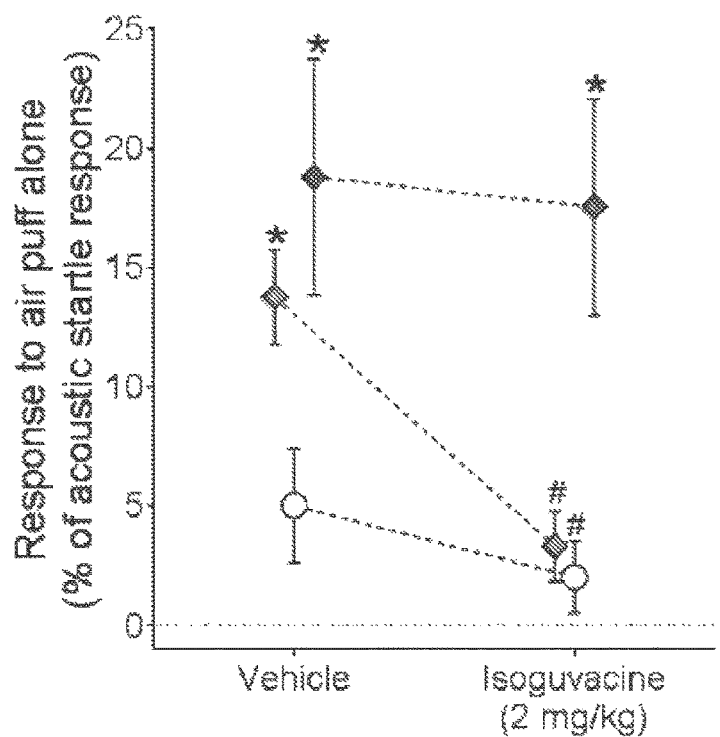
FIG. 20N: Response to a light air puff stimulus alone in mice following i.p. administration of either saline or 2 mg/kg isoguvacine treatment. Responses are expressed as percent of startle response to a 125 dB noise. Two-way ANOVA with post-hoc Sidak's test, *, p<0.05.

Consistent with these electrophysiological measurements, while mice with heterozygous loss of Gabrb3 in sensory neurons (Advillin$^{Cre}$; Gabrb3$^{f/+}$ mice) showed improved tactile hypersensitivity following isoguvacine injection, as measured using the tactile PPI assay, mice with homozygous deletion of Gabrb3 in peripheral sensory neurons (Advillin$^{Cre}$; Gabrb3$^{f/f}$ mice) exhibited no reduction in hairy skin sensitivity following isoguvacine treatment (FIGS. 20J, 20K). As above, startle amplitude was unaffected by isoguvacine treatment in any of the genotypes (FIG. 20L), indicating that isoguvacine was not sedating these mice. These findings indicate that a peripherally-restricted GABA analogue, isoguvacine, which attenuates tactile over-reactivity in several genetic and environmental ASD mouse models, exerts its effects through direct activation of $GABA_A$ receptors expressed in primary somatosensory neurons to reduce LTMR firing properties.

Figure 21A:
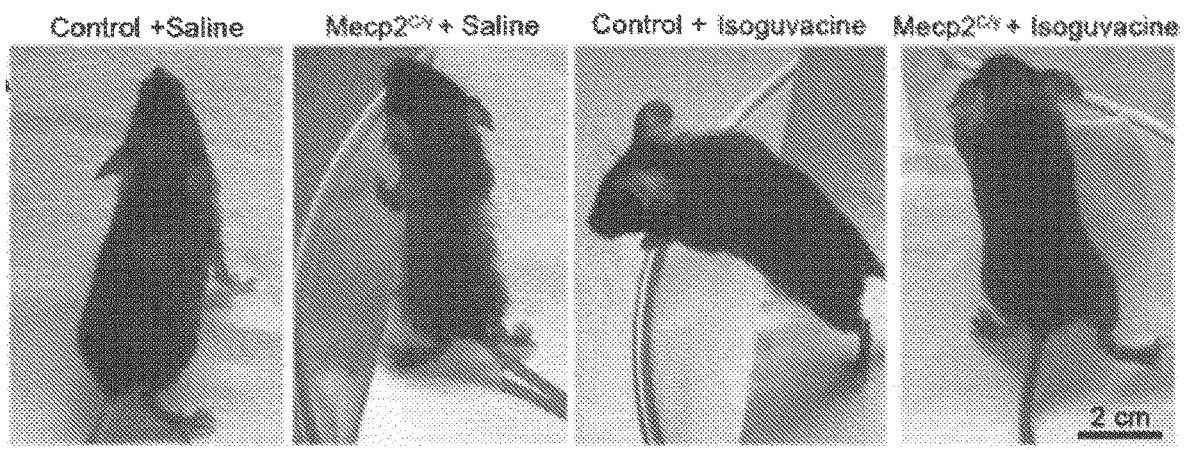
FIGS. 21A-21O show chronic administration of isoguvacine improves tactile over-reactivity, region-selective cortical abnormalities, and some ASD-related behaviors in Mecp2 and Shank3 mutant mice.
Figure 21G:
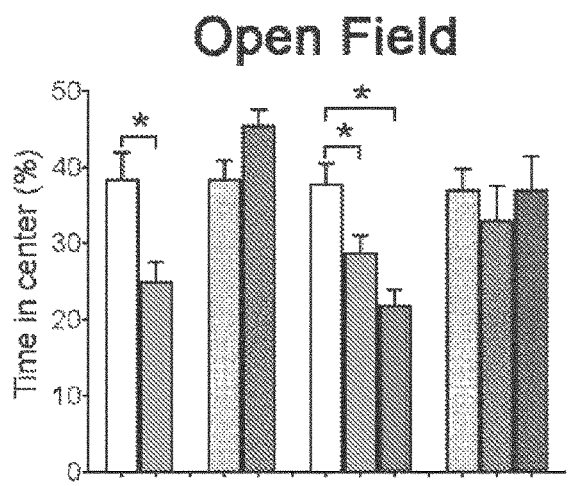
FIG. 21G: Percent time spent in the center of the OF chamber. One-way ANOVA with post-hoc Tukey's test, *, p<0.05.
Figure 21H:
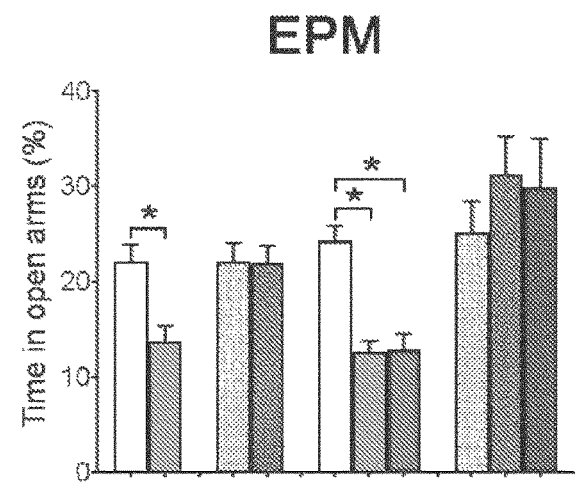
FIG. 21H: Percent time spent in the open arms of the EPM. One-way ANOVA with post-hoc Tukey's test, *, p<0.05.
Figure 21I:
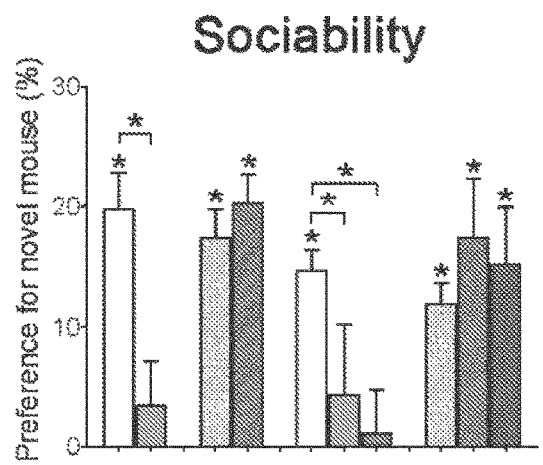
FIGS. 21I-21J: Preference index for the percentage of time spent investigating the novel mouse in the "Sociability" (FIG. 21I) or "Social Novelty Recognition Preference" (FIG. 21J) portion of the 3-chamber social interaction test. One-way ANOVA with post-hoc Tukey's test, *, p<0.05.
Figure 21J:
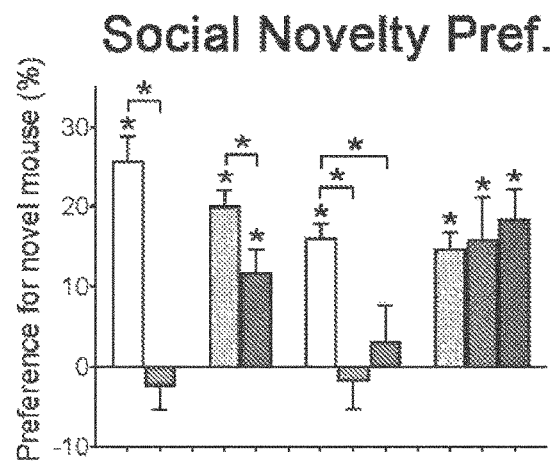
Figure 21K:
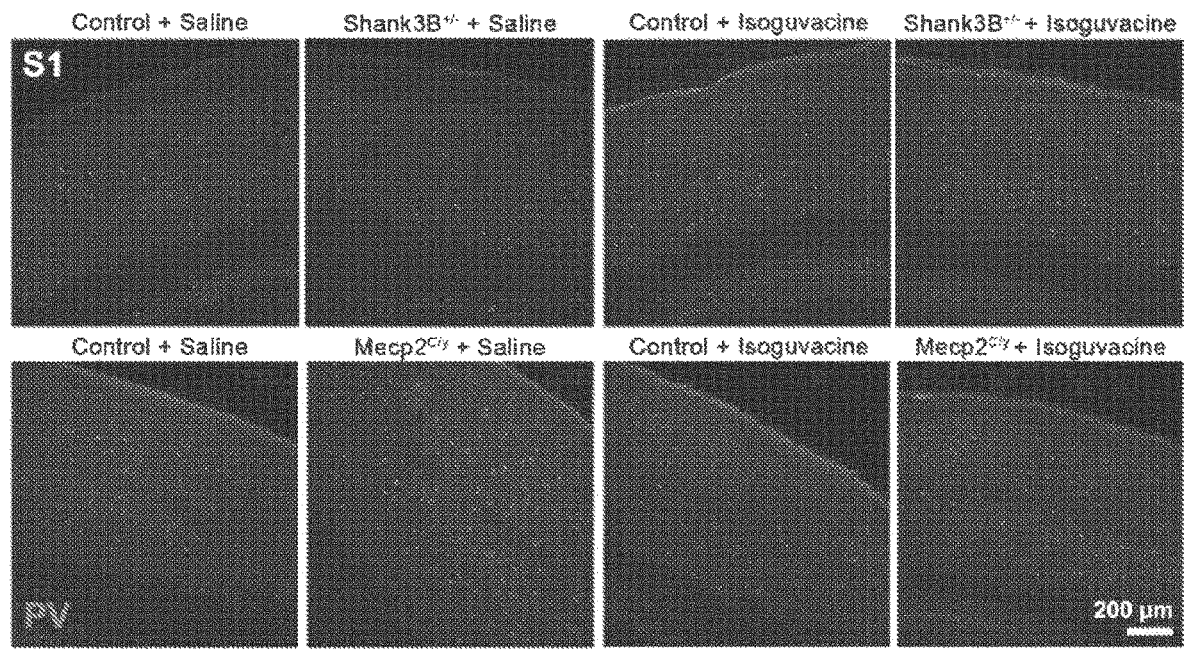
FIG. 21K: Representative IHC images of transverse S1 brain sections, showing PV immunoreactivity in Shank3B$^{+/-}$ or Mecp2$^{C/y}$ mutant mice and control littermates treated daily from P1-42 with either saline or isoguvacine (2 mg/kg).
Figure 21L:
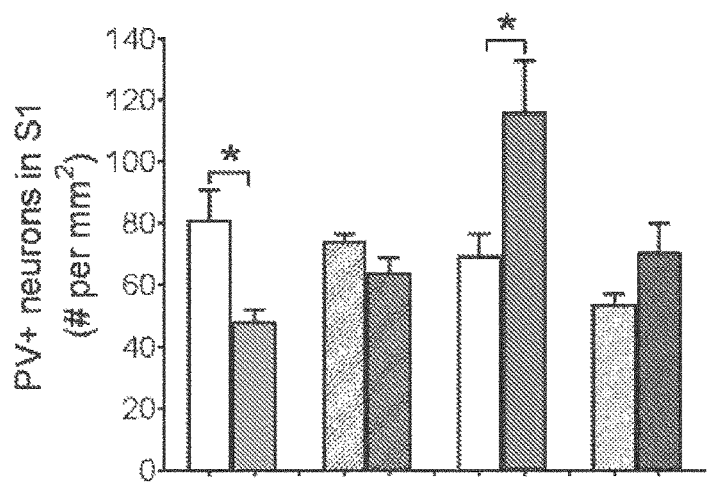
FIGS. 21L-21M: Quantification of the number of PV-positive (PV$^+$) neurons in S1 (FIG. 21L) and V1 (FIG. 21M). One-way ANOVA with post-hoc Tukey's test, *, p<0.05.
Figure 21M:
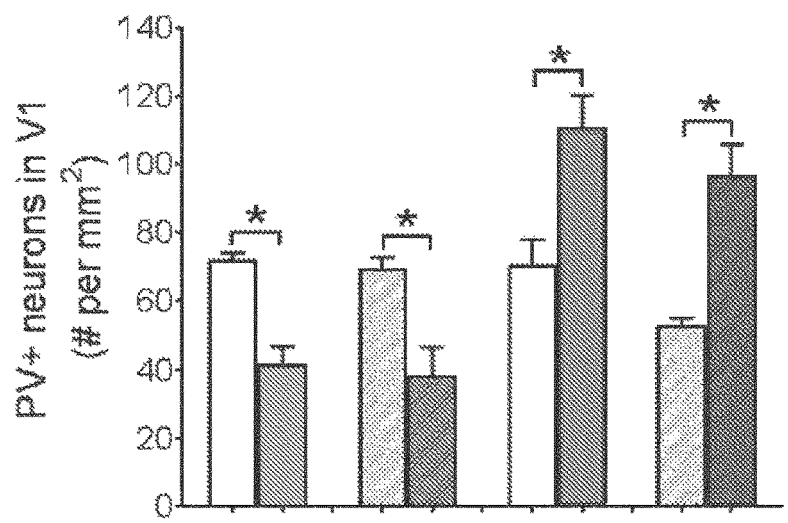
Figure 21N:
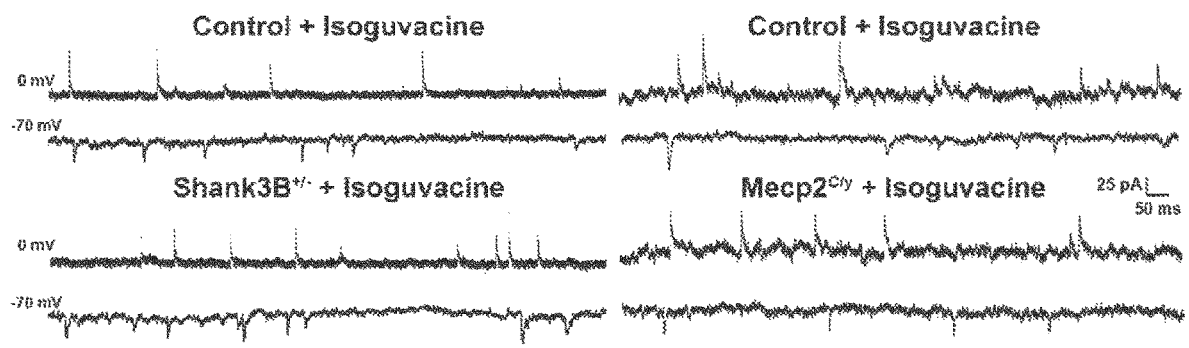
FIG. 21N: Representative traces showing ePSCS (-70 my hold) and iPSCs (0 mV hold) from S1 slices from Shank3B$^{+/-}$ or Mecp2$^{C/y}$ mutant mice and control littermates treated daily from P1-42 with either saline or isoguvacine (2 mg/kg).
Figure 21O:
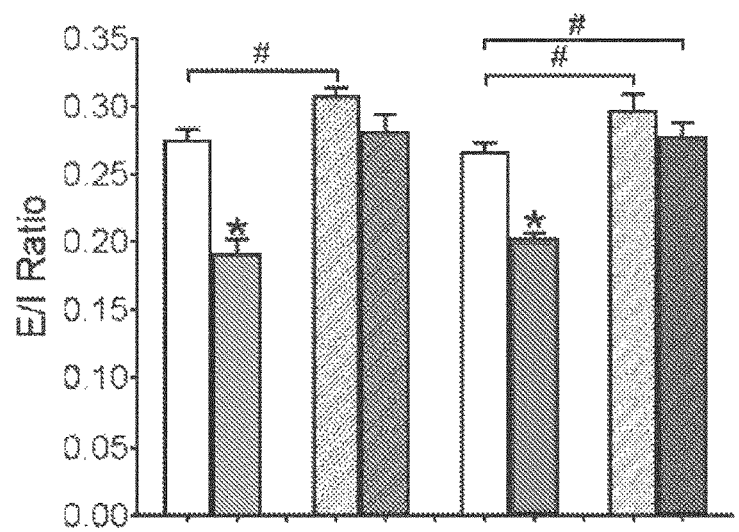
Figure 28A:
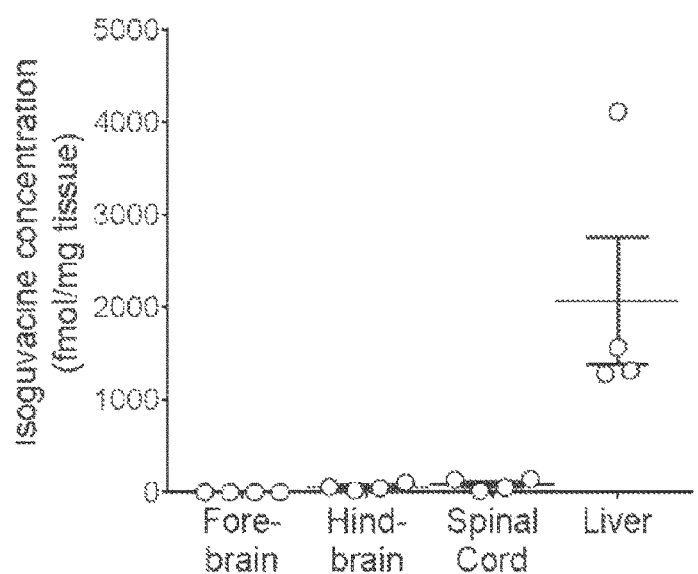
FIGS. 28A-28U are related to FIGS. 21A-21O.
Figure 28B:
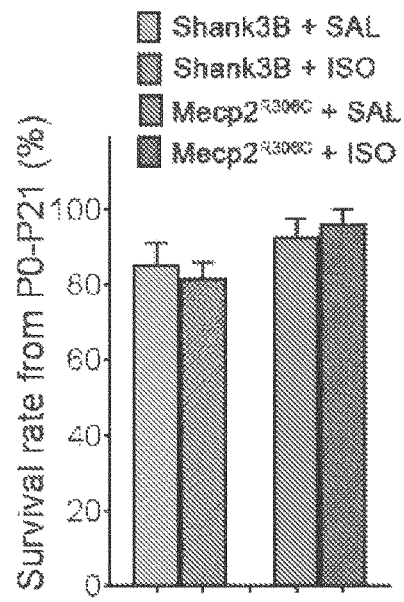
FIG. 28B: Percent of pups surviving to P21 in litters from Shank3B$^{+/-}$ or Mecp2$^{R/C}$ female mice, in which litters were treated daily with either saline or isoguvacine (2 mg/kg).
Figure 28C:
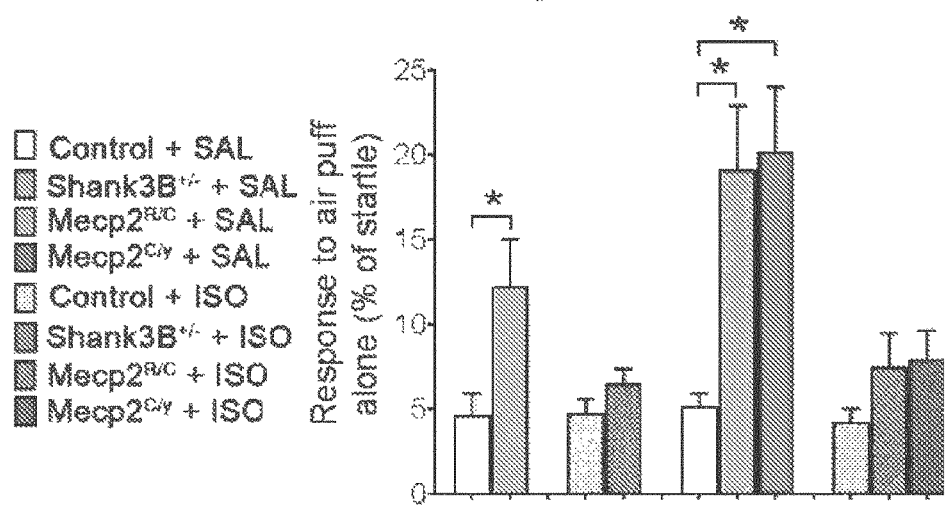
FIG. 28C: Response to a light air puff stimulus alone in Shank3B$^{+/-}$, Mecp2$^{R/C}$ or Mecp2$^{C/y}$ mutant mice and control littermates treated daily from P1-42 with either saline or isoguvacine (2 mg/kg). One-way ANOVA with post-hoc Tukey's test, *, p<0.05.
Figure 28D:
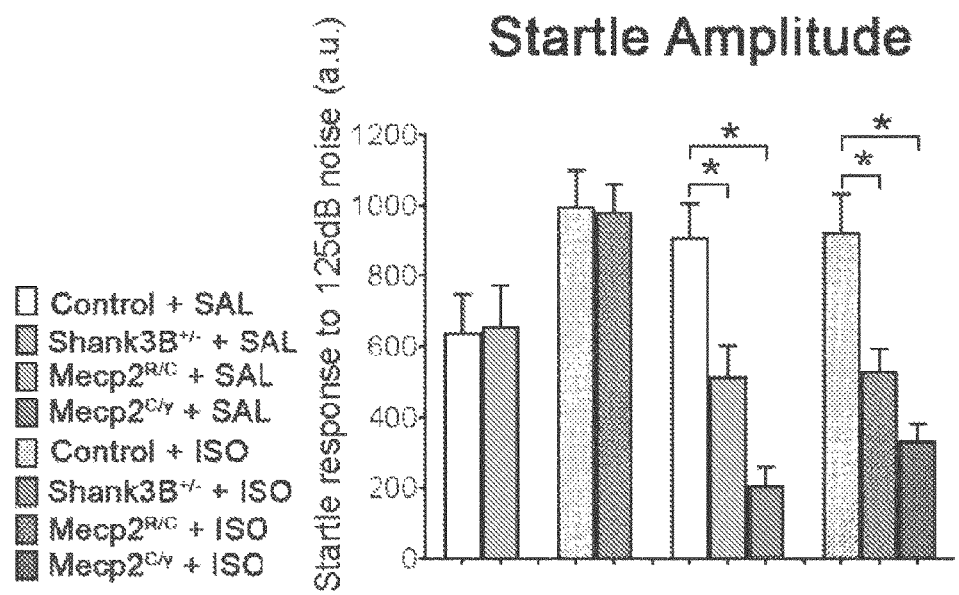
FIG. 28D: Magnitude of startle response to a 125 dB noise in Shank3B$^{+/-}$, Mecp2$^{R/C}$ or Mecp2$^{C/y}$ mutant mice and control littermates treated daily from P1-42 with either saline or isoguvacine (2 mg/kg). One-way ANOVA with post-hoc Tukey's test, *, p<0.05.
Figure 28E:
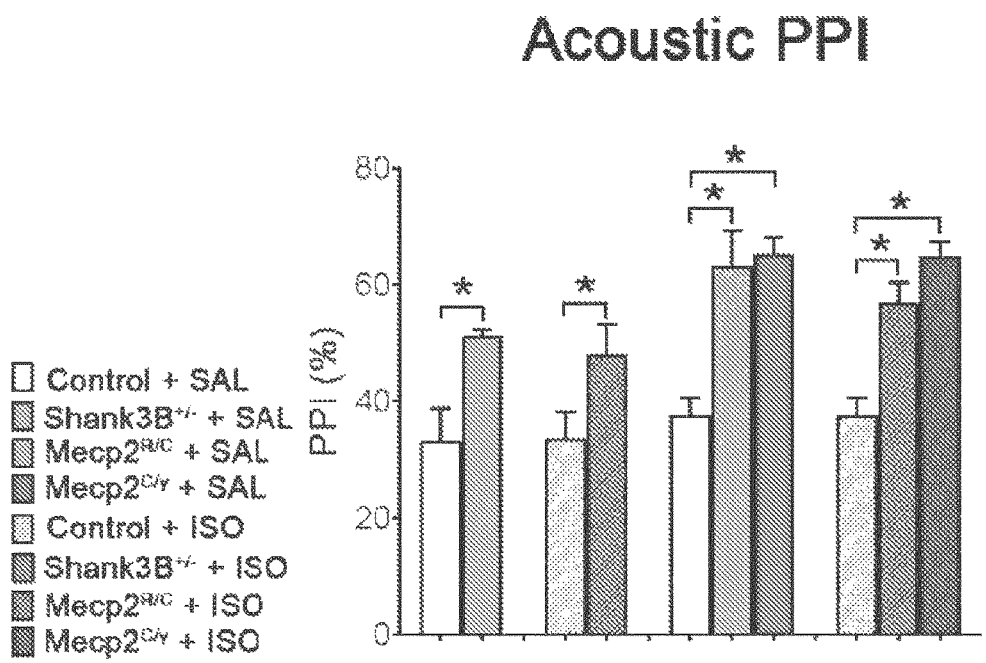
FIG. 28E: Percent inhibition of the startle response to a 125 dB noise (pulse), when the startle noise is preceded by tone prepulse in Shank3B$^{+/-}$, Mecp2$^{R/C}$ or Mecp2$^{C/y}$ mutant mice and control littermates treated daily from P1-42 with either saline or isoguvacine (2 mg/kg). One-way ANOVA with post-hoc Tukey's test, *, p<0.05.
Figure 28F:
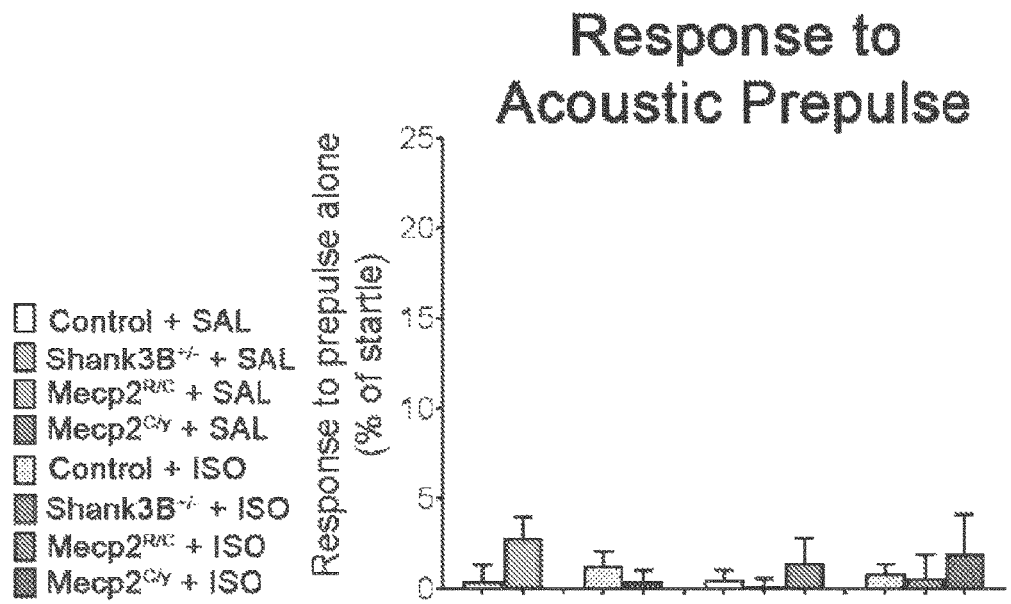
FIG. 28F: Response to a non-startling acoustic noise (80 dB, 20 ms) in Shank3B$^{+/-}$, Mecp2$^{R/C}$ or Mecp2$^{C/y}$ mutant mice and control littermates treated daily from P1-42 with either saline or isoguvacine (2 mg/kg). Responses are expressed as percent of startle response to a 125 dB startle noise.
Figure 28G:
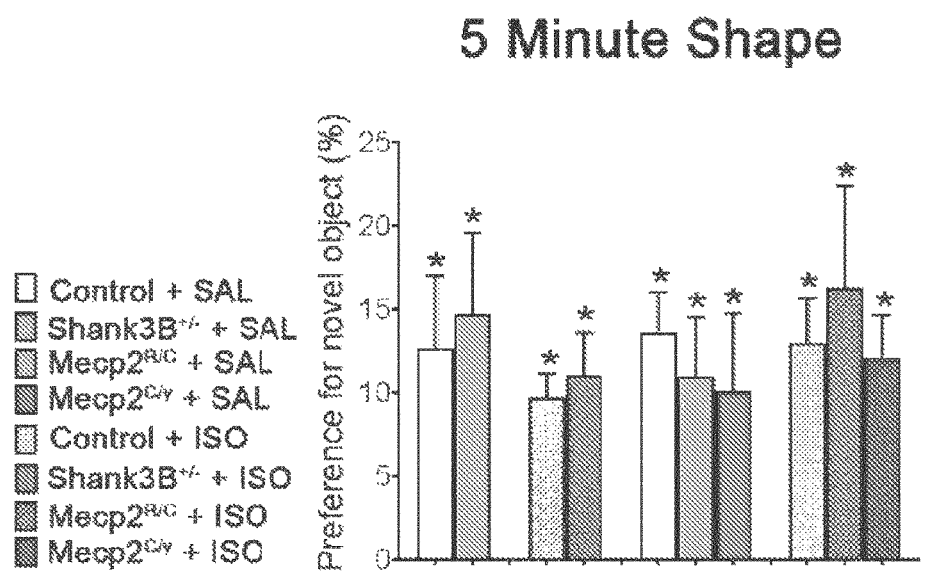
FIG. 28G: Discrimination index for 5-minute NORT in Shank3B$^{+/-}$, Mecp2$^{R/C}$ or Mecp2$^{C/y}$ mutant mice and control littermates treated daily from P1-42 with either saline or isoguvacine (2 mg/kg).
Figure 28H:
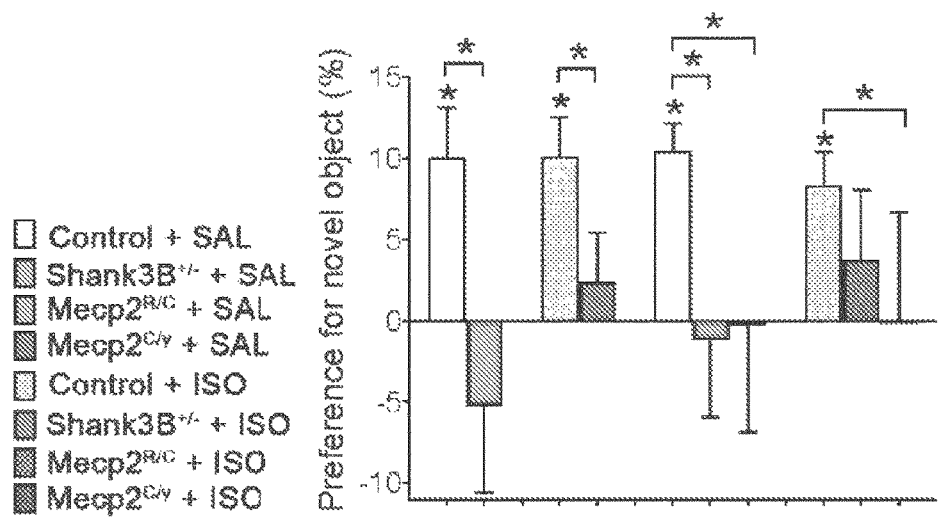
FIG. 28H: Discrimination index for 1-hour NORT in Shank3B$^{+/-}$, Mecp2$^{R/C}$ or Mecp2$^{C/y}$ mutant mice and control littermates treated daily from P1-42 with either saline or isoguvacine (2 mg/kg). One-way ANOVA with post-hoc Tukey's test, *, p<0.05.
Figure 28I:
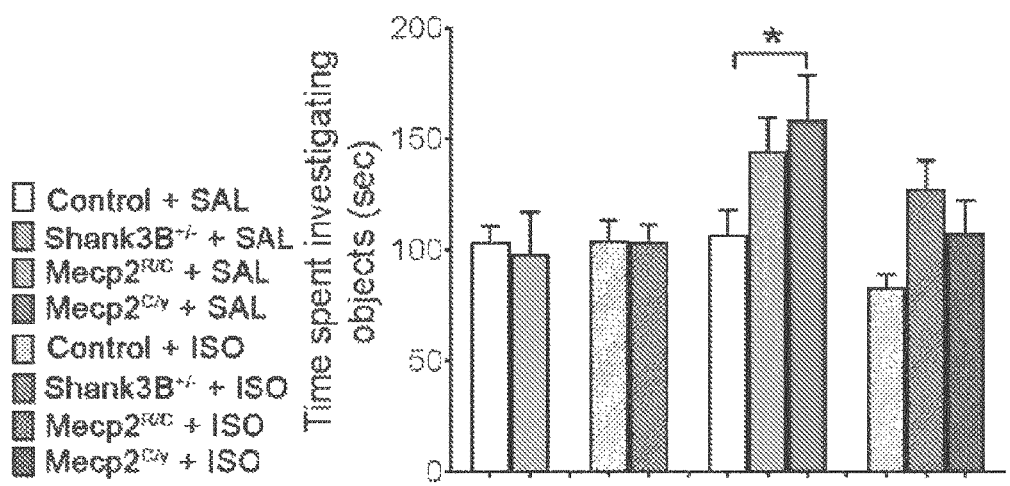
FIG. 28I: Average amount of time (seconds) spent physically interacting with both the familiar and novel object in the NOR tests Shank3B$^{+/-}$, Mecp2$^{R/C}$ or Mecp2$^{C/y}$ mutant mice and control littermates treated daily from P1-42 with either saline or isoguvacine (2 mg/kg).
Figure 28J:
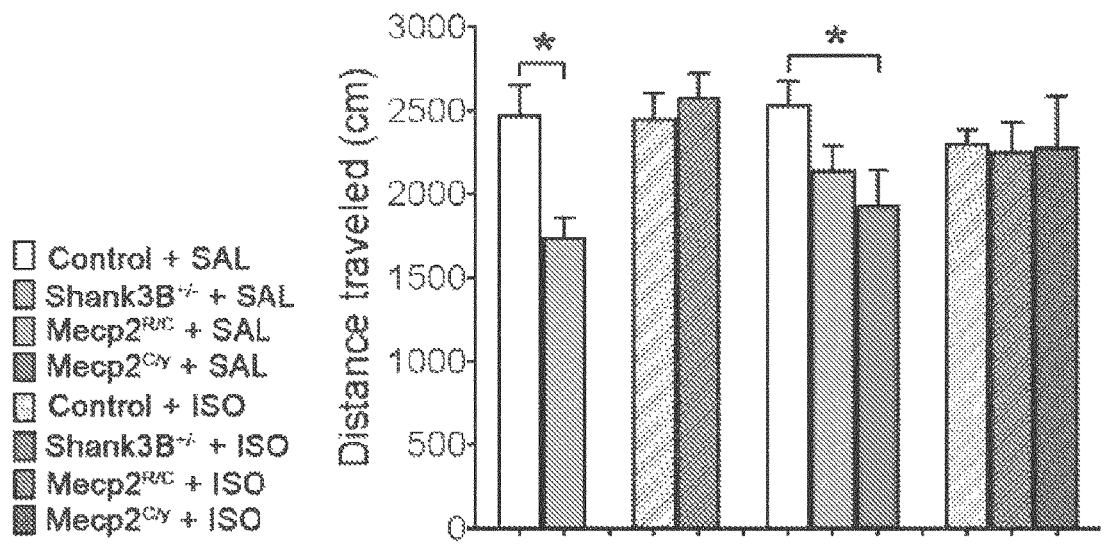
FIG. 28J: Average total distance traveled in the open field chamber for Shank3B$^{+/-}$, Mecp2$^{R/C}$ or Mecp2$^{C/y}$ mutant mice and control littermates treated daily from P1-42 with either saline or isoguvacine (2 mg/kg). One-way ANOVA with post-hoc Tukey's test, *, p<0.05.
Figure 28K:
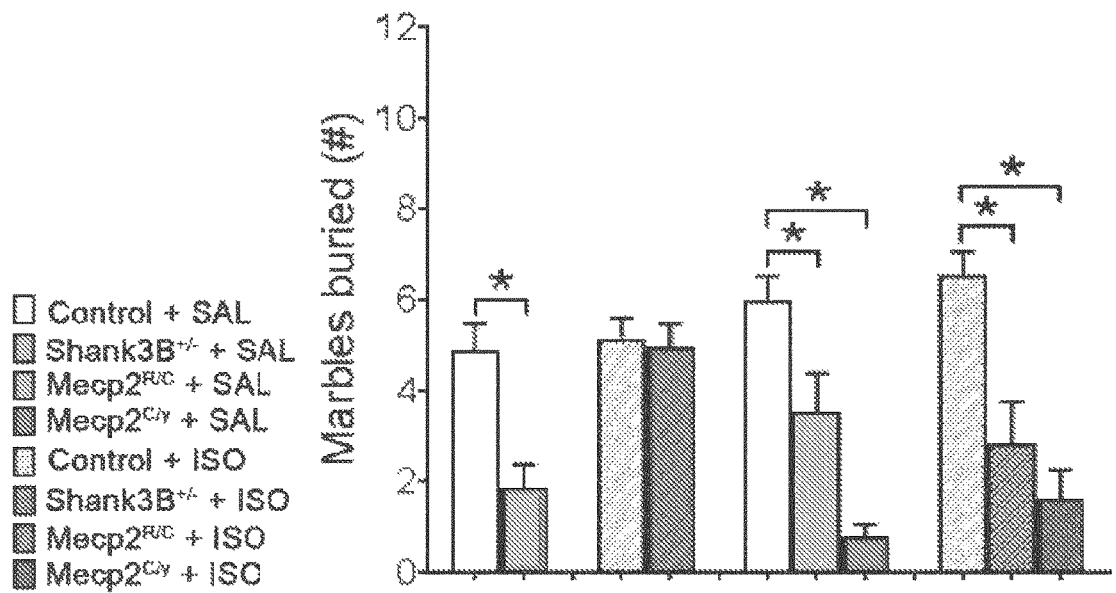
FIG. 28K: Average number of marbles buried (out of 12) during a twenty-minute assay for Shank3B$^{+/-}$, Mecp2$^{R/C}$ or Mecp2$^{C/y}$ mutant mice and control littermates treated daily from P1-42 with either saline or isoguvacine (2 mg/kg). One-way ANOVA with post-hoc Tukey's test, *, p<0.05.
Figure 28L:
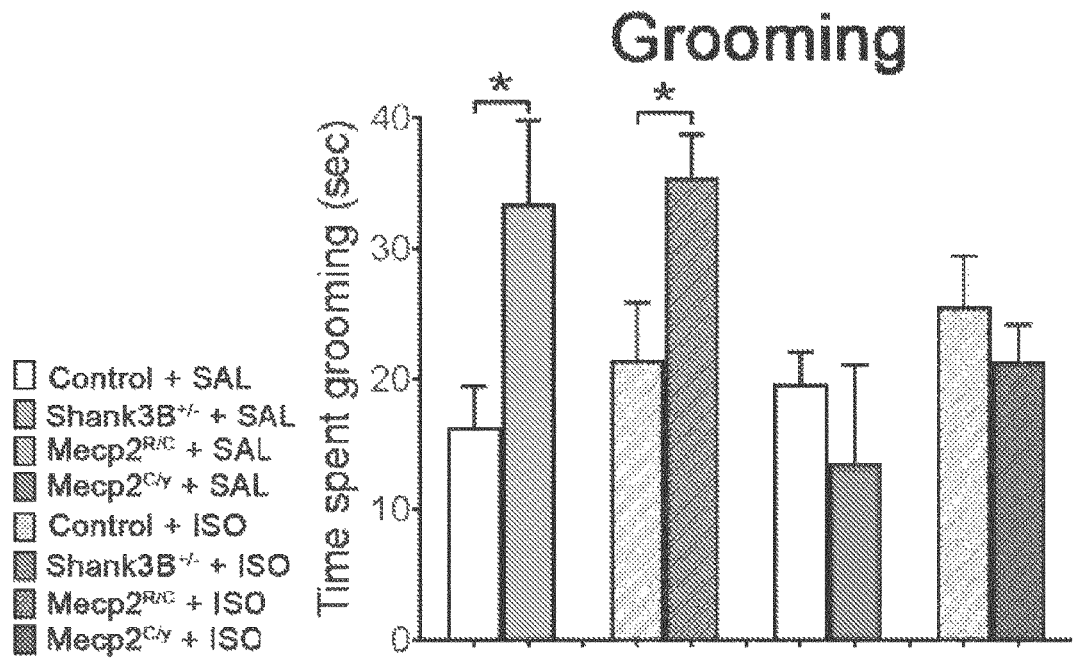
FIG. 28L: Average amount of time spent grooming during a 10-minute open field assessment for Shank3B$^{+/-}$, Mecp2$^{R/C}$ or Mecp2$^{C/y}$ mutant mice and control littermates treated daily from P1-42 with either saline or isoguvacine (2 mg/kg). One-way ANOVA with post-hoc Tukey's test, *, p<0.05.
Figure 28M:
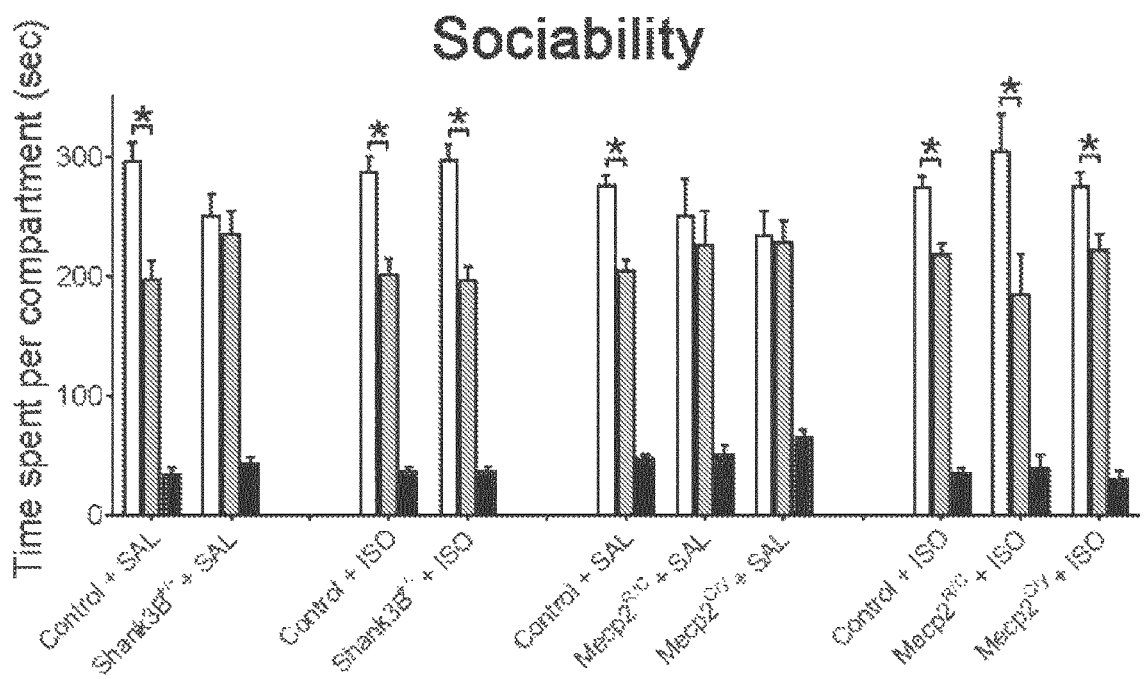
FIG. 28M: Time spent per compartment in the 3-chamber social interaction test during the "Sociability" portion of the assay for Shank3B$^{+/-}$, Mecp2$^{R/C}$ or Mecp2$^{C/y}$ mutant mice and control littermates treated daily from P1-42 with either saline or isoguvacine (2 mg/kg). One-way ANOVA with post-hoc Tukey's test, *, p<0.05.
Figure 28N:
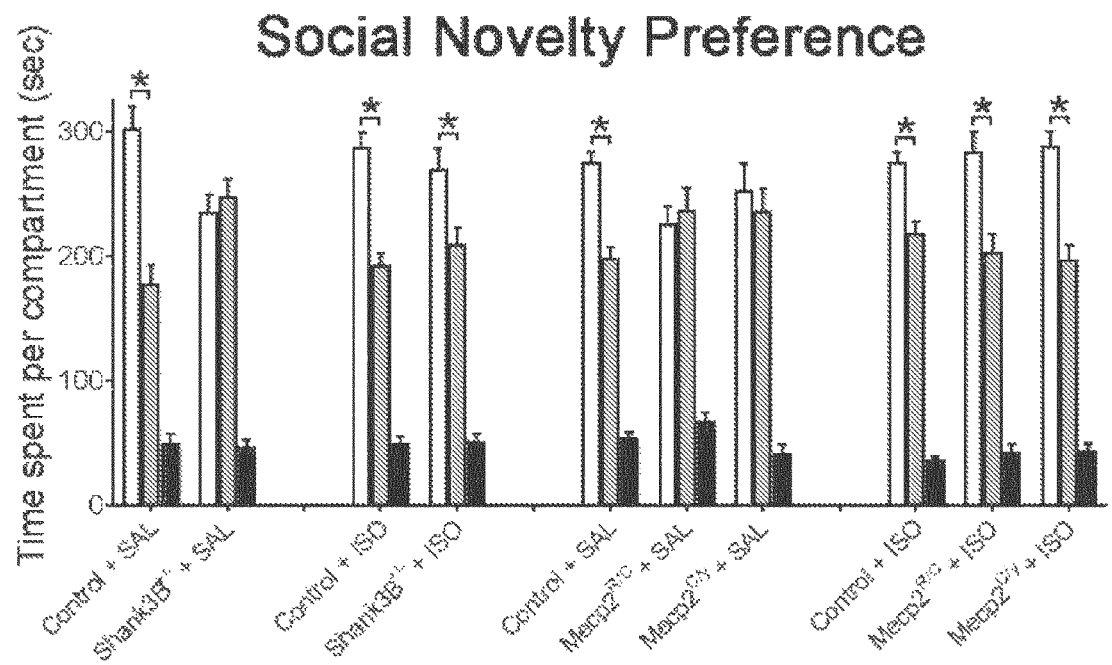
FIG. 28N: Time spent per compartment in the 3-chamber social interaction test during the "Social Novelty Preference" portion of the assay for Shank3B$^{+/-}$, Mecp2$^{R/C}$ or Mecp2$^{C/y}$ mutant mice and control littermates treated daily from P1-42 with either saline or isoguvacine (2 mg/kg). One-way ANOVA with post-hoc Tukey's test, *, p<0.05.
Figure 28O:
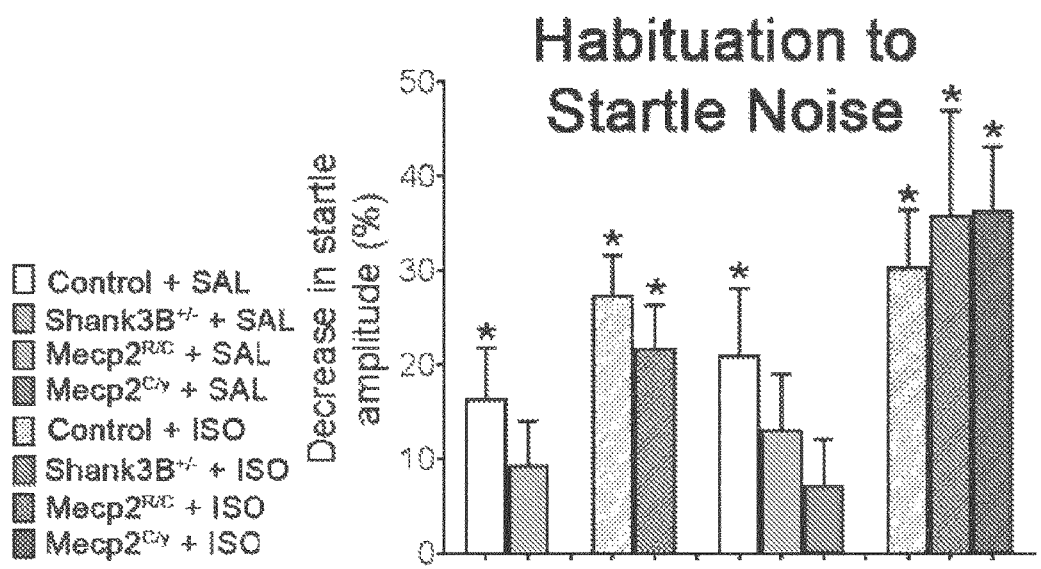
FIG. 28O: Percent decrease in startle response to a 125 dB noise during a 30-minute tactile PPI session, when comparing the first five startle responses to the last five responses to a 125 dB noise for Shank3B$^{+/-}$, Mecp2$^{R/C}$ or Mecp2$^{C/y}$ mutant mice and control littermates treated daily from P1-42 with either saline or isoguvacine (2 mg/kg). One-way ANOVA with post-hoc Tukey's test, *, p<0.05.
Figure 28P:
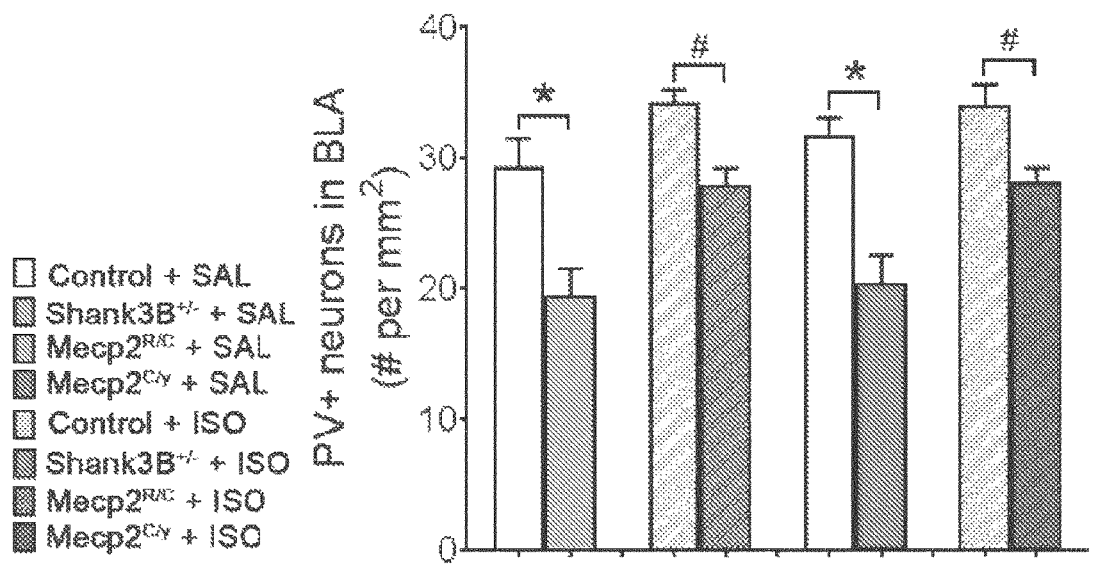
FIG. 28P: Quantification of the number of PV$^+$ neurons in BLA of Shank3B$^{-/-}$, Mecp2$^{R/C}$ or Mecp2$^{C/y}$ mutant mice and control littermates treated daily from P1-42 with either saline or isoguvacine (2 mg/kg). One-way ANOVA with post-hoc Tukey's test, *, p<0.05.
Figure 28Q:
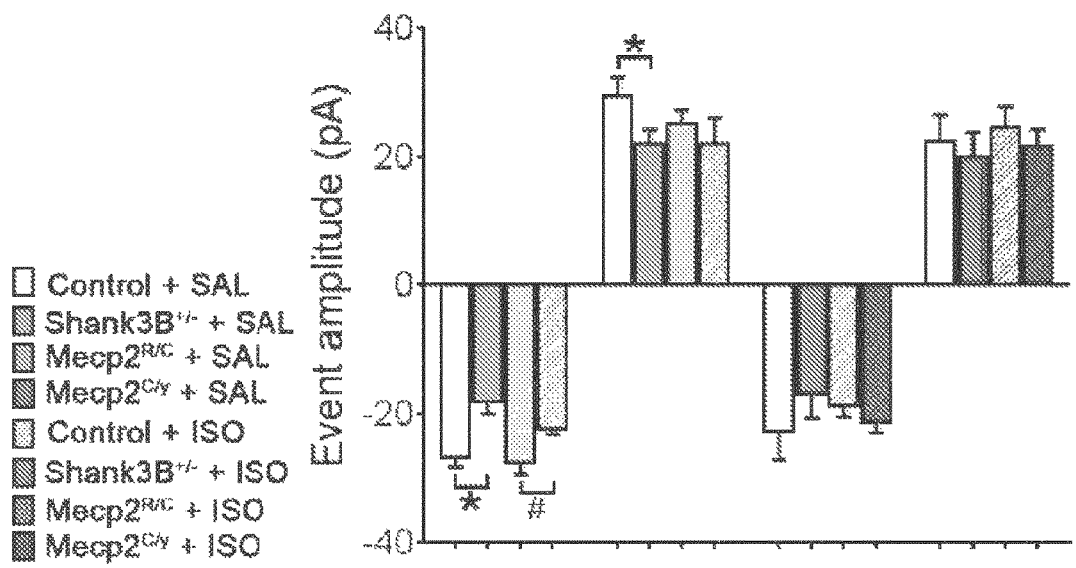
FIG. 28Q: Quantification of ePSC and iPSC event amplitude in S1 slices from Shank3B$^{+/-}$, Mecp2$^{R/C}$ or Mecp2$^{C/y}$ mutant mice and control littermates treated daily from P1-42 with either saline or isoguvacine (2 mg/kg). Two-way ANOVA with post-hoc Sidak's test, *, p<0.05.
Figure 28R:
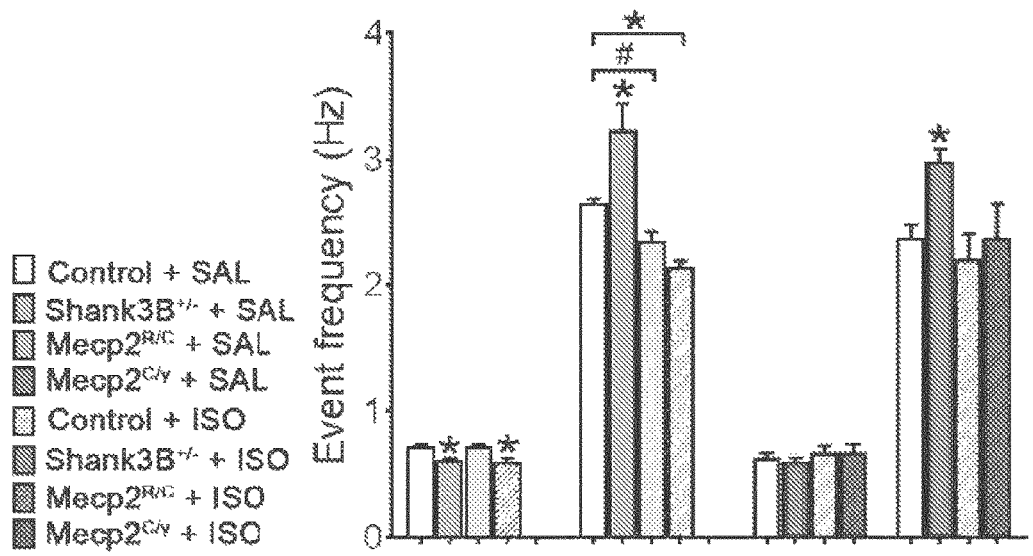
FIG. 28R: Quantification of ePSC and iPSC event frequency in S1 slices from Shank3B$^{+/-}$, Mecp2$^{R/C}$ or Mecp2$^{C/y}$ mutant mice and control littermates treated daily from P1-42 with either saline or isoguvacine (2 mg/kg). Two-way ANOVA with post-hoc Sidak's test, *, p<0.05.
Figure 28S:
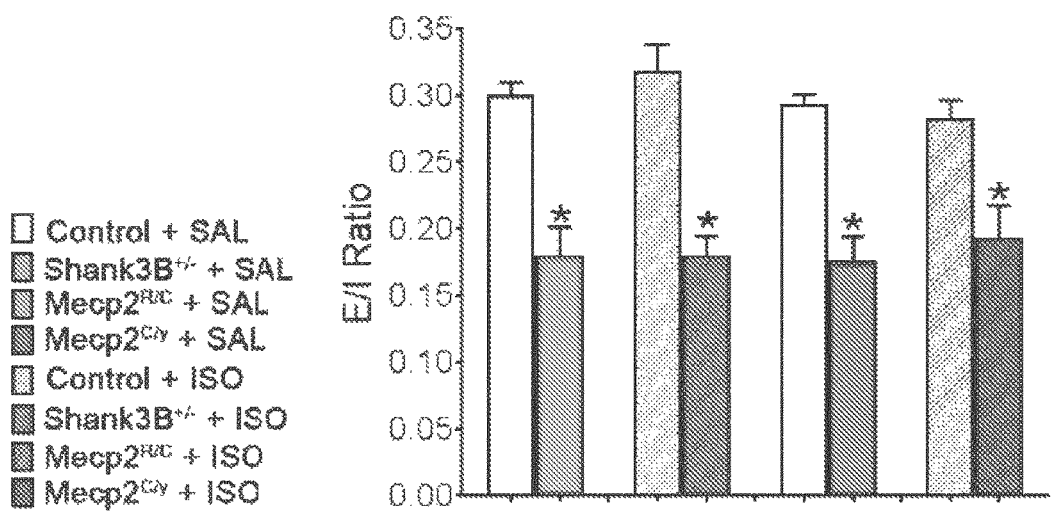
FIG. 28S: Quantification of excitatory/inhibitory (E/I) ratios in S1 or V1 slices from Shank3B$^{-/-}$, Mecp2$^{R/C}$ or Mecp2$^{C/y}$ mutant mice and control littermates treated daily from P1-42 with either saline or isoguvacine (2 mg/kg). Two-way ANOVA with post-hoc Sidak's test, *, p<0.05.
Figure 28T:
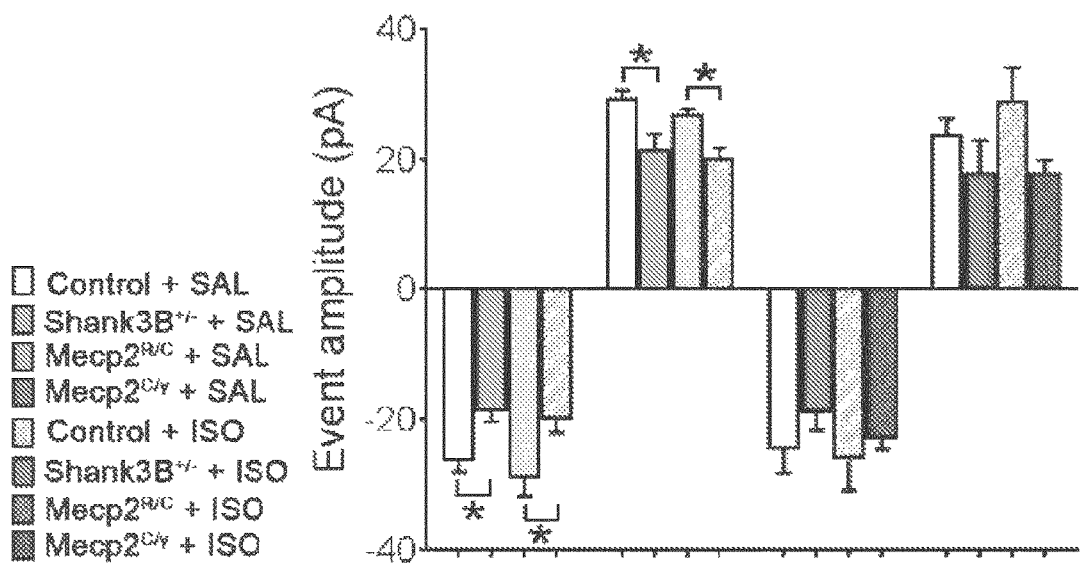
FIG. 28T: Quantification of ePSC and iPSC event amplitude in V1 slices from Shank3B$^{+/-}$, Mecp2$^{R/C}$ or Mecp2$^{C/y}$ mutant mice and control littermates treated daily from P1-42 with either saline or isoguvacine (2 mg/kg). Two-way ANOVA with post-hoc Sidak's test, *, p<0.05.
Figure 28U:
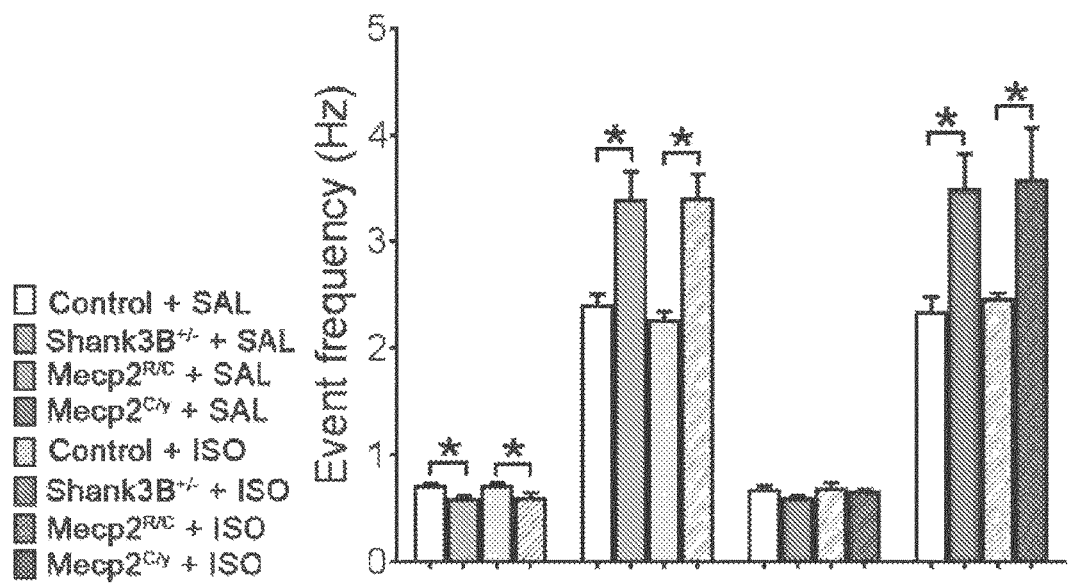
Figure 2:
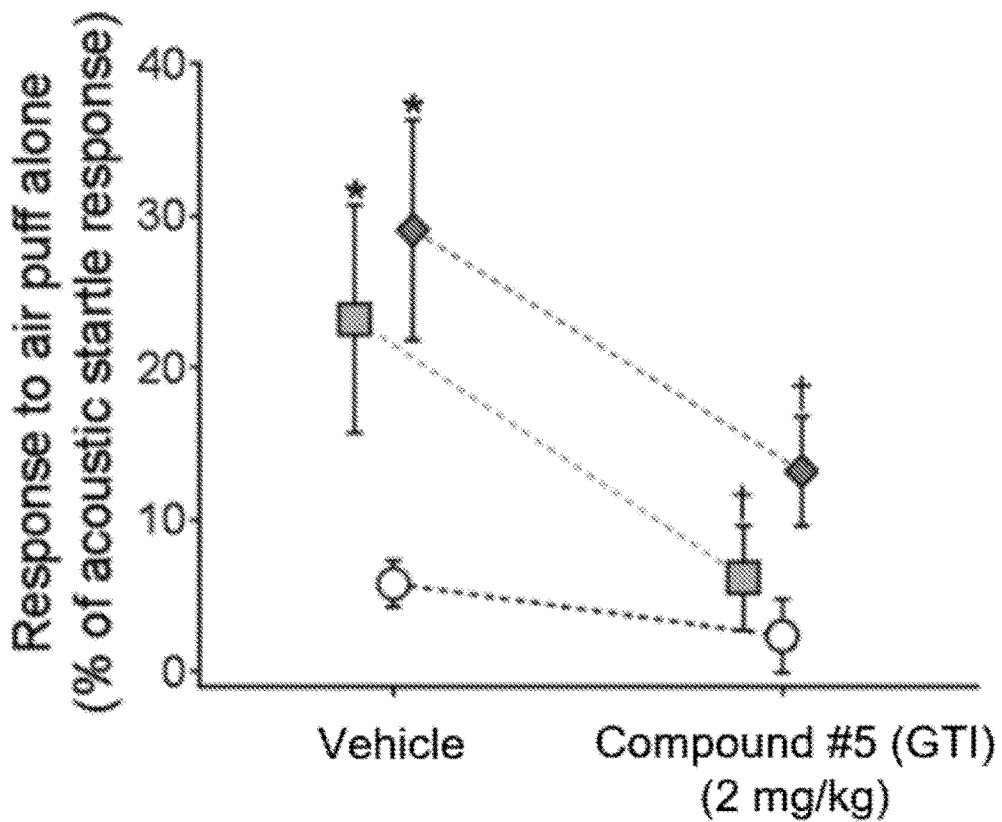
Figure 11A:
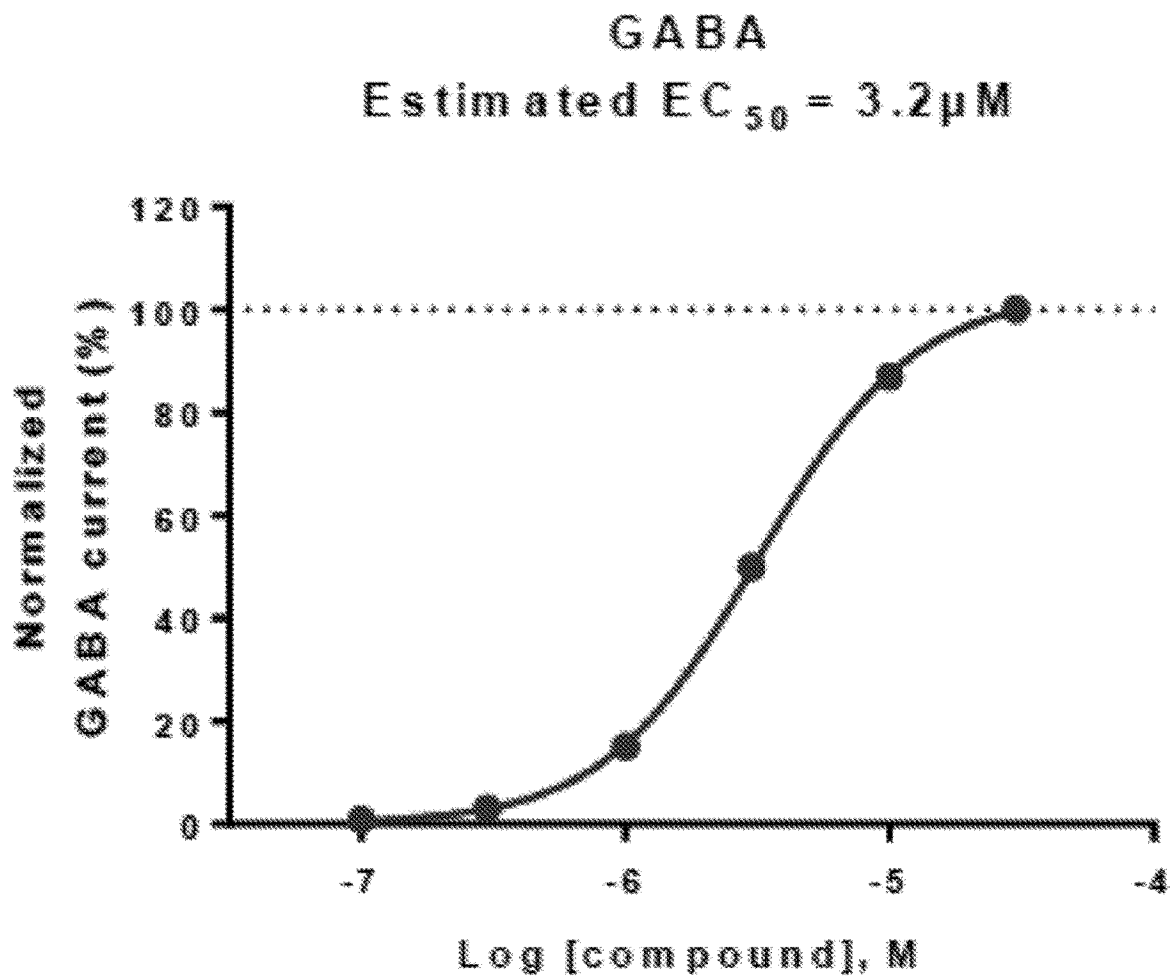

Chronic Treatment with a Peripherally-Restricted $GABA_A$ Receptor Agonist Improves Multiple ASD Phenotypes in Several Animal Models of ASD These results indicate that peripherally restricted $GABA_A$ receptor agonists, which act directly on $GABA_A$ receptors expressed on LTMRs to attenuate responses to tactile stimuli, may be useful for treating tactile over-reactivity and thus anxiety and social impairments in ASD mouse models, if treatment is administered during early postnatal development. Therefore, it was tested whether chronic treatment of Mecp2 and Shank3 germline mutant mice with isoguvacine beginning shortly after birth (i.p. administration, 2 mg/kg per daily, from P0-P42) improves any of the ASD-related phenotypes commonly observed in adulthood. Mecp2$^{R306C}$ and Shank3B$^{+/-}$ mice were chosen for these analyses because both are well established models of ASD that exhibit behavioral abnormalities with high penetrance and severity. Following a six-week isoguvacine treatment regimen, starting at P0, isoguvacine was detected in liver, but not the brain or spinal cord (FIG. 28A). When isoguvacine-treated mice were first compared to saline-treated groups at weaning age (P21), it was noticed a substantial improvement in their overall body appearance, or phenotypic score, which incorporates measures of coat appearance, posture, and general health (FIGS. 21A, 21B; See Experimental Procedures). Moreover, while saline-treated Shank3B and Mecp2 mutant mice displayed reduced bodyweight at P21, compared to control littermates, isoguvacine-treated mutant mice had increased bodyweight and were not different in weight from control mice (FIG. 21C). Chronic administration of isoguvacine also significantly improved multiple ASD-associated behavioral phenotypes, including tactile over-reactivity, anxiety-like behaviors, social impairments, as well as PV$^+$ neuron abnormalities in S1 and BLA and normalized E/I ratios in S1 of 8-week-old mice (FIGS. 21D, 21F-21O, 28C, 28P-28R). On the other hand, chronic administration of isoguvacine did not improve textured discrimination deficits, increased acoustic PPI performance, memory impairments, PV$^+$ neuron abnormalities in V1 or altered E/I ratios in V1 in either Shank3 or Mecp2 mutants (FIGS. 21E, 28E, 28G, 28S-28U). Motor impairments were also not improved in Mecp2 mutants, nor was the overgrooming phenotype rescued in Shank3 mutants (FIGS. 28G, 28L). Taken together, treatment with a peripherally restricted $GABA_A$ receptor agonist during early postnatal development may provide an effective therapeutic strategy for improving tactile over-reactivity and a subset of other key features of ASD, including anxiety, without causing sedation and other undesirable effects of activating brain $GABA_A$ receptors during development.

DISCUSSION

Sensory over-reactivity is now regarded as a hallmark, diagnostic feature of ASDs. The present study adds to a growing body of work demonstrating that peripheral somatosensory neurons are dysfunctional and contribute to behavioral phenotypes in a wide range of genetic and environmental models of ASD, including Mecp2, Gabrb3, Shank3, Cntnap2, Fmr1, and MIA models of ASD [present study, (Bhattacherjee et al., 2017; Chen et al., 2014; Dawes et al., 2018; Han et al., 2016; Oginsky et al., 2017; Orefice et al., 2016; Perche et al., 2018; Price and Melemedjian, 2012)]. These findings, together with evidence of impaired peripheral sensory neuron function in humans with both syndromic and non-syndromic forms of ASD (Bader et al., 1989; Boyle and Kaufmann, 2010; Brandt and Rosen, 1998; Haas and Love, 1988; Hagerman et al., 2007; Jellinger et al., 1988; Khalfa et al., 2001; Torres et al., 2013) have led to the consideration that targeting peripheral sensory neurons may provide an opportunity for therapeutic intervention. Indeed, it was found that pharmacological targeting of $GABA_A$ receptors expressed in peripheral mechanosensory neurons to attenuate their sensitivity reduced tactile over-reactivity and improved aspects of both aberrant brain development and behavioral deficits in multiple ASD models. Importantly, restricting $GABA_A$ receptor drug action to the periphery is potentially beneficial because it avoids sedation and undesirable effects of long-term BBB-penetrating $GABA_A$ receptor treatments. Therefore, it is proposed that peripherally-restricted pharmacological augmentation of $GABA_A$ receptor activity as a therapeutic strategy to combat tactile over-reactivity and possibly core behavioral deficits in ASD patients.

An important finding of the present work is that tactile over-reactivity in ASD models can arise from distinct cell-autonomous, pathophysiological mechanisms. Tactile over-reactivity may result from loss of $GABA_A$ receptor signaling, as is the case for Mecp2 and Gabrb3 mutants, or loss of K channel function leading to hyper-excitability, as seen in Shank3 mutants. The latter observation is consistent with prior work indicating that alterations in $I_h/I_m$ lead to hyper-excitability of neurons (Crozier et al., 2007; Watanabe et al., 2000; Yi et al., 2016; Zheng et al., 2013). It is noteworthy that mutations in Mecp2 and Shank3 may differentially affect sensitivity of LTMRs and nociceptive neurons, which may help to explain the seemingly paradoxical findings that many patients can exhibit both hypersensitivity and aversion to light touch but also decreased responsiveness to noxious stimuli (Downs et al., 2010; Tomchek and Dunn, 2007). Consistent with this, reduced sensitivity to painful thermal and chemical stimuli is observed in mice with conditional deletion of Shank3 in nociceptive neurons (Han et al., 2016). Thus, GABA drugs that target LTMRs without compromising nociceptor or proprioceptor function may be desirable in order to avoid alterations in pain sensitivity or proprioception. The observation that $GABA_A$ receptor expression is high in LTMRs and relatively low in small diameter neurons and proprioceptors may therefore be fortuitous for therapeutic interventions targeting this receptor.

A second principle to emerge from the present work is that loss of either Mecp2 or Shank3 in peripheral sensory neurons leads to changes in neurochemical and functional properties of forebrain circuits. It was found that $PV^+$ interneurons in S1 and BLA are adversely affected in mice lacking either Mecp2 or Shank3 in peripheral somatosensory neurons. Moreover, consistent with recent findings (Antoine et al., 2018), these results suggest that changes in sensory cortex E/I balance observed in ASD models may reflect adaptations to altered sensory input from the periphery. It is speculated that alterations in the number of $PV^+$ neurons or PV expression in the cortex reflect homeostatic mechanisms for increasing inhibitory neuron response rates under conditions of enhanced sensory drive to the cortex. It is important to note, however, that the anatomical and functional phenotypes observed in S1 of mice with loss of Mecp2 or Shank3 in peripheral sensory neurons are less severe than those observed in germline mutants. Thus, while peripheral sensory neuron dysfunction contributes to altered cortical circuitry development, loss of ASD-related genes within the brain are also likely contribute to altered cortical microcircuit function in ASD models. Moreover, loss of Mecp2 or Shank3 in peripheral sensory neurons does not recapitulate all ASD behavioral phenotypes observed in the germline mutation models, including memory impairments and over-grooming behaviors observed in Shank3 mutants. These findings are consistent with prior studies that implicated striato-pallidal and cortico-striatal circuit dysfunction in the genesis of repetitive behaviors in Shank3 mutant mice (Peixoto et al., 2016; Wang et al., 2017). It is proposed that alterations in sensory neuron function and sensory information processing at the earliest stages of sensory pathways contribute to abnormal brain development in a region-specific manner and a subset of ASD behaviors.

A third general finding of the present work is that the extent to which sensory neuron dysfunction contributes to aberrant behavior in disparate ASD models varies greatly with respect to the timing or developmental onset of sensory dysfunction. While early developmental restoration of either Mecp2 or Shank3 function in peripheral sensory neurons improves hairy skin sensitivity, some aspects of social behavior, and anxiety-like behaviors, postnatal weaning age (P28) restoration improves hairy skin sensitivity and sociability, but has no effect on social novelty recognition preference or anxiety-like behaviors. Thus, tactile processing defects in ASDs that manifest during early postnatal periods more profoundly affect both brain development and behavior. This is consistent with prior studies in which global restoration of Shank3 at P21 was sufficient to normalize sociability behaviors but not anxiety-like behaviors (Mei et al., 2016; Wang et al., 2017). The implications of this are profound when considering the pathophysiological mechanisms of ASDs, the contributions of sensory dysfunction to brain development and behavior, and potential therapeutic approaches. Based on these findings, it is proposed that for therapeutic strategies that target the peripheral nervous system to be maximally effective, treatments should be administered early postnatally.

This analysis of the contributions of peripheral mechanosensory neuron dysfunction in ASD mouse models to tactile reactivity, brain development and behavior, together with molecular and physiological analyses of LTMRs, have led to the consideration of a pharmacological approach to augment $GABA_A$ receptor signaling in LTMRs during early postnatal development as a novel therapy for ASD. The logic behind the "LTMR $GABA_A$ receptor hypothesis" for treating tactile over-reactivity and associated behaviors in ASD patients is based on the following observations: 1) ASD gene dysfunction in mechanosensory neurons causes altered physiological properties of LTMRs, including hypersensitivity and reduced presynaptic inhibition in the spinal cord, which contribute to tactile over-reactivity in ASD mouse models (present study); (Orefice et al., 2016); 2) $GABA_A$ receptors are present all along myelinated axons of peripheral nerves (Zeilhofer et al., 2012), and peripheral release of GABA controls somatosensory neuron sensitivity (Carlton et al., 1999; Hanack et al., 2015; Obradovic et al., 2015); (present study); 3) The ASD-associated gene Gabrb3, which encodes the principal obligatory beta subunit of $GABA_A$ receptors in DRG neurons in both mouse (present study) and humans (Flegel et al., 2015; Ray et al., 2018), functions cell autonomously in mechanosensory neurons to control LTMR function as well as tactile sensitivity measured behaviorally (Orefice et al., 2016); 4) GABA acts directly on DRG neurons to reduce excitability in vitro (present study); (Du et al., 2017); 5) Administration of the peripherally-restricted GABA analogue, isoguvacine, attenuates LTMR firing properties and tactile sensitivity in vivo in a manner that is dependent on $GABA_A$ receptors present on LTMRs (present study); 6) Isoguvacine normalizes tactile over-reactivity in five genetic and one environmental model of ASD (present study); and 7) Chronic treatment with isoguvacine beginning at early postnatal ages in two genetically distinct models of ASD improves overall body condition, body weight, $PV^+$ interneuron alterations in S1 and the amygdala, E/I ratios in S1, as well as anxiety-like behaviors and some social impairments in young adult mice (present study). In line with the LTMR $GABA_A$ receptor hypothesis for treating tactile over-reactivity in ASD, other new treatment strategies that show promise for ASD may also work through affecting peripheral nerve function. A recent study reported that i.p. administration of bumetanide from P0-P10 significantly improves functional abnormalities in the somatosensory cortex of Fmr1 knockout mice (He et al., 2018). Because systemic administration of bumetanide leads to extremely low brain concentrations (Romermann et al., 2017), it is likely that bumetanide, akin to isoguvacine, exerts its effects outside of the brain, perhaps directly on peripheral somatosensory neurons, which express the bumetanide target NKCC1, to affect sensitivity and/or development. It is suggest that a significant benefit of peripheral restriction of drug action is that it enables effective peripheral target engagement and optimal dosing without the complications of brain actions and adverse effects on brain development. In line with this, it was found that peripheral administration of isoguvacine, while attenuating LTMR firing and tactile over-reactivity, fails to penetrate the brain to an appreciable extent and does not lead to sedation, as compared to brain-penetrating $GABA_A$ receptor PAMs including benzodiazepines. Therefore, it is hypothesizee that potent GABA drugs that are peripherally restricted to limit or eliminate brain exposure will minimize or avoid entirely the potentially detrimental effects on brain development observed in clinical use of the classical, FDA-approved $GABA_A$ drug arsenal (Jevtovic-Todorovic et al., 2003; Kodish et al., 2011), all of which penetrate the brain (Groeneveld et al., 2016; Pajouhesh and Lenz, 2005; Rudolph and Knoflach, 2011). Whether acute treatment of children or adult ASD patients with peripherally-restricted GABA analogues, $GABA_A$ receptor PAMs, or GABA reuptake inhibitors normalize tactile over-reactivity, and whether chronic treatment beginning at early postnatal ages ameliorates ASD-associated behaviors must await the development of new peripherally restricted compounds and their testing in patient trials.

REFERENCES

Akyol, A., Hinoi, T., Feng, Y., Bommer, G. T., Glaser, T. M., and Fearon, E. R. (2008). Generating somatic mosaicism with a Cre recombinase-microsatellite sequence transgene. Nature methods 5, 231-233. Amaral, D. G. (2003). The amygdala, social behavior, and danger detection. Ann N Y Acad Sci 1000, 337-347.

Amaral, D. G., Bauman, M. D., and Schumann, C. M. (2003). The amygdala and autism: implications from non-human primate studies. Genes Brain Behav 2, 295-302.

Anagnostou, E., Soorya, L., Chaplin, W., Bartz, J., Halpern, D., Wasserman, S., Wang, A. T., Pepa, L., Tanel, N., Kushki, A., et al. (2012). Intranasal oxytocin versus placebo in the treatment of adults with autism spectrum disorders: a randomized controlled trial. Mol Autism 3, 16.

Antoine, M. W., Schnepel, P., Langberg, T., and Feldman, D. E. (2018). Increased excitation-inhibition ratio stabilizes synapse and circuit excitability in four autism mouse models. 317693.

Bader, G. G., Witt-Engerstrom, I., and Hagberg, B. (1989). Neurophysiological findings in the Rett syndrome, I: EMG, conduction velocity, EEG and somatosensory-evoked potential studies. Brain Dev 11, 102-109.

Baio, J., Wiggins, L., Christensen, D. L., Maenner, M. J., Daniels, J., Warren, Z., Kurzius-Spencer, M., Zahorodny, W., Robinson Rosenberg, C., White, T., et al. (2018). Prevalence of Autism Spectrum Disorder Among Children Aged 8 Years—Autism and Developmental Disabilities Monitoring Network, 11 Sites, United States, 2014. MMWR Surveill Summ 67, 1-23.

Bhattacherjee, A., Mu, Y., Winter, M. K., Knapp, J. R., Eggimann, L. S., Gunewardena, S. S., Kobayashi, K., Kato, S., Krizsan-Agbas, D., and Smith, P. G. (2017). Neuronal cytoskeletal gene dysregulation and mechanical hypersensitivity in a rat model of Rett syndrome. Proceedings of the National Academy of Sciences of the United States of America 114, E6952-E6961.

Bowery, N. G., Hill, D. R., and Hudson, A. L. (1983). Characteristics of $GABA_B$ receptor binding sites on rat whole brain synaptic membranes. Br J Pharmacol 78, 191-206.

Boyle, L., and Kaufmann, W. E. (2010). The behavioral phenotype of FMR1 mutations. Am J Med Genet C Semin Med Genet 154C, 469-476.

Brandt, B. R., and Rosen, I. (1998). Impaired peripheral somatosensory function in children with Prader-Willi syndrome. Neuropediatrics 29, 124-126.

Carlton, S. M., Zhou, S., and Coggeshall, R. E. (1999). Peripheral GABA(A) receptors: evidence for peripheral primary afferent depolarization. Neuroscience 93, 713-722.

Chen, J. T., Guo, D., Campanelli, D., Frattini, F., Mayer, F., Zhou, L., Kuner, R., Heppenstall, P. A., Knipper, M., and Hu, J. (2014). Presynaptic GABAergic inhibition regulated by BDNF contributes to neuropathic pain induction. Nature communications 5, 5331.

Choi, G. B., Yim, Y. S., Wong, H., Kim, S., Kim, H., Kim, S. V., Hoeffer, C. A., Littman, D. R., and Huh, J. R. (2016). The maternal interleukin-17a pathway in mice promotes autism-like phenotypes in offspring. Science 351, 933-939.

Coury, D. L., Anagnostou, E., Manning-Courtney, P., Reynolds, A., Cole, L., McCoy, R., Whitaker, A., and Perrin, J. M. (2012). Use of psychotropic medication in children and adolescents with autism spectrum disorders. Pediatrics 130 Suppl 2, S69-76.

Crozier, R. A., Ajit, S. K., Kaftan, E. J., and Pausch, M. H. (2007). MrgD activation inhibits KCNQ/M-currents and contributes to enhanced neuronal excitability. The Journal of neuroscience: the official journal of the Society for Neuroscience 27, 4492-4496.

Dawes, J. M., Weir, G. A., Middleton, S. J., Patel, R., Chisholm, K. I., Pettingill, P., Peck, L. J., Sheridan, J., Shakir, A., Jacobson, L., et al. (2018). Immune or Genetic-Mediated Disruption of CASPR2 Causes Pain Hypersensitivity Due to Enhanced Primary Afferent Excitability. Neuron 97, 806-822 e810.

Dorrn, A. L., Yuan, K., Barker, A. J., Schreiner, C. E., and Froemke, R. C. (2010). Developmental sensory experience balances cortical excitation and inhibition. Nature 465, 932-936.

Downs, J., Geranton, S. M., Bebbington, A., Jacoby, P., Bahi-Buisson, N., Ravine, D., and Leonard, H. (2010). Linking MECP2 and pain sensitivity: the example of Rett syndrome. Am J Med Genet A 152A, 1197-1205.

DSM-V (2013). Diagnostic and statistical manual of mental disorders: DSM-5 (Fifth edition. Arlington, Va.: American Psychiatric Publishing, [2013] ©2013).

Du, X., Hao, H., Yang, Y., Huang, S., Wang, C., Gigout, S., Ramli, R., Li, X., Jaworska, E., Edwards, I., et al. (2017). Local GABAergic signaling within sensory ganglia controls peripheral nociceptive transmission. J Clin Invest 127, 1741-1756.

Enna, S. J., and McCarson, K. E. (2006). The role of GABA in the mediation and perception of pain. Adv Pharmacol 54, 1-27.

Erickson, C.A., Veenstra-Vanderweele, J. M., Melmed, R. D., McCracken, J. T., Ginsberg, L. D., Sikich, L., Scahill, L., Cherubini, M., Zarevics, P., Walton-Bowen, K., et al. (2014). STX209 (arbaclofen) for autism spectrum disorders: an 8-week open-label study. J Autism Dev Disord 44, 958-964.

Filice, F., Vorckel, K. J., Sungur, A. O., Wohr, M., and Schwaller, B. (2016). Reduction in parvalbumin expression not loss of the parvalbumin-expressing GABA interneuron subpopulation in genetic parvalbumin and shank mouse models of autism. Mol Brain 9, 10.

Flegel, C., Schobel, N., Altmuller, J., Becker, C., Tannapfel, A., Hatt, H., and Gisselmann, G. (2015). RNA-Seq Analysis of Human Trigeminal and Dorsal Root Ganglia with a Focus on Chemoreceptors. PLoS One 10, e0128951.

Fukuda, T., Itoh, M., Ichikawa, T., Washiyama, K., and Goto, Y. (2005). Delayed maturation of neuronal architecture and synaptogenesis in cerebral cortex of Mecp2-deficient mice. J Neuropathol Exp Neurol 64, 537-544.

Golombok, S., Moodley, P., and Lader, M. (1988). Cognitive impairment in long-term benzodiazepine users. Psychol Med 18, 365-374.

Groeneveld, G. J., Hay, J. L., and Van Gerven, J. M. (2016). Measuring blood-brain barrier penetration using the NeuroCart, a CNS test battery. Drug Discov Today Technol 20, 27-34.

Guastella, A. J., Gray, K. M., Rinehart, N. J., Alvares, G. A., Tonge, B. J., Hickie, I. B., Keating, C. M., Cacciotti-Saija, C., and Einfeld, S. L. (2015). The effects of a course of intranasal oxytocin on social behaviors in youth diagnosed with autism spectrum disorders: a randomized controlled trial. J Child Psychol Psychiatry 56, 444-452.

Gudex, C. (1991). Adverse effects of benzodiazepines. Soc Sci Med 33, 587-596.

Haas, R. H., and Love, S. (1988). Peripheral nerve findings in Rett syndrome. J Child Neurol 3 Suppl, S25-30.

Hadjikhani, N., Asberg Johnels, J., Lassalle, A., Zurcher, N. R., Hippolyte, L., Gillberg, C., Lemonnier, E., and Ben-Ari, Y. (2018). Bumetanide for autism: more eye contact, less amygdala activation. Sci Rep 8, 3602.

Hagerman, R. J., Coffey, S. M., Maselli, R., Soontarapornchai, K., Brunberg, J. A., Leehey, M. A., Zhang, L., Gane, L. W., Fenton-Farrell, G., Tassone, F., et al. (2007). Neuropathy as a presenting feature in fragile X-associated tremor/ataxia syndrome. Am J Med Genet A 143A, 2256-2260.

Han, Q., Kim, Y. H., Wang, X., Liu, D., Zhang, Z. J., Bey, A. L., Lay, M., Chang, W., Berta, T., Zhang, Y., et al. (2016). SHANKS Deficiency Impairs Heat Hyperalgesia and TRPV1 Signaling in Primary Sensory Neurons. Neuron 92, 1279-1293.

Hanack, C., Moroni, M., Lima, W.C., Wende, H., Kirchner, M., Adelfinger, L., Schrenk-Siemens, K., Tappe-Theodor, A., Wetzel, C., Kuich, P. H., et al. (2015). GABA blocks pathological but not acute TRPV1 pain signals. Cell 160, 759-770.

Hasegawa, H., Abbott, S., Han, B. X., Qi, Y., and Wang, F. (2007). Analyzing somatosensory axon projections with the sensory neuron-specific Advillin gene. The Journal of neuroscience: the official journal of the Society for Neuroscience 27, 14404-14414.

Hashemi, E., Ariza, J., Rogers, H., Noctor, S. C., and Martinez-Cerdeno, V. (2017). The Number of Parvalbumin-Expressing Interneurons Is Decreased in the Medial Prefrontal Cortex in Autism. Cereb Cortex 27, 1931-1943.

He, Q., Arroyo, E. D., Smukowski, S. N., Xu, J., Piochon, C., Savas, J. N., Portera-Cailliau, C., and Contractor, A. (2018). Critical period inhibition of NKCC1 rectifies synapse plasticity in the somatosensory cortex and restores adult tactile response maps in fragile X mice. Mol Psychiatry.

Hill, D. R., and Bowery, N. G. (1981). 3H-baclofen and 3H-GABA bind to bicuculline-insensitive GABA B sites in rat brain. Nature 290, 149-152.

Howes, O. D., Rogdaki, M., Findon, J. L., Wichers, R. H., Charman, T., King, B. H., Loth, E., McAlonan, G. M., McCracken, J. T., Parr, J. R., et al. (2018). Autism spectrum disorder: Consensus guidelines on assessment, treatment and research from the British Association for Psychopharmacology. J Psychopharmacol 32, 3-29.

Hubel, D. H., and Wiesel, T. N. (1970). The period of susceptibility to the physiological effects of unilateral eye closure in kittens. The Journal of physiology 206, 419-436.

Janak, P. H., and Tye, K. M. (2015). From circuits to behaviour in the amygdala. *Nature* 517, 284-292.

Jaramillo, T. C., Speed, H. E., Xuan, Z., Reimers, J. M., Escamilla, C. O., Weaver, T. P., Liu, S., Filonova, I., and Powell, C. M. (2017). Novel Shank3 mutant exhibits behaviors with face validity for autism and altered striatal and hippocampal function. Autism Res 10, 42-65.

Jellinger, K., Armstrong, D., Zoghbi, H. Y., and Percy, A. K. (1988). Neuropathology of Rett syndrome. Acta Neuropathol 76, 142-158.

Jevtovic-Todorovic, V., Hartman, R. E., Izumi, Y., Benshoff, N. D., Dikranian, K., Zorumski, C. F., Olney, J. W., and Wozniak, D. F. (2003). Early exposure to common anesthetic agents causes widespread neurodegeneration in the developing rat brain and persistent learning deficits. The Journal of neuroscience: the official journal of the Society for Neuroscience 23, 876-882.

Jiao, Y., Zhang, Z., Zhang, C., Wang, X., Sakata, K., Lu, B., and Sun, Q. Q. (2011). A key mechanism underlying sensory experience-dependent maturation of neocortical GABAergic circuits in vivo. Proceedings of the National Academy of Sciences of the United States of America 108, 12131-12136.

Khalfa, S., Bruneau, N., Roge, B., Georgieff, N., Veuillet, E., Adrien, J. L., Barthelemy, C., and Collet, L. (2001). Peripheral auditory asymmetry in infantile autism. Eur J Neurosci 13, 628-632.

King, B. H., Hollander, E., Sikich, L., McCracken, J. T., Scahill, L., Bregman, J. D., Donnelly, C. L., Anagnostou, E., Dukes, K., Sullivan, L., et al. (2009). Lack of efficacy of citalopram in children with autism spectrum disorders and high levels of repetitive behavior: citalopram ineffective in children with autism. Arch Gen Psychiatry 66, 583-590.

Kodish, I., Rockhill, C., and Varley, C. (2011). Pharmacotherapy for anxiety disorders in children and adolescents. Dialogues in clinical neuroscience 13, 439-452.

Konig, P., Engel, A. K., and Singer, W. (1996). Integrator or coincidence detector? The role of the cortical neuron revisited. Trends Neurosci 19, 130-137.

Krishnan, K., Wang, B. S., Lu, J., Wang, L., Maffei, A., Cang, J., and Huang, Z. J. (2015). MeCP2 regulates the timing of critical period plasticity that shapes functional connectivity in primary visual cortex. Proceedings of the National Academy of Sciences of the United States of America 112, E4782-4791.

Krogsgaard-Larsen, P., and Johnston, G. A. (1978). Structure-activity studies on the inhibition of GABA binding to rat brain membranes by muscimol and related compounds. J Neurochem 30, 1377-1382.

Krogsgaard-Larsen, P., Johnston, G. A., Lodge, D., and Curtis, D. R. (1977). A new class of GABA agonist. Nature 268, 53-55.

Krogsgaard-Larsen, P., Schultz, B., Mikkelsen, H., Aaes-Jorgensen, T., and Bogeso, K. P. (1981). THIP, isoguvacine, isoguvacine oxide, and related GABA agonists. Adv Biochem Psychopharmacol 29, 69-76.

Lau, J., Minett, M. S., Zhao, J., Dennehy, U., Wang, F., Wood, J. N., and Bogdanov, Y. D. (2011). Temporal control of gene deletion in sensory ganglia using a tamoxifen-inducible Advillin-Cre-ERT2 recombinase mouse. Mol Pain 7, 100.

Lemonnier, E., Villeneuve, N., Sonie, S., Serret, S., Rosier, A., Roue, M., Brosset, P., Viellard, M., Bernoux, D., Rondeau, S., et al. (2017). Effects of bumetanide on neurobehavioral function in children and adolescents with autism spectrum disorders. Transl Psychiatry 7, e1056.

Levy, R. A., and Anderson, E. G. (1972). The effect of the GABA antagonists bicuculline and picrotoxin on primary afferent terminal excitability. Brain research 43, 171-180.

Lyst, M. J., Ekiert, R., Ebert, D. H., Merusi, C., Nowak, J., Selfridge, J., Guy, J., Kastan, N. R., Robinson, N. D., de Lima Alves, F., et al. (2013). Rett syndrome mutations abolish the interaction of MeCP2 with the NCoR/SMRT co-repressor. Nature neuroscience 16, 898-902.

Mammen, M. A., Moore, G. A., Scaramella, L. V., Reiss, D., Ganiban, J. M., Shaw, D. S., Leve, L. D., and Neiderhiser, J. M. (2015). Infant Avoidance during a Tactile Task Predicts Autism Spectrum Behaviors in Toddlerhood. Infant Ment Health J 36, 575-587.

Marin, O. (2012). Interneuron dysfunction in psychiatric disorders. Nat Rev Neurosci 13, 107-120.

Mazurek, M. O., Vasa, R. A., Kalb, L. G., Kanne, S. M., Rosenberg, D., Keefer, A., Murray, D. S., Freedman, B., and Lowery, L. A. (2013). Anxiety, sensory over-responsivity, and gastrointestinal problems in children with autism spectrum disorders. J Abnorm Child Psychol 41, 165-176.

Mei, Y., Monteiro, P., Zhou, Y., Kim, J. A., Gao, X., Fu, Z., and Feng, G. (2016). Adult restoration of Shank3 expression rescues selective autistic-like phenotypes. Nature 530, 481-484.

Nelson, S. B., and Valakh, V. (2015). Excitatory/Inhibitory Balance and Circuit Homeostasis in Autism Spectrum Disorders. Neuron 87, 684-698.

Obradovic, A. L., Scarpa, J., Osuru, H. P., Weaver, J. L., Park, J. Y., Pathirathna, S., Peterkin, A., Lim, Y., Jagodic, M. M., Todorovic, S. M., et al. (2015). Silencing the alpha2 subunit of gamma-aminobutyric acid type A receptors in rat dorsal root ganglia reveals its major role in antinociception posttraumatic nerve injury. Anesthesiology 123, 654-667.

Oginsky, M. F., Cui, N., Zhong, W., Johnson, C. M., and Jiang, C. (2017). Hyperexcitability of Mesencephalic Trigeminal Neurons and Reorganization of Ion Channel Expression in a Rett Syndrome Model. J Cell Physiol 232, 1151-1164.

Orefice, L. L., Zimmerman, A. L., Chirila, A. M., Sleboda, S. J., Head, J. P., and Ginty, D. D. (2016). Peripheral Mechanosensory Neuron Dysfunction Underlies Tactile and Behavioral Deficits in Mouse Models of ASDs. Cell 166, 299-313.

Page, A. J., and Blackshaw, L. A. (1999). GABA(B) receptors inhibit mechanosensitivity of primary afferent endings. The Journal of neuroscience: the official journal of the Society for Neuroscience 19, 8597-8602.

Pajouhesh, H., and Lenz, G. R. (2005). Medicinal chemical properties of successful central nervous system drugs. NeuroRx 2, 541-553.

Peca, J., Feliciano, C., Ting, J. T., Wang, W., Wells, M. F., Venkatraman, T. N., Lascola, C. D., Fu, Z., and Feng, G. (2011). Shank3 mutant mice display autistic-like behaviours and striatal dysfunction. Nature 472, 437-442.

Peixoto, R. T., Wang, W., Croney, D. M., Kozorovitskiy, Y., and Sabatini, B. L. (2016). Early hyperactivity and precocious maturation of corticostriatal circuits in Shank3B (−/−) mice. Nature neuroscience 19, 716-724.

Perche, O., Felgerolle, C., Ardourel, M., Bazinet, A., Paris, A., Rossignol, R., Meyer-Dilhet, G., Mausset-Bonnefont, A. L., Hebert, B., Laurenceau, D., et al. (2018). Early Retinal Defects in Fmr1(−/y) Mice: Toward a Critical Role of Visual Dys-Sensitivity in the Fragile X Syndrome Phenotype? Front Cell Neurosci 12, 96. Phelan, K., and McDermid, H. E. (2012). The 22q13.3 Deletion Syndrome (Phelan-McDermid Syndrome). Mol Syndromol 2, 186-201.

Price, T. J., and Melemedjian, O. K. (2012). Fragile X mental retardation protein (FMRP) and the spinal sensory system. Results Probl Cell Differ 54, 41-59.

Ray, P., Torck, A., Quigley, L., Wangzhou, A., Neiman, M., Rao, C., Lam, T., Kim, J. Y., Kim, T. H., Zhang, M. Q., et al. (2018). Comparative transcriptome profiling of the human and mouse dorsal root ganglia: an RNA-seq-based resource for pain and sensory neuroscience research. Pain 159, 1325-1345.

Romermann, K., Fedrowitz, M., Hampel, P., Kaczmarek, E., Tollner, K., Erker, T., Sweet, D. H., and Loscher, W. (2017). Multiple blood-brain barrier transport mechanisms limit bumetanide accumulation, and therapeutic potential, in the mammalian brain. Neuropharmacology 117, 182-194.

Rudolph, U., and Knoflach, F. (2011). Beyond classical benzodiazepines: novel therapeutic potential of $GABA_A$ receptor subtypes. Nat Rev Drug Discov 10, 685-697.

Schulz, S. E., and Stevenson, R. A. (2018). Sensory hypersensitivity predicts repetitive behaviours in autistic and typically-developing children. Autism: the international journal of research and practice, 1362361318774559.

Simons, D. J., and Land, P. W. (1987). Early experience of tactile stimulation influences organization of somatic sensory cortex. Nature 326, 694-697.

Sohal, V. S., Zhang, F., Yizhar, O., and Deisseroth, K. (2009). Parvalbumin neurons and gamma rhythms enhance cortical circuit performance. Nature 459, 698-702.

Tata, P. R., Rollings, J., Collins, M., Pickering, A., and Jacobson, R. R. (1994). Lack of cognitive recovery following withdrawal from long-term benzodiazepine use. Psychol Med 24, 203-213.

Tomassy, G. S., Morello, N., Calcagno, E., and Giustetto, M. (2014). Developmental abnormalities of cortical interneurons precede symptoms onset in a mouse model of Rett syndrome. J Neurochem 131, 115-127.

Tomchek, S. D., and Dunn, W. (2007). Sensory processing in children with and without autism: a comparative study using the short sensory profile. Am J Occup Ther 61, 190-200.

Torres, E. B., Brincker, M., Isenhower, R. W., Yanovich, P., Stigler, K. A., Nurnberger, J. I., Metaxas, D. N., and Jose, J. V. (2013). Autism: the micro-movement perspective. Front Integr Neurosci 7, 32.

Usoskin, D., Furlan, A., Islam, S., Abdo, H., Lonnerberg, P., Lou, D., Hjerling-Leffler, J., Haeggstrom, J., Kharchenko, O., Kharchenko, P. V., et al. (2015). Unbiased classification of sensory neuron types by large-scale single-cell RNA sequencing. Nature neuroscience 18, 145-153.

Veenstra-VanderWeele, J., Cook, E. H., King, B. H., Zarevics, P., Cherubini, M., Walton-Bowen, K., Bear, M. F., Wang, P. P., and Carpenter, R. L. (2017). Arbaclofen in Children and Adolescents with Autism Spectrum Disorder: A Randomized, Controlled, Phase 2 Trial. Neuropsychopharmacology 42, 1390-1398.

Wang, W., Li, C., Chen, Q., van der Goes, M.-S., Hawrot, J., Yao, A. Y., Gao, X., Lu, C., Zang, Y., Zhang, Q., et al. (2017). Striatopallidal dysfunction underlies repetitive behavior in Shank3-deficient model of autism. The Journal of Clinical Investigation 127, 1978-1990.

Watanabe, H., Nagata, E., Kosakai, A., Nakamura, M., Yokoyama, M., Tanaka, K., and Sasai, H. (2000). Disruption of the epilepsy KCNQ2 gene results in neural hyperexcitability. J Neurochem 75, 28-33.

Wiesel, T. N., and Hubel, D. H. (1965). Extent of recovery from the effects of visual deprivation in kittens. Journal of neurophysiology 28, 1060-1072.

Wiggins, L. D., Robins, D. L., Bakeman, R., and Adamson, L. B. (2009). Brief report: sensory abnormalities as distinguishing symptoms of autism spectrum disorders in young children. J Autism Dev Disord 39, 1087-1091.

Womelsdorf, T., Valiante, T. A., Sahin, N. T., Miller, K. J., and Tiesinga, P. (2014). Dynamic circuit motifs underlying rhythmic gain control, gating and integration. Nature neuroscience 17, 1031-1039.

Yatawara, C. J., Einfeld, S. L., Hickie, I. B., Davenport, T. A., and Guastella, A. J. (2016). The effect of oxytocin nasal spray on social interaction deficits observed in young children with autism: a randomized clinical crossover trial. Mol Psychiatry 21, 1225-1231.

Yi, F., Danko, T., Botelho, S. C., Patzke, C., Pak, C., Wernig, M., and Sudhof, T. C. (2016). Autism-associated SHANKS haploinsufficiency causes $I_h$ channelopathy in human neurons. Science 352, aaf2669.

Zeilhofer, H. U., Wildner, H., and Yevenes, G. E. (2012). Fast synaptic inhibition in spinal sensory processing and pain control. Physiological reviews 92, 193-235.

Zheng, Q., Fang, D., Liu, M., Cai, J., Wan, Y., Han, J. S., and Xing, G. G. (2013). Suppression of KCNQ/M (Kv7) potassium channels in dorsal root ganglion neurons contributes to the development of bone cancer pain in a rat model. Pain 154, 434-448.

Zikopoulos, B., and Barbas, H. (2013). Altered neural connectivity in excitatory and inhibitory cortical circuits in autism. Front Hum Neurosci 7, 609.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound having the structure of Formula (I):

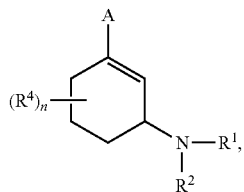

wherein n=1, 2, 3, 4, 5, 6, 7, or 8;

each of $R^1$ and $R^2$ is, independently, hydrogen, deuterium, optionally substituted $C_{1-6}$ alkyl, or optionally substituted $C_{3-6}$ cycloalkyl wherein $R^1$ and $R^2$ are covalently linked;

each $R^4$ is, independently, hydrogen, deuterium, halogen, optionally substituted $C_{1-4}$ alkoxy, optionally substituted $C_{1-6}$ alkyl, $CF_3$, $CH_3S$, $CH_3SO_2$, or $NO_2$; and A is a carboxylic acid, or has the structure of:

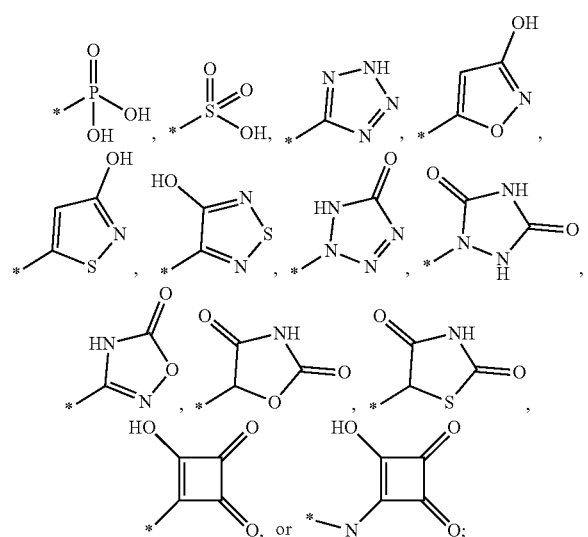

or a pharmaceutically acceptable salt thereof wherein when A is a carboxylic acid, and each occurrence of $R^4$ is hydrogen, at least one of $R^1$ and $R^2$ is not hydrogen.

2. The compound of claim 1, wherein the compound has the structure of Formula (Ia) or (Ib):

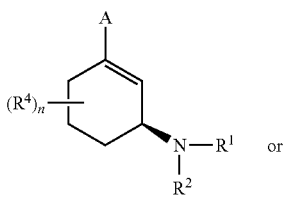

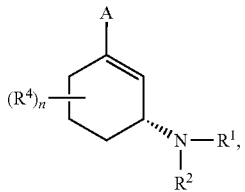

or a pharmaceutically acceptable salt thereof.

3. The compound of claim 1, wherein each of $R^1$ and $R^2$ is, independently, hydrogen or $C_{1-4}$ alkyl; and A is carboxylic acid.

4. The compound of claim 3, wherein each of $R^1$ and $R^2$ is, independently, hydrogen or $C_{1-2}$ alkyl; and A is carboxylic acid.

5. The compound of claim 4, wherein the compound has the structure of:

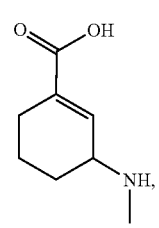

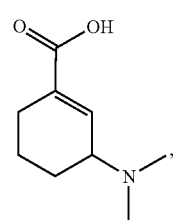

or a pharmaceutically acceptable salt thereof.

6. A compound of the structure 5a:

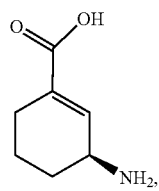

or a pharmaceutically acceptable salt thereof.

7. The compound of claim 5, wherein the compound has the structure of:

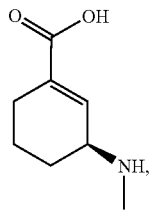
3a

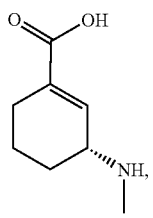
3b

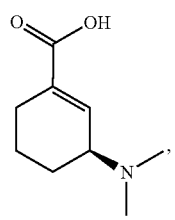
4a

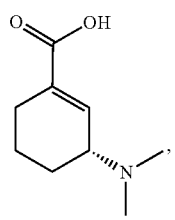
4b or a pharmaceutically acceptable salt thereof.

8. A pharmaceutical composition comprising a compound of claim 1, and a pharmaceutically acceptable excipient.

9. A method of reducing tactile dysfunction in a human subject diagnosed with Autism Spectrum Disorder (ASD), Rett syndrome (RTT), Phelan McDermid syndrome (PMS), or Fragile X syndrome, the method comprising administering to the subject the compound of claim 1 in an amount and for a duration sufficient to reduce the tactile dysfunction.

10. A method of reducing anxiety or social impairment in a human subject diagnosed with ASD, RTT, PMS, or Fragile X syndrome, the method comprising administering to the subject the compound of claim 1 in an amount and for a duration sufficient to reduce the anxiety or social impairment.

11. A method of treating touch over-reactivity and/or pain and/or mechanical allodynia in a human subject in need thereof, the method comprising administering to the subject a compound of claim 1 in an amount and for a duration sufficient to reduce the touch over-reactivity and/or pain and/or mechanical allodynia.

12. The method of claim 11, wherein the touch over-reactivity and/or pain is associated with a disease state selected from Sensory Processing Disorder (SPD) and fibromyalgia.

13. The method of claim 11, wherein the mechanical allodynia is associated with nerve injury, shingles, diabetic neuropathy, chemotherapy-induced neuropathy, or a neuropathic pain state.

14. The method of claim 9, wherein the subject is a child.

15. A kit comprising a compound of claim 1 and instructions for use.

16. A pharmaceutical composition comprising a compound of claim 6, and a pharmaceutically acceptable excipient.

17. A method of reducing tactile dysfunction in a human subject diagnosed with Autism Spectrum Disorder (ASD), Rett syndrome (RTT), Phelan McDermid syndrome (PMS), or Fragile X syndrome, the method comprising administering to the subject the compound of claim 6 in an amount and for a duration sufficient to reduce the tactile dysfunction.

18. A method of reducing anxiety or social impairment in a human subject diagnosed with ASD, RTT, PMS, or Fragile X syndrome, the method comprising administering to the subject the compound of claim 6 in an amount and for a duration sufficient to reduce the anxiety or social impairment.

19. A method of treating touch over-reactivity and/or pain and/or mechanical allodynia in a human subject in need thereof, the method comprising administering to the subject a compound of claim 6 in an amount and for a duration sufficient to reduce the touch over-reactivity and/or pain and/or mechanical allodynia.

20. The method of claim 19, wherein the touch over-reactivity and/or pain is associated with a disease state selected from Sensory Processing Disorder (SPD) and fibromyalgia.

21. The method of claim 19, wherein the mechanical allodynia is associated with nerve injury, shingles, diabetic neuropathy, chemotherapy-induced neuropathy, or a neuropathic pain state.

22. A kit comprising a compound of claim 6 and instructions for use.

* * * * *

UNITED STATES PATENT AND TRADEMARK OFFICE
CERTIFICATE OF CORRECTION

PATENT NO. : 12,252,457 B2
APPLICATION NO. : 17/056069
DATED : March 18, 2025
INVENTOR(S) : David D. Ginty et al.

It is certified that error appears in the above-identified patent and that said Letters Patent is hereby corrected as shown below:

In the Drawings

Sheet 2 of 112, Figure 2 should be replaced with attached Figure 2.

Sheet 11 of 112, Figure 11A should be replaced with the attached Figure 11A.

Signed and Sealed this
Fifteenth Day of July, 2025

Coke Morgan Stewart
*Acting Director of the United States Patent and Trademark Office*